United States Patent
Naidu et al.

(10) Patent No.: US 7,511,037 B2
(45) Date of Patent: *Mar. 31, 2009

(54) N-[[4-FLUORO-2-(5-METHY-1H-1,2,4-TRIAZOL-1-YL)PHENYL]METHYL]-4-,6,7,9-TETRAHYDRO-3-HYDROXY-9,9-DIMETHYL-4-OXO-PYRIMIDO[2,1-C][1,4]OXAZINE-2-CARBOXAMIDE AS AN HIV INTEGRASE INHIBITOR

(75) Inventors: B. Narasimhulu Naidu, Durham, CT (US); Jacques Banville, St-Hubert (CA); Francis Beaulieu, Laprairie (CA); Timothy P. Connolly, Portland, CT (US); Mark R. Krystal, Westport, CT (US); John D. Matiskella, Wallingford, CT (US); Carl Ouellet, Boucherville (CA); Serge Plamondon, Ste-Catherine (CA); Roger Remillard, Napierville (CA); Margaret E. Sorenson, Meriden, CT (US); Yasutsugu Ueda, Clinton, CT (US); Michael A. Walker, Durham, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 176 days.

This patent is subject to a terminal disclaimer.

(21) Appl. No.: 11/505,149

(22) Filed: Aug. 16, 2006

(65) Prior Publication Data

US 2006/0276466 A1 Dec. 7, 2006

Related U.S. Application Data

(63) Continuation of application No. 11/126,891, filed on May 11, 2005, now Pat. No. 7,176,196.

(60) Provisional application No. 60/603,371, filed on Aug. 20, 2004, provisional application No. 60/575,513, filed on May 28, 2004.

(51) Int. Cl.
*A61K 31/5365* (2006.01)
*A61K 38/16* (2006.01)
*A61K 35/76* (2006.01)
*A61K 31/5513* (2006.01)
*A61K 31/662* (2006.01)
*A61P 31/18* (2006.01)
*C07D 498/04* (2006.01)

(52) U.S. Cl. ............... 514/230.5; 514/12; 514/220; 514/117; 514/81; 544/105

(58) Field of Classification Search ............ 514/233.2, 514/230.5
See application file for complete search history.

(56) References Cited

FOREIGN PATENT DOCUMENTS

WO WO 2006/060731 6/2006
WO WO 2006/103399 10/2006

OTHER PUBLICATIONS

Summa, V. et al. J. Med. Chem. Published on website: Oct. 25, 2006.

*Primary Examiner*—Brenda Coleman
*Assistant Examiner*—Susanna Moore
(74) *Attorney, Agent, or Firm*—James Epperson

(57) ABSTRACT

The invention encompasses a series of bicyclic pyrimidinone compounds of Formula I which inhibit HIV integrase and prevent viral integration into human DNA. This action makes the compounds useful for treating HIV infection and AIDS. The invention also encompasses pharmaceutical compositions and methods for treating those infected with HIV.

4 Claims, No Drawings

N-[[4-FLUORO-2-(5-METHY-1H-1,2,4-TRIAZOL-1-YL)PHENYL]METHYL]-4-,6,7,9-TETRAHYDRO-3-HYDROXY-9,9-DIMETHYL-4-OXO-PYRIMIDO[2,1-C][1,4]OXAZINE-2-CARBOXAMIDE AS AN HIV INTEGRASE INHIBITOR

CROSS REFERENCE TO RELATED APPLICATIONS

This application is a continuation of U.S. Nonprovisional application Ser. No. 11/126,891 filed May 11, 2005 now U.S. Pat. No. 7,176,196 and claims the benefit of U.S. Provisional Application Ser. Nos. 60/603,371 filed Aug. 20, 2004 and 60/575,513 filed May 28, 2004.

BACKGROUND OF THE INVENTION

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics (UNAIDS: Report on the Global HIV/AIDS Epidemic, December 1998), indicate that as many as 33 million people worldwide are infected with the virus. In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into three classes based on the viral protein they target and their mode of action. In particular, saquinavir, indinavir, ritonavir, nelfinavir and amprenavir are competitive inhibitors of the aspartyl protease expressed by HIV. Zidovudine, didanosine, stavudine, lamivudine, zalcitabine and abacavir are nucleoside reverse transcriptase inhibitors that behave as substrate mimics to halt viral cDNA synthesis. The non-nucleoside reverse transcriptase inhibitors, nevaripine, delavirdine and efavirenz inhibit the synthesis of viral cDNA via a non-competitive (or uncompetitive) mechanism. Used alone these drugs are effective in reducing viral replication. The effect is only temporary as the virus readily develops resistance to all known agents. However, combination therapy has proven very effective at both reducing virus and suppressing the emergence of resistance in a number of patients. In the US, where combination therapy is widely available, the number of HIV-related deaths has declined (Palella, F. J.; Delany, K. M.; Moorman, A. C.; Loveless, M. O.; Furher, J.; Satten, G. A.; Aschman, D. J.; Holmberg, S. D. N. *Engl. J. Med.* 1998, 338, 853-860).

Unfortunately, not all patients are responsive and a large number fail this therapy. In fact, approximately 30-50% of patients ultimately fail combination therapy. Treatment failure in most cases is caused by the emergence of viral resistance. Viral resistance in turn is caused by the rapid turnover of HIV-1 during the course of infection combined with a high viral mutation rate. Under these circumstances incomplete viral suppression caused by insufficient drug potency, poor compliance to the complicated drug regiment as well as intrinsic pharmacological barriers to exposure provides fertile ground for resistance to emerge. More disturbing are recent findings which suggest that low-level replication continues even when viral plasma levels have dropped below detectable levels (<50 copies/ml) (Carpenter, C. C.; Cooper, D. A.; Fischl, M. A.; Gatell, J. M.; Gazzard, B. G.; Hammer, S. M.; Hirsch, M. S.; Jacobsen, D. M.; Katzenstein, D. A.; Montaner, J. S.; Richman, D. D.; Saag, M. S.; Schechter, M.; Schooley, R. T.; Thompson, M. A.; Vella, S.; Yeni, P. G.; Volberding, P. A. *JAMA* 2000, 283, 381-390). Clearly there is a need for new antiviral agents, preferably targeting other viral enzymes to reduce the rate of resistance and suppress viral replication even further.

HIV expresses three enzymes, reverse transcriptase, an aspartyl protease, and integrase. All three are targets for treating AIDS and HIV infection. HIV integrase catalyzes insertion of the viral cDNA into the host cell genome, which is a critical step in the viral life cycle. HIV integrase inhibitors belonging to a class of diketo acid compounds prevented viral integration and inhibited HIV-1 replication in cells (Hazuda et al. *Science* 2000, 287, 646). And recently, HIV integrase inhibitors have been accepted into clinical trials for treating AIDS and HIV infection (Neamati *Expert. Opin. Ther. Patents* 2002, 12, 709, Pais and Burke *Drugs Fut.* 2002, 27, 1101).

DESCRIPTION OF THE INVENTION

The invention encompasses compounds of Formula I, including pharmaceutically acceptable salts and solvates, their pharmaceutical compositions, and their use in inhibiting HIV integrase and treating those infected with HIV or AIDS.

One aspect of the invention are compounds of Formula I

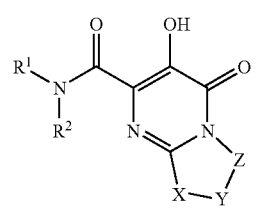

wherein:
$R^1$ is $C_{1-6}(Ar^1)$alkyl, $C_{1-6}(Ar^1)(CON(R^8)(R^9))$alkyl, $C_{1-6}(Ar^1)(CO_2R^{14})$alkyl, $C_{1-6}(Ar^1)$hydroxyalkyl, or $C_{1-6}(Ar^1)$oxyalkyl;

$R^2$ is hydrogen, $C_{1-6}$alkyl, or $OR^{14}$;

$R^3$ is hydrogen, halo, hydroxy, cyano, $C_{1-6}$alkyl, $C_{3-7}$cycloalkyl, $C_{5-7}$cycloalkenyl, $C_{1-6}$haloalkyl, $C_{1-6}$alkoxy, $C_{1-6}$alkylthio, $C_{1-6}$haloalkoxy, $N(R^8)(R^9)$, $NHAr^2$, $N(R^6)SO_2R^7$, $N(R^6)COR^7$, $N(R^6)CO_2R^7$, $OCOR^7$, $OCO_2R^7$, $OCON(R^8)(R^9)$, $OCH_2CO_2R^7$, $OCH_2CON(R^8)(R^9)$, $COR^6$, $CO_2R^6$, $CON(R^8)(R^9)$, $SOR^7$, $S(=N)R^7$, $SO_2R^7$, $SO_2N(R^6)(R^6)$, $PO(OR^6)_2$, $C_{2-4}(R^{12})$alkynyl, $R^{13}$, $Ar^2$, or $Ar^3$;

$R^4$ is hydrogen, halo, hydroxy, cyano, $C_{1-6}$alkyl, $C_{1-6}$alkoxy, $C_{1-6}$haloalkyl, $C_{1-6}$haloalkoxy, or $N(R^6)(R^6)$;

$R^5$ is hydrogen, halo, hydroxy, cyano, $C_{1-6}$alkyl, $C_{1-6}$alkoxy, $C_{1-6}$haloalkyl, $C_{1-6}$haloalkoxy, or $N(R^6)(R^6)$;

$R^6$ is hydrogen, $C_{1-6}$alkyl, or $C_{3-7}$cycloalkyl;

$R^7$ is $C_{1-6}$alkyl or $C_{3-7}$cycloalkyl;

$R^8$ is hydrogen, $C_{1-6}$alkyl, $C_{1-6}$hydroxyalkyl, $C_{1-6}(C_{1-6}$alkoxy)alkyl or $C_{1-6}(C_{1-6}$dialkylamino)alkyl;

$R^9$ is hydrogen, $C_{1-6}$alkyl, $C_{1-6}$hydroxyalkyl, $C_{1-6}(C_{1-6}$alkoxy)alkyl or $C_{1-6}(C_{1-6}$dialkylamino)alkyl; or $N(R^8)(R^9)$ taken together is azetidinyl, pyrrolidinyl, $(R^{10})$-piperidinyl, $N-(R^{11})$-piperazinyl, morpholinyl, thiomorpholinyl, or dioxothiazinyl;

$R^{10}$ is hydrogen, $C_{1-6}$alkyl, or $C_{1-6}$hydroxyalkyl;

$R^{11}$ is hydrogen, $C_{1-6}$alkyl, $C_{3-7}$cyclolkyl, $COR^6$, or $CO_2R^6$;

$R^{12}$ is hydrogen, hydroxy, $N(R^6)(R^6)$, $SO_2R^7$, $OSO_2R^7$, or dioxothiazinyl;

$R^{13}$ is azetidinonyl, pyrrolidinonyl, valerolactamyl, caprolactamyl, maleimido, oxazolidonyl, or dioxothiazinyl, and is substituted with 0-1 substituents selected from the group consisting of hydroxymethyl, acetoxymethyl, and aminomethyl;

$R^{14}$ is hydrogen or $C_{1-6}$alkyl;

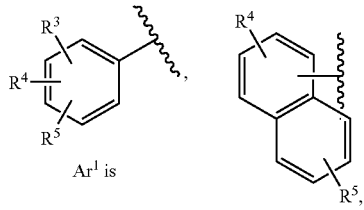

$Ar^1$ is

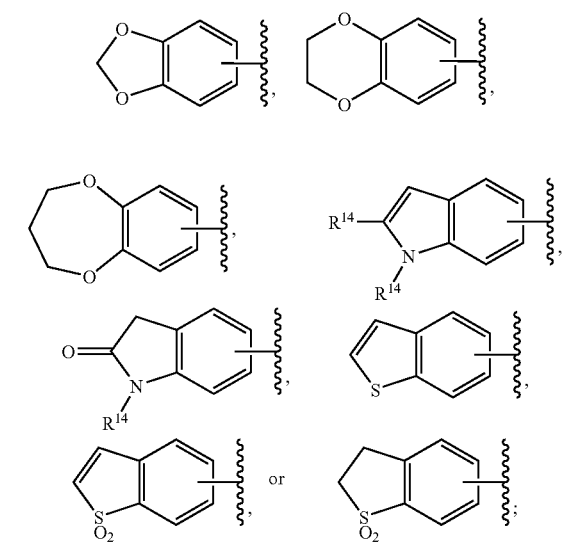

$Ar^2$ is tetrazolyl, triazolyl, oxadiazolyl, thiadiazolyl, pyrazolyl, imidazolyl, oxazolyl, thiazolyl, isoxazolyl, isothiazolyl, furanyl, thienyl, pyrrolyl, pyrimidinyl, pyrazinyl, pyridinyl, hydroxypyridinyl, quinolinyl, isoquinolinyl, or indolyl, and is substituted with 0-2 substituents selected from the group consisting of halo, cyano, benzyl, $C_{1-6}$alkyl, $C_{1-6}$alkoxy, $N(R^8)(R^9)$, $CON(R^8)(R^9)$, $CO_2R^6$, $CONHSO_2N(R^6)(R^6)$, $CONHSO_2N(R^6)$(phenyl), and $CONHSO_2N(R^6)$(halophenyl);

$Ar^3$ is phenyl substituted with 0-2 substituents selected from the group consisting of halo, cyano, hydroxy, $C_{1-6}$alkyl, $C_{1-6}$alkoxy, $(C_{1-6}$alkoxy)methyl, $C_{1-6}$haloalkyl, $C_{1-6}$haloalkoxy, $N(R^8)(R^9)$, $CON(R^6)(R^6)$, and $CH_2N(R^8)(R^9)$, or is dioxolanylphenyl; and X—Y—Z is $C(R^{14})_2OC(R^{14})_2$, $C(R^{14})_2OC(R^{14})_2C(R^{14})_2$, or $C(R^{14})_2OC(R^{14})_2C(R^{14})_2C(R^{14})_2$;

or a pharmaceutically acceptable salt or solvate thereof.

Another aspect of the invention is a compound of Formula I where $R^1$ is $C_{1-6}(Ar^1)$alkyl.

Another aspect of the invention is a compound of Formula I where $R^1$ is

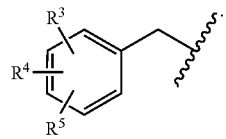

Another aspect of the invention is a compound of Formula I where $R^1$ is

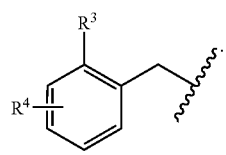

Another aspect of the invention is a compound of Formula I where $R^2$ is hydrogen.

Another aspect of the invention is a compound of Formula I where $R^3$ is hydrogen, halo, $N(R^8)(R^9)$, $N(R^6)COR^7$, $OCON(R^8)(R^9)$, $CON(R^8)(R^9)$, $SOR^7$, $SO_2R^7$, $SO_2N(R^6)(R^6)$, $PO(OR^6)_2$, $R^{13}$, or $Ar^2$.

Another aspect of the invention is a compound of Formula I where X—Y—Z is $C(R^{14})_2OCH_2$, $C(R^{14})_2OCH_2CH_2$, or $C(R^{14})_2OCH_2CH_2CH_2$.

Another aspect of the invention is a compound of Formula I where X—Y—Z is $CH_2OCH_2$, $C(CH_3)HOCH_2$, $C(CH_3)_2OCH_2$, $CH_2OCH_2CH_2$, $C(CH_3)HOCH_2CH_2$, $C(CH_3)_2OCH_2CH_2$, $CH_2OCH_2CH_2CH_2$, $C(CH_3)HOCH_2CH_2CH_2$, or $C(CH_3)_2OCH_2CH_2CH_2$.

For a compound of Formula I, any scope of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $Ar^1$, $Ar^2$, $Ar^3$, and X—Y—Z can be used independently with any scope of any other substituent.

"Alkyl," "alkoxy," "hydroxyalkyl," and related terms with an alkyl moiety include straight and branched configurations. A term such as "$C_{1-6}(R)$alkyl" means a straight or branched alkyl group of one to six carbons substituted with the substituent R. "Haloalkyl" and "halophenyl" include all permutations of halogenated alkyl or phenyl groups, from monohalo to perhalo. "Aryl" means an aromatic ring system and includes carbocyclic and heterocyclic systems. Some substituents are divalent, such as X—Y—Z. Asymmetric divalent substituents may be attached in either of the two configurations.

"$C_{1-6}(Ar^1)$oxyalkyl" means $Ar^1$ is attached at the oxygen. "Dioxolanyphenyl" means

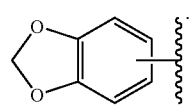

"Dioxothiazinyl" means

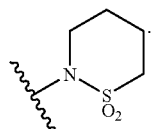

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

Some of the compounds of the invention exist in stereoisomeric forms. The invention includes all stereoisomeric forms of the compounds including enantiomers and diastereomers. An example of enantiomers is shown below. Methods of making and separating stereoisomers are known in the art.

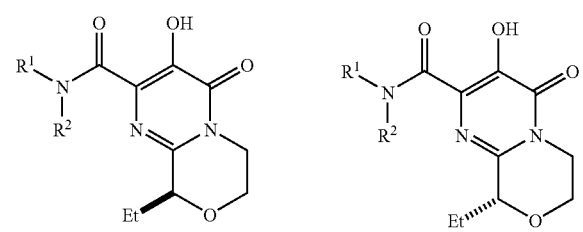

The invention includes all tautomeric forms of the compounds. An example of a tautomeric pair is shown below.

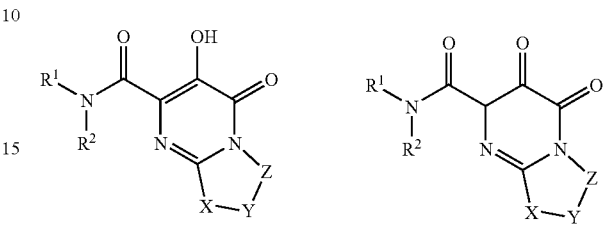

The compounds of this invention can be made by various methods known in the art including those of the following schemes and in the specific embodiments section. The variables shown in the synthetic schemes are distinct from and should not be confused with the variables in the claims or the rest of the specification. The variables in the schemes are meant only to illustrate how to make some of the compounds of this invention.

Some compounds can be synthesized from an appropriately substituted heterocycle I-1 according to Scheme I, where $R_a$ and P can serve as protecting groups (see Greene, T. W. and Wutz, P. G. M. Protective Groups in Organic Synthesis, Second Edition, 1991, John Wiley and Sons, New York). When P is benzyl or substituted benzyl it can be removed by hydrogenolysis ($H_2$—Pd/C) or acid hydrolysis (trifluoroacetic acid) to yield intermediate I-2. I-2 can be transaminated to I-4 by reaction with amine I-3. In a number of cases this reaction can be carried out by heating I-3 and I-2 together in the presence of base. Alternatively, standard amide coupling reagents can be used to effect the formation of the amide bond. When $R_a$ is a lower alkyl group, $R_a$ can be removed under ester hydrolysis conditions, such as treatment with NaOH, LiOH, or KOH to deliver the corresponding carboxylic acid I-5. Alternatively, $R_a$ can be removed by nucleophilic displacement using NaI. When $R_a$ is benzyl and substituted benzyl, $R_a$ can be removed by hydrogenolysis. Intermediate I-5 can be coupled using amide bond forming reagents such as BOP, DCC, EDCI, PyBrop, PyBop or other reagents (see March, J. Advanced Organic Chemistry, Fourth Edition 1992 John Wiley & Sons, New York). The resulting intermediate I-6 can be deprotected as described for intermediate I-1.

Scheme I.

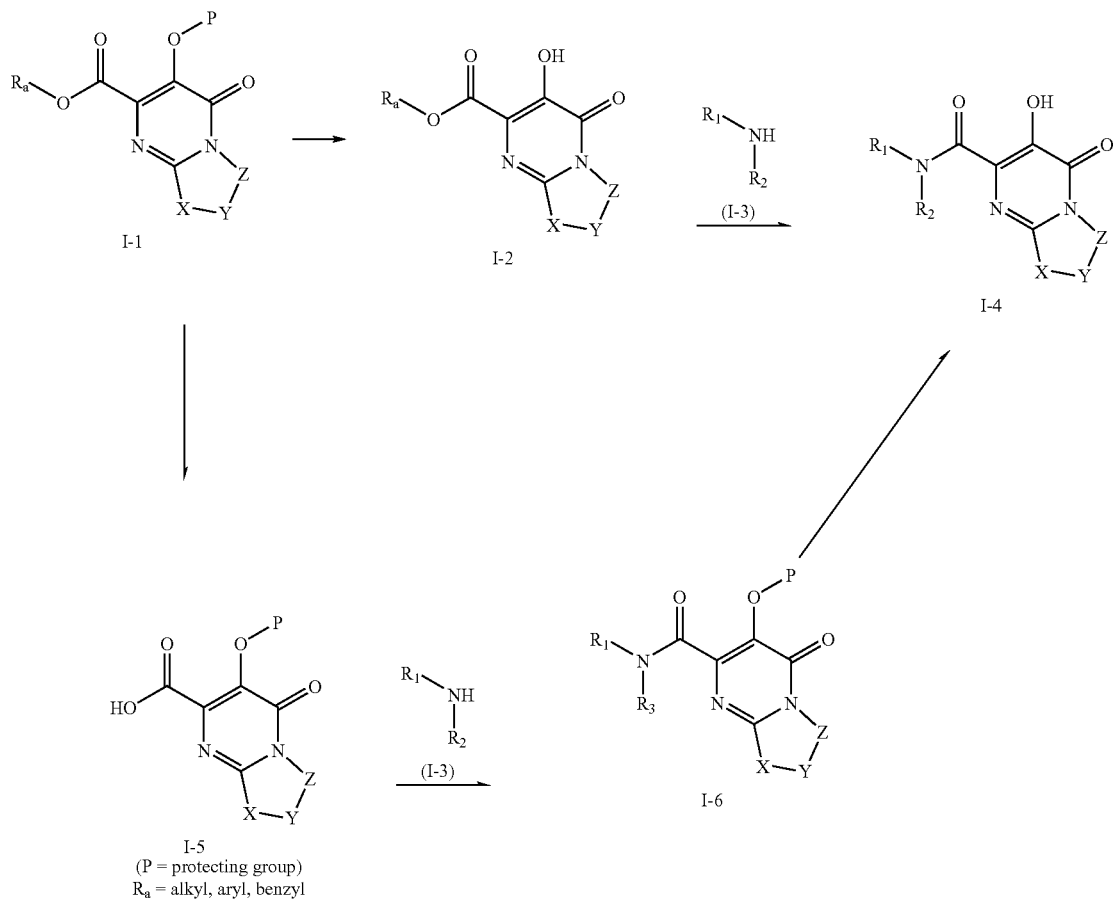

In Scheme II, intermediate II-3 can be prepared using methods similar to those described in Sunderland, J. S.; Botta, M.; Aime, S.; Raymond, K. N. Inorg. Chem. (2001), 40, 6756-6756, where II-1 and II-2 are condensed, to provide intermediate II-3. This reaction is usually conducted in the presence of a base such as sodium hydride (NaH), sodium ethoxide (EtONa) or lithium hexamethyldisilazide (LiHMDS). Using the methods described in the reference, II-3 can be condensed with an appropriately substituted amidine II-4 to form II-5. Substituent B can be a leaving group, such as -halo (Cl, Br or I) or can be converted to a leaving group under appropriate conditions such as by forming the corresponding methylsulfonate ester. When substituent B is a methyl sulphide group it can be treated with iodomethane to form a dimethylsulfonium intermediate which is activated towards nucleophilic attack to effect ring closure.

Scheme II.

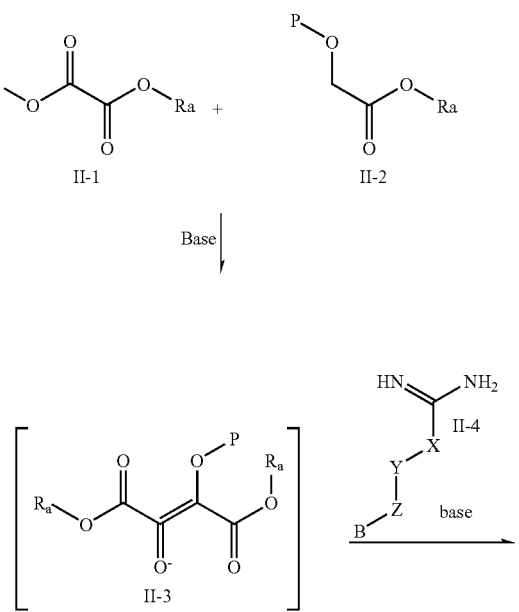

-continued

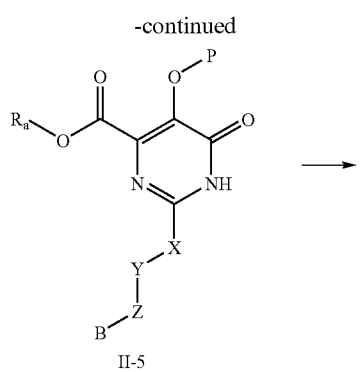

II-5

In Scheme III, intermediate II-3 can be condensed with a cyclic-amidine to yield intermediate I-1. Intermediate III-1 can be prepared using known methods (see Patai, S. and Rappoport, Z. The Chemistry of Amidines and Imidates, Volume 2, 1991, John Wiley & Sons, New York).

Scheme III.

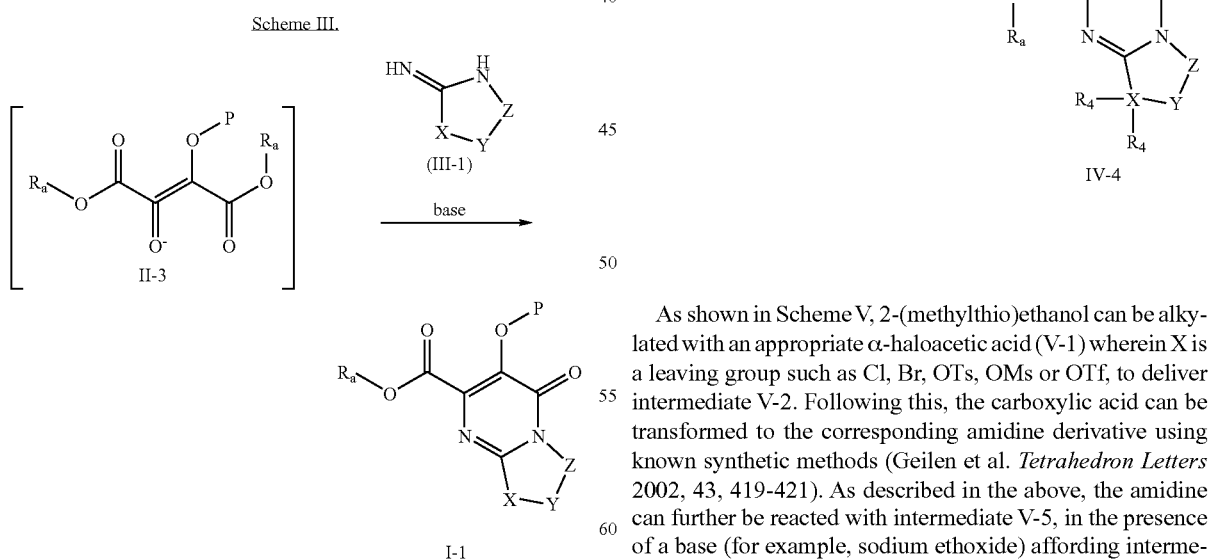

In Scheme IV, nitrile IV-1; possessing a potential leaving group B, can be reacted with hydroxylamine to form intermediate IV-2. This intermediate can be reacted with a suitably protected alkyne to form IV-3 which can rearrange to from intermediate IV-4 according to literature methods (Culbertson, T. P. *Journal of Heterocyclic Chemistry*, 1979, 16, 1423-1424).

Scheme IV.

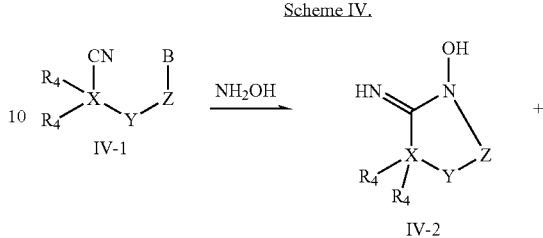

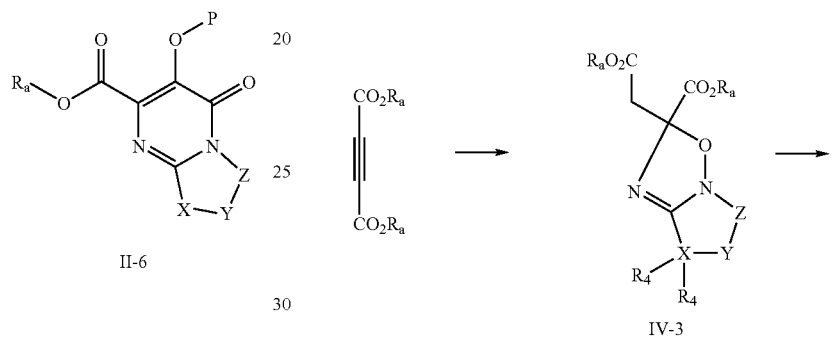

As shown in Scheme V, 2-(methylthio)ethanol can be alkylated with an appropriate α-haloacetic acid (V-1) wherein X is a leaving group such as Cl, Br, OTs, OMs or OTf, to deliver intermediate V-2. Following this, the carboxylic acid can be transformed to the corresponding amidine derivative using known synthetic methods (Geilen et al. *Tetrahedron Letters* 2002, 43, 419-421). As described in the above, the amidine can further be reacted with intermediate V-5, in the presence of a base (for example, sodium ethoxide) affording intermediate V-6. Methylation of the sulphide ether can be accomplished by treating V-6 with iodomethane and the resulting sulfonium derivative (V-7) treated with base to form the bicyclic template V-8. This intermediate can be used in the synthesis of final compounds using methods described in Scheme I.

Scheme V
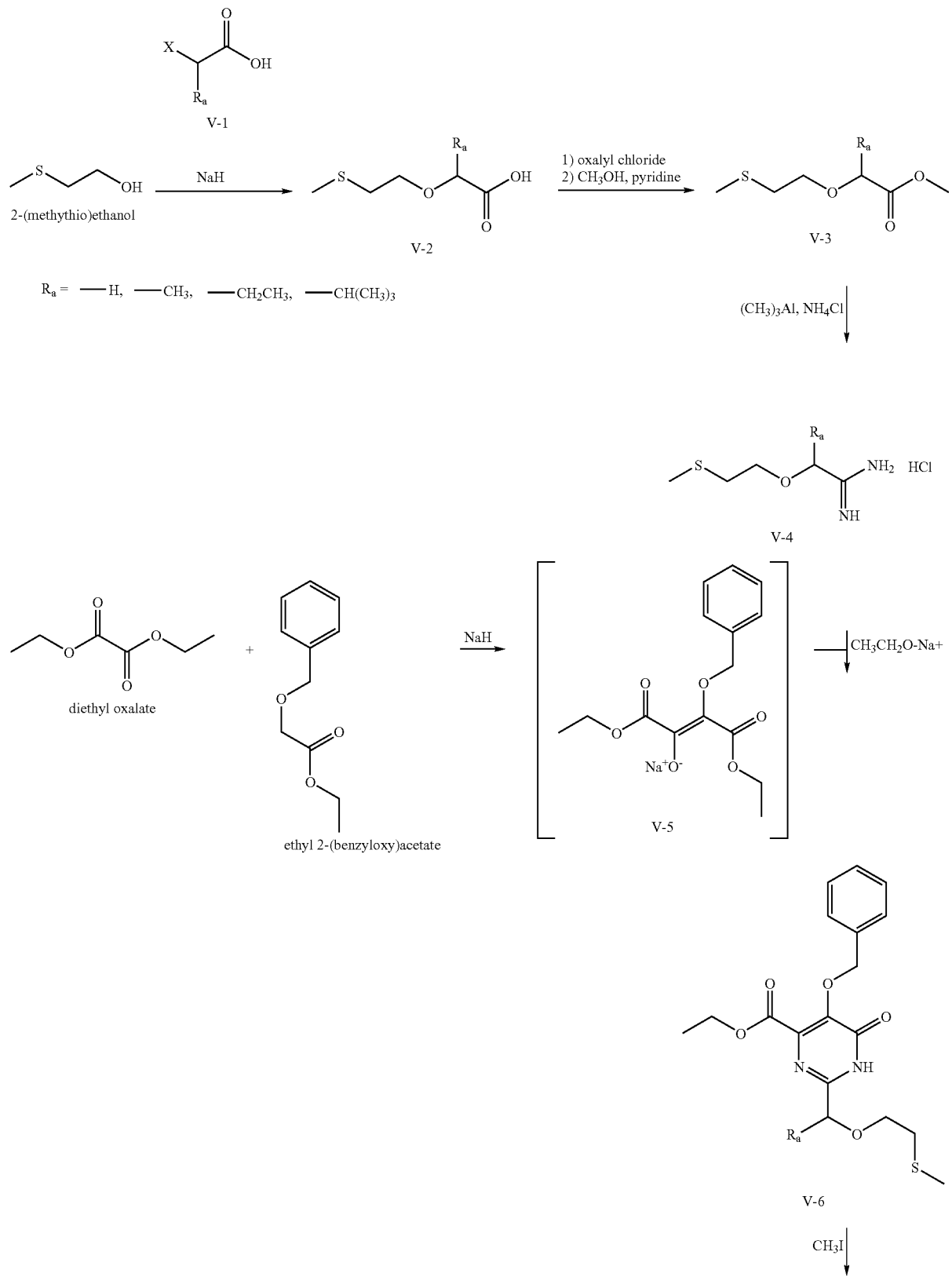

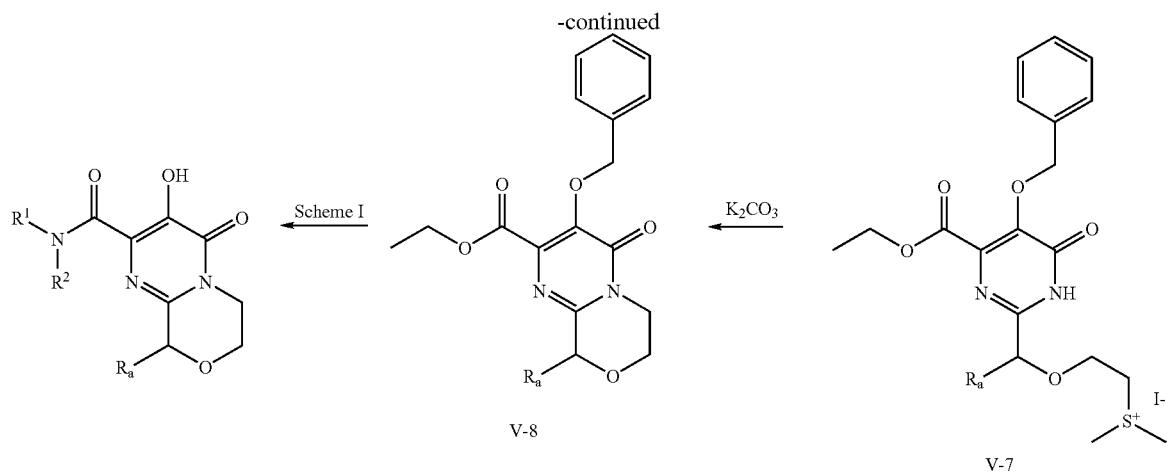

In Scheme VI, 3-methylthiopropanal is converted to dioxolane VI-1 using well known chemistry. Treatment with trimethylsilylcyanide (TMSCN), in the presence of zinc iodide (ZnI$_2$) produces intermediate VI-2. Reaction with ammonia provides amidine VI-3 which is used in the synthesis of pyrimidinone VI-4 according to the methods described in the previous schemes. Subsequent treatment with CH$_3$SO$_2$Cl and triethylamine (Et$_3$N) results in the corresponding bicyclic intermediate VI-5. Completion of the synthesis can be carried out as illustrated in Scheme I.

Scheme VI

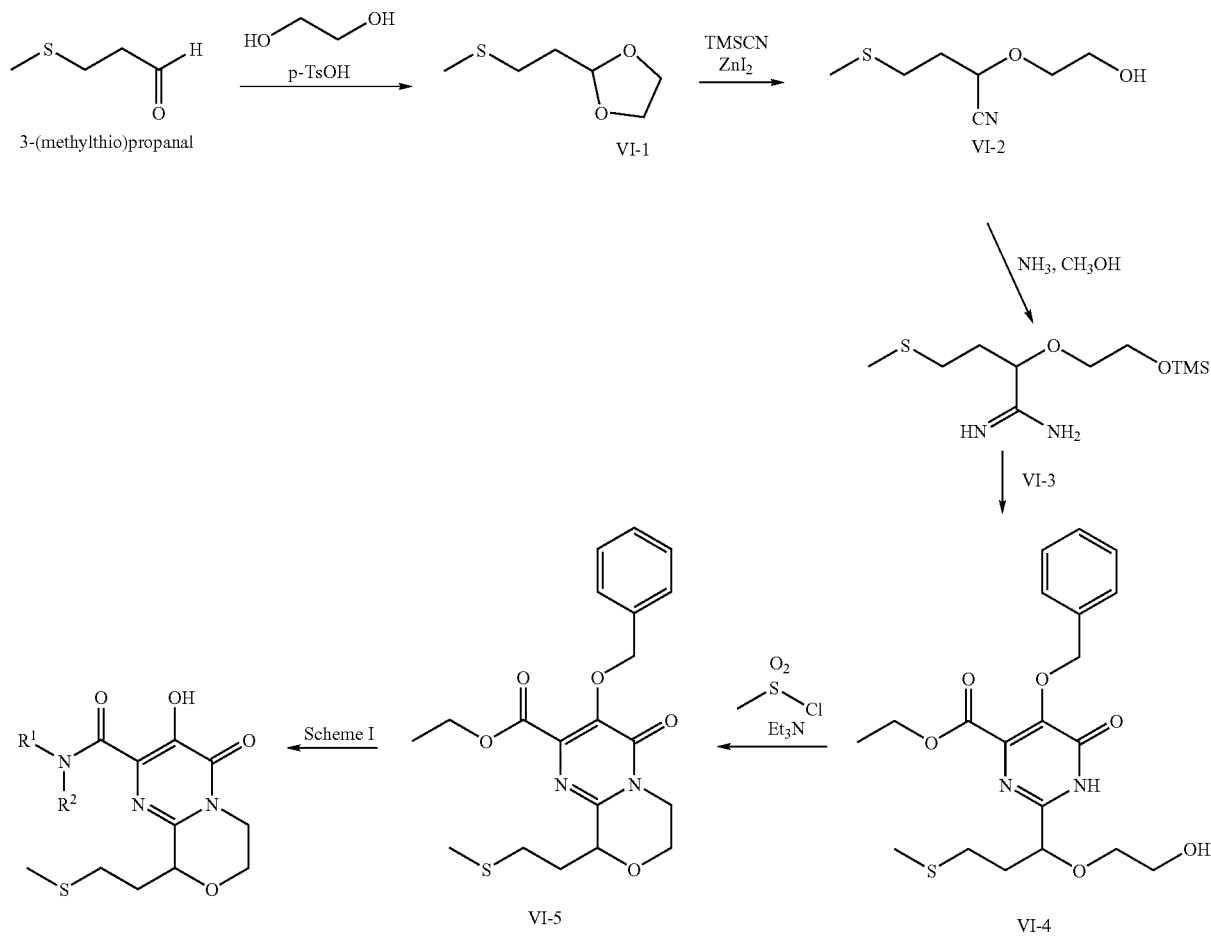

Another method is illustrated in Scheme VII. This synthetic path begins with an appropriately substituted ketone which can be transformed to the corresponding nitrile intermediate VII-1. This in turn can be reacted with 2-chloroethanol to produce compound VII-2, which can be reacted with hydroxylamine and an acetylene dicarboxylate ester to yield intermediate VII-4. Heating of the intermediate can yield intermediate VII-5. Synthesis of the corresponding amide derivatives can be accomplished according to Scheme I.

In Scheme VIII, benzylation of the hydroxyl group of VII-5, as a means of functional group protection, can be achieved using benzyl bromide under basic conditions (for example, $K_2CO_3$ or NaH). Saponification of the ester group of VIII-1 can provide VIII-2 which can be coupled with appropriately substituted amines ($R^1R^2NH$) using well known amide bond forming reagents, such as benzotriazole-1-yloxy-tris-pyrrolidino-phosphonium hexafluorophosphate (PyBOP) or O-(7-azabenzotriazol-1-yl)-N,N,N',N'-tetram-

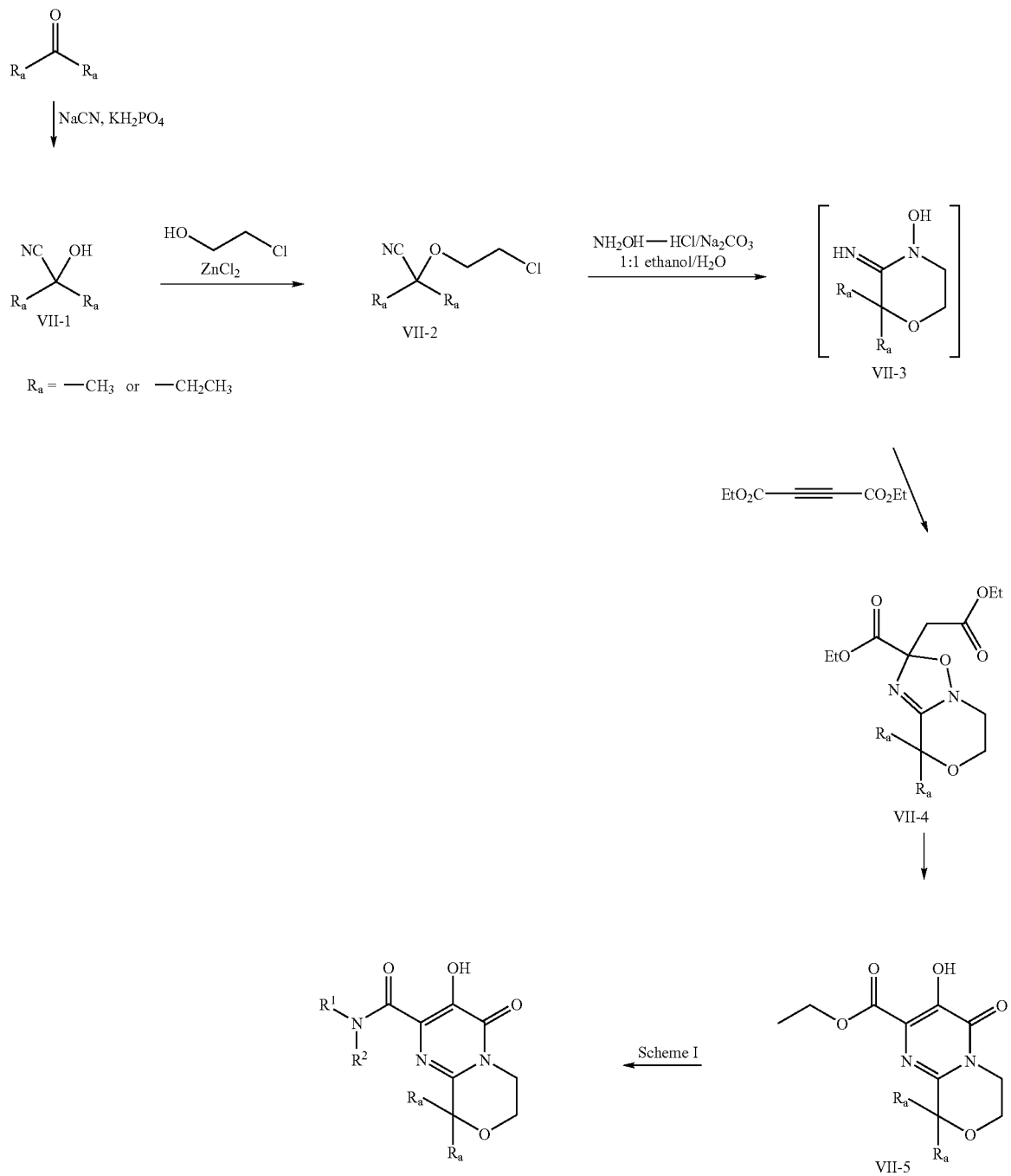

ethyluronium hexafluorophosphate (HATU). Alternatively, the corresponding acid chloride can be formed, by treatment with oxalyl chloride, and reacted with an appropriate amine to form the amide bond. Removal of the benzyl group can be accomplished under a variety of conditions including treatment with $CF_3CO_2H$ or $H_2$ (Pd—C).

those described in the previous schemes. This intermediate can be carried on to the final product according to a variety of paths. In one, the hydroxyl group can be benzoylated to provide intermediate IX-4 which can be further treated with $K_2CO_3$ to effect ring closure to form the bicyclic template IX-5. Alternatively, direct treatment of IX-3 with $K_2CO_3$ can

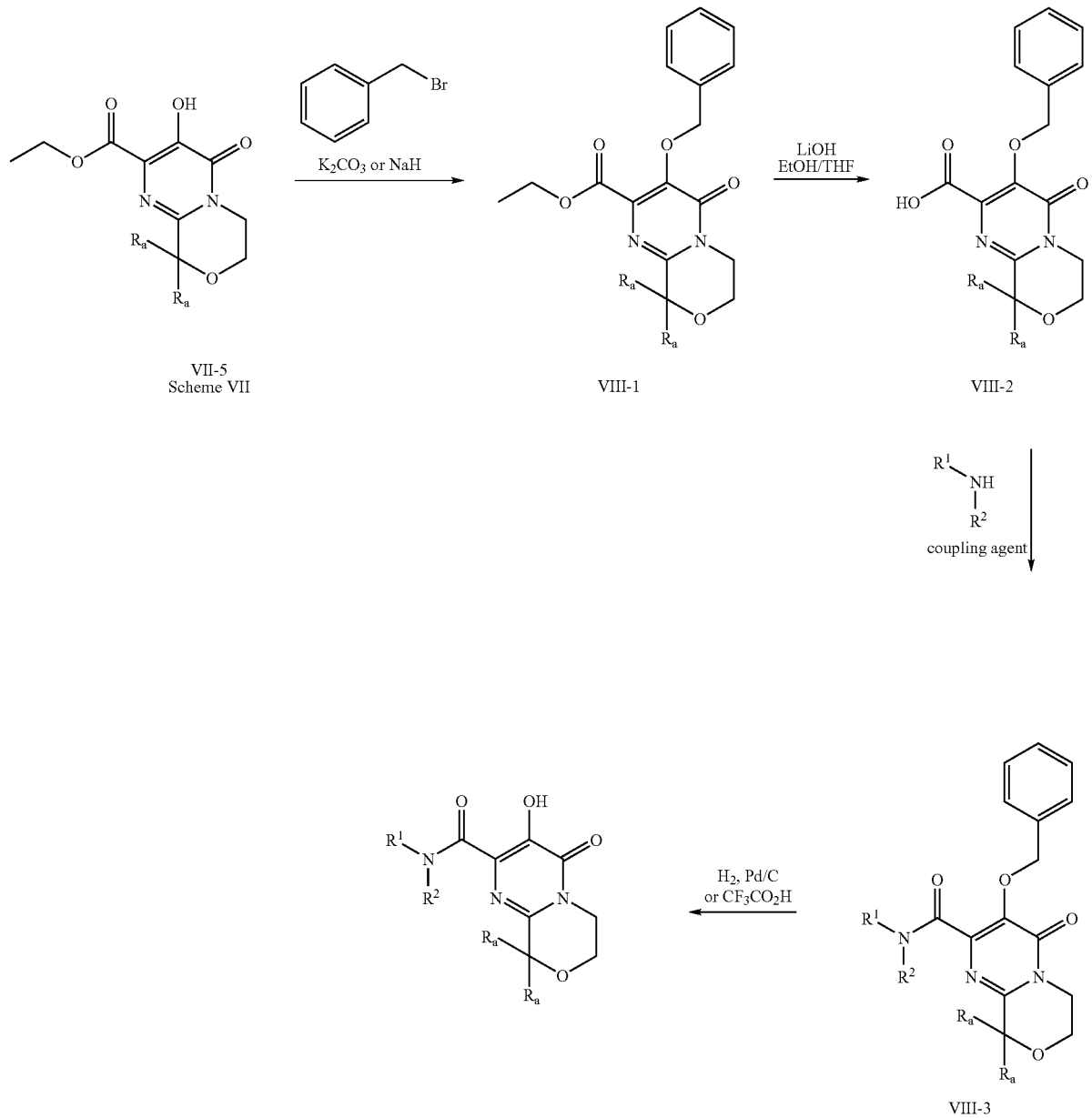

In yet another method, some compounds of this invention can be synthesized according to Scheme IX. In Scheme IX, pyrimidinone IX-3, can be produced using methods similar to provide intermediate IX-6. Intermediates IX-5, an IX-6 can be used in the synthesis the final products using the methods described in Scheme I.

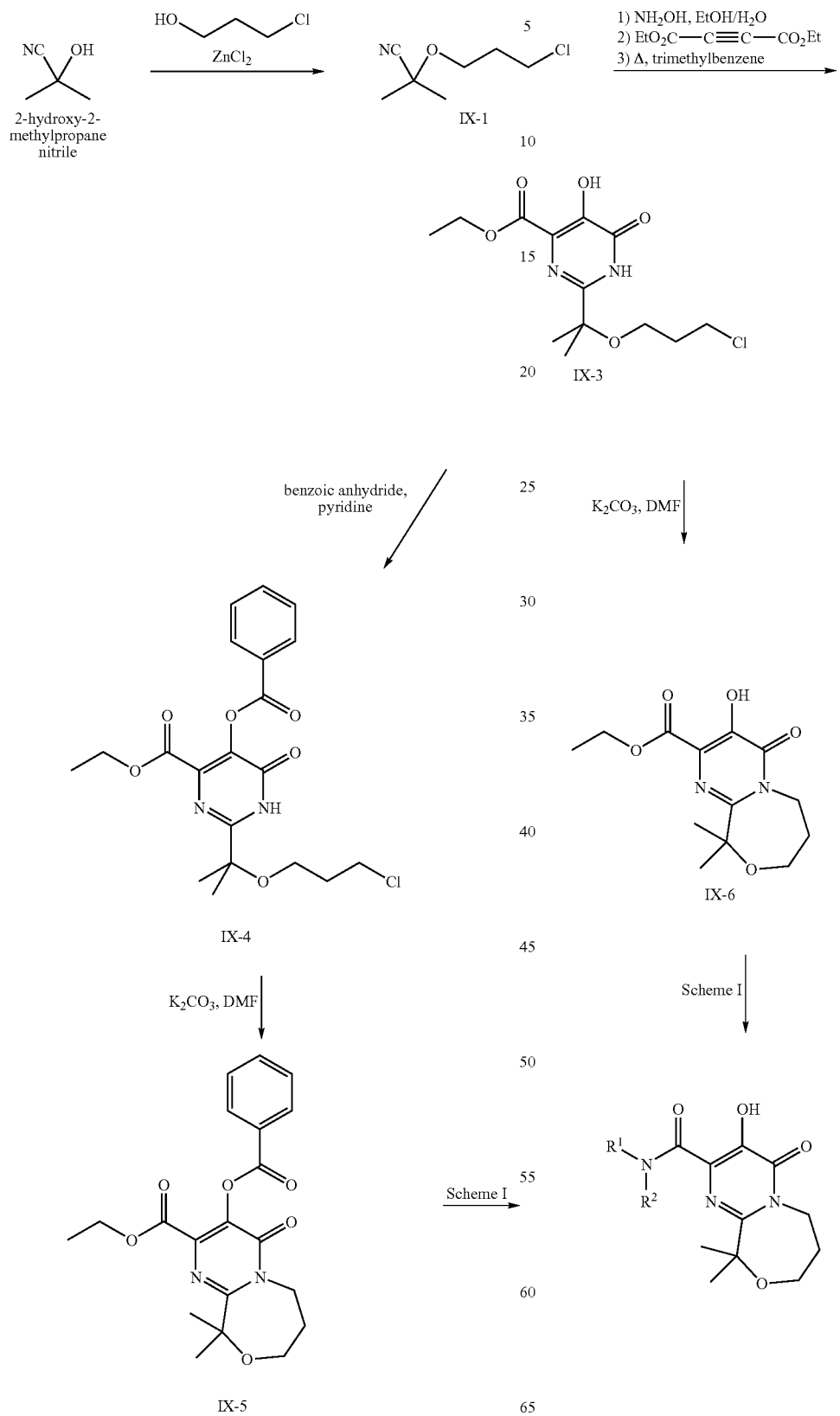

In Scheme X, IX-3 can be used to synthesize the benzylated intermediate X-1. This intermediate can be carried on to final product using methods analogous to those described in Scheme VIII.
Scheme X
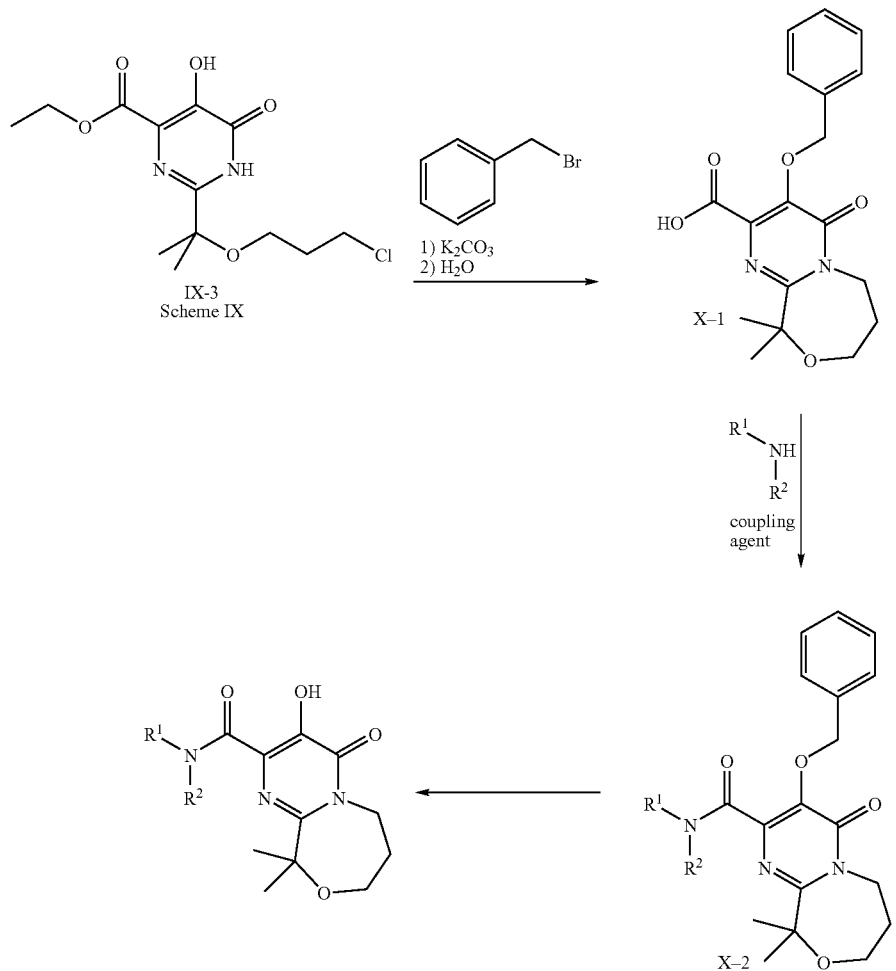
The synthesis of (2-(aminomethyl)-5-fluorophenyl)(morpholino)methanone hydrochloride is illustrated in Scheme XI.
Scheme XI
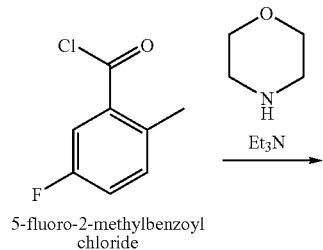

-continued

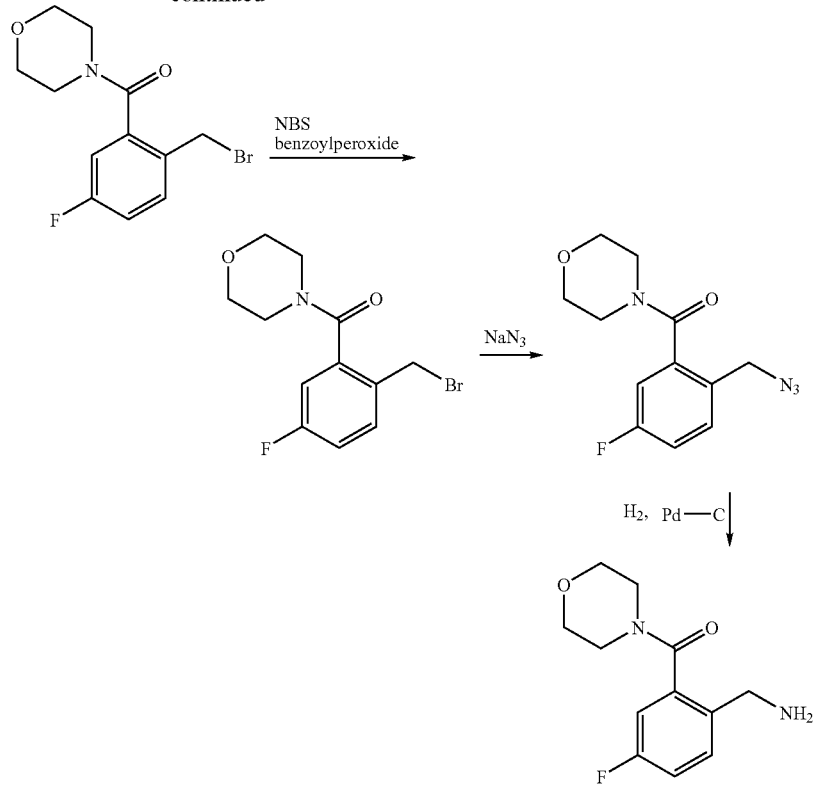

In Scheme XII, bicyclic intermediate XII-1, prepared according to the methods described above, can be saponified using well known methods. The resulting carboxylic acid, XII-3, can then be coupled to amine XII-2 using standard amide bond forming reagents and methods. Removal of the benzyl group, by hydrogenolysis or acid mediated hydrolysis provides the final products.

Scheme XII

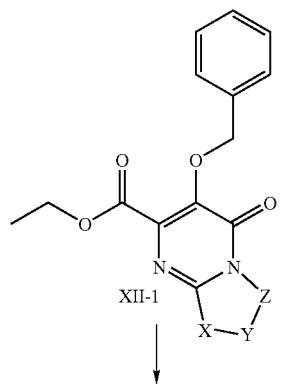

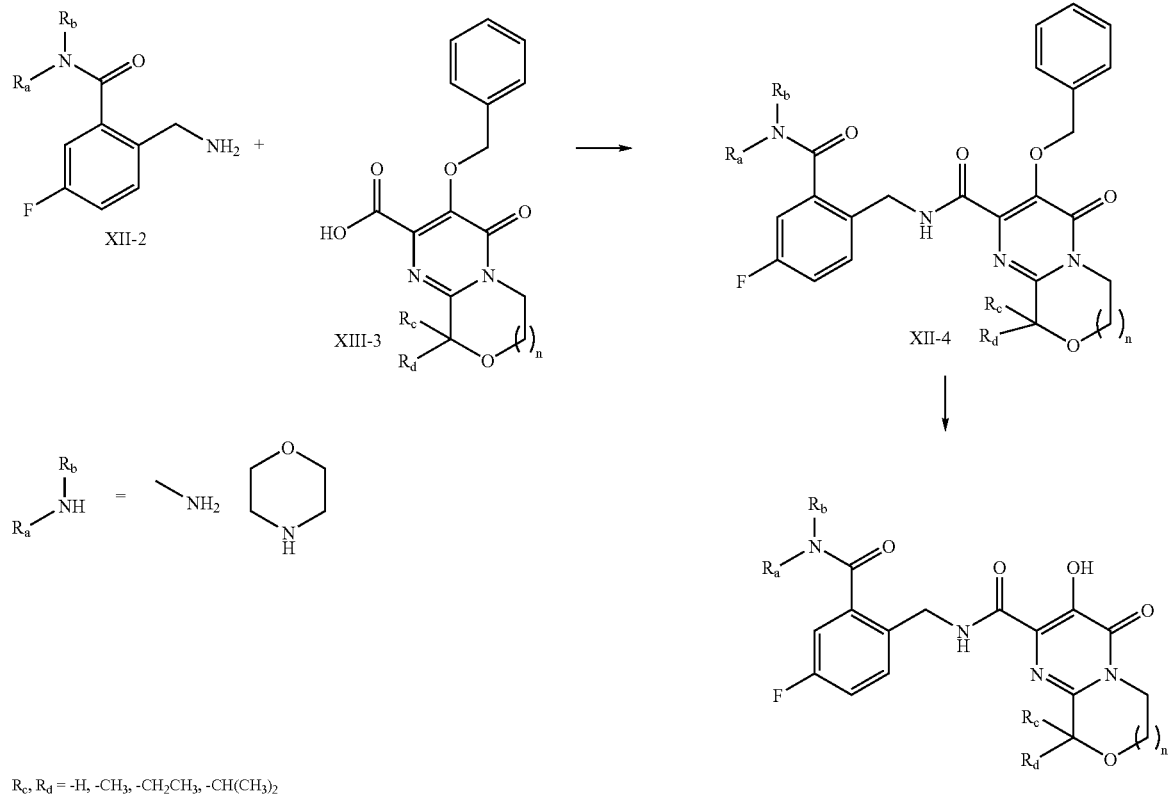

An alternative route to compounds similar to those presented in Scheme XII is given in Scheme XIII. In this scheme the ester group of XIII-1 can be hydrolyzed and the resulting carboxylic acid coupled to methyl 2-(aminomethyl)-5-fluorobenzoate. A second hydrolysis reaction can produce XIII-4 which can be coupled with a second amine. This is followed by removal of the benzyl group to provide the final products.

Scheme XIII

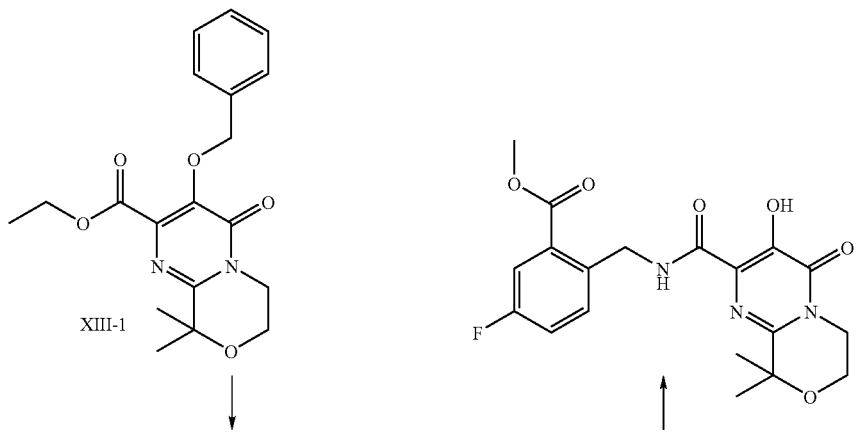

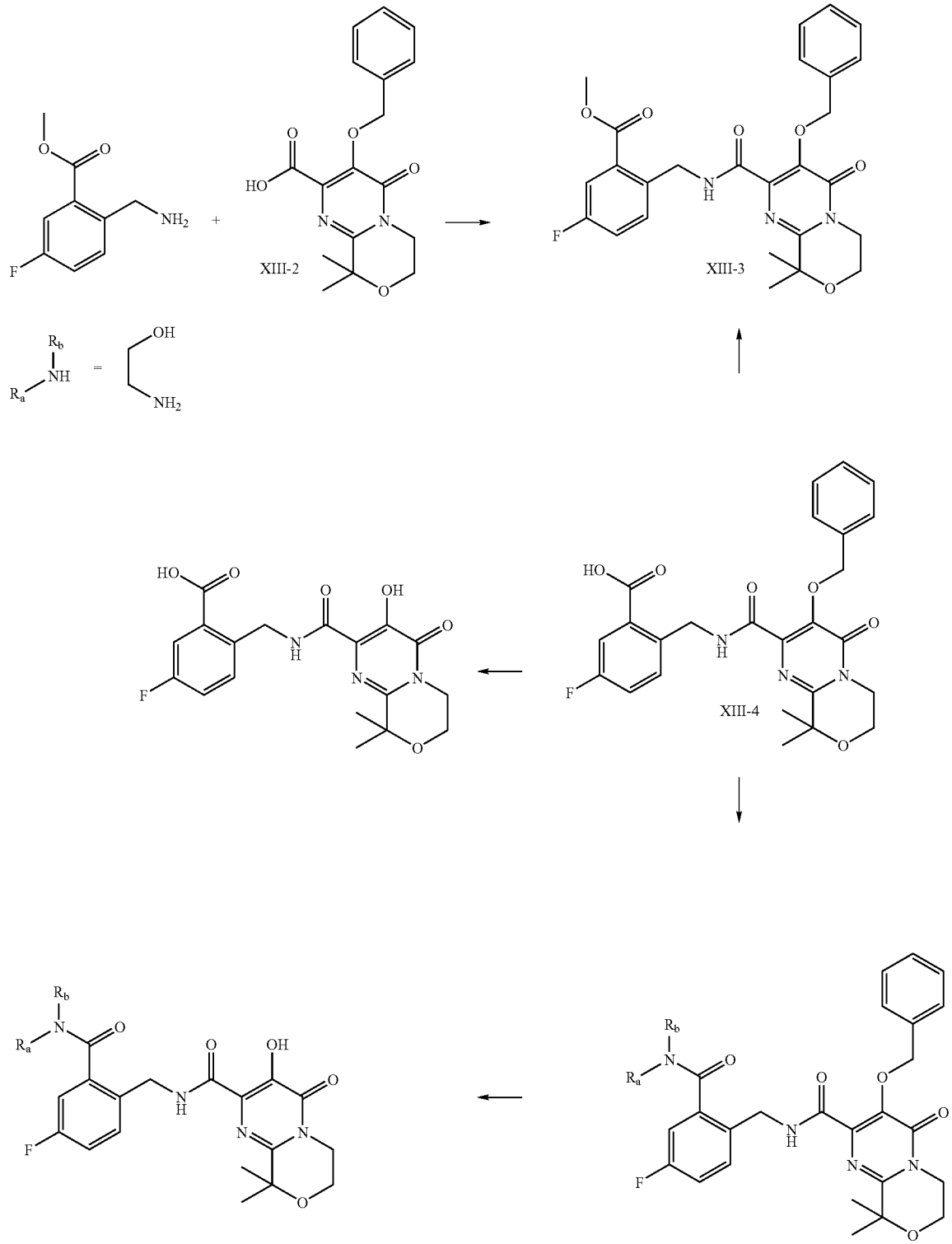
In yet another method, Scheme XIV illustrates the synthesis of sulfonamide containing examples, starting from 5-fluoro-2-methylbenzen-1-sulfonlyl chloride.

Scheme XIV
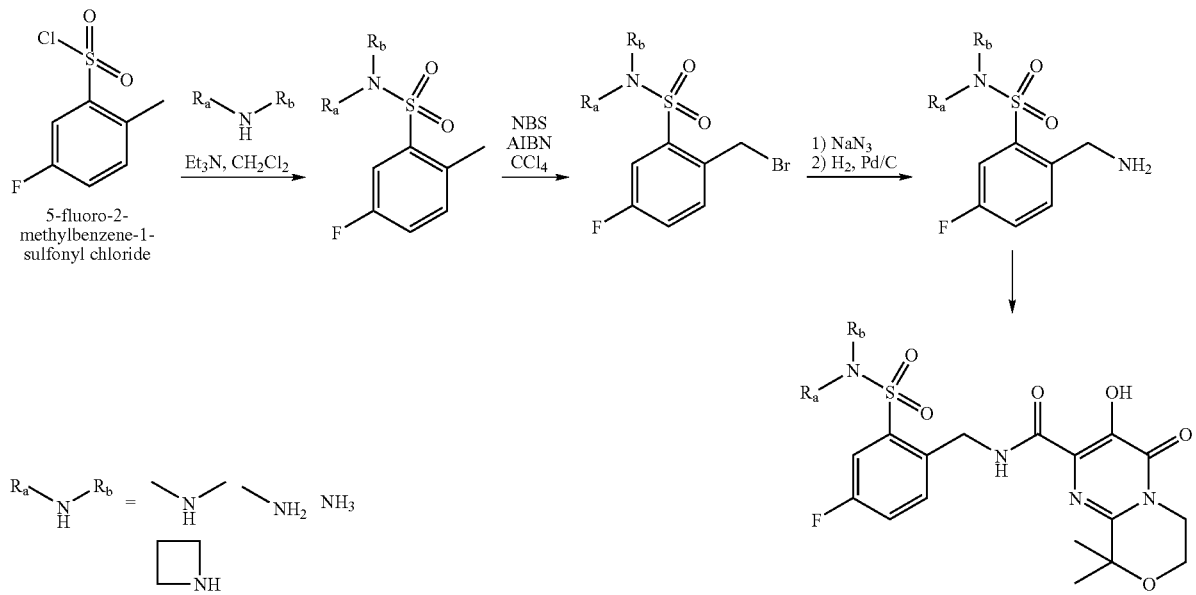
Further illustration of methods used for the synthesis of certain compounds of the invention is shown in Scheme XV. Methylation of 5-(2-bromo-5-fluorophenyl)-1H-tetrazole can yield a mixture of XV-1 and XV-2 that can be separated and each of the compounds carried on to the corresponding final products.
Scheme XV
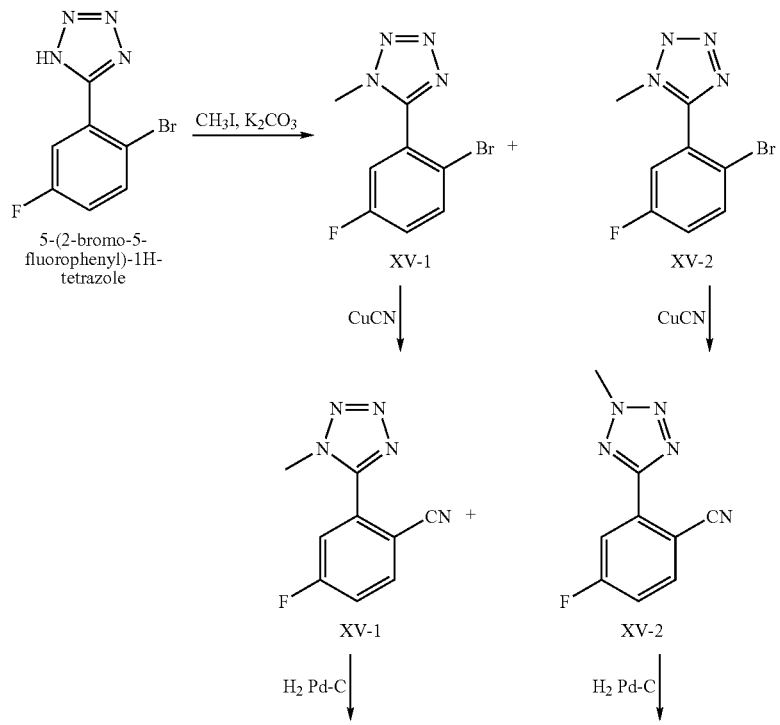

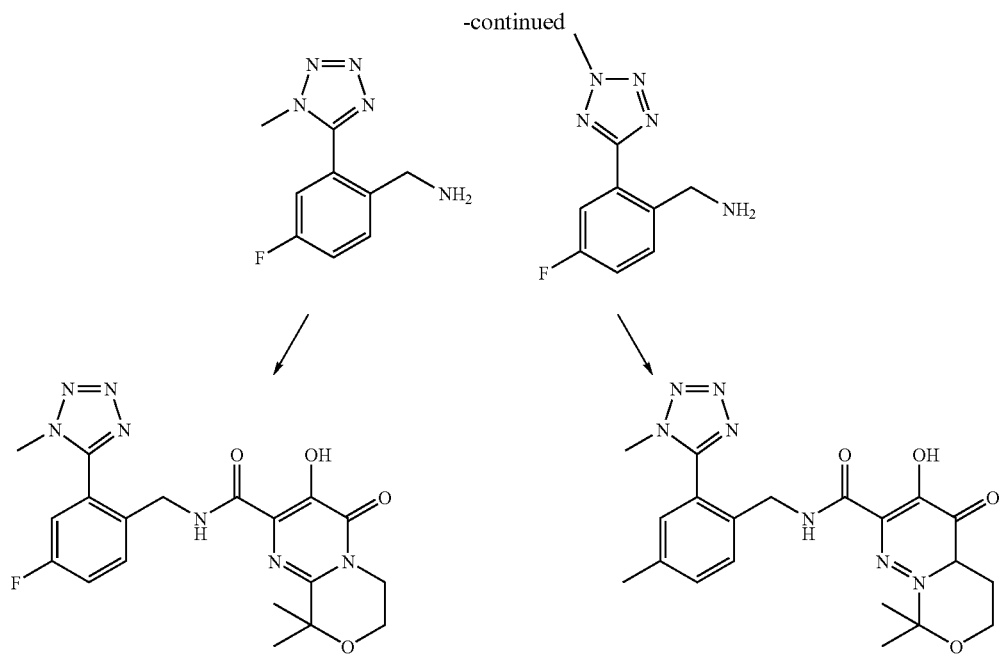
Some diazarine and diaziradine analogues can be synthesized according to Scheme XVI.
Scheme XVI
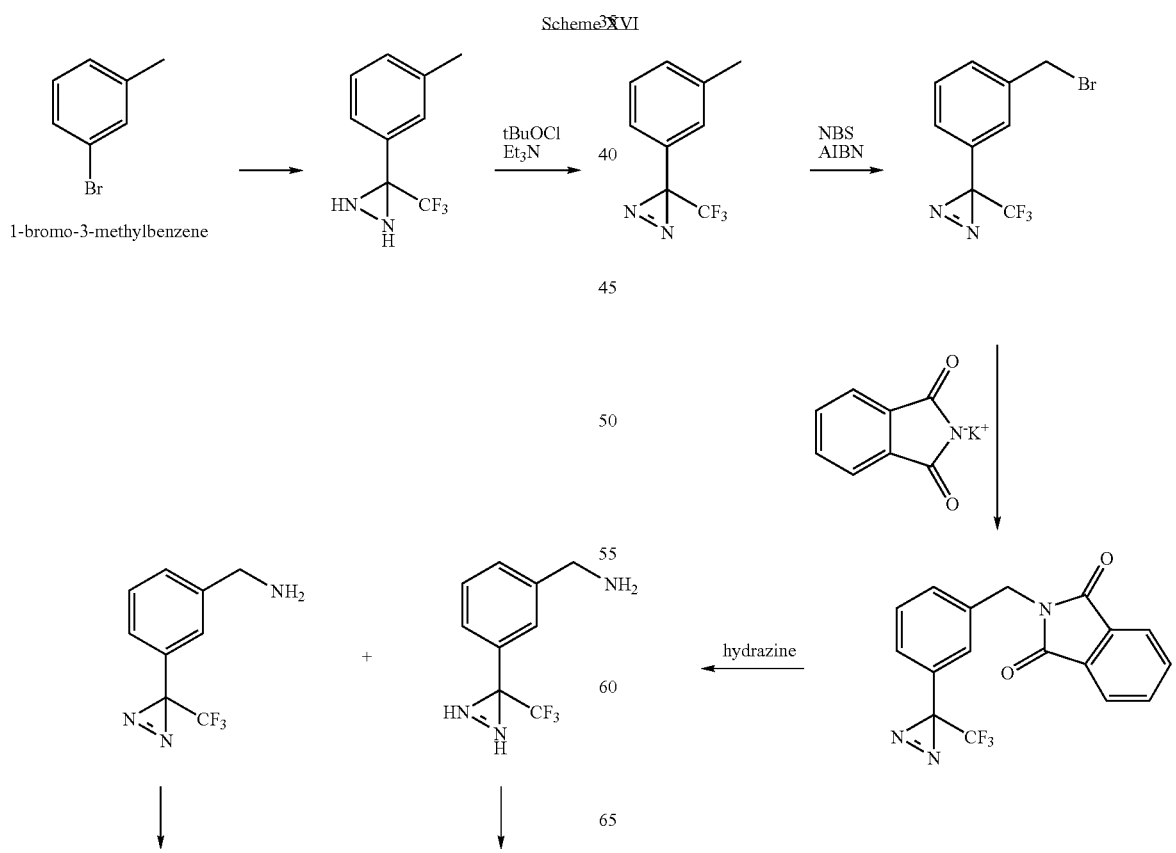

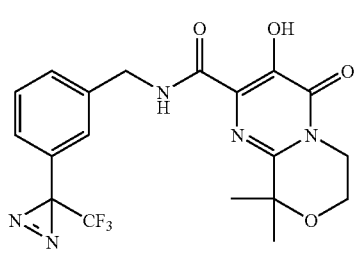
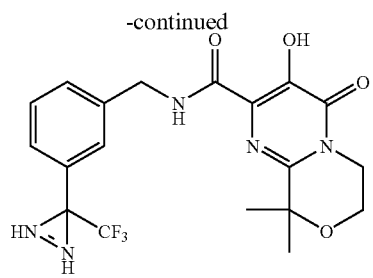
Some examples of the invention can be synthesized according to the methods illustrated in Schemes XVII-XX.
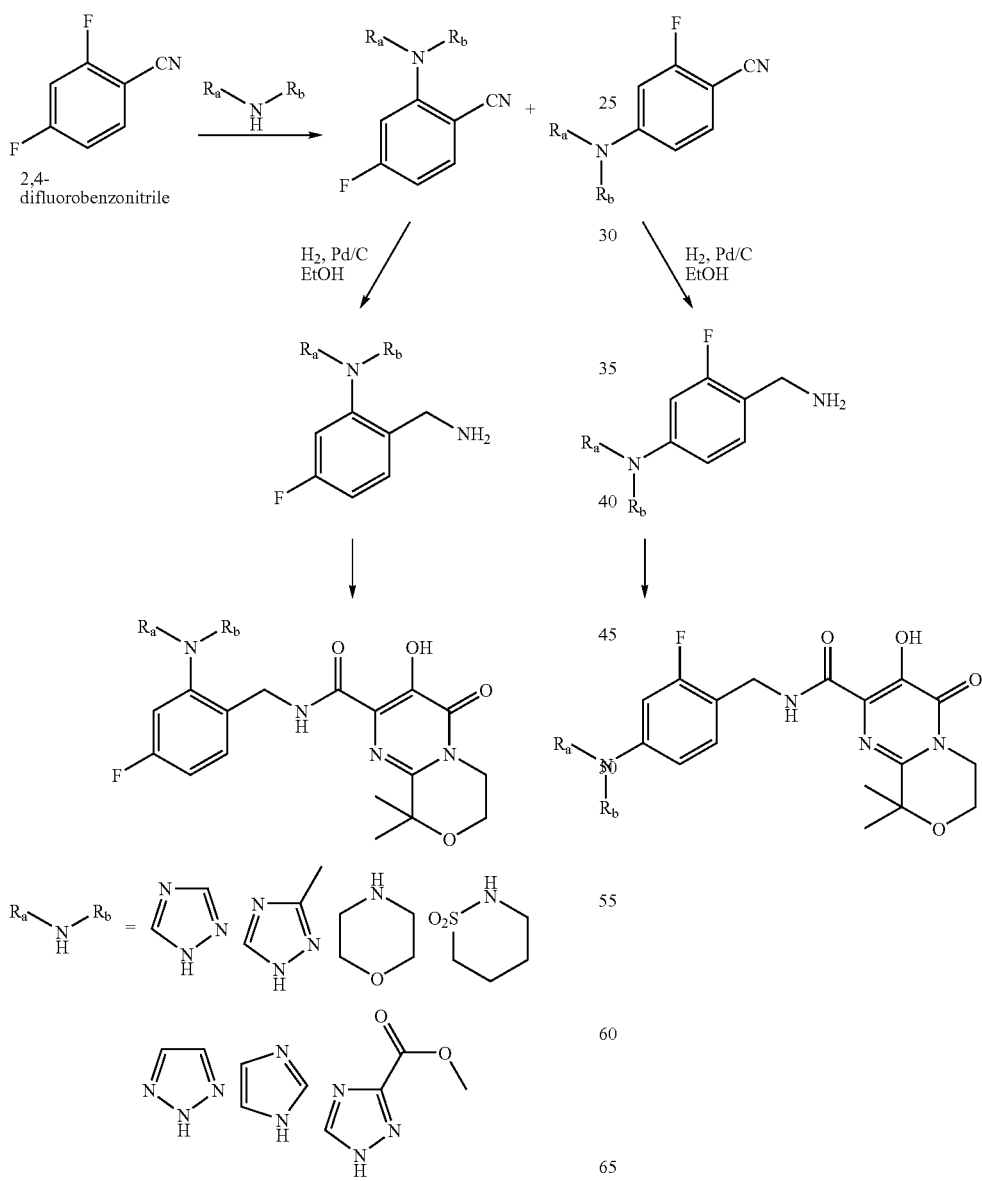
Scheme XVII Scheme XVIII
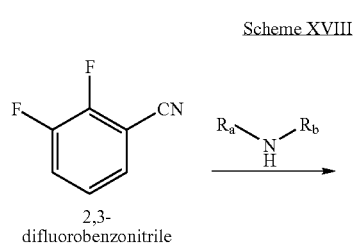
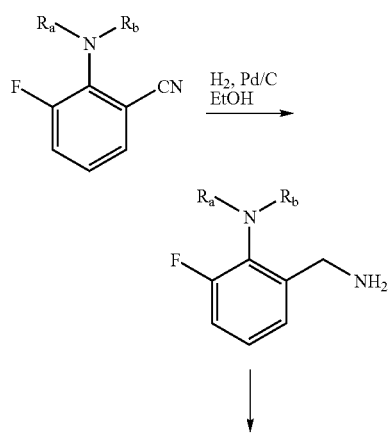
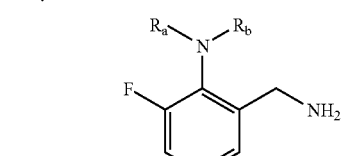
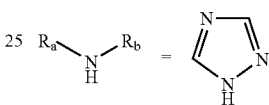
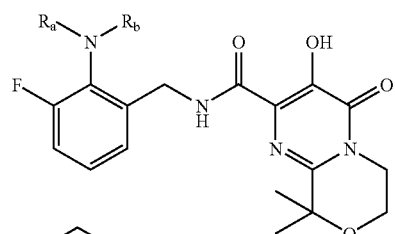
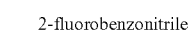
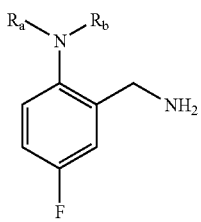
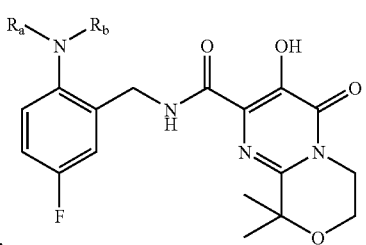
Scheme XIX
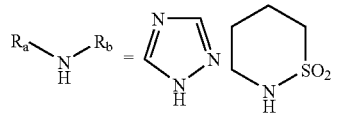
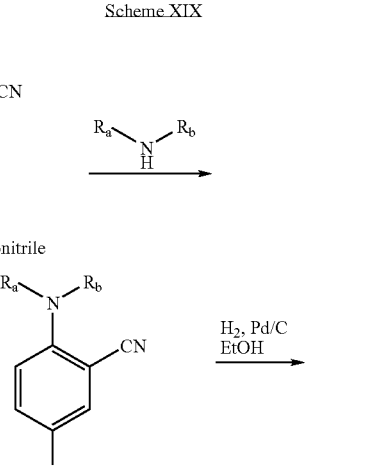
Scheme XX
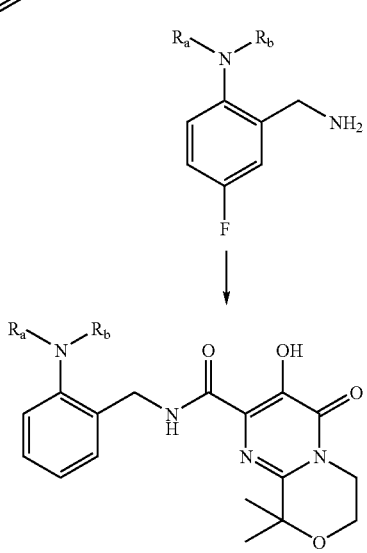

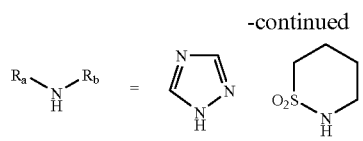

In Scheme XXI, 2-bromo-benzonitrile or 2-bromo-4-fluoro-benzonitrile can be coupled with an appropriate amide to provide XXI-1. Reduction of the nitrile group provides XXI-2 which can be used in the synthesis of the final product according to the methods described in the previous schemes. In most cases, compound XXI-1 need not be isolated but can be carried directly into the coupling reaction to form XXI-3.

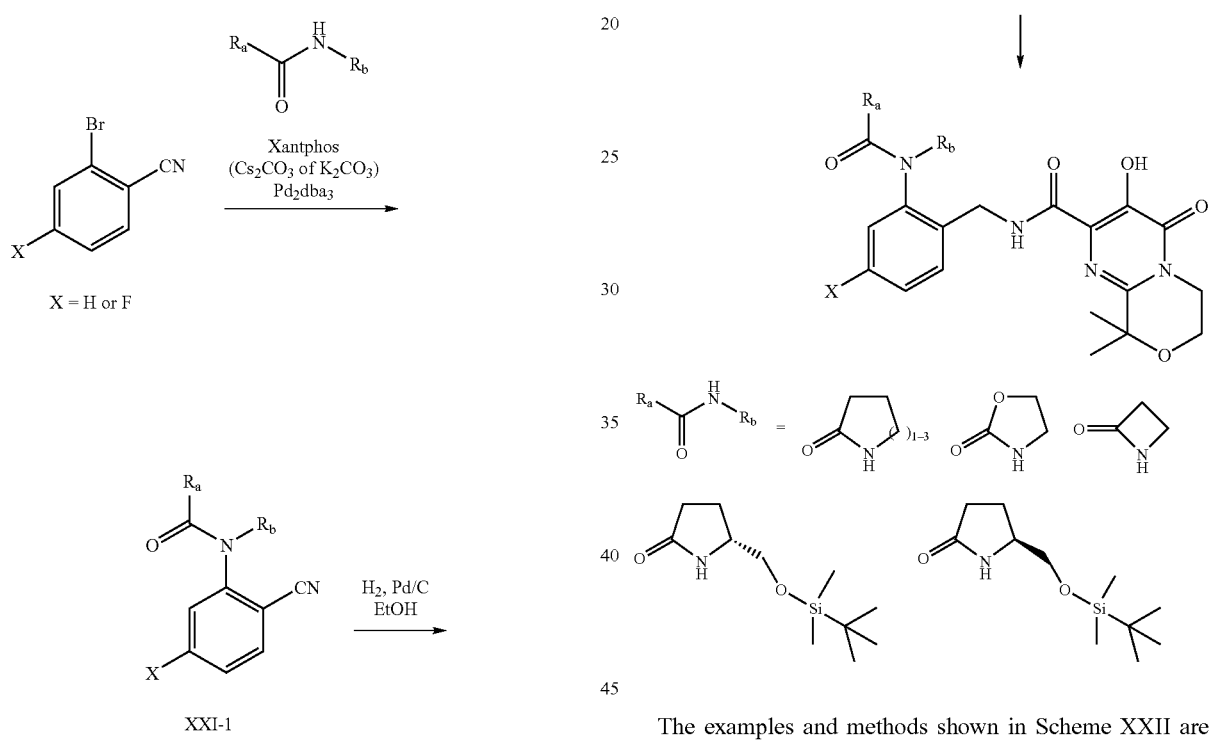

The examples and methods shown in Scheme XXII are similar to those depicted in Scheme XXI.

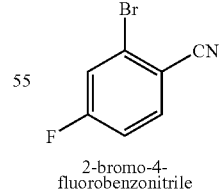

2-bromo-4-fluorobenzonitrile

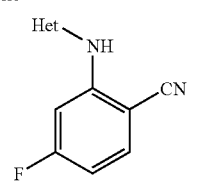

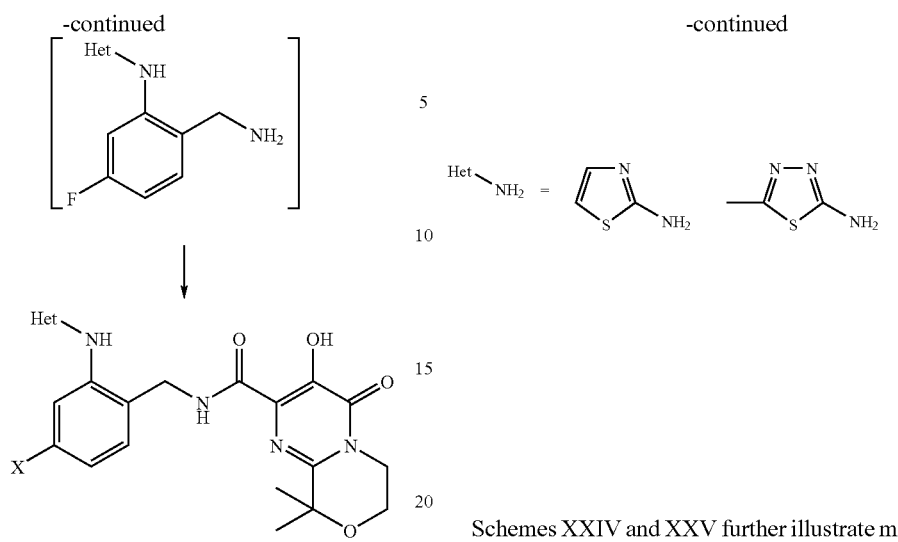
Schemes XXIV and XXV further illustrate methods useful for the synthesis of some compounds of the invention.
Scheme XXIV
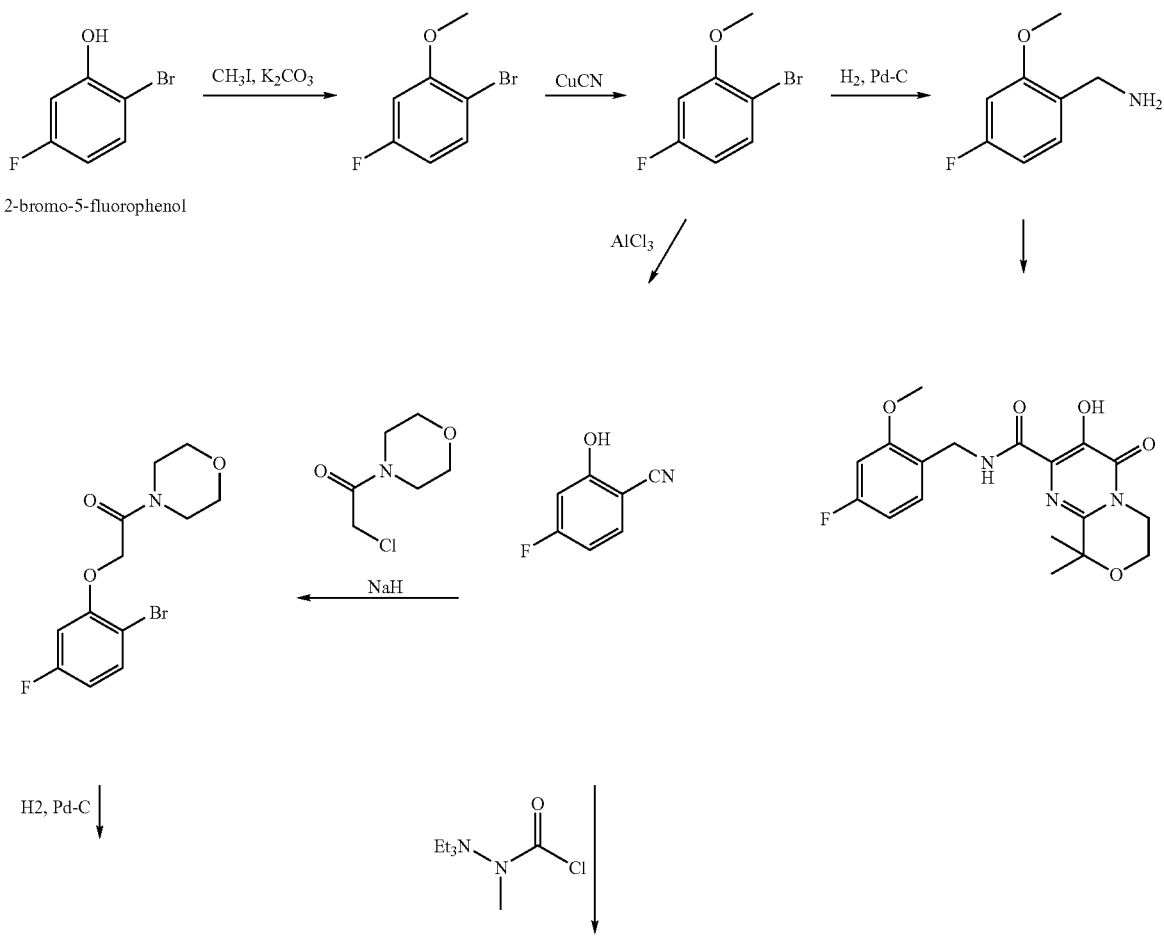

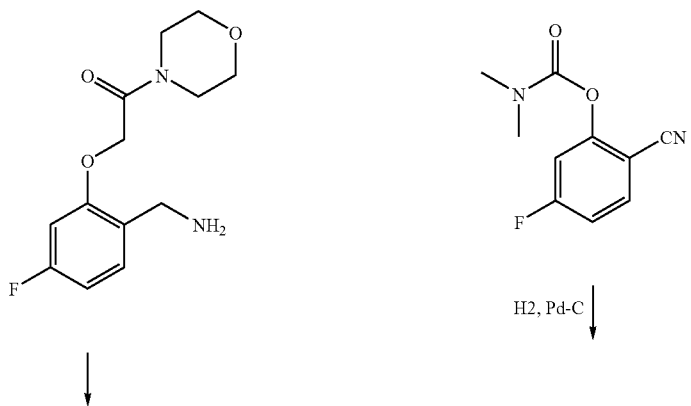
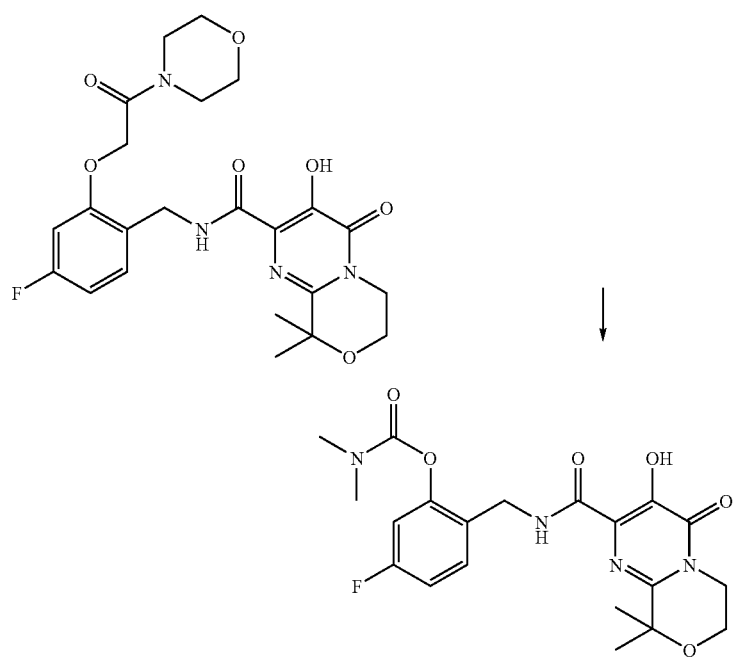
Scheme XXV
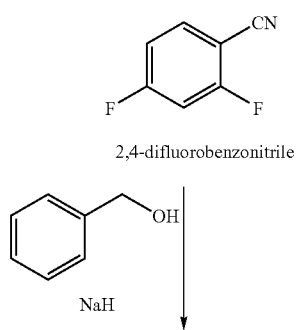
2,4-difluorobenzonitrile
NaH

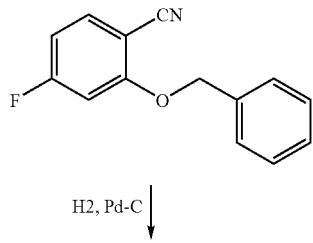
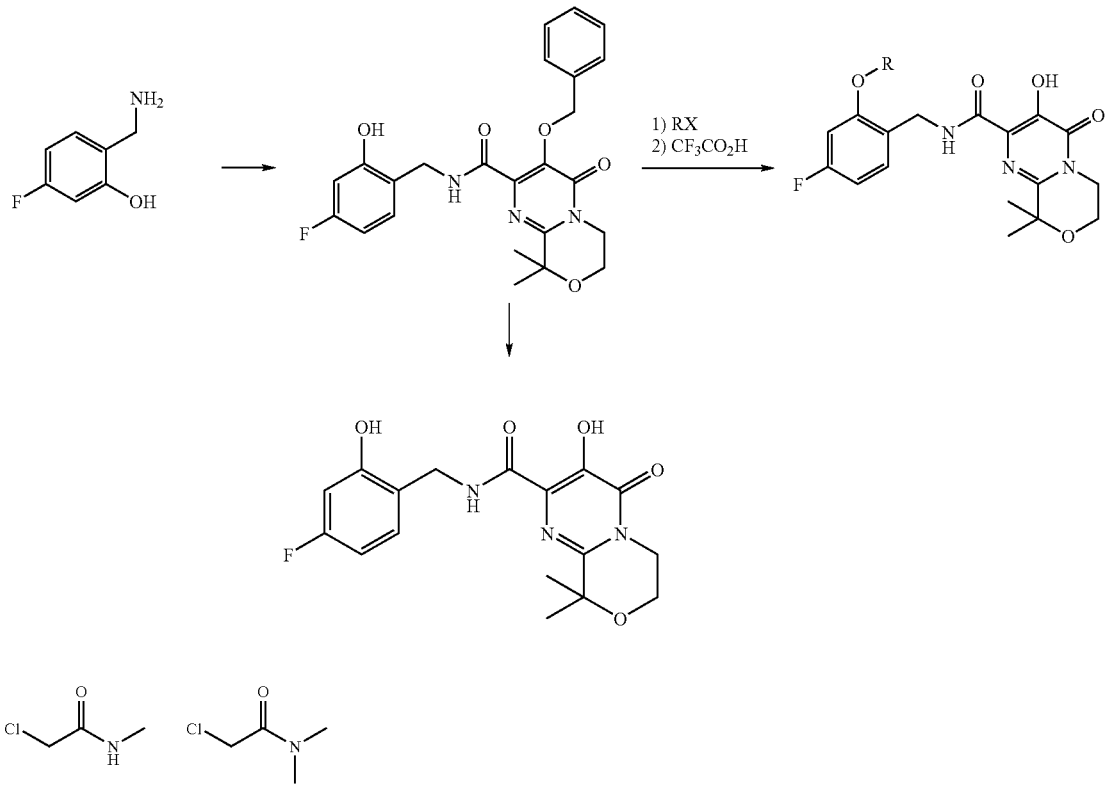
In Scheme XXVI, intermediate XXVI-1 can be used to synthesize intermediates XXVI-2 via palladium catalyzed coupling. These intermediates can be further modified to provide some of the compounds of this invention.
Scheme XXVI
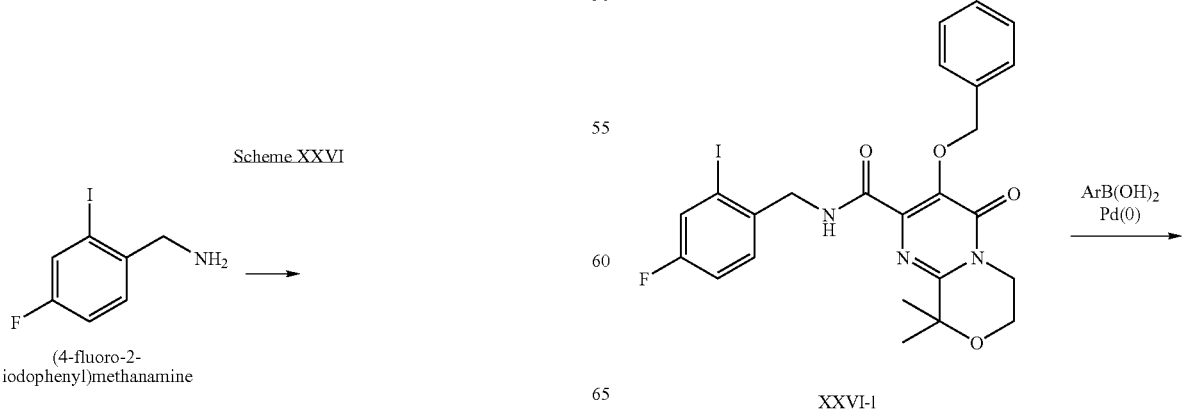

-continued
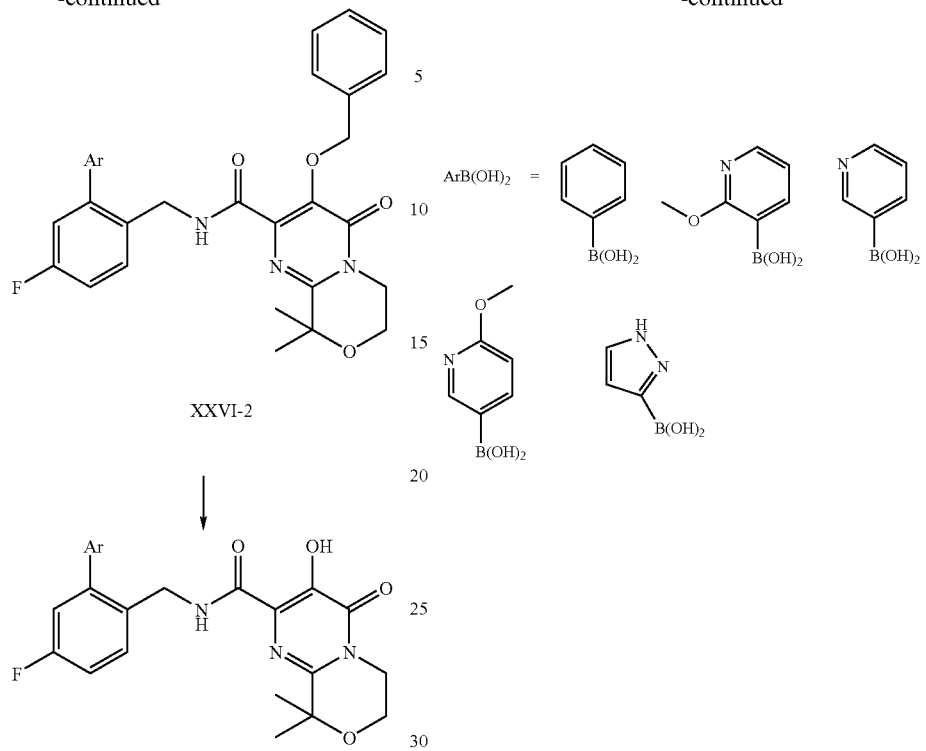
Another method is illustrated in Scheme XXVII.
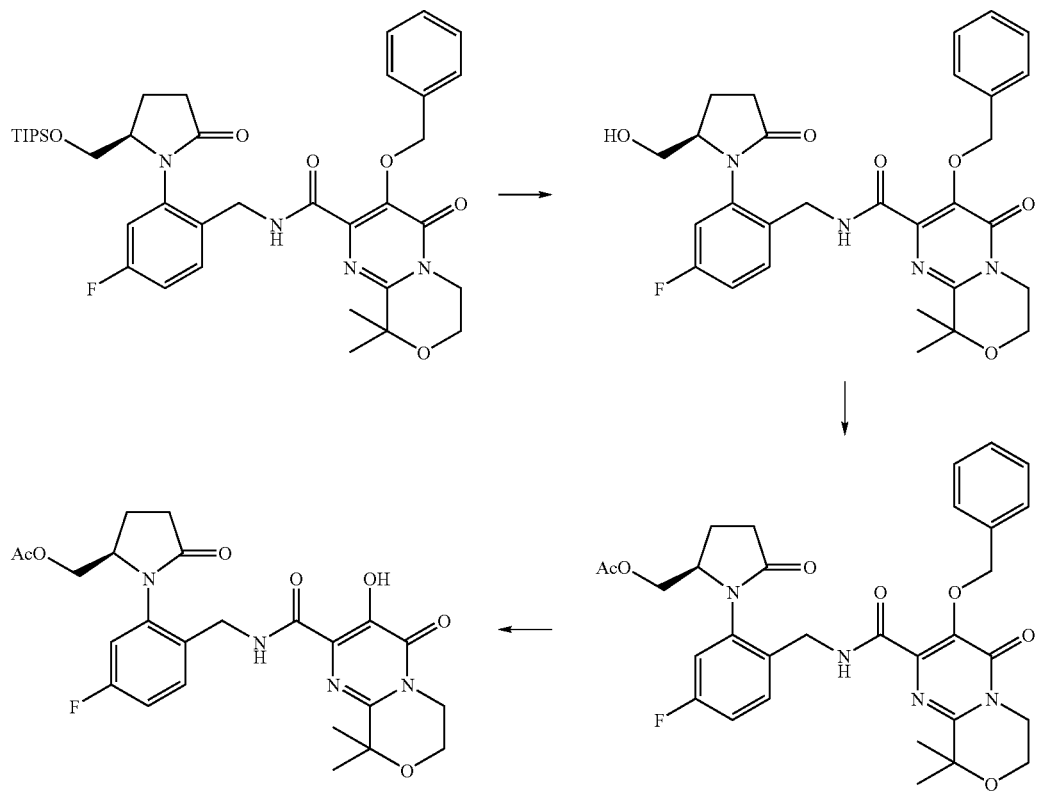

In Scheme XXVIII, compound XXVIII-1 can be converted to the corresponding methylsulfonate derivate, XXVIII-2, which can be subsequently treated with sodium azide to yield XXVIII-3. This compound in turn can serve as an intermediate for further transformation as illustrated in the scheme.
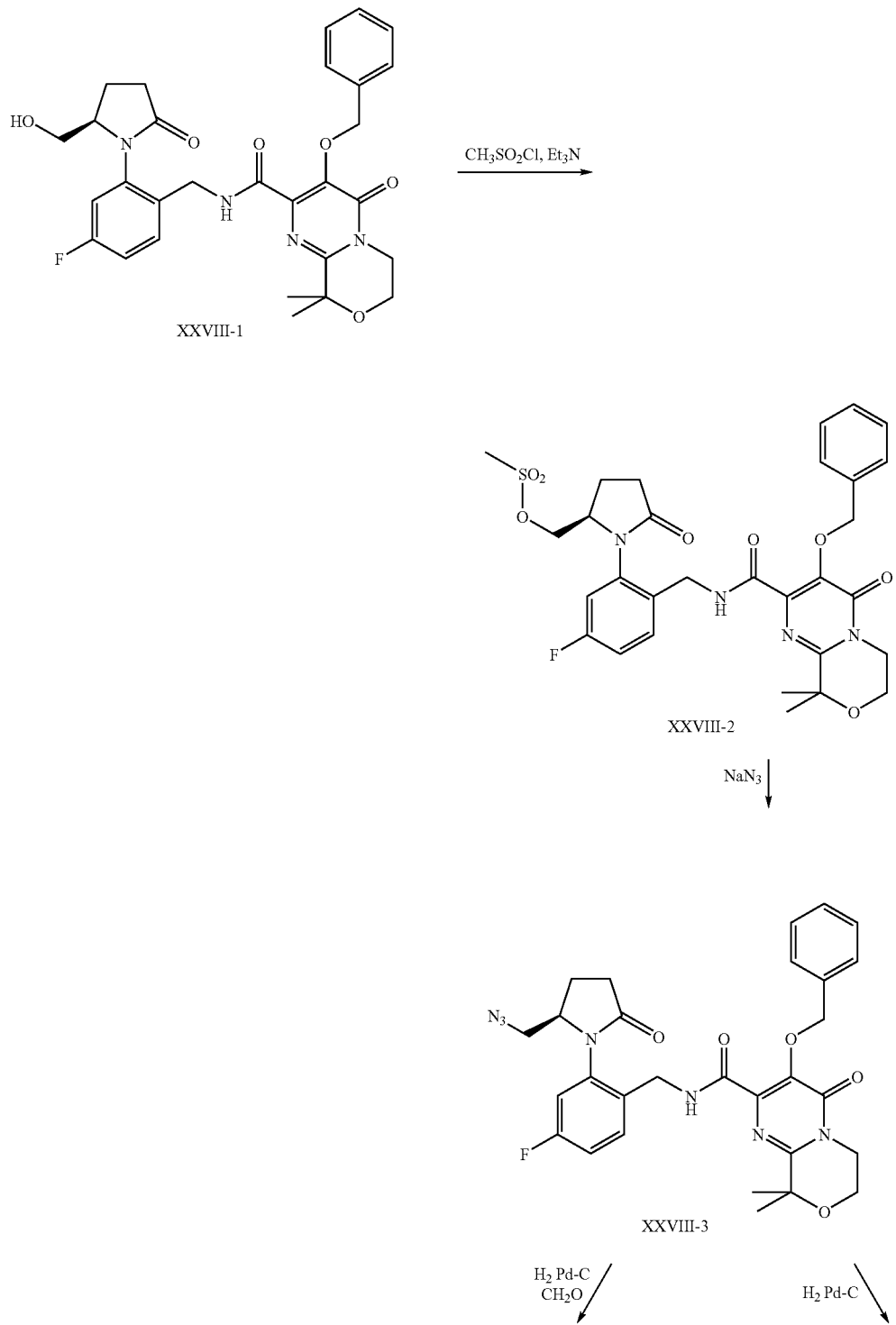

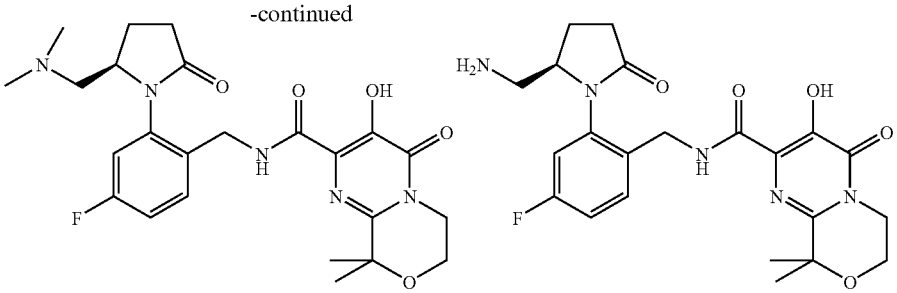
Certain examples of the current invention can be synthesized according to the methods illustrated in Schemes XXIX-XXXVIII.
Scheme XXIX
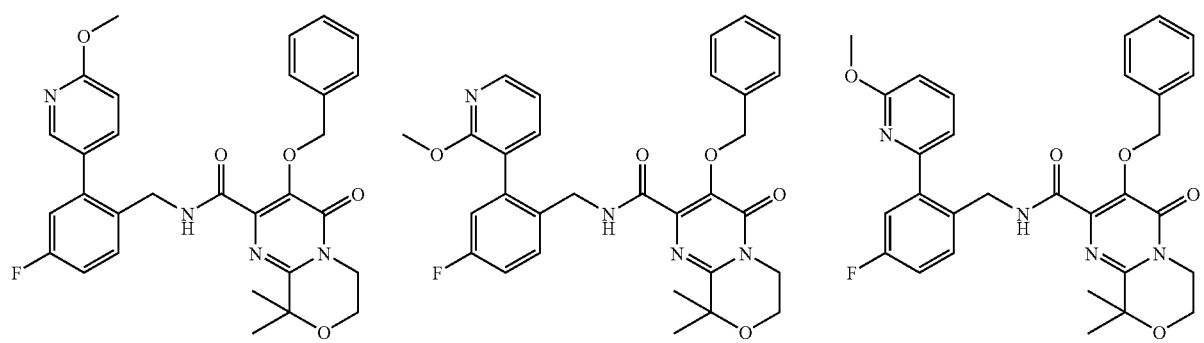
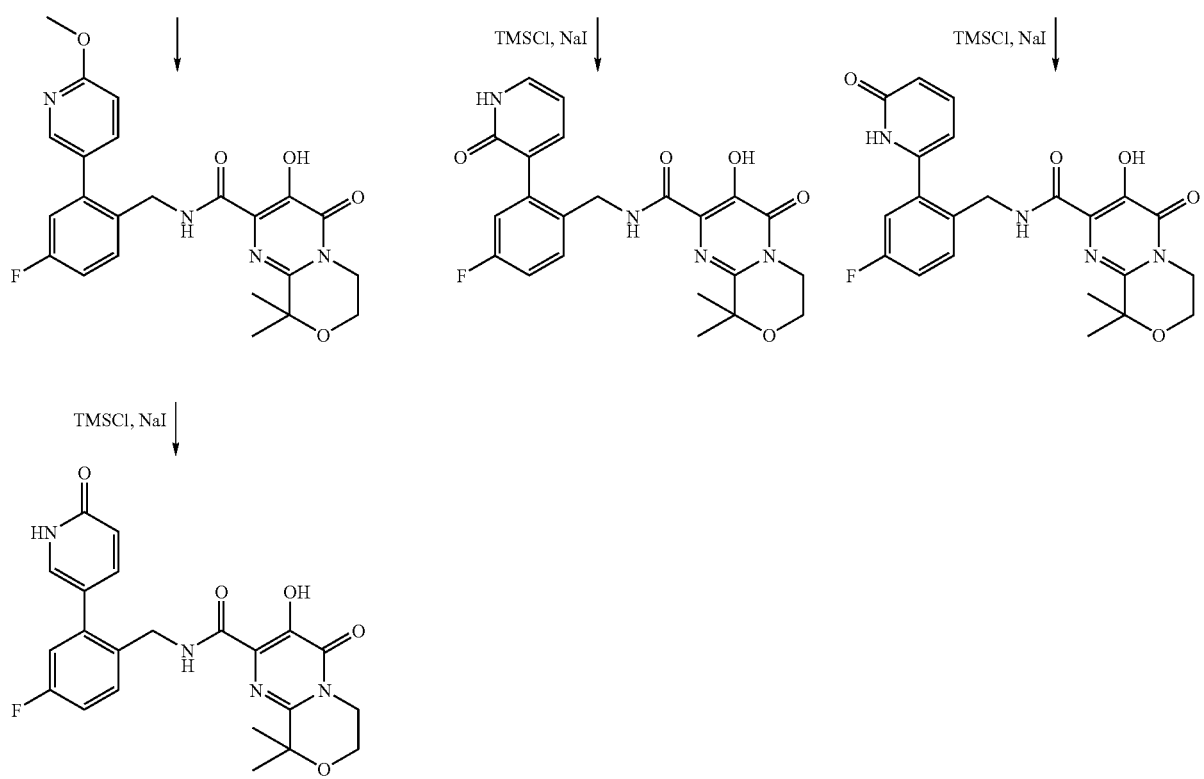

Scheme XXX
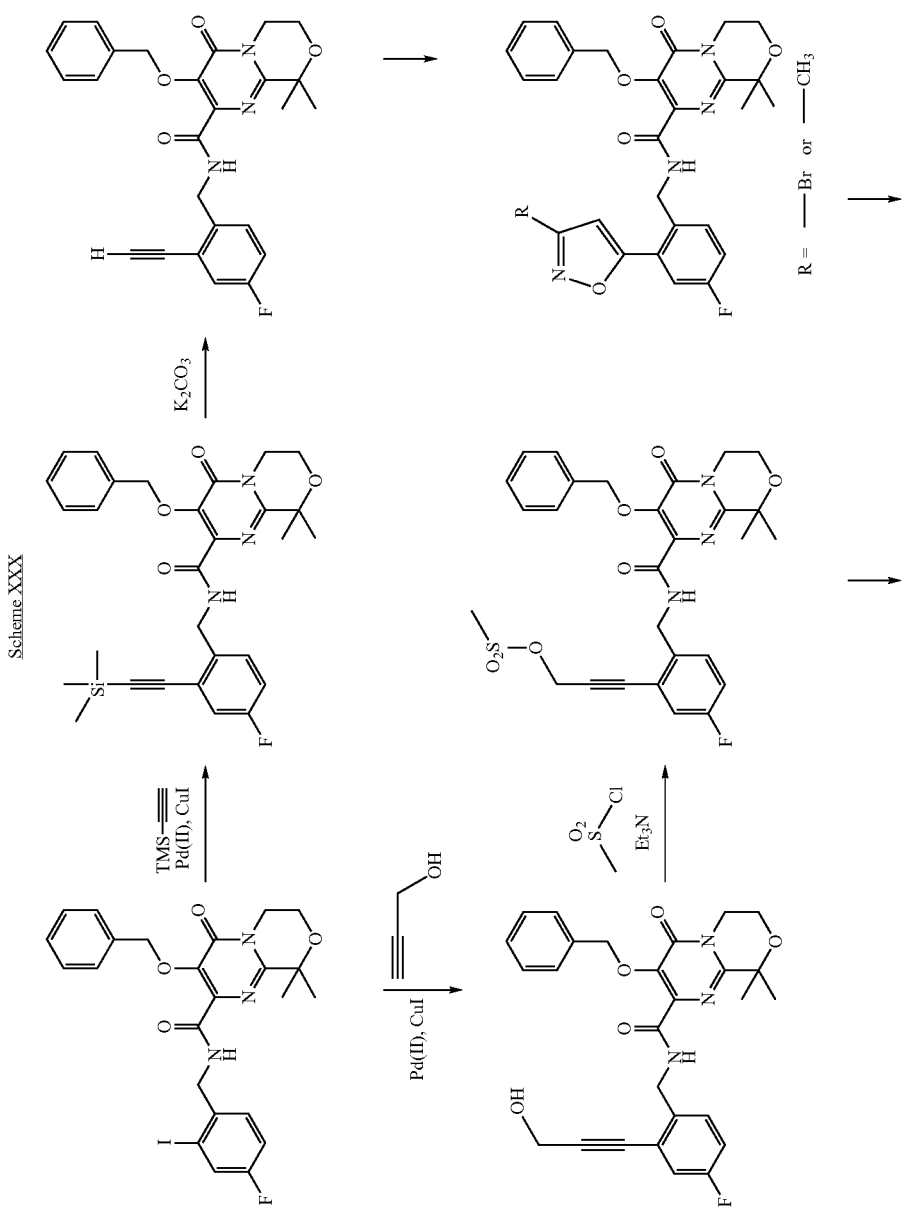

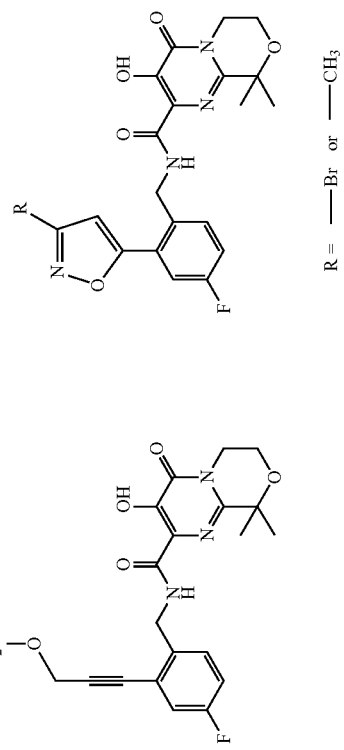

Scheme XXXI
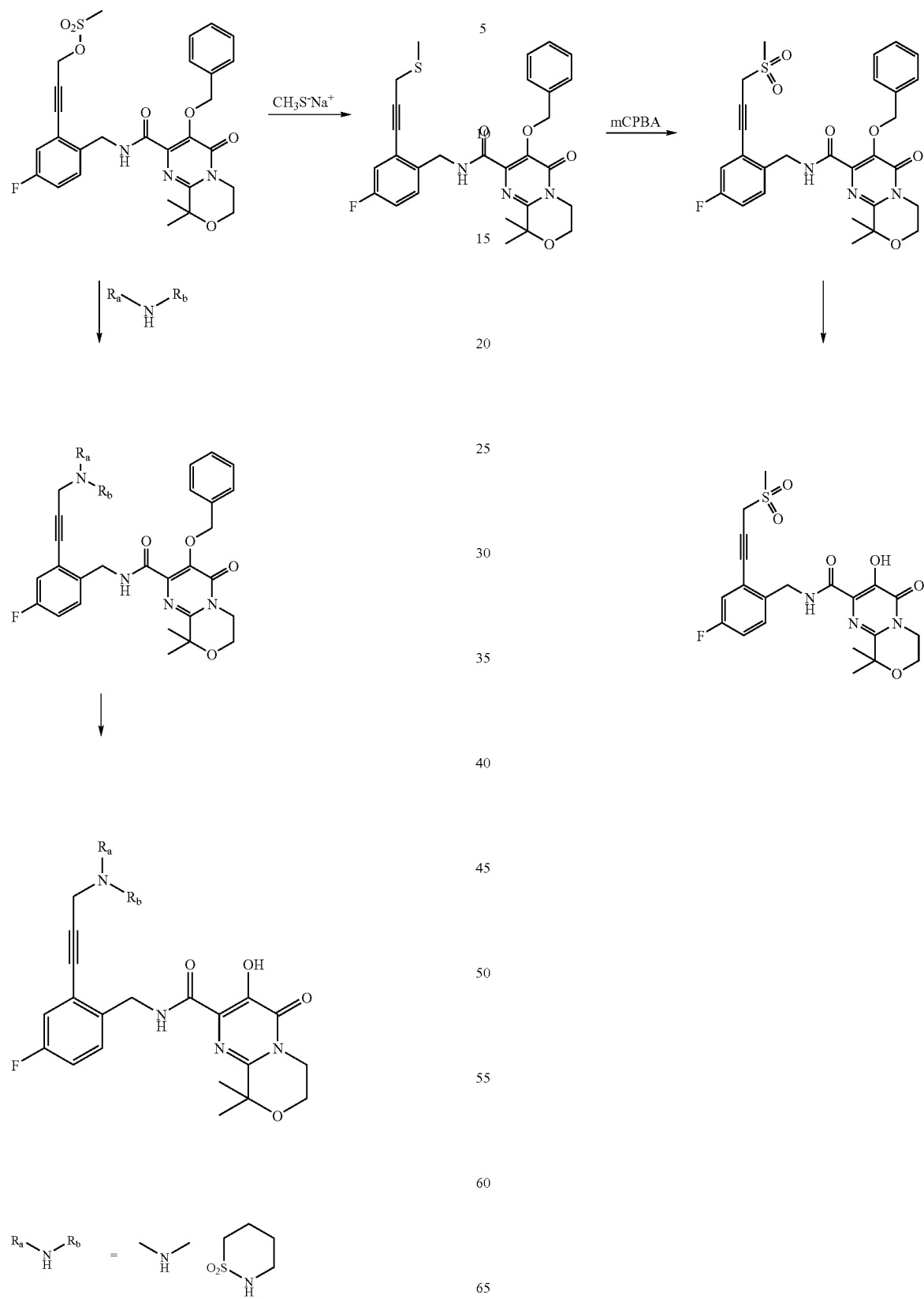

Scheme XXXII
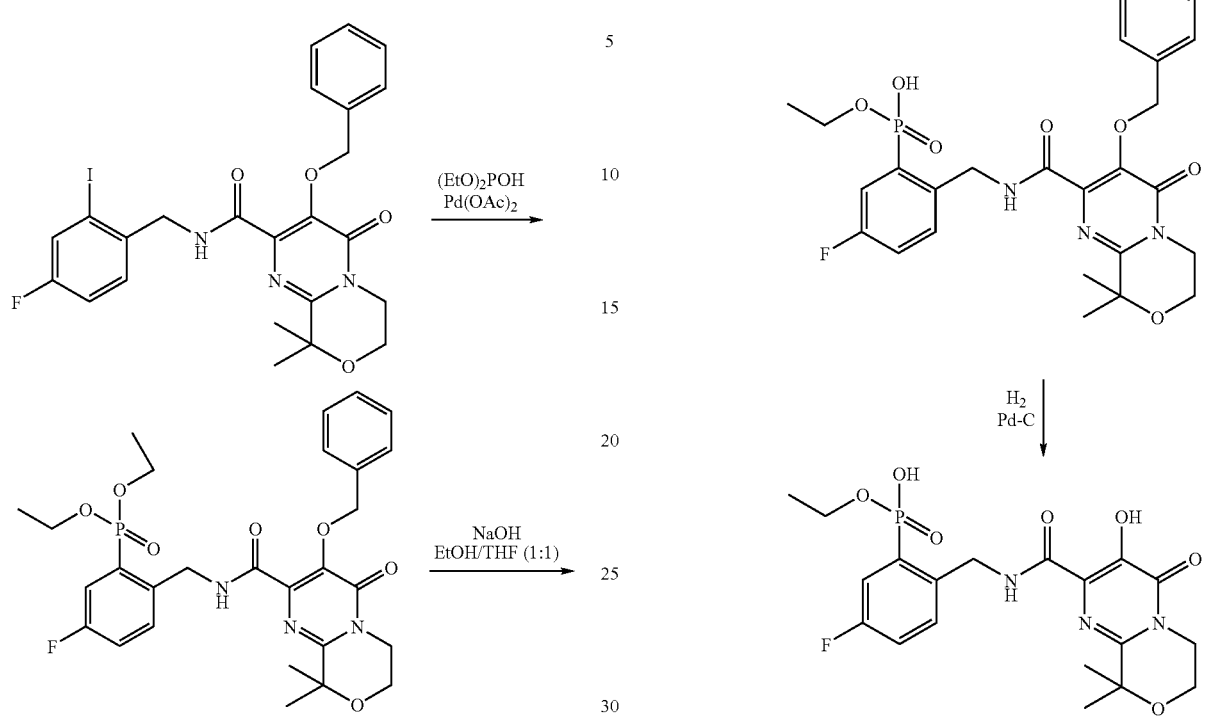
Scheme XXXIII
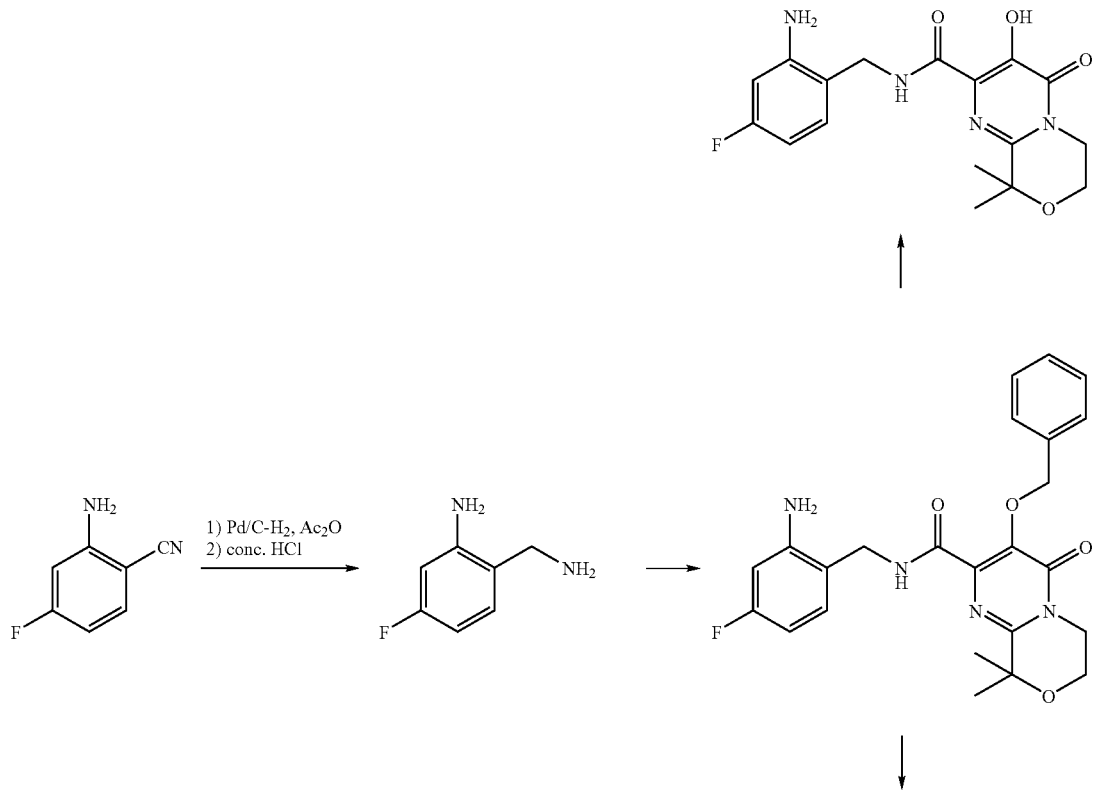

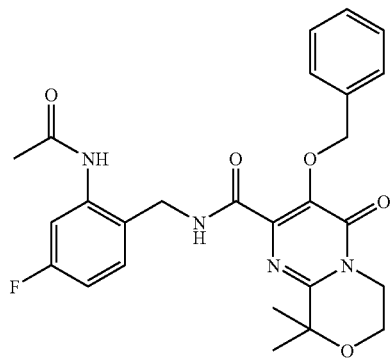
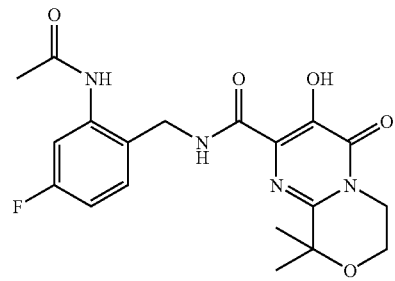
Scheme XXXIV
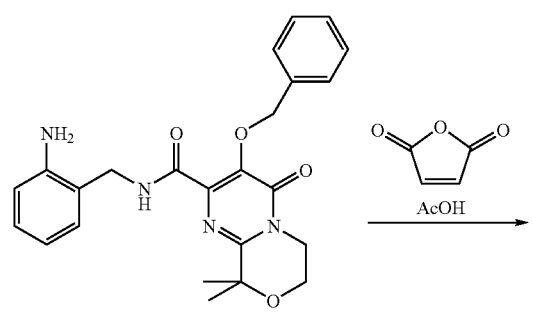
Scheme XXXV
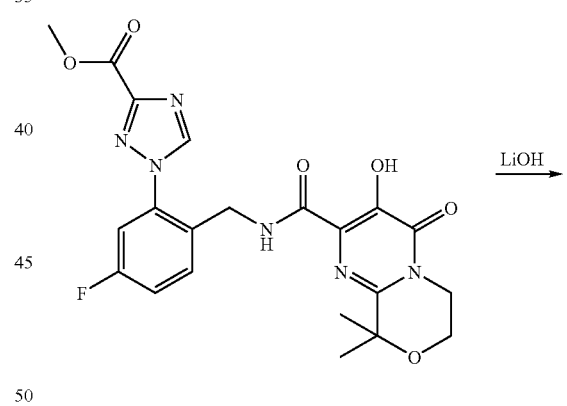
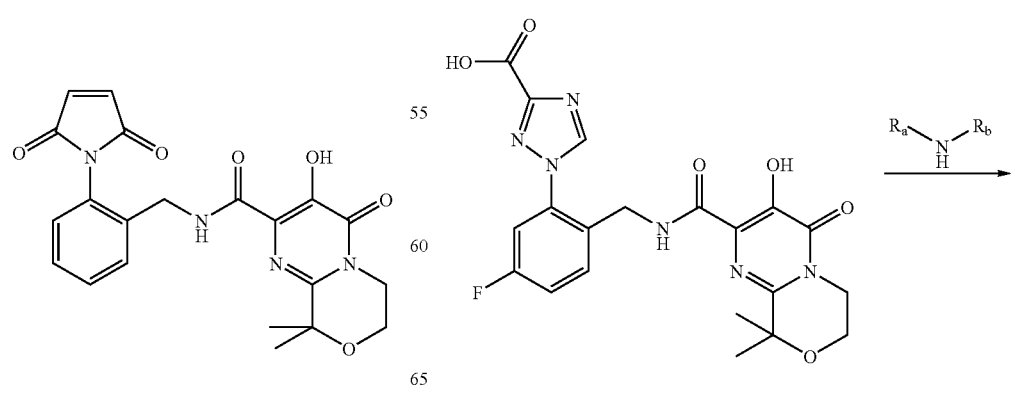

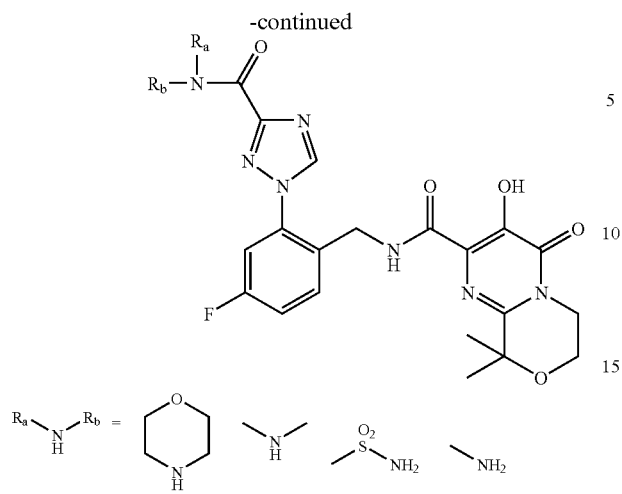
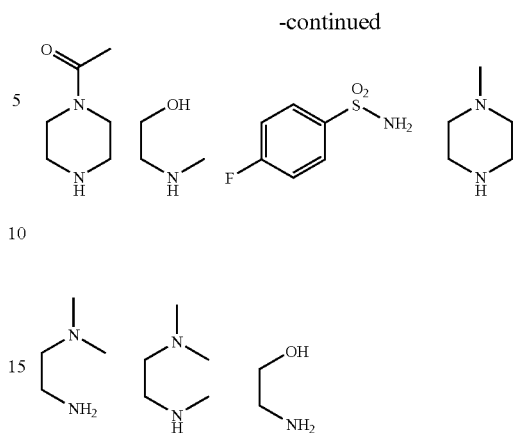
Schemes XXXVI
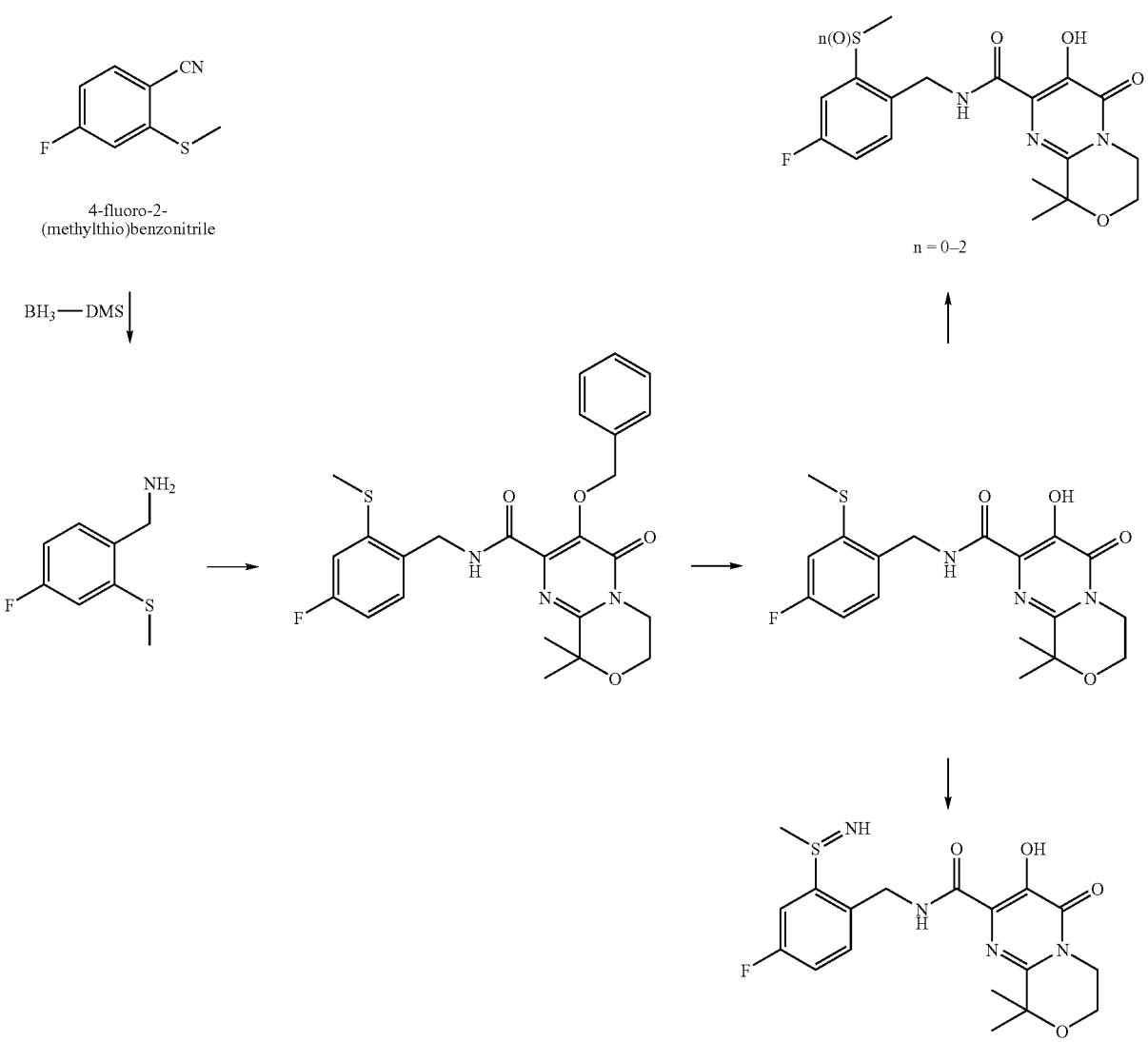

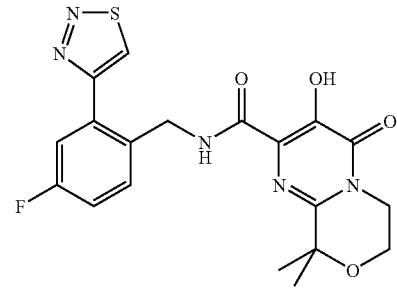
Scheme XXXVII
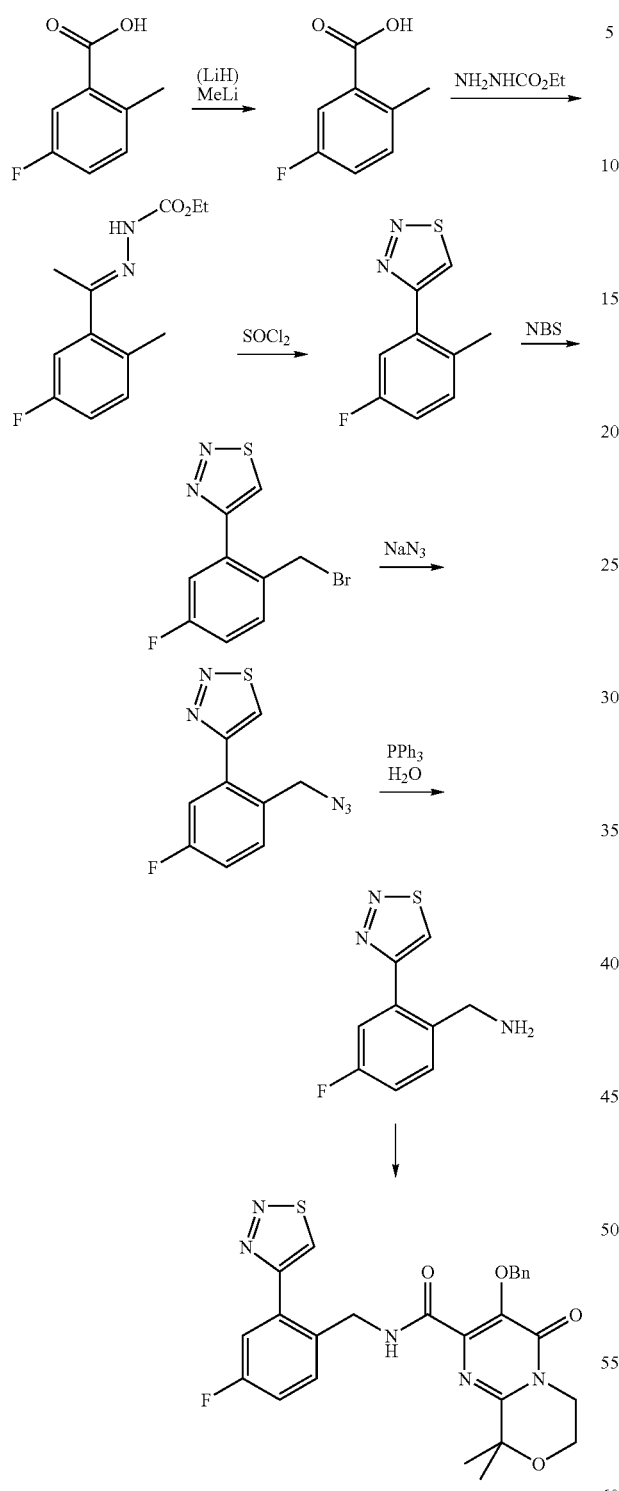
Scheme XXXVIII
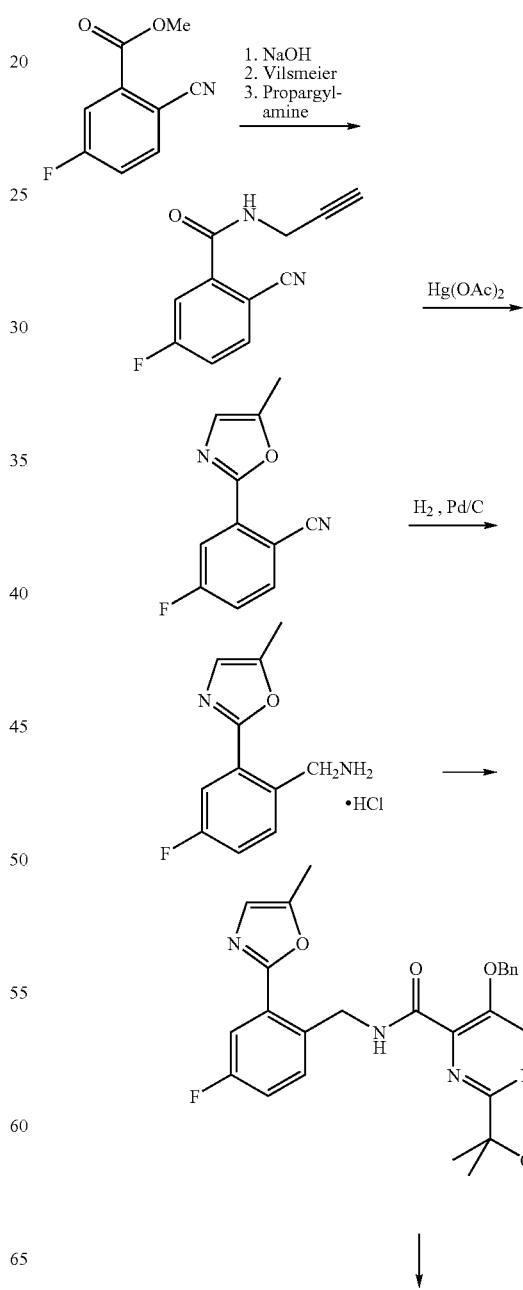

-continued

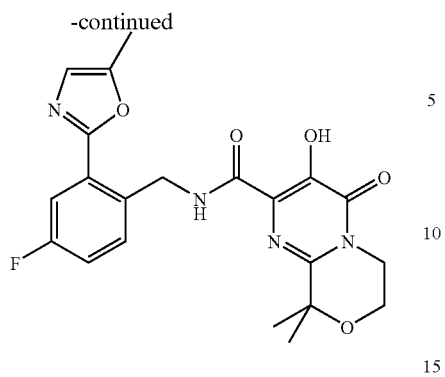

Biological Methods

HIV-Integrase InhibitionActivity. To evaluate in-vitro activity against HIV-integrase, 5 pmole of biotin labeled substrate DNA was bound to 100 μg of Streptavidin coated PVT SPA beads (Amersham Pharmacia Biotech). Recombinant integrase (0.26 ng) was incubated with the beads for 90 min at 37° C. Unbound enzyme was removed by washing the complex followed by addition of inhibitors and 0.1 fmol of P33 labeled target DNA. The reaction was stopped by adding EDTA to a final concentration of 10 mM. Samples were counted in TopCountNXT (Packard) and the CPM was used as a measure of integration. The reaction condition was as described in A. Engelman and R. Craigie, *J. Virol* 69, 5908-5911 (1995). The sequences of substrate and target DNA were described in *Nucleic Acid Research* 22,1121-1122 (1994). Results are shown in the Table 1. Activity equal to A refers to a compound having $IC_{50}=0.002$ to $0.10$ μM while B and C denote compounds having $IC_{50}=0.1$ to $1.0$ μM and $IC_{50} \geqq 1.0$ μM respectively.

TABLE 1

| Example | Activity |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | B |
| 23 | A |
| 24 | B |
| 25 | B |
| 26 | A |
| 27 | A |
| 28 | A |
| 29 | A |
| 30 | A |
| 31 | A |

TABLE 1-continued

| Example | Activity |
|---|---|
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | C |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 103 | A |
| 104 | B |
| 105 | A |
| 106 | A |
| 107 | A |
| 108 | A |

TABLE 1-continued

| Example | Activity |
|---|---|
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 131 | B |
| 132 | A |
| 133 | B |
| 134 | A |
| 135 | A |
| 136 | A |
| 137 | A |
| 138 | A |
| 139 | A |
| 140 | A |
| 141 | A |
| 142 | A |
| 143 | A |
| 144 | B |
| 145 | C |
| 146 | A |
| 147 | A |
| 148 | B |
| 149 | A |
| 150 | A |
| 151 | A |
| 152 | A |
| 153 | A |
| 154 | A |
| 155 | A |
| 156 | A |
| 157 | A |
| 158 | A |
| 159 | B |
| 160 | A |
| 161 | A |
| 162 | A |
| 163 | A |
| 164 | A |
| 165 | A |
| 166 | B |
| 167 | A |
| 168 | A |
| 169 | A |
| 170 | A |
| 171 | A |
| 172 | A |
| 173 | A |
| 174 | A |
| 175 | A |
| 176 | A |
| 177 | A |
| 178 | A |
| 179 | A |
| 180 | A |
| 181 | A |
| 187 | A |
| 188 | A |
| 189 | A |
| 190 | A |

TABLE 1-continued

| Example | Activity |
|---|---|
| 191 | A |
| 192 | A |
| 193 | A |
| 194 | A |
| 195 | A |
| 196 | A |
| 197 | A |
| 198 | A |
| 199 | A |
| 200 | A |
| 201 | A |
| 202 | A |
| 203 | A |
| 204 | A |
| 205 | A |
| 206 | A |
| 207 | A |
| 208 | A |
| 209 | A |
| 210 | A |
| 211 | A |
| 212 | A |
| 213 | A |
| 214 | C |
| 215 | A |
| 216 | A |
| 217 | A |
| 218 | A |
| 219 | A |
| 220 | A |
| 221 | A |
| 222 | A |
| 223 | A |
| 224 | A |
| 225 | A |
| 226 | A |
| 227 | A |
| 228 | A |
| 229 | A |
| 230 | A |
| 231 | A |
| 232 | A |
| 233 | A |
| 234 | A |
| 235 | A |
| 236 | A |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | A |
| 249 | A |
| 250 | A |
| 251 | A |
| 252 | B |
| 253 | C |
| 254 | A |
| 255 | A |
| 256 | B |
| 257 | A |
| 258 | A |
| 259 | A |
| 260 | A |
| 261 | A |
| 262 | A |
| 263 | A |
| 264 | A |
| 265 | A |
| 266 | A |
| 267 | A |

TABLE 1-continued

| Example | Activity |
|---|---|
| 268 | A |
| 269 | A |
| 270 | A |
| 271 | A |
| 272 | A |
| 273 | A |
| 274 | A |
| 275 | A |
| 276 | A |
| 277 | A |
| 278 | A |
| 279 | A |
| 280 | A |
| 281 | A |
| 282 | A |

Inhibition of HIV replication. A recombinant NL-Rluc virus was constructed in which a section of the nef gene from NL4-3 was replaced with the Renilla Luciferase gene. The NL-RLuc virus was prepared by co-transfection of two plasmids, pNLRLuc and pVSVenv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to PVSVenv on 293T cells using the LipofectAMINE PLUS kit from Invitrogen (Carlsbad, Calif.) according to manufactures instruction, and the pseudotype virus generated was titered in MT-2 cells.

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/\text{drug conc.})^m]$ (Johnson V A, Byington R T. Infectivity Assay. In *Techniques in HIV Research* ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in the Table 2. Activity equal to A refers to a compound having $EC_{50}=0.003$ to $0.10$ μM while B and C denote compounds with $EC_{50}=0.1$ to $1.0$ μM and $EC_{50}\geq 1.0$ μM respectively.

TABLE 2

| Example | Activity |
|---|---|
| 1 | B |
| 2 | A |
| 3 | C |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | B |
| 23 | A |
| 24 | C |
| 25 | C |
| 26 | A |
| 27 | A |
| 28 | B |
| 29 | A |
| 30 | A |
| 31 | A |
| 32 | A |
| 33 | A |
| 34 | A |
| 35 | A |
| 36 | A |
| 37 | B |
| 38 | A |
| 39 | A |
| 40 | A |
| 41 | A |
| 42 | A |
| 43 | A |
| 44 | A |
| 45 | A |
| 46 | A |
| 47 | A |
| 48 | B |
| 49 | A |
| 50 | A |
| 51 | A |
| 52 | A |
| 53 | B |
| 54 | A |
| 55 | A |
| 56 | A |
| 57 | A |
| 58 | A |
| 59 | B |
| 60 | A |
| 61 | B |
| 62 | A |
| 63 | A |
| 64 | C |
| 65 | A |
| 66 | B |
| 67 | A |
| 68 | C |
| 69 | A |
| 70 | B |
| 71 | B |
| 72 | B |
| 73 | A |
| 74 | A |
| 75 | A |
| 76 | B |
| 77 | A |
| 78 | A |
| 79 | B |
| 80 | B |
| 81 | A |
| 82 | A |
| 83 | C |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |

TABLE 2-continued

| Example | Activity |
|---|---|
| 99 | A |
| 100 | A |
| 101 | A |
| 102 | A |
| 103 | B |
| 104 | B |
| 105 | A |
| 106 | A |
| 107 | A |
| 108 | A |
| 109 | A |
| 110 | A |
| 111 | A |
| 113 | A |
| 114 | A |
| 115 | A |
| 116 | A |
| 117 | A |
| 118 | A |
| 119 | A |
| 120 | A |
| 121 | A |
| 122 | A |
| 123 | A |
| 124 | A |
| 125 | A |
| 126 | A |
| 127 | A |
| 128 | A |
| 129 | A |
| 130 | A |
| 132 | A |
| 133 | B |
| 134 | A |
| 135 | A |
| 136 | A |
| 137 | B |
| 138 | A |
| 139 | A |
| 140 | A |
| 141 | C |
| 142 | B |
| 144 | C |
| 146 | A |
| 147 | B |
| 148 | B |
| 149 | B |
| 150 | B |
| 151 | B |
| 152 | B |
| 153 | B |
| 154 | B |
| 155 | B |
| 156 | B |
| 157 | A |
| 158 | A |
| 159 | A |
| 160 | B |
| 161 | B |
| 162 | A |
| 163 | B |
| 164 | B |
| 165 | A |
| 166 | C |
| 167 | B |
| 168 | A |
| 169 | A |
| 170 | A |
| 171 | B |
| 172 | B |
| 173 | A |
| 174 | A |
| 175 | B |
| 176 | A |
| 177 | A |
| 178 | A |
| 179 | B |

TABLE 2-continued

| Example | Activity |
|---|---|
| 180 | C |
| 181 | A |
| 187 | B |
| 188 | B |
| 189 | A |
| 190 | A |
| 191 | B |
| 192 | B |
| 193 | C |
| 194 | B |
| 195 | B |
| 196 | A |
| 197 | C |
| 198 | B |
| 199 | B |
| 200 | A |
| 201 | B |
| 202 | A |
| 203 | A |
| 204 | A |
| 205 | A |
| 206 | A |
| 207 | A |
| 208 | A |
| 209 | B |
| 210 | A |
| 211 | A |
| 212 | A |
| 213 | A |
| 214 | B |
| 215 | A |
| 216 | A |
| 217 | A |
| 218 | A |
| 219 | A |
| 220 | A |
| 221 | A |
| 222 | A |
| 223 | A |
| 224 | B |
| 225 | A |
| 226 | A |
| 227 | B |
| 228 | B |
| 229 | A |
| 230 | A |
| 231 | A |
| 232 | A |
| 233 | A |
| 234 | A |
| 235 | A |
| 236 | B |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | A |
| 249 | A |
| 250 | A |
| 251 | A |
| 252 | C |
| 253 | C |
| 254 | A |
| 255 | A |
| 256 | B |
| 257 | A |
| 258 | A |
| 259 | A |
| 260 | A |
| 262 | A |

TABLE 2-continued

| Example | Activity |
|---|---|
| 263 | B |
| 265 | B |
| 266 | A |
| 267 | A |
| 268 | A |
| 270 | A |
| 273 | B |
| 279 | A |
| 281 | A |
| 282 | A |

Combination Studies

Example 19 demonstrated synergistic or additive-synergistic HIV antiviral activity when used in a conjunction with a variety of other antiviral agents, as described below.

Virus and cell lines. The T-cell line, MT-2, was obtained through the AIDS Research and Reference Reagent Program. MT-2 cells were sub-cultured twice a week in RPMI 1640 medium supplemented with 10% fetal bovine serum, 2 mM L-glutamine, and 10 mM HEPES buffer pH 7.5. The HIV-1 303B virus is a molecular clone derived from the NL4-3 strain of HIV-1 that was obtained from the NIH AIDS Research and Reference Reagent Program. For combinations with enfavirtide, the NL36G virus was used. This NL4-3 derivative has the naturally occurring enfuvirtide resistance mutation in gp41 (36D) changed to a sensitive phenotype (D36G). Virus stocks were made by transfecting 293T cells with a proviral DNA clone using LipofectAMINE PLUS (Invitrogen), according to the manufacturer's instructions. Three days post-transfection, virus was harvested and passaged once in MT-2 cells before titration in MT-2 cells.

Chemicals. Example 19, atazanavir, didanosine, stavudine, efavirenz, and enfuvirtide (T-20) were synthesized by Bristol-Myers Squibb using published or known reactions. Amprenavir, indinavir, nelfinavir, nevirapine, lopinavir, lamivudine, ritonavir, tenofovir, saquinavir, delavirdine and abacavir were extracted from commercial formulations of the prescribed drugs and purified using published or common techniques. Tenofovir was tested as tenofovir disopoxil flimerate. Zidovudine and zalcitabine were purchased from Sigma, and emtricitabine from Moravek Biochemicals.

Drug Susceptibility and Cytotoxicity Assays. For drug susceptibility assays, MT-2 cells were infected with HIV-1 303B (or NL36G), at an MOI of 0.001, and seeded into 96-well microtiter plates ($2.5 \times 10^5$ cells/ml) containing serial dilutions of test compounds. The drug combinations were set up using ratios of the two drugs of 1:1, 1:2.5 and 2.5:1 times the $EC_{50}$ value determined for each drug in prior experiments. Each drug ratio consisted of an array of 3-fold serial dilutions, and was performed with eight or more replicas on separate multi-well plates. HIV infected cells were incubated at 37° C. in 5% $CO_2$, and on day five post-infection, the extent of virus replication was measured by determining cell viability using the CellTiter 96 Aqueous Non-Radioactive Cell Proliferation Assay (Promega). Maximal cell protection was typically seen in samples treated with the highest drug concentration. In the cell viability assay, the tetrazolium compound MTS (3-(4,5-dimethylthiazol-2-yl)-5-(3-carboxymethoxyphenyl)-2-4-sulphophenyl-2H-tetrazolium) is added to cells, whereby enzymes in metabolically active cells convert it into a colored formazan product, which is quantitated by reading absorbance at 490 nm. Cytotoxicity assays were performed in parallel with the combination experiments. Here, uninfected cells were exposed to the same drug combinations, and assayed after five days for cell viability using the MTS assay.

Analysis of Drug Combination Effects. For determination of combination index (CI) values, drugs were diluted in a fixed ratio and multiple ratios were analyzed. The drug serial dilutions spanned a range of concentrations near the $EC_{50}$ value of each compound, so that equivalent antiviral activities could be compared. The normalized responses from each therapy are fit to the four-parameter logistic model with a common minimum and maximum across all therapies. Conceptually, this equation can be written as $$Fa_i = A + \frac{D - A}{1 + \left(\frac{C_1^{I_1} C_2^{I_2} C_3^{I_3} C_4^{I_4} C_5^{I_5}}{concentration_i}\right)^{B_1^{I_1} B_2^{I_2} B_3^{I_3} B_4^{I_4} B_5^{I_5}}}$$

where $I_j = \begin{cases} 1 & \text{if therapy} = j \\ 0 & \text{otherwise} \end{cases}$ for $j = 1, 2, 3, 4,$ or $5$.

In this equation, Fa stands for "fraction affected," and represents the fraction of the viral load that has been inactivated. For example, Fa of 0.75 indicates that viral replication had been inhibited by 75%, relative to the no-drug controls. The $EC_{50}$, represented by the $C_i$ in the above equation, is the drug concentration that is expected to reduce the amount of virus by 50%, and the $B_i$ are the parameters that reflects the slope of the concentration-response curve. For this assay, A is the bottom plateau common to all curves, D is the common top plateau, $B_j$ is the "slope" parameter for the jth therapy, and $C_j$ is the concentration that produces an effect equal to the average of A and D for the jth therapy. Therapies 1 and 2 correspond to mono therapies 1 and 2, respectively. Therapies 3, 4, and 5 correspond to the three combination therapies. $EC_{50}$ values for each drug were determined from the single drug experiments, using the above equation. The equation was fit using a nonlinear regression routine (Proc Nlin) in PC SAS version 8.2 (SAS Institute Inc.).

To assess antiviral effects of different drug combination treatments, combination indices (CIs) were calculated according to Chou and Rideout. The combination index was computed as $$CI = \frac{[D]_1}{[Dm]_1} + \frac{[D]_2}{[Dm]_2}$$

In this equation $[Dm]_1$ and $[Dm]_2$ are the concentrations of drugs that would individually produce a specific level of effect, while $[D]_1$ and $[D]_2$ are the concentrations of drugs in combination that would produce the same level of effect.

Theoretically, additivity is implied if the CI is equal to one, synergy if the CI is less than one, and antagonism if the CI is greater than one. However, extensive experience with combination studies indicates that there are inherent laboratory variables that must be taken into account in interpreting the CIs. At best, a range can be constructed that contains the likely values for the CI, given the noise in the data. In this report, these ranges are reported in parentheses next to each point estimate of the CI. For example, when a CI of "0.52 (0.36, 0.69)" is reported this means that the best estimate of the CI is 0.52, but due to noise in the data, values from 0.36 to 0.69 are also reasonable values for the CI. This range, 0.36 to 0.69 falls entirely below the value of 1.0, and hence all likely values for the CI are less than 1.0. Therefore, synergistic behavior can be inferred for this combination. If the range fell entirely above 1.0, we would infer antagonistic behavior. If the range were to include 1.0, we would infer additivity.

In carrying out the combination experiments, the $EC_{50}$ for Example 19 and each comparator compound was determined during the course of each study, and used in the subsequent data analysis. The determined values are consistent with previously published data and are shown in Table 3.

TABLE 3

Anti-HIV Activity of Compounds in Two-Drug Combination Studies

| Compound | $EC_{50}$ (µM) | Highest Drug Concentration (µM) |
|---|---|---|
| Example19 | 0.022 | 2.5 |
| Zidovudine | 0.012 | 2.5 |
| Didanosine | 10.7 | 100 |
| Stavudine | 0.241 | 15 |
| Lamivudine | 0.203 | 15 |
| Abacavir | 1.04 | 30 |
| Tenofovir | 0.018 | 2.5 |
| Emtricitabine | 0.053 | 20 |
| Zalcitabine | 0.124 | 10 |
| Efavirenz | 0.0016 | 0.2 |
| Nevirapine | 0.095 | 5 |
| Delavirdine | 0.043 | 5 |
| Ritonavir | 0.048 | 2.5 |
| Indinavir | 0.026 | 2.5 |
| Nelfinavir | 0.022 | 2.5 |
| Saquinavir | 0.011 | 2.5 |
| Amprenavir | 0.062 | 2.5 |
| Atazanavir | 0.010 | 1 |
| Lopinavir | 0.017 | 2.5 |
| Enfuvirtide | 0.061 | 2.2 |

Two-Drug Combinations of Example 19 with Nucleoside Reverse Transcriptase Inhibitors. Eight nucleoside RT inhibitors (didanosine, stavudine, zidovudine, lamivudine, abacavir, zalcitabine, emtricitibine and the nucleoside phosphonate, tenofovir) were combined with Example 19 at a range of concentrations near the $EC_{50}$ value of each compound, so that equivalent antiviral activities could be compared. All estimates were computed using SAS Proc NLIN, and a two-parameter logistic. Data is presented in Table 4 as the combination indices and the asymptotic confidence intervals for RT inhibitors at different molar ratios.

Four nucleoside RT inhibitors; didanosine, stavudine, abacavir and emtricitibine, show synergistic antiviral effects in combination with Example 19 at all effective levels and all molar ratios. The other four RT inhibitors: zidovudine, lamivudine, tenofovir and zalcitabine all have combination indices suggestive of synergistic behavior with Example 19. However, the upper ranges of the confidence intervals for some of the effective levels are greater than 1, so the overall effects of these compounds with Example 19 are classified as synergistic to additive. No significant antagonism of anti-HIV activity is observed. No enhanced cytotoxicity was encountered at the highest concentrations tested with any of the drug combinations, as measured by the XTT reduction assay.

TABLE 4

Two-Drug Combinations using Example 19 and Nucleoside Reverse Transcriptase Inhibitors.

| Molar Ratio | Combination Indices at % HIV Inhibition[b] (Confidence Interval) | | |
|---|---|---|---|
| ($EC_{50}$ Ratio)[a] | 50% | 75% | 90% |
| Zidovudine | | | |
| 1:1 (1:1) | 0.59 (0.49, 0.69) | 0.56 (0.41, 0.70) | 0.54 (0.36, 0.70) |
| 2:5 (1:2.5) | 0.65 (0.56, 0.75) | 0.73 (0.59, 0.86) | 0.81 (0.57, 1.06) |
| 5:2 (2.5:1) | 0.72 (0.61, 0.83) | 0.83 (0.64, 1.02) | 0.96 (0.63, 1.30) |
| Didanosine | | | |
| 1:1000 (1:1) | 0.58 (0.53, 0.63) | 0.47 (0.35, 0.60) | 0.39 (0.22, 0.56) |
| 1:2500 (1:2.5) | 0.56 (0.51, 0.62) | 0.46 (0.40, 0.52) | 0.38 (0.32, 0.44) |
| 1:400 (2.5:1) | 0.50 (0.46, 0.54) | 0.49 (0.44, 0.53) | 0.48 (0.42, 0.54) |
| Stavudine | | | |
| 1:6 (1:1) | 0.52 (0.43, 0.61) | 0.46 (0.36, 0.56) | 0.42 (0.26, 0.57) |
| 1:15 (1:2.5) | 0.60 (0.48, 0.71) | 0.60 (0.46, 0.74) | 0.61 (0.40, 0.83) |
| 5:12 (2.5:1) | 0.70 (0.57, 0.84) | 0.63 (0.48, 0.79) | 0.58 (0.37, 0.81) |
| Lamivudine | | | |
| 1:6 (1:1) | 0.80 (0.63, 0.98) | 0.80 (0.55, 1.05) | 0.81 (0.42, 1.21) |
| 1:15 (1:2.5) | 1.09 (0.88, 1.31) | 1.00 (0.72, 1.27) | 0.92 (0.52, 1.33) |
| 5:12 (2.5:1) | 0.94 (0.80, 1.08) | 0.84 (0.65, 1.03) | 0.75 (0.49, 1.02) |
| Abacavir | | | |
| 1:30 (1:1) | 0.68 (0.59, 0.76) | 0.67 (0.56, 0.79) | 0.67 (0.49, 0.84) |
| 1:75 (1:2.5) | 0.87 (0.77, 0.97) | 0.74 (0.63, 0.85) | 0.63 (0.50, 0.77) |
| 1:12 (2.5:1) | 0.86 (0.76, 0.96) | 0.82 (0.68, 0.96) | 0.79 (0.58, 0.99) |
| Tenofovir | | | |
| 1:1 (1:1) | 0.66 (0.57, 0.75) | 0.54 (0.45, 0.62) | 0.43 (0.33, 0.53) |
| 2:5 (1:2.5) | 0.68 (0.59, 0.77) | 0.60 (0.48, 0.72) | 0.52 (0.36, 0.69) |
| 5:2 (2.5:1) | 0.90 (0.77, 1.04) | 0.84 (0.67, 1.01) | 0.79 (0.55, 1.03) |
| Zalcitabine | | | |
| 1:4 (1:1) | 0.61 (0.48, 0.73) | 0.56 (0.39, 0.73) | 0.53 (0.28, 0.79) |
| 1:10 (1:2.5) | 0.55 (0.44, 0.66) | 0.40 (0.31, 0.49) | 0.30 (0.18, 0.42) |
| 5:8 (2.5:1) | 0.80 (0.62, 0.97) | 0.82 (0.58, 1.07) | 0.86 (0.46, 1.26) |
| Emtricitabine | | | |
| 1:8 (1:1) | 0.31 (0.27, 0.36) | 0.23 (0.18, 0.28) | 0.18 (0.12, 0.24) |
| 1:20 (1:2.5) | 0.31 (0.26, 0.37) | 0.23 (0.19, 0.29) | 0.17 (0.12, 0.28) |
| 5:16 (2.5:1) | 0.33 (0.28, 0.38) | 0.25 (0.20, 0.30) | 0.19 (0.13, 0.25) |

[a]Ratio of Example 19 to comparator compound
[b]A lower bound of the asymptotic confidence interval greater than 1 indicates antagonism, an upper bound of less than 1 indicates synergism and a value of 1 being contained in the interval indicates additivity. The 95% confidence intervals are shown in parenthesis, and represent a measure of variability in the data.

Two-Drug Combinations of Example 19 with Non-Nucleoside Reverse Transcriptase Inhibitors. Three non-nucleoside RT inhibitors were combined with Example 19 at a range of concentrations near the $EC_{50}$ value of each compound, as described above for nucleoside RT inhibitors. Data is presented in Table 5 as the combination indices and the asymptotic confidence intervals at different molar ratios. Of the three, nevaripine shows strong synergistic effects in combination with Example 19. Synergy is seen at all effective concentrations and at all molar ratios. Sustiva and nevirapine also exhibit combination indices indicative of synergism at most effective concentrations and molar ratios. However, in some cases, the upper range of the asymptotic confidence interval is greater than 1, so an additive effect can not be ruled out. No enhanced cytotoxicity was observed at the highest concentrations tested with any of the drug combinations, suggesting a potential for therapeutic efficacy of Example 19 combinations with non-nucleoside RT inhibitors.

TABLE 5

Two-Drug Combinations using Example 19 and Non-Nucleoside Reverse Transcriptase Inhibitors.

| Molar Ratio | Combination Indices at % HIV Inhibition[b] (Confidence Interval) | | |
|---|---|---|---|
| (EC$_{50}$ Ratio)[a] | 50% | 75% | 90% |
| Efavirenz | | | |
| 5:2 (1:1) | 0.83 (0.75, 0.92) | 0.76 (0.64, 0.88) | 0.70 (0.54, 0.85) |
| 1:1 (1:2.5) | 0.95 (0.86, 1.04) | 0.93 (0.85, 1.02) | 0.93 (0.79, 1.06) |
| 25:4 (2.5:1) | 1.01 (0.92, 1.10) | 0.96 (0.83, 1.10) | 0.94 (0.73, 1.14) |
| Nevirapine | | | |
| 1:2 (1:1) | 0.72 (0.62, 0.82) | 0.69 (0.55, 0.83) | 0.66 (0.46, 0.87) |
| 1:5 (1:2.5) | 0.76 (0.64, 0.87) | 0.81 (0.64, 0.97) | 0.87 (0.59, 1.15) |
| 5:4 (2.5:1) | 0.73 (0.62, 0.83) | 0.68 (0.55, 0.81) | 0.64 (0.45, 0.84) |
| Delavirdine | | | |
| 1:2 (1:1) | 0.76 (0.64, 0.89) | 0.60 (0.47, 0.74) | 0.48 (0.31, 0.64) |
| 1:5 (1:2.5) | 0.68 (0.58, 0.77) | 0.44 (0.32, 0.54) | 0.28 (0.17, 0.39) |
| 5:4 (2.5:1) | 0.80 (0.68, 0.92) | 0.53 (0.42, 0.63) | 0.35 (0.25, 0.45) |

[a]Ratio of Example 19 to comparator compound.
[b]A lower bound of the asymptotic confidence interval greater than 1 indicates antagonisms, an upper bound of less than 1 indicates synergism, and a value of 1 being contained in the interval indicates additivity. The 95% confidence intervals are shown in parenthesis, and represent a measure of variability in the data.

Two-Drug Combinations Involving Example 19 and HIV Protease Inhibitors. Evaluation of Example 19 for drug combination therapy with protease inhibitors was carried out using indinavir, amprenavir, nelfinavir, lopinavir, saquinavir, ritonavir and atazanavir. Results from this two-drug combination study are summarized in Table 6. Again, the combination indices observed with Example 19 and all protease inhibitors at almost all effective levels and molar ratios are suggestive of a synergistic relationship. This is especially true for saquinavir and atazanavir, where the confidence interval is below one at all concentrations and effective levels. Meanwhile, the upper range of the confidence interval is greater than one in only one condition for ritonavir, indinavir and lopinavir, so an additive relationship with Example 19 cannot be ruled out. In addition, the upper range of the confidence interval for nelfinavir and amprenavir are slightly greater than 1 under a few conditions, suggestive of a synergistic-additive effect for these compounds with Example 19. No cytotoxicity was observed at the highest concentrations used in any of these combination antiviral assays.

TABLE 6

Two-Drug Combination using Example 19 and Protease Inhibitors.

| Molar Ratio | Combination Indices at % HIV Inhibition[b] (Confidence Interval) | | |
|---|---|---|---|
| (EC$_{50}$ Ratio)[a] | 50% | 75% | 90% |
| Indinavir | | | |
| 1:1 (1:1) | 0.86 (0.80, 0.92) | 0.71 (0.62, 0.81) | 0.60 (0.46, 0.73) |
| 2:5 (1:2.5) | 0.92 (0.84, 0.99) | 0.84 (0.76, 0.92) | 0.77 (0.66, 0.89) |
| 5:2 (2.5:1) | 0.94 (0.87, 1.02) | 0.79 (0.71, 0.87) | 0.67 (0.57, 0.77) |
| Nelfinavir | | | |
| 1:1 (1:1) | 0.79 (0.73, 0.86) | 0.75 (0.67, 0.82) | 0.71 (0.56, 0.84) |
| 2:5 (1:2.5) | 0.97 (0.89, 1.06) | 0.87 (0.79, 0.95) | 0.78 (0.68, 0.88) |
| 5:2 (2.5:1) | 1.09 (1.00, 1.18) | 0.98 (0.89, 1.08) | 0.90 (0.76, 1.03) |

TABLE 6-continued

Two-Drug Combination using Example 19 and Protease Inhibitors.

| Molar Ratio | Combination Indices at % HIV Inhibition[b] (Confidence Interval) | | |
|---|---|---|---|
| (EC$_{50}$ Ratio)[a] | 50% | 75% | 90% |
| Saquinavir | | | |
| 1:1 (1:1) | 0.77 (0.70, 0.84) | 0.67 (0.58, 0.75) | 0.58 (0.47, 0.69) |
| 2:5 (1:2.5) | 0.43 (0.38, 0.48) | 0.51 (0.42, 0.59) | 0.59 (0.44, 0.74) |
| 5:2 (2.5:1) | 0.81 (0.72, 0.89) | 0.77 (0.66, 0.89) | 0.74 (0.57, 0.91) |
| Amprenavir | | | |
| 1:1 (1:1) | 0.83 (0.67, 1.00) | 0.84 (0.61, 1.08) | 0.89 (0.50, 1.23) |
| 2:5 (1:2.5) | 0.84 (0.69, 0.99) | 0.77 (0.58, 0.96) | 0.75 (0.46, 1.04) |
| 5:2 (2.5:1) | 0.90 (0.77, 1.04) | 0.62 (0.50, 0.74) | 0.44 (0.30, 0.57) |
| Atazanavir | | | |
| 5:2 (1:1) | 0.87 (0.79, 0.96) | 0.67 (0.55, 0.80) | 0.52 (0.37, 0.67) |
| 1:1 (1:2.5) | 0.65 (0.51, 0.78) | 0.45 (0.31, 0.58) | 0.31 (0.19, 0.44) |
| 25:4 (2.5:1) | 0.78 (0.69, 0.86) | 0.60 (0.54, 0.67) | 0.47 (0.40, 0.54) |
| Lopinavir | | | |
| 1:1 (1:1) | 0.74 (0.67, 0.82) | 0.77 (0.66, 0.88) | 0.84 (0.65, 1.02) |
| 2:5 (1:2.5) | 0.77 (0.66, 0.88) | 0.56 (0.36, 0.75) | 0.41 (0.19, 0.64) |
| 5:2 (2.5:1) | 0.76 (0.69, 0.83) | 0.62 (0.55, 0.70) | 0.54 (0.47, 0.61) |
| Ritonavir | | | |
| 1:1 (1:1) | 0.80 (0.67, 0.93) | 0.57 (0.41, 0.73) | 0.44 (0.23, 0.65) |
| 2:5 (1:2.5) | 0.73 (0.59, 0.88) | 0.64 (0.48, 0.80) | 0.61 (0.38, 0.85) |
| 5:2 (2.5:1) | 0.92 (0.72, 1.11) | 0.72 (0.50, 0.93) | 0.59 (0.32, 0.87) |

[a]Ratio of Example 19 to comparator compound.
[b]A lower bound of the asymptotic confidence interval greater than 1 indicates antagonisms, an upper bound of less than 1 indicates synergism, and a value of 1 being contained in the interval indicates additivity. The 95% confidence intervals are shown in parenthesis, and represent a measure of variability in the data.

Two-Drug Combination of Example 19 with Enfuvirtide. Enfuvirtide (T-20) is an HIV gp41 fusion inhibitor and the first approved entry class inhibitor. The results presented in Table 7 indicate that the combination of Example 19 with T-20 is synergistic. No significant cytotoxicity was observed at the highest concentration of the combined drugs.

TABLE 7

Two-Drug Combination study of Example 19 with Enfuvirtide.

| Molar Ratio | Combination Indices at % HIV Inhibition[b] (Confidence Interval) | | |
|---|---|---|---|
| (EC$_{50}$ Ratio)[a] | 50% | 75% | 90% |
| Enfuvirtide | | | |
| 5:44 (1:1) | 0.68 (0.59, 0.77) | 0.59 (0.48, 0.70) | 0.52 (0.37, 0.67) |
| 1:22 (1:2.5) | 0.75 (0.65, 0.85) | 0.60 (0.49, 0.70) | 0.48 (0.34, 0.61) |
| 25:88 (2.5:1) | 0.76 (0.65, 0.86) | 0.73 (0.59, 0.86) | 0.71 (0.50, 0.92) |

[a]Ratio of Example 19 to comparator compound.
[b]A lower bound of the asymptotic confidence interval greater than 1 indicates antagonisms, an upper bound of less than 1 indicates synergism, and a value of 1 being contained in the interval indicates additivity. The 95% confidence intervals are shown in parenthesis, and represent a measure of variability in the data.

Pharmaceutical Composition and Methods of Use

The compounds of this invention inhibit HIV integrase. HIV integrase inhibitors belonging to a class of diketo acid compounds prevented viral integration and inhibited HIV-1 replication in cells (Hazuda et al. Science 2000, 287, 646). Recently, HIV integrase inhibitors have been accepted into clinical trials for treating AIDS and HIV infection (Neamati Expert. Opin. Ther. Patents 2002, 12, 709, Pais and Burke Drugs Fut. 2002, 27, 1101).

Accordingly, another aspect of the invention is a method for treating HIV infection in a human patient comprising administering a therapeutically effective amount of a compound of Formula I, or a pharmaceutically acceptable salt or solvate thereof, with a pharmaceutically acceptable carrier.

Another aspect of the invention is a method for treating HIV infection in a human patient comprising the administration of a therapeutically effective amount of a compound of Formula I, or a pharmaceutically acceptable salt or solvate thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt or solvate thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable salt or solvate thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt or solvate thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt or solvate thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt or solvate thereof.

Another aspect of the invention is a method wherein the agent is a CXCR4 inhibitor.

Another aspect of the invention is a method wherein the CXCR4 inhibitor is AMD-3100, or a pharmaceutically acceptable salt or solvate thereof.

Another aspect of the invention is a method wherein the agent is an HIV budding or maturation inhibitor.

Another aspect of the invention is a method wherein the budding or maturation inhibitor is PA-457, or a pharmaceutically acceptable salt, or solvate thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt or solvate thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt or solvate thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt or solvate thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt or solvate thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt or solvate thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt or solvate thereof.

Another aspect of the invention is a method wherein the agent is a CXCR4 inhibitor.

Another aspect of the invention is a method wherein the CXCR4 inhibitor is AMD-3100 or a pharmaceutically acceptable salt or solvate thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt or solvate thereof.

Another aspect of the invention is the composition wherein the agent is an HIV integrase inhibitor.

"Combination," "coadministration," "concurrent," and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Table 8 lists some agents useful in treating AIDS and HIV infection which are suitable for this invention.

TABLE 8

| DRUG NAME | MANUFACTURER | INDICATION |
|---|---|---|
| ANTIVIRALS | | |
| 097 (non-nucleoside reverse transcriptase inhibitor) | Hoechst/Bayer | HIV infection, AIDS, ARC |
| Amprenavir 141 W94 GW 141 (protease inhibitor) | Glaxo Wellcome | HIV infection, AIDS, ARC |
| Abacavir (1592U89) GW 1592 (RT inhibitor) | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection, ARC, PGL HIV positive, AIDS |
| Alpha Interferon HIV in combination w/Retrovir | Glaxo Wellcome | Kaposi's sarcoma |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |

TABLE 8-continued

| DRUG NAME | MANUFACTURER | INDICATION |
|---|---|---|
| AR177 | Aronex Pharm | HIV infection, AIDS, ARC |
| Beta-fluoro-ddA | Nat'l Cancer Institute | AIDS-associated diseases |
| BMS-232623 (CGP-73547) (protease inhibitor) | Bristol-Myers Squibb/ Novartis | HIV infection, AIDS, ARC |
| BMS-234475 (CGP-61755) (protease inhibitor) | Bristol-Myers Squibb/Novartis | HIV infection, AIDS, ARC |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight threatening CMV peripheral, CMV retinitis |
| Delaviridine (RT inhibitor) | Pharmacia-Upjohn | HIV infection, AIDS, ARC |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 (protease inhibitor) | AVID (Camden, NJ) | HIV infection, AIDS, ARC |
| Efavirenz (DMP 266) (−)6-Chloro-4-(S)-cyclopropylethynyl-4(S)-trifluoro-methyl-1,4-dihydro-2H-3,1-benzoxazin-2-one, STOCRINE (non-nucleoside RT inhibitor) | DuPont Merck | HIV infection, AIDS, ARC |
| EL10 | Elan Corp, PLC (Gainesville, GA) | HIV infection |
| Famciclovir | Smith Kline | herpes zoster, herpes simplex |
| FTC (reverse transcriptase inhibitor) | Emory University | HIV infection, AIDS, ARC |
| GS 840 (reverse transcriptase inhibitor) | Gilead | HIV infection, AIDS, ARC |
| HBY097 (non-nucleoside reverse transcriptase inhibitor) | Hoechst Marion Roussel | HIV infection, AIDS, ARC |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-associated diseases |
| Lamivudine, 3TC (reverse transcriptase inhibitor) | Glaxo Wellcome | HIV infection, AIDS, ARC, also with AZT |
| Lobucavir | Bristol-Myers Squibb | CMV infection |
| Nelfinavir (protease inhibitor) | Agouron Pharmaceuticals | HIV infection, AIDS, ARC |
| Nevirapine (RT inhibitor) | Boeheringer Ingleheim | HIV infection, AIDS, ARC |
| Novapren | Novaferon Labs, Inc. (Akron, OH) | HIV inhibitor |
| Peptide T Octapeptide | Peninsula Labs (Belmont, CA) | AIDS |

TABLE 8-continued

| DRUG NAME | MANUFACTURER | INDICATION |
|---|---|---|
| Sequence Trisodium Phosphonoformate | Astra Pharm. Products, Inc. | CMV retinitis, HIV infection, other CMV infections |
| PNU-140690 (protease inhibitor) | Pharmacia Upjohn | HIV infection, AIDS, ARC |
| Probucol | Vyrex | HTV infection, AIDS |
| RBC-CD4 | Sheffield Med. Tech (Houston, TX) | HIV infection, AIDS, ARC |
| Ritonavir (protease inhibitor) | Abbott | HIV infection, AIDS, ARC |
| Saquinavir (protease inhibitor) | Hoffmann-LaRoche | HIV infection, AIDS, ARC |
| Stavudine; d4T Didehydrodeoxythymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV-positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) (reverse transcriptase inhibitor) | Gilead | HIV infection, AIDS |
| Combivir ® (reverse transcriptase inhibitor) | GSK | HIV infection, AIDS |
| abacavir succinate (or Ziagen ®) (reverse transcriptase inhibitor) | GSK | HIV infection, AIDS |
| Reyataz ® (atazanavir) | Bristol-Myers Squibb | HIV infection, AIDS |
| Fuzeon (Enfuvirtide, T-20) | Roche/Trimeris | HIV infection, AIDS, viral fusion inhibitor |
| Trizivir ® | | HIV infection, AIDS |
| Kaletra ® | Abbott | HIV infection, AIDS, ARC |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 | Chiron | AIDS, increase in CD4 cell counts |

TABLE 8-continued

| DRUG NAME | MANUFACTURER | INDICATION |
|---|---|---|
| (aldeslukin) | | |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma AIDS, in combination w/AZT |
| Granulocyte Colony Stimulating Factor | Amgen | |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche in combination w/AZT | Kaposi's sarcoma, AIDS, ARC |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Description of Specific Embodiments

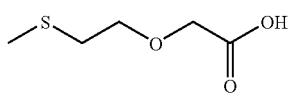

Intermediate 1

2-(2-(Methylthio)ethoxy)acetic acid. A solution of 2-methylthioethanol (10.0 g, 0.108 mol) in dry tetrahydrofuran (25 ml) was added dropwise, over 30 min, to a suspension of sodium hydride (9.54 g of a 60% dispersion in mineral oil, 0.238 mol, washed twice with hexane) in dry tetrahydrofuran (250 ml) at 22° C. After 30 min, a solution of chloroacetic acid (10.25 g, 0.108 mol) in dry tetrahydrofuran (20 ml) was added dropwise, over 30 min at 22° C., and the resulting mixture was then heated under reflux for 5 h. The cooled mixture was treated with 250 ml of 1 N hydrochloric acid and sodium chloride added to the aqueous phase until saturation. The organic phase was separated and the aqueous phase washed with ethyl acetate. The combined organic extracts were washed with brine, dried over anhydrous magnesium sulfate and concentrated under reduced pressure. Distillation of the resulting residue in vacuo gave 11.27 g (69% yield) of the title acid as a clear oil; bp 85-95° C./0.3 torr (bulb to bulb distillation, air bath temperature). $^1$HNMR 400 MHz (CDCl$_3$) δ ppm: 2.18 (3H, s, SCH$_3$), 2.76 (2H, t, J=6.6 Hz, CH$_2$), 3.77 (2H, t, J=6.6 Hz, CH$_2$), 4.20 (2H, s, OCH$_2$).

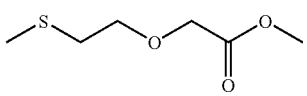

Intermediate 2

Methyl 2-(2-(methylthio)ethoxy)acetate. A solution of intermediate 1, 2-(2-(methylthio)ethoxy)acetic, (11.27 g, 0.075 mol) in dry dichloromethane (50 ml) was treated with oxalylchloride (13.0 ml, 0.15 mol) followed by a drop of N,N-dimethylformamide and the resulting mixture stirred at 22° C. for 5 h. The solvent and excess reagent were then evaporated under reduced pressure and the residual acid chloride was added dropwise to a cold mixture(0-5° C.) of methanol (30 ml) and pyridine (10 ml) in dichloromethane (50 ml). After 1 h at 22° C., the solvent was evaporated under reduced pressure. The resulting residue was diluted with ethyl acetate, washed with 1 N hydrochloric acid, saturated sodium bicarbonate and brine, dried over anhydrous magnesium sulfate and then concentrated under reduced pressure. Distillation of the resulting residue in vacuo gave 11.42 g (93% yield) of the title ester as a clear oil; bp 65-75° C./0.1 torr (bulb to bulb distillation, air bath temperature). $^1$HNMR 400 MHz (CDCl$_3$) δ ppm: 2.17 (3H, s, SCH$_3$), 2.75 (2H, t, J=6.9 Hz, CH$_2$), 3.74 (2H, t, J=6.9 Hz, CH$_2$), 3.77 (3H, s, OCH$_3$), 4.15 (2H, s, OCH$_2$).

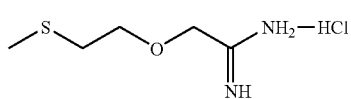

Intermediate 3

2-(2-(Methylthio)ethoxy)acetamidine hydrochloride salt. Intermediate 2, methyl 2-(2-(methylthio)ethoxy)acetate, (4.69 g, 28.6 mmol) was added to a solution of methylchloroaluminum amide (H. Geilen, C. Alonso-Alija, M. Hendrix, U. Niewohner and D. Schauss, Tetrahedron Lett., 2002, 43, 419-421)(0.114 mol; prepared in toluene (50 ml) from ammonium chloride 6.30 g (0.117 mol) and 57.0 ml (0.114 mol) of a 2 M solution of trimethylaluminum in toluene) and the resulting mixture was heated at 80° C. for 18 h. The reaction mixture was then cooled to 0° C., treated dropwise with methanol (100 ml) and stirred for another hour at 25° C. The solid which was formed was filtered and washed with methanol (300 ml). The combined filtrate was concentrated to give a white paste which was diluted with isopropanol (160 ml) and acetone (40 ml) and stirred at 25° C. for 1 h. The solid was then filtered off and the filtrate concentrated in vacuo to give 3.50 g (62% yield) of the title compound as an oil. $^1$HNMR 400 MHz (DMSO-d$_6$) δ ppm: 2.10 (3H, s, SCH$_3$), 2.71 (2H, t, J=6.8 Hz, CH$_2$), 3.66 (2H, t, J=6.8 Hz, CH$_2$), 4.34 (2H, s, OCH$_2$). MS (ESI$^+$) m/z 149 [M+H$^+$].

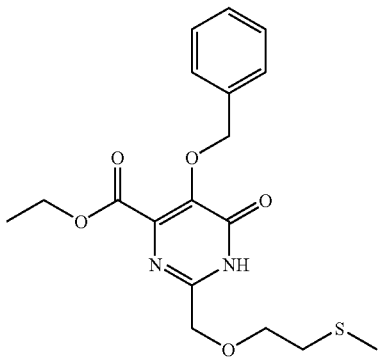

Intermediate 4

Ethyl 5-benzyloxy-2-{(2-(methylthio)ethoxy)methyl}-6-oxo-1,6-dihydropyrimidine-4-carboxylate. Diethyl oxalate (2.77 g, 19.0 mmol) and ethyl benzyloxyacetate (3.69 g, 19.0 mmol) in dry tetrahydrofuran (30 ml) were treated at 22° C. with sodium hydride (0.83 g of a 60% dispersion in mineral oil, 20.9 mmol) followed by ethanol (10 μl) and the resulting mixture was stirred at 22° C. for 18 h. The tetrahydrofuran was evaporated under reduced pressure to give an orange syrup. A mixture of intermediate 3, 2-(2-(methylthio)ethoxy) acetamidine hydrochloride salt, (3.50 g, 19.0 mmol) in a solution of sodium ethoxide (9.5 mmol, prepared from 0.22 g of sodium in ethanol 25 ml) was then added all at once to the above adduct and the resulting mixture heated at 60° C. for 3 h. Acetic acid (2 ml) was added and the ethanol was evaporated under reduced pressure. The residue was diluted with ethyl acetate washed successively with saturated sodium bicarbonate and brine, then dried over anhydrous magnesium sulfate and concentrated under reduced pressure. Chromatography on silica gel (elution with a gradient of ethyl acetate 20-30% in toluene) gave 0.728 g (10% yield) of the title ester as a clear oil. $^1$HNMR 400 MHz (CDCl$_3$) δ (ppm): 1.33 (3H, t, J=7.1 Hz, CH$_3$), 2.18 (3H, s, SCH$_3$), 2.78 (2H, t, J=6.0 Hz, CH$_2$), 3.78 (2H, t, J=6.0 Hz, CH$_2$), 4.36 (2H, q, J=7.1 Hz, OCH$_2$), 4.54 (2H, s, OCH$_2$), 5.35 (2H, s, OCH$_2$), 7.37 (3H, m, aromatics), 7.48 (2H, m, aromatics). HRMS (ESI$^+$) calculated for C$_{18}$H$_{23}$N$_2$O$_5$S [M+H$^+$]: 379.1328: found: 379.1314.

Intermediate 5

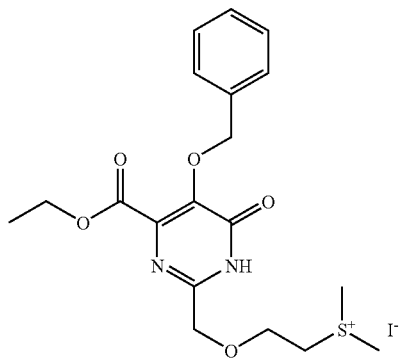

Ethyl 5-benzyloxy-2-{(2-(dimethylsulfonium)ethoxy)methyl}-6-oxo-1,6-dihydropyrimidine-4-carboxylate iodide. A solution of intermediate 4, ethyl 5-benzyloxy-2-{(2-(methylthio)ethoxy)methyl}-6-oxo-1,6-dihydropyrimidine-4-carboxylate, (0.555 g, 1.47 mmol) in dichloromethane (10 ml) was treated at 22° C. with iodomethane (2.0 ml, 21.5 mmol) for 10 days. Evaporation of the solvent and excess reagent gave the title compound (0.76 g) as an oil which was used without further purification. $^1$HNMR 400 MHz (CDCl$_3$) δ (ppm): 1.32 (3H, t, J=7.1 Hz, CH$_3$), 3.26 (6H, s, SCH$_3$), 4.02 (2H, m, CH$_2$), 4.23 (2H, m, CH$_2$), 4.34 (2H, q, J=7.1 Hz, OCH$_2$), 4.69 (2H, s, OCH$_2$), 5.23 (2H, s, OCH$_2$), 7.35-7.5 (5H, m, aromatics). MS (ESI$^+$) m/z 393 [M$^+$].

Intermediate 6

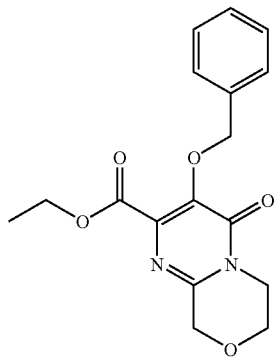

Ethyl 3-benzyloxy-4-oxo-4,6,7,9-tetrahydropyrimido[2,1-c][1,4]oxazine-2-carboxylate. A solution of intermediate 5, ethyl 5-benzyloxy-2-{(2-(dimethylsulfonium)ethoxy)methyl}-6-oxo-1,6-dihydropyrimidine-4-carboxylate iodide, (0.76 g, 1.47 mmol) in dry N,N-dimethylformamide (10 ml) was treated at 22° C. with powdered anhydrous potassium carbonate (2.5 g) and the resulting mixture stirred for 48 h. The solid was then filtered and the filtrate evaporated in vacuo. The residue was diluted with ethyl acetate washed successively with 0.1 N hydrochloric acid, saturated sodium bicarbonate, brine and dried over anhydrous magnesium sulfate. Evaporation of the solvent followed by chromatography on silica gel (elution with a gradient of ethyl acetate 20-50% in toluene) gave 0.347 g (72% yield) of the title ester as white prisms; mp 103-104° C. (ethyl acetate-hexane). $^1$HNMR 400 MHz (CDCl$_3$) δ ppm: 1.34 (3H, t, J=7.1 Hz, CH$_3$), 4.03 (2H, t, J=5.6 Hz, CH$_2$), 4.11 (2H, t, J=5.6 Hz, CH$_2$), 4.37 (2H, q, J=7.1 Hz, OCH$_2$), 4.74 (2H, s, OCH$_2$), 5.30 (2H, s, OCH$_2$), 7.38 (3H, m, aromatics), 7.50 (2H, m, aromatics). Anal. Calcd for C$_{17}$H$_{18}$N$_2$O$_5$: C, 61.81; H, 5.49; N 8.48. Found: C, 61.55; H, 5.53; N, 8.39.

Intermediate 7

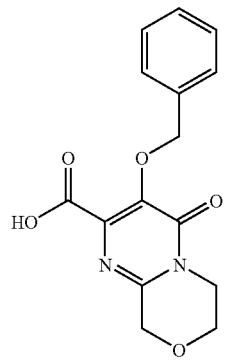

3-(Benzyloxy)-4-oxo-4, 6,7,9-tetrahydropyrimido[2, 1-c][1,4]oxazine-2-carboxylic acid. A solution of intermediate 6, ethyl 3-(benzyloxy)-4-oxo-4,6,7,9-tetrahydropyrimido[2, 1-c][1,4]oxazine-2-carboxylate (0.300 g, 0.91 mmol) in ethanol (10 ml) was treated with 3 ml (3.0 mmol) of 1 N sodium hydroxide and stirred at 25° C. for 30 min. The solution was then acidified with 1 N hydrochloric acid, extracted with ethyl acetate, washed with brine and dried over anhydrous magnesium sulfate. Evaporation of the solvent gave 0.264 g (96% yield) of the title acid as white crystals; mp 171° C. (ethyl acetate). $^1$HNMR 400 MHz (CDCl$_3$) δ (ppm):.4.03 (2H, t, J=5.3 Hz, CH$_2$), 4.12 (2H, t, J=5.3 Hz, CH$_2$), 4.73 (2H, s, OCH$_2$), 5.53 (2H, s, OCH$_2$), 7.35-7.42 (3H, m, aromatics), 7.53 (2H, m, aromatics). Anal. Calcd for C$_{15}$H$_{14}$N$_2$O$_5$: C, 59.60; H, 4.67; N, 9.27. Found: C, 59.35; H, 4.69; N, 9.10.

Intermediate 8

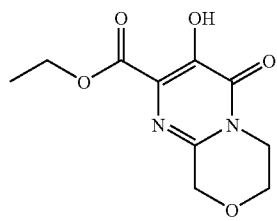

Ethyl 3-hydroxy-4-oxo-4,6,7,9-tetrahydropyrimido[2,1-c][1,4]oxazine-2-carboxylate. A solution of intermediate 6, ethyl 3-benzyloxy-4-oxo-4,6,7,9-tetrahydropyrimido[2,1-c][1,4]oxazine-2-carboxylate, (0.236 g, 0.714 mmol) in a mixture of ethyl acetate (60 ml) and ethanol (20 ml) was treated with 1 atm of hydrogen at 25° C. over 10% palladium on activated carbon (0.10 g) for 2.5 h to give 0.160 g (94% yield) of the title compound as white needles; mp 172-174° C. (ethyl acetate). $^1$HNMR 400 MHz (CDCl$_3$) δ ppm: 1.47 (3H, t, J=7.3 Hz, CH$_3$), 4.08 (4H, m, 2×CH$_2$), 4.54 (2H, q, J=7.3 Hz, OCH$_2$), 4.72 (2H, s, OCH$_2$), 10.75 (1H, s, OH). Anal. Calcd for C$_{10}$H$_{12}$N$_2$O$_5$: C, 50.00; H, 5.03; N, 11.66. Found: C, 50.01; H, 4.95; N, 11.54.

Intermediate 9

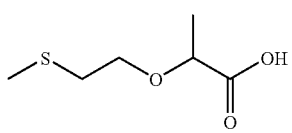

2-(2-(Methylthio)ethoxy)propanoic acid. Addition of 2-methylthioethanol (10.0 g, 0.108 mol) to sodium hydride (9.54 g of a 60% dispersion in mineral oil, 0.238 mol, washed twice with hexane) followed by reaction with 2-bromopropionic acid (16.6 g, 0.108 mol) gave 13.81 g (78% yield) of the title compound as a clear oil; bp 80-90° C./0.2 torr (bulb to bulb distillation, air bath temperature). $^1$HNMR 400 MHz (CDCl$_3$) δ ppm: 1.49 (3H, d, J=7.0 Hz, CH$_3$), 2.18 (3H, s, SCH$_3$), 2.76 (2H, t, J=6.6 Hz, CH$_2$), 3.74 (2H, t, J=6.6 Hz, CH$_2$), 4.07 (1H, d, J=7.0 Hz, OCH).

Intermediate 10

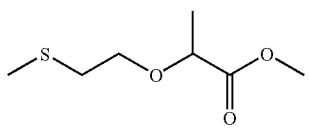

Methyl 2-(2-(methylthio)ethoxy)propanoate. Reaction of intermediate 9, 2-(2-(methylthio)ethoxy)propanoic acid, (13.70 g, 0.083 mol) with oxalyl chloride followed by reaction with methanol gave 14.27 g (96% yield) of the title ester as a clear oil; bp 55-60° C./0.3 torr (bulb to bulb distillation, air bath temperature). $^1$HNMR 400 MHz (CDCl$_3$) δ ppm: 1.42 (3H, d, J=7.0 Hz, CH$_3$), 2.15 (3H, s, SCH$_3$), 2.71 (2H, t, J=6.8 Hz, CH$_2$), 3.56 (1H, m, CH), 3.75 (3H, s, OCH$_3$), 3.78 (1H, m, CH), 4.15 (1H, q, J=7.0 Hz, OCH).

Intermediate 11

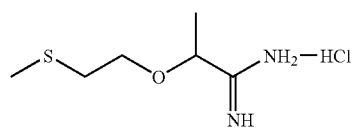

2-(2-(Methylthio)ethoxy)propanamidine hydrochloride salt. Intermediate 10, methyl 2-(2-(methylthio)ethoxy)propanoate, (10.00 g, 56.1 mmol) was added to a solution of methylchloroaluminum amide (0.224 mol; prepared in toluene (100 ml) from ammonium chloride 12.36 g (0.231 mol) and 112.0 ml (0.224 mol) of a 2 M solution of trimethylaluminum in toluene} as described in the preparation of intermediate 3 to give 7.70 g (69% yield) of the title compound as an oil. $^1$HNMR 400 MHz (D$_2$O) δ ppm: 1.37 (3H, d, J=6.6 Hz, CH$_3$), 2.01 (3H, s, SCH$_3$), 2.65 (2H, t, J=5.6 Hz, CH$_2$), 3.64 (2H, m, CH$_2$), 4.30 (1H, q, J=6.6 Hz, OCH). MS (ESI$^+$) m/z 163 [M+H$^+$].

Intermediate 12

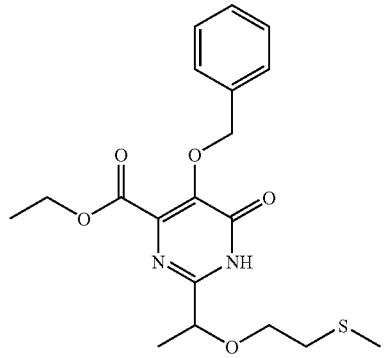

Ethyl 5-benzyloxy-2-{1-(2-(methylthio)ethoxy)ethyl}-6-oxo-1,6-dihydropyrimidine-4-carboxylate. Diethyl oxalate (5.66 g, 38.7 mmol) and ethyl benzyloxyacetate (7.52 g, 38.7 mmol) in dry tetrahydrofuran (60 ml) were treated at 22° C. with sodium hydride (1.70 g of a 60% dispersion in mineral oil, 42.5 mmol) and the condensation product was reacted with a mixture of intermediate 11, 2-(2-(methylthio)ethoxy) propanamidine hydrochloride salt, (7.70 g, 38.7 mmol) in a solution of sodium ethoxide (19.3 mmol, prepared from 0.445 g of sodium) in ethanol (50 ml) to give 2.29 g (15% yield) of the title ester as a clear oil after chromatography on silica gel. $^1$HNMR 400 MHz (CDCl$_3$) δ ppm: 1.33 (3H, t, J=7.1 Hz, CH$_3$), 1.54 (3H, d, J=7.1 Hz, CH$_3$), 2.16 (3H, s, SCH$_3$), 2.7-2.8 (2H, m, CH$_2$), 3.54 (1H, m, CH), 3.86 (1H, m, CH), 4.37 (2H, q, J=7.1 Hz, OCH$_2$), 4.47 (1H, q, J=7.1 Hz, OCH), 5.34 (2H, ABq, J$_{AB}$=11.0 Hz, OCH$_2$), 7.37 (3H, m, aromatics), 7.49 (2H, m, aromatics). MS (ESI$^+$) m/z 393 [M+H$^+$].

Intermediate 13

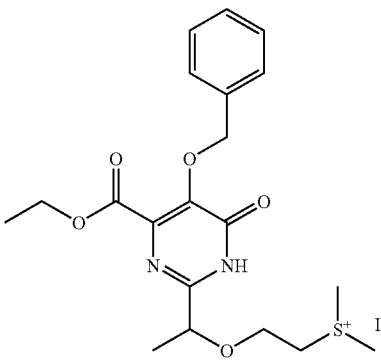

Ethyl 5-benzyloxy-2-{1-(2-(dimethylsulfonium)ethoxy) ethyl}-6-oxo-1,6-dihydropyrimidine-4-carboxylate iodide. A solution of intermediate 12, ethyl 5-benzyloxy-2-{1-(2-(methylthio)ethoxy)ethyl}-6-oxo-1,6-dihydropyrimidine-4-carboxylate, (1.63 g, 4.15 mmol) in dichloromethane (5 ml) was treated at 22° C. with iodomethane (5.0 ml, 53.9 mmol) for 5 days as described for the preparation of intermediate 5, to give the title compound (2.22 g) as an oil which was used without further purification. $^1$HNMR 400 MHz (CDCl$_3$) δ ppm: 1.32 (3H, t, J=7.1 Hz, CH$_3$), 1.66 (3H, d, J=6.6 Hz, CH$_3$), 3.15 (3H, s, SCH$_3$), 3.32 (3H, s, SCH$_3$), 3.4 (1H, m, CH), 4.01 (2H, m, CH$_2$), 4.37 (2H, q, J=7.1 Hz, OCH$_2$), 4.45 (1H, m, CH), 4.63 (1H, q, J=6.6 Hz, OCH), 5.28 (2H, OCH$_2$), 7.38 (3H, m, aromatics), 7.50 (2H, m, aromatics). MS (ESI$^+$) m/z 407 [M$^+$].

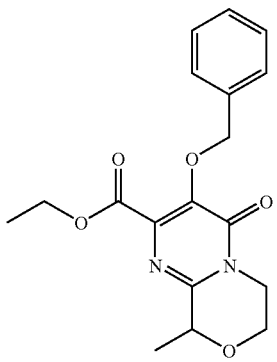

Intermediate 14

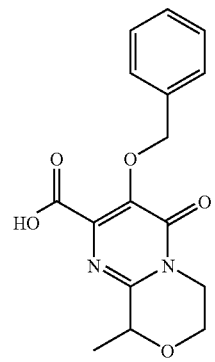

Intermediate 16

Ethyl 3-(benzyloxy)-9-methyl-4-oxo-4,6,7,9-tetrahydropyrimido[2,1-c][J,4]oxazine-2-carboxylate. A solution of intermediate 13, ethyl 5-benzyloxy-2-{1-(2-(dimethylsulfonium)ethoxy)ethyl}-6-oxo-1,6-dihydropyrimidine-4-carboxylate iodide (2.22 g, 4.15 mmol) in dry N,N-dimethylformamide (30 ml) was treated at 22° C. with powdered anhydrous potassium carbonate (6 g) and stirred for 40 h. The solid was then filtered and the filtrate was concentrated in vacuo. The residue was diluted with ethyl acetate, washed with 0.1 N hydrochloric acid, saturated sodium bicarbonate and brine then dried over anhydrous magnesium sulfate. Evaporation of the solvent and chromatography of the residue on silica gel (elution toluene-ethyl acetate 7:3) gave 1.0 g (70% yield) of the title ester as white crystals; mp 48-50° C. (ethyl acetate-hexane). $^1$HNMR 400 MHz (CDCl$_3$) δ (ppm): 1.33 (3H, t, J=7.1 Hz, CH$_3$), 1.68 (3H, d, J=6.6 Hz, CH$_3$), 3.91 (2H, m, CH$_2$), 4.17-4.31 (2H, m, CH$_2$), 4.37 (2H, q, J=7.1 Hz, OCH$_2$), 4.73 (1H, q, J=6.6 Hz, OCH), 5.30 (2H, ABq, J$_{AB}$=11.0 Hz, OCH$_2$), 7.38 (3H, m, aromatics), 7.50 (2H, m, aromatics). Anal. Calcd for C$_{18}$H$_{20}$N$_2$O$_5$: C, 62.78; H, 5.85; N, 8.13. Found: C, 62.69; H, 6.01; N, 8.16.

3-Benzyloxy-9-methyl-4-oxo-4,6,7,9-tetrahydropyrimido[2,1-c][1,4]oxazine-2-carboxylic acid. Saponification of intermediate 14, ethyl 3-benzyloxy-9-methyl-4-oxo-4,6,7,9-tetrahydropyrimido[2,1-c][1,4]oxazine-2-carboxylate, (0.225 g, 0.65 mmol) as described in the preparation of intermediate 7 gave 0.198 g (96% yield) of the title acid as white crystals; mp 167-168° C. (ethyl acetate-hexane). $^1$HNMR 400 MHz (CDCl$_3$) δ ppm: 1.68 (3H, d, J=6.6 Hz, CH$_3$), 3.93 (2H, m, CH$_2$), 4.12-4.21 (1H, m, CH), 4.27-4.35 (1H, m, CH), 4.70 (1H, q, J=6.6 Hz, OCH), 5.53 (2H, ABq, J$_{AB}$=11.1 Hz, OCH$_2$), 7.39 (3H, m, aromatics), 7.55 (2H, m, aromatics). MS (ESI$^+$) m/z 317 [M+H$^+$]. Anal. Calcd for C$_{16}$H$_{16}$N$_2$O$_5$: C, 60.75; H, 5.10; N, 8.86. Found: C, 60.65; H, 5.05; N, 8.72.

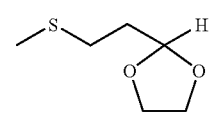

Intermediate 17

2-(2-(Methylthio)ethyl)-1,3-dioxolane. A solution of 3-(methylthio)propanal (5.2 g, 0.05 mol) and ethyleneglycol (3.4g. 0.055 mol) in 100 mL of benzene was treated with 300 mg p-toluenesulfonic acid and heated at reflux for 4 hrs. The solution was cooled and decanted. Concentration and drying in vacuo provided the title compound as a light yellow oil. $^1$H NMR (300 MHz, CDCl$_3$) δ ppm:4.93 (1 H, t, J=4.76 Hz) 3.74-4.03 (4 H, m) 2.46-2.68 (2 H, m) 2.08 (3 H, s) 1.83-2.00 (2 H, m).

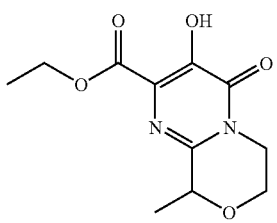

Intermediate 15

Ethyl 3-hydroxy-9-methyl-4-oxo-4,6,7,9-tetrahydropyrimido[2,1-c][1,4]oxazine-2-carboxylate. Hydrogenolysis of intermediate 14, ethyl 3-benzyloxy-9-methyl-4-oxo-4,6,7,9-tetrahydropyrimido[2,1-c][1,4]oxazine-2-carboxylate, (0.610 g, 1.77 mmol) in a mixture of ethyl acetate (75 ml) and ethanol (75 ml) at 25° C. over 10% palladium on activated carbon (0.20 g) under 1 atm of hydrogen for 2 h gave 0.430 g (95% yield) of the title ester as white crystals; mp 119-121° C. (ethyl acetate-hexane). $^1$HNMR 400 MHz (CDCl$_3$) δ ppm: 1.46 (3H, t, J=7.1 Hz, CH$_3$), 1.67 (3H, d, J=6.6 Hz, CH$_3$), 3.90 (2H, m, CH$_2$), 4.13-4.32 (2H, m, CH$_2$), 4.51 (2H, m, OCH$_2$), 4.70 (1H, q, J=6.6 Hz, CH), 10.7 (1H, broad, OH). Anal. Calcd for C$_{11}$H$_{14}$N$_2$O$_5$: C, 51.96; H, 5.55; N, 11.01. Found: C, 51.60; H, 5.61; N, 10.70.

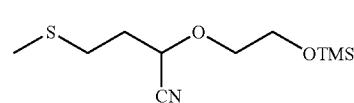

Intermediate 18

4-(Methylthio)-2-(2-(trimethylsilyloxy)ethoxy)butanenitrile. Intermediate 17, 2-(2-(methylthio)ethyl)-1,3-dioxolane, (2.96g, 0.02mol), trimethylsilylcyanide (1.98 g, 0.02 mol) and 20mg zinc iodide were combined under N$_2$ and stirred for 16 hrs at room temperature. The mixture was then concentrated in vacuo to provide 4.9 g (approximately 100% yield) of the title compound as a yellow oil. $^1$H NMR (300 MHz, CDCl$_3$) δ ppm:4.37-4.49 (1 H, m) 3.50-3.88 (4 H, m) 2.57-2.74 (2 H, m) 1.98-2.26 (5 H, m) 0.06-0.22 (9 H, m): LC/MS 198 (−TMS+Na).

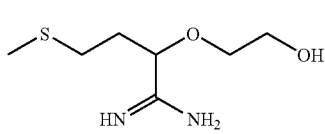

Intermediate 19

4-(Methylthio)-2-(2-(trimethylsilyloxy)ethoxy)butanamidine. A solution of intermediate 18, 4-(methylthio)-2-(2-(trimethylsilyloxy)ethoxy)butanenitrile, (4.9 g, 0.02 mol) in 30 mL of methanol was saturated with ammonia. The flask was then sealed and heated in an oil bath at 80-90° C. for 16 hrs. After cooling, the flask was opened and the mixture concentrated in vacuo to give the title compound in essentially quantitative yield as a very viscous oil. $^1$H NMR (300 MHz, CDCl$_3$) δ ppm:3.94-4.02 (1 H, m) 3.76-3.94 (3 H, m) 3.68-3.77 (2 H, m) 3.52-3.62 (2 H, m) 2.53-2.67 (2 H, m) 2.07 (3 H, s) 1.89-2.01 (2 H, m); LC/MS 193 (M+H).

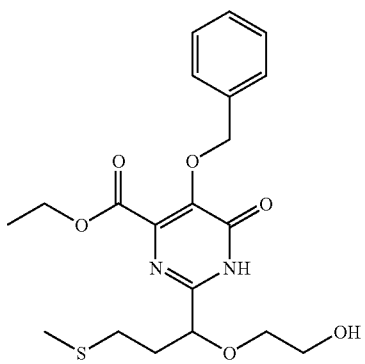

Intermediate 20

Ethyl 5-(benzyloxy)-2-(]-(2-hydroxyethoxy)-3-(methylthio)propyl)-6-oxo-1,6-dihydropyrimidine-4-carboxylate. Ethyl 2-(benzyloxy)acetate (7.76 g, 0.04 mole) and diethyloxalate (5.84 g, 0.04 mole) in 80 mL of tetrahydrofuran were treated with one equivalent of NaH and a few drops of ethanol. The resulting mixture was stirred for 1.5 hours after which the solvent was removed under vacuum and replaced with 30 mL of ethanol. Intermediate 19, 2-(2-hydroxyethoxy)-4 methylthio)butanamidine, in 30 mL ethanol was added to the mixture followed by NaH (60% in mineral oil, 800 mg, 0.02 mol). This was stirred for 20 hrs at room temperature and 3 hrs at 60° C. then concentrated under reduced pressure. The residue was dissolved in CH$_2$Cl$_2$ and washed with water. The CH$_2$Cl$_2$ layer was dried over MgSO$_4$, filtered and concentrated under vacuum. Chromatography on silica gel, eluting with 4:1 CH$_2$Cl$_2$; ether and ethyl acetate, gave 760 mg of the title compound (9% yield). $^1$H NMR (300 MHz, CDCl$_3$) δ ppm: 7.24-7.54 (5 H, m) 5.17-5.36 (2 H, s) 4.50 (1 H, m) 4.30 (2 H, q, J=7.32 Hz) 3.38-4.00 (4 H, m) 2.59 (2 H, m) 1.95-2.11 (5 H, m) 1.20-1.36 (3 H, t, J=7.32 Hz); LC/MS m/z 423 (M+H).

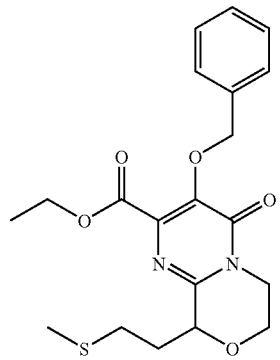

Intermediate 21

Ethyl 3-(benzyloxy)-9-(2-(methylthio)ethyl)-4-oxo-4,6,7,9-tetrahydropyrimido[2,1-c][1,4]oxazine-2-carboxylate. To a solution of intermediate 20, ethyl 5-(benzyloxy)-2-(1-(2-hydroxyethoxy)-3-(methylthio)propyl)-6-oxo-1,6-dihydropyrimidine-4-carboxylate, (527 mg, 1.25 mmol) and Et$_3$N (505 mg, 5 mmol) dissolved in 10 mL of CH$_2$Cl$_2$ was added a solution of CH$_3$SO$_2$CI (288 mg, 2.5 mmol) dissolved in 2 mL of CH$_2$Cl$_2$. This was stirred for 20 hrs then concentrated. The crude product was purified by chromatography on silica gel, using 10:1 CH$_2$Cl$_2$:ether as eluent, to give the title compound 265 mg (52% yield). (500 MHz, CDCl$_3$) δ ppm: 7.31-7.55 (5 H, m) 5.30 (2 H, s) 4.75 (1 H, dd, J=3.66 Hz) 4.32-4.40 (2 H, q, J=7.17 Hz) 4.13-4.30 (2 H, m) 3.75-3.97 (2 H, m) 2.20-2.84 (4 H, m) 2.06 (3 H, s)1.32 (3 H, t, J=7.17 Hz); LC/MS m/z 405 (M+H).

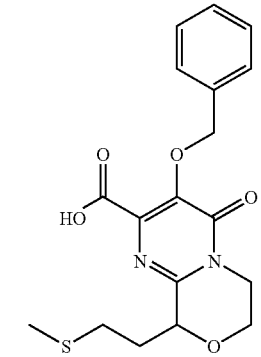

Intermediate 22

3-(Benzyloxy)-9-(2-(methylthio)ethyl)-4-oxo-4,6,7,9-tetrahydropyrimido[2,1-c][1,4]oxazine-2-carboxylic acid. To a stirred solution of intermediate 21, ethyl 3-(benzyloxy)-9-(2-(methylthio)ethyl)-4-oxo-4,6,7,9-tetrahydropyrimido[2,1-c][1,4]oxazine-2-carboxylate (97 mg, 0.2mmol) in 3 mL tetrahydrofuran was added lithium hydroxide (1 5 mg, 0.6 mmol) in 3 mL water. After 20 min the reaction mixture was acidified with 1N HCl and extracted with CH$_2$Cl$_2$. The extract was dried over MgSO$_4$, filtered and concentrated to give 82 mg of the title compound (88% yield). LC/MS m/e 377.

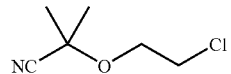

Intermediate 23

2-(2-Chloroethoxy)-2-methylpropanenitrile. (Navalokina, R. Et al J. Org. Chem. USSR (Engl. Trans.), 1980, 16, 1382-1386. 2) Ramalingam, K. U.S. Pat. No. 4,864,051, 1989.). A 250 mL round bottom flask was charged with $ZnCl_2$ (68.14 g, 0.5 mole) which was then fused by heating under vacuum. After returning to room temperature the material was placed under an atmosphere of $N_2$. To this was added acetone cyanohydrin (45.66 mL, 0.5 mole) followed by 2-chloroethanol (50.24 mL, 0.75 mole) and the mixture placed in a preheated oil bath (60° C.). After stirring for 18-20 h at 60° C., the reaction mixture was cooled, diluted with water (300 mL) and washed with $CH_2Cl_2$ (5×100 mL). The combined $CH_2Cl_2$ extracts were dried ($Na_2SO_4$), filtered and concentrated under vacuum to afford the crude product as a yellow liquid. Purification was accomplished by vacuum distillation (10 mm Hg) using a vigreux column. The fraction boiling between 65-75° C. was collected to afford the desired product as a colorless oil (47.1 g, 63.8% yield). $^1$H NMR (500 MHz, $CDCl_3$) δ ppm: 3.85 (2H, t, J=5.8 Hz), 3.64 (2H, t, J=5.8 Hz), 1.60 (6H, s).

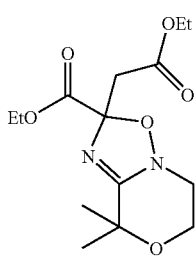

Intermediate 24

Ethyl 2-(2-ethoxy-2-oxoethyl)-8, 8-dimethyl-2,5,6, 8-tetrahydro-[1,2,4]oxadiazolo[3,2-c][1,4]oxazine-2-carboxylate. To a stirred solution of intermediate 23, 2-(2-chloroethoxy)-2-methylpropanenitrile (14.7 g, 0.10 mole) and NaI (1.5 g, 10 mmol) in ethanol (50 mL) was added an aqueous solution (50%) of hydroxylamine (18.4 g, 0.30 mole) resulting in an exothermic reaction. Following this the reaction mixture was heated at 80° C. for 2 h. Upon cooling to room temperature the solvent was removed. The resulting residue was dissolved in 1:1 ethanol/$H_2O$ (100 mL) and cooled in an ice bath. To this was added diethyl acetylenedicarboxylate (17.6 mL, 0.110 mole) over 10 min. The reaction mixture was allowed to warm to room temperature and stirred for 1 h. Following this, it was diluted with ethyl acetate (250 mL), washed with $H_2O$ (2×100 mL), brine (50 mL), dried over $Na_2SO_4$, filtered and concentrated to give the crude product as a yellow oil. Flash chromatography on a silica gel column, eluting with 20-40% ethyl acetate/Hexanes, provided the title compound as a viscous pale yellow oil (15.29 g, 48.6% yield). $^1$H NMR (500 MHz, $CDCl_3$) δ ppm: 4.35-4.28 (2H, m), 4.18-4.12 (2H, m), 3.60-3.56 (1H, m), 3.51-3.47 (1H, m), 3.30 (1H, d, J=16.2 Hz), 2.94 (1H, d, J=16.2 Hz), 1.52 (3H, s), 1.51 (3H, s), 1.29 (3H, t, J=7.0 Hz), 1.24 (3H, t, J=7.0 Hz). LCMS (M+H) calcd for $C_{14}H_{23}N_2O_7$: 315.16; found: 315.33.

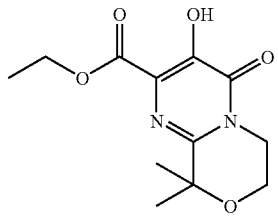

Intermediate 25

Ethyl 3-hydroxy-9,9-dimethyl-4-oxo-4,6,7,9-tetrahydropyrimido[2,1-c][1,4]oxazine-2-carboxylate. A solution of intermediate 24, ethyl 2-(2-ethoxy-2-oxoethyl)-8,8-dimethyl-2,5,6,8-tetrahydro-[1,2,4]oxadiazolo[3,2-c][1,4]oxazine-2-carboxylate (31.16 g) in 1,2,4-trimethylbenzene (200 mL) was heated at 180° C. for 5 h. The resulting dark reaction solution was cooled then concentrated to give a dark brown paste which was taken up into ethyl acetate (250 mL) and extracted with 0.5 M aq $Na_2CO_3$ (4×50 mL). The organic layer was discarded and the aqueous layer acidified by carefully adding conc. HCl (20 mL) before being extracted with $CH_2Cl_2$ (4×50 mL). The combined $CH_2Cl_2$ layers were dried ($Na_2SO_4$), filtered and concentrated to give a dark paste which was dissolved in ether (100 mL) and allowed to stand at room temperature in a open flask. The brown/light yellow solid that formed was filtered to afford the title compound. The mother liquor that contained product was re-processed to afford additional material (combined yield ~18-20% over two steps). $^1$H NMR (500 MHz, $CDCl_3$) δ: 10.55 (1H, s), 4.45 (2H, q, J=7.0 Hz), 4.02 (4H, s), 1.61 (6H, s), 1.43 (3H, t, J=7.0 Hz). HRMS (M+H) calcd for $C_{12}H_{17}N_2O_5$: 269.1138; found: 269.1149. Anal calcd for $C_{12}H_{16}N_2O_5$: C, 53.72; H, 6.01; N, 10.44. Found: C, 53.71; H, 6.04; N, 10.30.

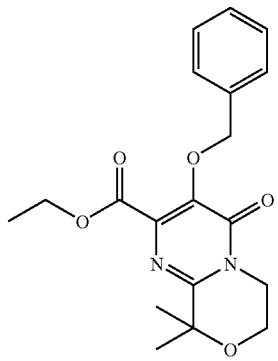

Intermediate 26

Ethyl 3-(benzyloxy)-9,9-dimethyl-4-oxo-4,6,7,9-tetrahydropyrimido[2,1-c][1,4]oxazine-2-carboxylate. To a stirred solution of intermediate 25, ethyl 3-hydroxy-9,9-dimethyl-4-oxo-4,6,7,9-tetrahydropyrimido[2,1-c][1,4]oxazine-2-carboxylate, (2.68 g, 10 mmol) and benzyl bromide (1.43 mL, 12 mmol) in DMF (40 mL) was added $K_2CO_3$ (2.07 g, 20 mmol). After stirring 48 h at ambient temperature, the reaction mixture was diluted with ether (100 mL), then washed with water (3×30 mL) and brine (20 mL). The organic layer was dried ($Na_2SO_4$/activated carbon), filtered and concentrated to give a yellow solid. Trituration with hexanes/ether (9: 1) afforded the title compound as an off-white solid (2.79 g, 78% yield). $^1$H NMR (500 MHz, $CDCl_3$) δ ppm: 7.48-7.45 (2H, m), 7.37-7.30 (3H, m), 5.25 (2H, s), 4.33 (2H, q, J=7.3 Hz), 4.05-3.99 (4H, m), 1.62 (6H, s), 1.29 (3H, t, J=7.3 Hz). HRMS (M+H) calcd for $C_{19}H_{23}N_2O_5$: 359.1607; found: 359.1611. Anal calcd for $C_{19}H_{22}N_2O_5$: C, 63.67; H, 6.18; N, 7.81; found: C, 63.63; H, 6.16; N, 7.78.

Intermediate 27

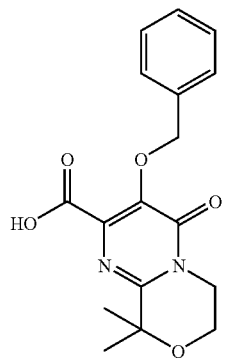

3-(Benzyloxy)-9,9-dimethyl-4-oxo-4,6,7,9-tetrahydropyrimido[2,1-c][1,4]oxazine-2-carboxylic acid. A mixture of intermediate 26, ethyl 3-(benzyloxy)-9,9-dimethyl-4-oxo-4,6,7,9-tetrahydropyrimido[2,1-c][1,4] oxazine-2-carboxylate, (2.93 g, 8.2 mmol) and $LiOH \cdot H_2O$ (0.84 g, 20 mmol) in 4:1 ethanol/tetrahydrofuran (50 mL) was stirred for 2 h at ambient temperature then concentrated under vacuum. The resulting yellow residue was treated with 1N HCl (25 mL) providing a precipitate that was filtered and dried under vacuum to yield the title compound as a white powder (2.68 g, 99% yield). $^1$H NMR (500 MHz, $CDCl_3$) δ ppm: 7.54-7.48 (2H, m), 7.37-7.27 (3H, m), 5.44 (2H, s), 4.05-3.93 (4H, m), 1.60 (6H, s).). HRMS (M+H) calcd for $C_{17}H_{19}N_2O_5$: 331.1294; found: 331.1308. Anal calcd for $C_{17}H_{18}N_2O_5$: C, 61.81; H, 5.49; N, 8.48; found: C, 61.84; H, 5.36; N, 8.25.

Intermediate 28

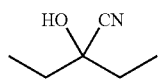

2-Ethyl-2-hydroxybutanenitrile. To a solution of potassium phosphate monobasic (140 g, 1.11 mole) in water (250 mL) was added 3-pentanone (75.8 g, 0.88 mole), followed by a solution of sodium cyanide (54 g, 1.10 mole) in water (250 mL), and the resulting mixture stirred for 3 hours. The mixture was extracted with diethyl ether (1×250 mL, then 2×100 mL) and the combined ether layers washed with 1.0 N HCl (200 mL). The ether solution was dried ($Na_2SO_4$), filtered, and concentrated in-vacuo. The crude product was purified by vacuum distillation (bp 87° C., 10 mmHg) to give the title compound (72.4 g, 3% yield) as a clear oil. $^1$H NMR (500 MHz, $CDCl_3$) δ ppm: 2.71 (1H, s), 1.82 (2H, q, J=7.5 Hz), 1.76 (2H, q, J=7.5 Hz), 1.10 (6H, t, J=7.5 Hz). $^{13}$C NMR (500 MHz, $CDCl_3$) δ ppm: 121.21, 73.53, 32.81, 8.27.

Intermediate 29

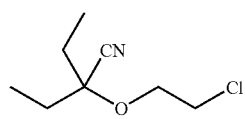

2-(2-Chloroethoxy)-2-ethylbutanenitrile. Zinc chloride (68.1 g, 0.5 mol) was fused under vacuum as described in the procedure for the synthesis of intermediate 23. The molten zinc was cooled and the evacuated flask was flushed with nitrogen. The flask was loaded with intermediate 28, 2-ethyl-2-hydroxybutanenitrile, (40.3 g, 0.5 mol) and 2-chloroethanol (50.5 mL, 0.75 mmol) then stirred at 60° C. for 20 hours. The reaction mixture was diluted with water (250 mL) and extracted with dichloromethane (1×250 mL, 4×100 mL). The combined organic layers were dried (sodium sulfate), filtered, and concentrated in-vacuo. The crude product was purified by vacuum distillation (bp 83° C., 10 mmHg) to give the title compound (52 g) containing unreacted intermediate 28. $^1$H NMR (500 MHz, $CDCl_3$) δ ppm: 3.82 (2H, t, J=5.8 Hz), 3.64 (2H, t, J=5.8 Hz), 1.83 (4H, J=7.3 Hz), 1.03 (6H, t, J=7.6 Hz).

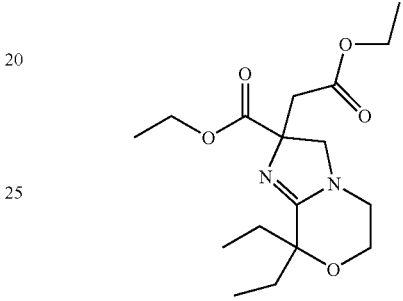

Diethyl 2-(2,2-diethyl-3-iminomorpholinooxy)but-2-enedioate. A solution of the product mixture obtained in the synthesis of intermediate 29, 2-(2-chloroethoxy)-2-ethylbutanenitrile, (0.171 mol) in absolute ethanol (150 mL) was added dropwise to a solution of hydroxylamine (50% aqueous solution, 33.8 mL, 0.51 mol), sodium carbonate (9.1 g, 0.086 mol) and sodium iodide (2.55 g, 0.017 mol) over 15 minutes. The mixture was heated at 80° C. for 3 hours. The reaction was then concentrated to a thick paste and azeotroped under vacuum with ethanol/water (1:1, 100 mL), water (100 mL) and finally ethanol (100 mL). The residue was taken up in ethanol/water (1:1, 160 mL), cooled (0° C.), and treated with diethyl acetylenedicarboxylate (30.1 mL, 0.188 mol). The reaction was stirred at room temperature for 2 hours, then diluted with water (200 mL) and ethyl acetate (200 mL). The organic layer was separated, washed with water (200 mL) and brine (100 mL), then dried (sodium sulfate), filtered and concentrated in-vacuo. The crude product was purified by column chromatography over silica gel, eluting with 10% to 40% ethyl acetate in hexanes to afford the title compound (25.7 g) as a yellow oil.

Intermediate 31

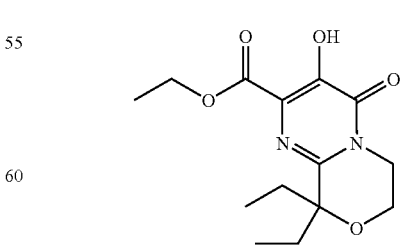

Ethyl 9,9-diethyl-3-hydroxy-4-oxo-4,6,7,9-tetrahydropyrimido[2,1-c][1,4]oxazine-2-carboxylate. A solution of intermediate 30, diethyl 2-(2,2-diethyl-3-iminomorpholinooxy)

but-2-enedioate, (25.7 g) in 1,2,4-trimethylbenzene (100 mL) was heated at reflux (180° C.) for 16 hours. The solvent was then removed in vacuo and the resulting oil placed in a freezer until crystal formation began. The oil-crystal mixture was triturated with diethyl ether (50 mL) and the solid was collected by filtration, washing with a small volume of ether to provide the title compound (9.02 g). A second crop (1.62 g) was obtained from the filtrate. $^1$H NMR (500 MHz, CDCl$_3$) δ ppm: 10.54 (1H, s), 4.44 (2H, q, J=7.0 Hz), 4.00 (4H, m), 2.00 (2H, m), 1.92 (2H, m), 1.42 (3H, t, J=7.0 Hz), 0.85 (6H, t, J=7.3 Hz). $^{13}$C NMR (500 MHz, CDCl$_3$) δ ppm: 169.53, 157.82, 151.40, 147.58, 125.35, 87.27, 62.62, 58.35, 43.24, 31.06, 14.17, 7.79. HRMS [M+H]$^+$ calcd for C$_{14}$H$_{21}$N$_2$O$_5$: 297.14506; found: 297.1464.

Intermediate 32

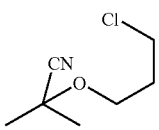

2-(3-Chloropropoxy)-2-methylpropanenitrle. Zinc chloride (68.1 g, 0.5 mol) was fused using the procedure described for the synthesis of intermediate 23, 2-(2-chloroethoxy)-2-methylpropanenitrile. The molten zinc was cooled and the flask flushed with nitrogen. The flask was loaded with acetone cyanohydrin (46 mL, 0.5 mol) and 3-chloropropanol (64 mL, 0.75 mmol) and the reaction mixture stirred at 60° C. for 30 hours. The mixture was then diluted with water (200 mL) and extracted with dichloromethane (1×200 mL and 3×100 mL). The combined organic layers were dried (sodium sulfate), filtered, and concentrated in-vacuo. The crude product was purified by vacuum distillation (bp 78-84° C., 10 mmHg) to give the title compound (41 g) as a 2:1 mixture with residual 3-chloropropanol. $^1$H NMR (500 MHz, CDCl$_3$) δ ppm: 3.72 (2H, t, J=5.8 Hz), 3.63 (2H, t, J=6.4 Hz), 2.04 (2H, m), 1.57 (6H, br s).

Intermediate 33

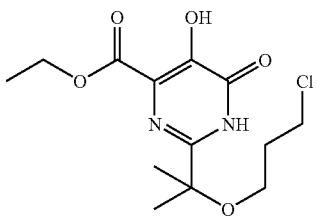

Ethyl 2-(2-(3-chloropropoxy)propan-2-yl)-5-hydroxy-6-oxo-1,6-dihydropyrimidine-4-carboxylate. A solution of intermediate 32, 2-(3-chloropropoxy)-2-methylpropanenitrle (0.186 mol) in absolute ethanol (40 mL) was added dropwise to a cold (0° C.) solution of hydroxylamine (50% aqueous solution, 17 mL, 0.278 mol), 20 mL H$_2$O, sodium carbonate (9.91 g, 0.093 mol) and sodium iodide (2.80 g, 0.019 mol) over 15 minutes. (In an alternative procedure, sodium carbonate was omitted from the mixture). The mixture was stirred at room temperature for 30 min, then additional hydroxylamine (17 mL, 0.278 mol) was added. The reaction was then heated at 80° C. for 16 hours. The mixture was concentrated to a thick paste which was azeotroped under vacuum with ethanol/water (1:1, 100 mL). The resulting residue was taken up in ethanol/water (1:1, 200 mL), cooled (0° C.), and treated with diethyl acetylenedicarboxylate (30.1 mL, 0.188 mol) by dropwise addition over 10 min. The reaction was allowed to stir at room temperature for 2.5 hours, then diluted with water (300 mL) and ethyl acetate (300 mL). The separated organic layer was washed with water (100 mL) and brine (100 mL), then dried (sodium sulfate), filtered and concentrated in-vacuo. The crude product was purified by silica gel column chromatography, eluting with 10% to 40% ethyl acetate in hexanes, to give 21.2 g of a yellow oil. A solution of this oil (15.6 g) in 1,2,4-trimethylbenzene (300 mL) was heated at reflux (180° C.) for 2.5 hours after which the solvent was removed in-vacuo. The resulting oil was taken up in ethyl acetate (300 mL) and extracted with saturated aqueous sodium bicarbonate (1×200 mL, then 4×100 mL). The combined aqueous layers were acidified to pH 1-2 using 6 N HCl then extracted with ethyl acetate (3×150 mL). The organic extracts were dried (sodium sulfate), filtered, then concentrated in vacuo. The resulting oil was triturated with diethyl ether (50 mL) and the resulting solid collected by filtration and washed with a small volume of ether to afford the title compound (2.05 g). A second crop (0.70 g) was obtained from the filtrate. $^1$H NMR (500 MHz, CDCl$_3$) δ ppm: 10.83 (1H, br), 10.02 (1H, br), 4.46 (2H, q, J=7.0 Hz), 3.66 (2H, t, J=6.1 Hz), 3.58 (2H, t, J=5.8 Hz), 2.06 (2H, m), 1.55 (6H, s), 1.44 (3H, t, J=7.0 Hz).

Intermediate 34

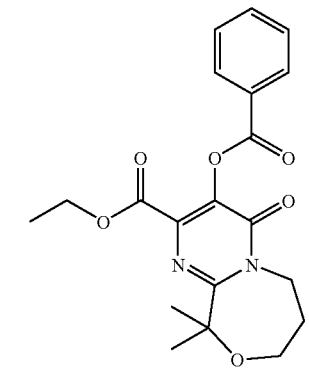

Ethyl 3-(benzoyloxy)-10,10-dimethyl-4-oxo-6,7,8,10-tetrahydro-4H-pyrimido[2,1-c][1,4]oxazepine-2-carboxylate.
A solution of intermediate 33, ethyl 2-(2-(3-chloropropoxy)propan-2-yl)-5-hydroxy-6-oxo-1,6-dihydropyrimidine-4-carboxylate, (0.064 g, 0.2 mmol) in pyridine (1 mL) was treated with benzoic anhydride (0.047 g, 0.2 mmol) and stirred for 1 hr at 60° C. The solvent was removed and the residue taken up in N,N-dimethylformamide (1 mL) and treated with potassium carbonate (0.036 g, 0.2 mmol). The mixture was stirred for 1 hr at 80° C., and solvent was removed to give the title compound.

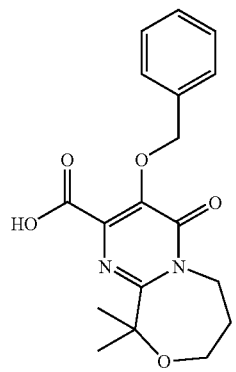

Intermediate 35

3-(Benzyloxy)-10,10-dimethyl-4-oxo-6,7,8,10-tetrahydro-4H-pyrimido[2,1-c][1,4]oxazepine-2-carboxylic acid. A suspension of intermediate 33, ethyl 2-(2-(3-chloropropoxy)propan-2-yl)-5-hydroxy-6-oxo-1,6-dihydropyrimidine-4-carboxylate, (0.205 g, 0.64 mmol) and anhydrous potassium carbonate (0.361 g, 2.6 mmol) in anhydrous dimethylformamide (4 mL) was stirred at 60° C. for 5 hours. The reaction mixture was treated with benzyl bromide (0.122 g, 0.71 mmol) and stirred for 16 hours. Following this, 2 mL of H$_2$O was added and the mixture stirred for an additional 24 hours. Solvent was removed by rotary evaporator and the resulting residue suspended in 0.5 N hydrochloric acid (16 mL). The crude product was extracted with ethyl acetate (2×15 mL), then dried (sodium sulfate), filtered, and concentrated to dryness by rotary evaporator to give 0.299 g (Yield >100%) of the title compound as a solid. LC/MS [M+H]$^+$=345.21.

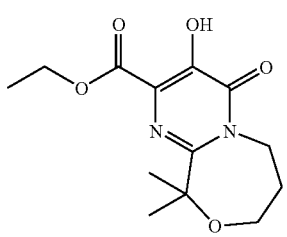

Intermediate 36

3-Hydroxy-10,10-dimethyl-4-oxo-6,7,8,10-tetrahydro-4H-pyrimido[2,1-c][1,4]oxazepine-2-carboxylate. A solution of intermediate 33, ethyl 2-(2-(3-chloropropoxy)propan-2-yl)-5-hydroxy-6-oxo-1,6-dihydropyrimidine-4-carboxylate, (7.01 g, 22 mmol) and anhydrous potassium carbonate (9.12 g, 66 mmol) in anhydrous dimethylformamide (50 mL) was stirred at 80° C. for 20 hours. Solvent was removed by rotary evaporator and the residue, dissolved in water (50 mL), was brought to pH 1 using 6.0 N HCl. The solution was extracted with ethyl acetate (4×25 mL). The combined organic layers were dried (sodium sulfate) and filtered. The solvent was removed by rotary evaporator to give the title compound (5.53 g, Yield 89%) as a brown solid: $^1$H NMR (500 MHz, CDCl$_3$) δ ppm 10.49 (1H, s), 4.56 (2H, br), 4.43 (2H, q, J=7.2 Hz), 3.69 (2H, t, J=6.4 Hz), 1.93-1.99 (2H, m), 1.61 (6H, s), 1.42 (3H, t, J=7.2 Hz); $^{13}$C NMR (126 MHz, CDCl$_3$) δ ppm 169.33, 158.30, 153.39, 148.73, 124.45, 82.85, 62.60, 60.71, 38.79, 27.67, 27.35, 14.15; HRMS (ESI) calcd for C$_{13}$H$_{19}$N$_2$O$_5$ (M+H) 283.1294, found 283.1305.

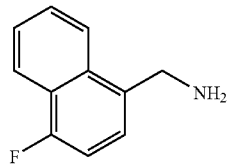

Intermediate 37

(4-Fluoronaphthalen-1-yl)methanamine hydrochloride. A solution of 1-cyano-4-fluoronapthalene (1.05 g, 6.12 mmol) and 1.5 mL of HCl (aq.) in absolute ethanol (50 mL) was stirred under a hydrogen atmosphere (balloon) with 10% palladium on carbon (0.20 g) for 16 hours. The catalyst was removed by filtration through Celite, and the filtrate concentrated under vacuum. The resulting solid was triturated with ether and collected by filtration to give the title compound (0.575 g, 44% yield) as an off white solid.

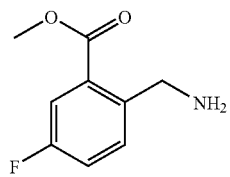

Intermediate 38

Methyl 2-(aminomethyl)-5-fluorobenzoate trifluoroacetic acid salt. Methyl 2-((tert-butoxycarbonyl)methyl)-5-fluorobenzoate, prepared according to literature methods, was treated with trifluoroacetic acid to provide the title compound. Yield 100%; $^1$H NMR (300 MHz, DMSO-d6) δ ppm: 3.89 (3H, s) 4.32 (2H, q, J=5.61 Hz) 7.51-7.71 (2H, m) 7.78 (1H, dd, J=9.33, 2.38 Hz) 8.13 (2H, brs); LC/MS m/z 184 (M+H).

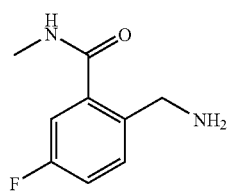

Intermediate 39

2-Aminomethyl-5-fluoro-N-methyl-benzamide trifluoroacetic acid salt. To a solution of tert-butyl 4-fluoro-2-(methylcarbamoyl)benzylcarbamate (7.70 g, 27.3 mmol; prepared from 2-bromo-5-fluorobenzoic acid using literature methods) in CH$_2$Cl$_2$ (100 mL) was added CF$_3$CO$_2$H (25 mL) and the mixture stirred at room temperature for 15 min. This was concentrated in vacuo and the residue triturated with diethyl ether to obtain 8.0 g (Yield 99%) of the title compound as a white powder. $^1$H NMR (300 MHz, D$_2$O) δ ppm: 2.93 (3 H, s) 4.20 (2 H, s) 7.35 (1 H, dt, J=8.5, 3 Hz) 7.42 (1 H, dd, J=9.0, 2.7 Hz) 7.57 (1 H, dd, J=8.4, 5.5 Hz); LC/MS m/z 183 (M+H).

Intermediate 40

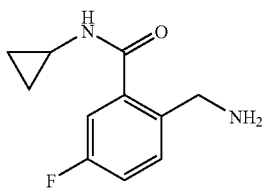

2-(Aminomethyl)-N-cyclopropyl-5-fluorobenzamide trifluoroacetic acid salt. A solution of tert-butyl 2-(cyclopropylcarbamoyl)-4-fluorobenzylcarbamate (130 mg, 0.42 mmol) prepared according to literature methods, in CH$_2$Cl$_2$ (5 mL) was stirred with trifluoroacetic acid (3 mL) at room temperature for 10 min, then concentrated in vacuo to give 140 mg (Yield 100%) of the title compound as a foam: $^1$H NMR (DMSO-d6, 300 MHz) δ ppm: 0.62 (2H, m, CH$_2$), 0.73 (2H, m, CH$_2$), 2.86 (1H, m, CH), 4.02-4.07 (2H, ABq, NCH$_2$), 7.46 (2H, m, Ar-Hs), 7.58 (1H, m, Ar—H), 8.11 (3H, br, NH3), 8.81 (1H, d, J=4.4 Hz, NH); LC/MS m/z 209 (M+H).

Intermediate 41

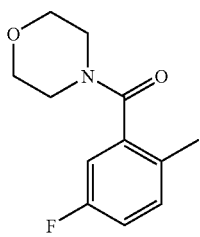

(5-Fluoro-2-methylphenyl)(morpholino)methanone. To a solution of morpholine (870 mg, 10 mmol) and triethylamine (1.1 g, 10.8 mmol) in CH$_2$Cl$_2$ (15 mL) was added a solution of 5-fluoro-2-methylbenzoyl chloride (1.72 g, 10 mmol) in CH$_2$Cl$_2$ (5 mL), dropwise, and the mixture stirred for 15 min. The mixture was then washed with water, and the organic phase dried (MgSO$_4$), filtered, and concentrated to obtain 2.19 g (Yield 98%) of the title compound as a solid: $^1$H NMR (500 MHz, CDCl$_3$) δ ppm: 2.27 (3H, s) 3.24 (2H, d, J=4 Hz) 3.58 (2H, s) 3.79 (4 H, dd, J=18, 3.8 Hz) 6.88 (1H, dd, J=8.2, 2.8 Hz) 6.92-7.05 (1 H, m) 7.18 (1 H, dd, J=8.4, 5.3 Hz).

Intermediate 42

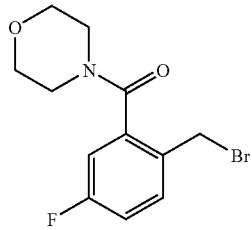

(2-(Bromomethyl)-5-fluorophenyl)(morpholino)methanone. A mixture of intermediate 41, (5-fluoro-2-methylphenyl)(morpholino)methanone, (2.1 g, 9.5 mmol) and N-bromosuccinimide (2.0 g, 11 mmol) in CCl$_{14}$ (30 mL) was heated at reflux. To this mixture was added benzoylperoxide (242 mg, 1 mmol) and the mixture heated at reflux for 2 hrs. After cooling, the insoluble materials were filtered and the filtrate purified by column chromatography (SiO$_2$, 0-10% ether in CH$_2$Cl$_2$) to give 1.1 g (Yield 38%) of the title compound as a clear oil: $^1$H NMR (300 MHz, CDCl$_3$) δ ppm: 3.31 (2H, t, J=4.94 Hz) 3.55-4.02 (6H, m) 4.56 (2H, dd, J=128.81, 9.51 Hz) 6.89 (1H, dd, J=8.23, 2.74 Hz) 6.96-7.12 (1H, m) 7.33-7.49 (1H, m); LC/MS m/z 302 (M+H).

Intermediate 43

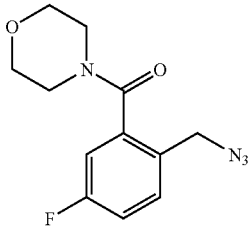

(2-(Azidomethyl)-5-fluorophenyl)(morpholino)methanone. To a solution of intermediate 42, (2-(bromomethyl)-5-fluorophenyl)(morpholino)methanone, (1.0 g, 3.32 mmol) in dimethylformamide (10 mL) was added sodium azide (230 mg, 3.5 mmol) and the mixture stirred under a nitrogen atmosphere for 1 h. The solvent was evaporated in vacuo, and the residue dissolved in CH$_2$Cl$_2$, then washed with water. The organic phase was dried (Na$_2$SO$_4$), filtered, concentrated, and the residue purified by column chromatography (SiO$_2$, CH$_2$Cl$_2$) to provide 770 mg (Yield 88%) of the title compound as an oil: $^1$H NMR (300 MHz, CDCl$_3$) δ ppm: 3.27 (2H, s) 3.51-3.65 (2H, m) 3.66-3.97 (4H, m) 4.38 (2H, brs) 6.92 (1H, dd, J=8.2, 2.7 Hz) 7.07 (1H, dt, J=8.5, 3 Hz) 7.34 (1 H, dd, J=8.4, 5.5 Hz); LC/MS m/z 265 (M+H).

Intermediate 44

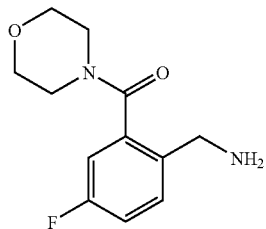

(2-(Aminomethyl)-5-fluorophenyl)(morpholino)methanone hydrochloride. To a solution of intermediate 43, (2-(azidomethyl)-5-fluorophenyl)(morpholino)methanone, (770 mg, 2.92 mmol,) in ethanol (20 mL) was added 4N HCl (1 mL) and 10% Pd—C (100 mg), and the mixture hydrogenated at 1 atm of H$_2$ for 3 hrs. The catalyst was removed by filtration and the filtrate concentrated. The residue was purified by C18 reverse phase silica gel column chromatography (YMC ODS, 0-5% CH$_3$CN/H$_2$O) to obtain 350 mg (Yield 44%) of the title compound, (2-(aminomethyl)-5-fluorophenyl)(morpholino)-methanone hydrochloride as a white powder: $^1$H NMR (300 MHz, DMSO-d$_6$) δ ppm: 3.0-4.0 (8H, m), 3.78 (2H, t, J=5 Hz), 7.32 (1 H, dd, J=8.8, 2.6 Hz), 7.35-7.44 (1H, t, J=8.5, 3 Hz), 7.75 (1H, dd, J=8.8, 5.5 Hz); LC/MS m/z 239 (M+H).

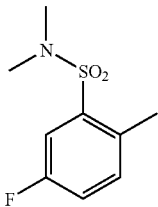

Intermediate 45

5-Fluoro-2,N,N-trimethyl-benzenesulfonamide. To a solution of 5-fluoro-2-methyl-benzenesulfonyl chloride (4.18 g, 20 mmol) in tetrahydrofuran (25 mL) was added, dropwise, a solution of dimethylamine in tetrahydrofuran (2M, 25 mL, 50 mmol) over 15 min. and the mixture stirred for 5 min. The insoluble materials were filtered and the filtrate concentrated. The residue was purified by column chromatography (SiO$_2$, 5% ether in CH$_2$Cl$_2$) to provide 4.3 g (Yield 90%) of the title compound as a clear oil: $^1$H NMR (500 MHz, CDCl$_3$) δ ppm: 2.57 (3 H, s) 2.82 (3 H, s) 2.82 (3 H, s) 7.12-7.18 (1 H, m) 7.28 (1 H, dd, J=8.2, 5.5 Hz) 7.59 (1 H, dd, J=8.2, 2.1 Hz); LC/MC m/z 218 (M+H).

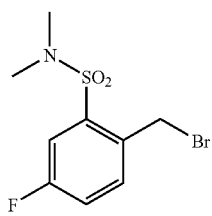

Intermediate 46

2-Bromomethyl-5-fluoro-N,N-dimethyl-benzenesulfonamide. Under nitrogen, a mixture of intermediate 45, 5-fluoro-2,N,N-trimethyl-benzenesulfonamide, (435 mg, 2.0 mmol) and N-bromosuccinimide (391 mg, 2.2 mmol) in CCl$_4$ (20 mL) was stirred at 80-90° C. for 5 min. To this mixture was added 2,2'-azobisisobutyronitrile (AIBN, 100 mg) and stirring continued at 80-90° C. for 30 min. After cooling, the insoluble precipitates were filtered and the filtrate concentrated and purified by column chromatography (SiO$_2$, CH$_2$Cl$_2$) to provide 440 mg (Yield 74%) of the title compound: $^1$H NMR (500 MHz, CDCl$_3$) δ ppm: 2.87 (6 H, s) 4.86 (2 H, s) 7.28 (1 H, dd, J=8.55, 2.75 Hz) 7.61-7.65 (2 H, m); LC/MC m/z 296/298 (M+H).

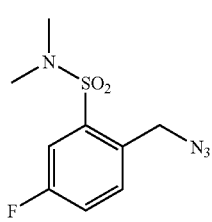

Intermediate 47

2-Azidomethyl-5-fluoro-N,N-dimethyl-benzenesulfonamide. A mixture of intermediate 46, 2-bromomethyl-5-fluoro-N,N-dimethyl-benzenesulfonamide, (880 mg, 2.97 mmol) and sodium azide (200 mg, 3 mmol) in dimethylformamide (4 mL) was stirred at 55-60° C. for 30 min after which the solvent was removed in vacuo. The residue was partitioned between CH$_2$Cl$_2$ and water, and the organic phase was washed with water, dried (Na$_2$SO$_4$), filtered and concentrated to provide 670 mg (Yield 87%) of the title compound as a yellow oil; $^1$H NMR (500 MHz, CDCl$_3$) δ ppm: 2.84 (6 H, s) 4.78 (2 H, s) 7.29-7.34 (1 H, m) 7.59-7.64 (2 H, m).

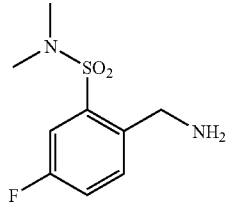

Intermediate 48

2-(Aminomethyl)-5-fluoro-N,N-dimethylbenzenesulfonamide. To a solution of intermediate 47, 2-azidomethyl-5-fluoro-N,N-dimethyl-benzenesulfonamide, (660 mg, 2.6 mmol) in tetrahydrofuran (10 mL) and water (2 mL) was added triphenylphosphine (740 mg, 2.8 mmol), and the mixture stirred under nitrogen for 1 hr. The tetrahydrofuran was evaporated in vacuo and a mixture of the residue and 6N HCl (3 mL) in MeOH (5 mL) was heated at 80° C. for 20 hrs. This was washed with CH$_2$Cl$_2$, and the aqueous phase basified with dilute NH4OH and extracted with CH$_2$Cl$_2$. The organic extract was dried (Na$_2$SO$_4$), filtered and concentrated to provide 210 mg (0.91 mmol, Yield 35%) of the title compound; $^1$H NMR (500 MHz, CDCl$_3$) δ ppm: 2.84 (6 H, s) 4.10 (2 H, s) 7.23-7.29 (1 H, m) 7.53-7.60 (2 H, m); LC/MS m/z 233 (M+H).

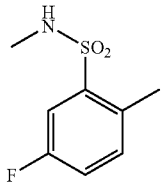

Intermediate 49

5-Fluoro-2,N-dimethyl-benzenesulfonamide. To a solution of 5-fluoro-2-methyl-benzenesulfonyl chloride (4.18 g, 20 mmol) in acetone (20 mL) was added a 40% aqueous solution of methylamine (4.5 mL, 60 mmol) under nitrogen and the mixture stirred for 5 min. Acetone was removed in vacuo and the aqueous residue extracted with CH$_2$Cl$_2$. The CH$_2$Cl$_2$ extract was dried (Na$_2$SO$_4$), filtered, concentrated and the residue purified by column chromatography (SiO$_2$, 10% ether in CH$_2$Cl$_2$) to provide 3.9 g (19.2 mmol, Yield 96%) of the title compound as a white solid; $^1$H NMR (500 MHz, CDCl$_3$) δ ppm: 2.59 (3H, s), 2.67 (3H, d, J=5.5 Hz), 4.41 (1H, brs), 7.13-7.20 (1H, m), 7.29 (1H, dd, J=8.2, 5.5 Hz), 7.69 (1H, J=8.6, 2.1 Hz); LC/MS m/z 204 (M+H).

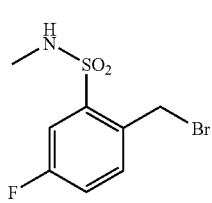

Intermediate 50

2-Bromomethyl-5-fluoro-N-methyl-benzenesulfonamide. The title compound can be prepared from intermediate 49, 5-fluoro-2,N-dimethyl-benzenesulfonamide, according to the method described for intermediate 46 and purified by column chromatography (SiO$_2$, 5% ether/CH$_2$Cl$_2$). $^1$H NMR (500 MHz, CDCl$_3$) δ ppm: 2.64 (3 H, d, J=5.19 Hz) 4.91 (1 H, d, J=3.66 Hz) 4.98 (2 H, s) 7.26-7.30 (1 H, m) 7.54 (1 H, dd, J=8.6, 5.2 Hz) 7.73 (1 H, dd, J=8.4, 2.6 Hz); LC/MS m/z 282/284.

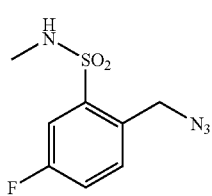

Intermediate 51

2-Azidomethyl-5-fluoro-N-methyl-benzenesulfonamide. The title compound can be prepared from intermediate 50, 2-bromomethyl-5-fluoro-N-methyl-benzenesulfonamide, according to the method described for intermediate 47 and purified by column chromatography (SiO$_2$, 5% ether—CH$_2$Cl$_2$). $^1$H NMR (500 MHz, CDCl$_3$) δ ppm: 2.65 (3 H, d, J=5.19 Hz) 4.81 (2 H, s) 4.86 (1 H, d, J=4.6 Hz) 7.27-7.33 (1 H, m) 7.49 (1 H, dd, J=8.2, 5.2 Hz) 7.76 (1 H, dd, J=8.2, 2.8 Hz).

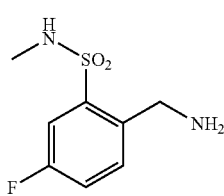

Intermediate 52

2-(Aminomethyl)-5-fluoro-N-methylbenzenesulfonamide hydrochloride. To a solution of intermediate 51, 2-azidomethyl-5-fluoro-N-methyl-benzenesulfonamide, (560 mg, 2.3 mmol) in ethanol (10 mL) was added 6N HCl (1 mL) and 10% Pd—C (100 mg) and the mixture hydrogenated with 1 atm of H$_2$ for 14 hrs. The catalyst was removed by filtration through Celite and the filtrate concentrated in vacuo to provide 630 mg (Yield >100%) of the title compound. $^1$H NMR (500 MHz, DMSO-D6) δ ppm: 4.36 (2 H, d, J=5.2 Hz) 7.63-7.70 (2 H, m) 7.77-7.83 (1 H, m) 8.11 (1 H, d, J=4.9 Hz) 8.41 (3 H, s); LC/MS m/z 219 (M+H).

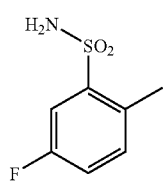

Intermediate 53

5-Fluoro-2-methyl-benzenesulfonamide. To a solution of 5-fluoro-2-methyl-benzenesulfonyl chloride (4.18 g, 20 mmol) in acetone (20 mL) was added, dropwise, concentrated NH$_4$OH (3 mL) and the resulting mixture stirred for 5 min. Acetone was removed in vacuo and the precipitates were filtered, washed thoroughly with water and dried in vacuo to provide 3.7 g (Yield 98%) of the title compound as a white solid; $^1$H NMR (500 MHz, DMSO-D6) δ ppm: 2.55 (3 H, s) 7.33-7.40 (1 H, m) 7.40-7.46 (1 H, m) 7.54 (2 H, s) 7.59 (1 H, dd, J=9.2, 2.7 Hz); LC/MS m/z 190 (M+H).

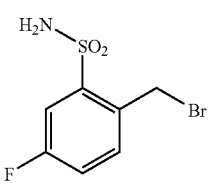

Intermediate 54

2-Bromomethyl-5-fluoro-benzenesulfonamide. The title compound can be prepared from intermediate 53, 5-fluoro-2-methyl-benzenesulfonamide, according to the method described for intermediate 46, and purified by column chromatography (SiO$_2$, 5% ether/CH$_2$Cl$_2$). $^1$H NMR (500 MHz, CDCl$_3$) δ ppm: 5.01 (2 H, s) 5.16 (2 H, brs) 7.25-7.31 (1 H, m) 7.53 (1 H, dd, J=8.5, 5.2 Hz) 7.80 (1 H, dd, J=8.5, 2.7 Hz). LC/MS m/z 268/270 (M+H).

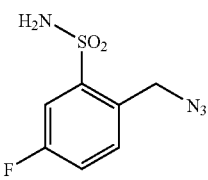

Intermediate 55

2-Azidomethyl-5-fluoro-N-methyl-benzenesulfonamide. The title compound can be prepared from intermediate 54, 2-bromomethyl-5-fluoro-benzenesulfonamide, according to the method described for the preparation of intermediate 47. $^1$H NMR (300 MHz, CDCl$_3$) δ ppm: 4.82 (2 H, s) 5.18 (2 H, s) 7.27 (1 H, m) 7.45 (1 H, dd, J=8.4, 5.5 Hz) 7.79 (1 H, dd, J=8.4, 2.6 Hz). LC/MS m/z 253 (M+Na).

Intermediate 56

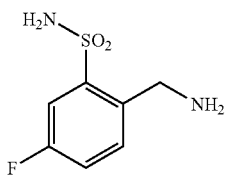

2-(Aminomethyl)-5-fluorobenzenesulfonamide hydrochloride. The title compound can be prepared from intermediate 55, 2-azidomethyl-5-fluoro-N-methyl-benzenesulfonamide, according to the method described for the preparation of intermediate 48. $^1$H NMR (500 MHz, DMSO-D6) δ ppm: 4.05 (2 H, s) 5.05 (3 H, br) 7.44 (1 H, dt, J=8.5, 3 Hz) 7.58 (1 H, dd, J=9.2, 2.7 Hz) 7.66 (1 H, dd, J=8.5, 5.5 Hz). LC/MS m/z 205 (M+H).

Intermediate 57

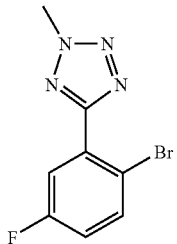

5-(2-Bromo-5-fluoro-phenyl)-2-methyl-2H-tetrazole. A mixture of 5-(2-bromo-5-fluoro-phenyl)-1H-tetrazole (1.0 g, 4.12 mmol), iodomethane (1.12 g, 10 mmol) and potassium carbonate (1.5 g) in dimethylformamide (5 mL) was stirred at room temperature for 16 hrs, then concentrated in vacuo. The residue was purified by column chromatography (SiO$_2$, CH$_2$Cl$_2$) to provide 650 mg (Yield 61%) of the title compound as a white powder. $^1$H NMR (500 MHz, CDCl$_3$) δ ppm: 4.45 (3 H, s) 7.03-7.11 (1 H, m) 7.63 (1 H, dd, J=8.9, 3.1 Hz) 7.69 (1 H, dd, J=8.9, 5.5 Hz); $^{13}$C NMR(126 MHz, CDCl$_3$) δ ppm: 39.86, 116.28, 118.66, 118.76, 130.13, 135.73, 161.74, 163.53; LC/MS m/z 257/259.

Intermediate 58

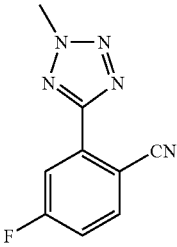

4-Fluoro-2-(2-methyl-2H-tetrazol-5-yl)-benzonitrile. A mixture of intermediate 57, 5-(2-bromo-5-fluoro-phenyl)-2-methyl-2H-tetrazole (650 mg, 2.53 mmol) and CuCN (224 mg, 2.5 mmol) in dimethylformamide (4 mL) was placed in a sealed tube and heated at 100-110° C. for 20 hrs. After cooling, the insoluble material was filtered, and the filtrate concentrated in vacuo. The residue was dissolved in CH$_2$Cl$_2$, washed with aq. 4N HCl and dil. NH$_4$OH, then dried (MgSO$_4$), filtered, and concentrated. The residual solid was purified by column chromatography (SiO$_2$, CH$_2$Cl$_2$) to obtain 375 mg (Yield 73%) of the title compound as an off-white solid; $^1$H NMR (500 MHz, CDCl$_3$) δ ppm: 4.48 (3 H, s) 7.29 (1 H, dd, J=7.6, 2.8 Hz) 7.85 (1 H, dd, J=8.6, 5.2 Hz) 8.00 (1 H, dd, J=9.0, 2.6 Hz); LC/MS m/z 204.

Intermediate 59

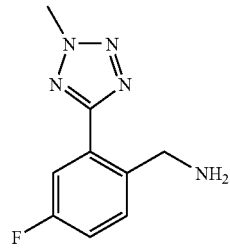

(4-Fluoro-2-(2-methyl-2H-tetrazol-5-yl)phenyl)methanamine hydrochloride. A solution of intermediate 58, 4-fluoro-2-(2-methyl-2H-tetrazol-5-yl)-benzonitrile, (330 mg, 1.62 mmol) in ethanol (15 mL) was mixed with 6N HCl (1 mL) and 10% Pd—C (200 mg) under nitrogen. The mixture was then stirred under hydrogen (1 atm) for 3 hrs. After removing the catalyst, the filtrate was concentrated in vacuo to provide 360 mg (Yield 91%) of the compound as an off-white solid; $^1$H NMR (500 MHz, DMSO-D6) δ ppm: 4.42 (2 H, d, J=2.75 Hz) 4.49 (3 H, s) 7.48-7.56 (1 H, m) 7.78 (1 H, dd, J=8.7, 5.7 Hz) 7.86 (1 H, dd, J=9.8, 2.8 Hz) 8.45 (3 H, s); LC/MS m/z 208.

Intermediate 60

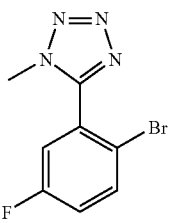

5-(2-Bromo-5-fluoro-phenyl)-1-methyl-2H-tetrazole. A mixture of 5-(2-bromo-5-fluoro-phenyl)-1H-tetrazole (1.0 g, 4.12 mmol), iodomethane (1.12 g, 10 mmol) and potassium carbonate (1.5 g) in dimethylformamide (5 mL) was stirred at room temperature for 16 hrs, then concentrated in vacuo. The residue was purified by column chromatography (SiO$_2$, CH$_2$Cl$_2$) to provide 350 mg (Yield 33%) of the title compound as white crystals. $^1$H NMR (500 MHz, CDCl$_3$) o ppm: 4.00 (3 H, s) 7.18-7.25 (2 H, m) 7.72 (1 H, dd, J=8.4, 5.0 Hz); $^{13}$C NMR (126 MHz, CDCl$_3$) δ ppm: 34.59, 117.73, 119.58, 120.43, 127.57, 135.11, 153.43, 161.69. LC/MS m/z 257/259.

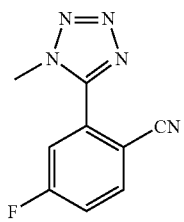

Intermediate 61

4-Fluoro-2-(]-methyl-2H-tetrazol-5-yl)-benzonitrile. $^1$H NMR (300 MHz, CDCl$_3$) δ ppm: 4.13 (3 H, s) 7.38-7.49 (2 H, m) 7.86-7.97 (1 H, m); LC/MS m/z 204 (M+H).

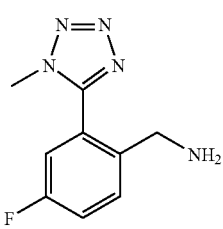

Intermediate 62

(4-Fluoro-2-(1-methyl-2H-tetrazol-5-yl)phenyl)methanamine hydrochloride. $^1$H NMR (500 MHz, DMSO-D6) δ ppm: 4.05 (2 H, s) 4.09 (3 H, s) 7.58-7.67 (1 H, m) 7.77 (1 H, dd, J=9.3, 2.6 Hz) 7.87 (1 H, dd, J=8.7, 5.7 Hz) 8.38 (3 H, s); LC/MS m/z 208.

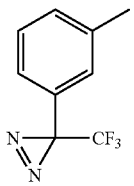

Intermediate 63

3-m-Tolyl-3-trifluoromethyl-3H-diazirine. To a cold stirring solution of 3-m-tolyl-3-trifluoromethyl-diaziridine (2.0 g, 10 mmol. prepared using the methods described in Doucet-Personeni C. et al., *J. Med. Chem.*, 2001, 44, 3203 and Nassal, M. *Liebigs Ann. Chem.* 1983, 1510-1523 or in Stromgaard, K et al., *J. Med. Chem.*, 2002, 45, 4038-46) in ethanol (20 mL) was added triethylamine (1.5 g, 15 mmol). To this mixture was added tert-butyl hypochlorite (3.25 g, 30 mmol), and the mixture stirred for 5 min. This mixture was poured into 10% aqueous sodium sulfite (100 mL), and extracted with ether. The ether extract was washed with brine, dried (MgSO$_4$), filtered and concentrated. The residue was purified by column chromatography (SiO$_2$, pentane) to provide 1.6 g (Yield 80%) of the title compound. $^1$H NMR (300 MHz, CDCl$_3$) δ ppm: 2.33 (3 H, s) 6.90-7.03 (2 H, m) 7.15-7.31 (2 H, m).

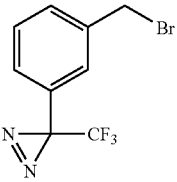

Intermediate 64

3-(3-Bromomethyl-phenyl)-3-trifluoromethyl-3H-diazirine. To a solution of intermediate 63, 3-m-tolyl-3-trifluoromethyl-3H-diazirine, (200 mg, 1 mmol) in CCl$_4$ (4 mL) was added N-bromosuccinimide (200 mg, 1.1 mmol, re-crystallized from water), and the stirred mixture heated at 85° C. To this was added AIBN (50 mg) and the mixture heated at reflux for an additional 2.5 hrs. After cooling, the mixture was purified by column chromatography (SiO$_2$, pentane) to provide 150 mg (Yield 54%) of the title compound as a clear oil. $^1$H NMR (300 MHz, CDCl$_3$) δ ppm: 4.42 (2 H, s) 7.10-7.17 (2 H, m) 7.31-7.45 (2 H, m).

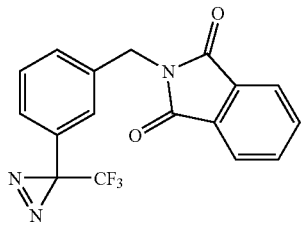

Intermediate 65

2-[3-(3-Trifluoromethyl-diaziridin-3-yl)-benzyl]-isoindole-1,3-dione. A mixture of intermediate 64, 3-(3-bromomethyl-phenyl)-3-trifluoromethyl-3H-diazirine, (140 mg, 0.5 mmol) and potassium phthalimide (95 mg, 0.5 mmol) in dimethylformamide (1.5 mL) was stirred at room temperature for 3 hrs. Dimethylformamide was removed in vacuo. The residue was extracted with CH$_2$Cl$_2$, washed with water, then dried (Na$_2$SO$_4$), filtered, and concentrated. The resulting residue was purified by column chromatography (SiO$_2$, 1:1 CH$_2$Cl$_2$/pentane) to provide 140 mg (Yield 82%) of the title compound as a solid; $^1$H NMR (300 MHz, CDCl$_3$) δ ppm: 4.80 (2 H, s) 7.09-7.21 (2 H, m) 7.32 (1 H, t, J=7.9 Hz) 7.41-7.49 (2 H, m) 7.66-7.71 (2 H, m) 7.81-7.85 (2 H, m); LC/MS m/z 346 (M+H).

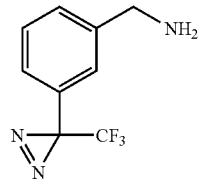

Intermediate 66

(3-(3-(Trifluoromethyl)diaziridin-3-yl)phenyl)methanamine. A stirred solution of intermediate 65, 2-[3-(3-trifluoromethyl-diaziridin-3-yl)-benzyl]-isoindole-1,3-dione, (150 mg, 0.43 mmol) in ethanol (2 mL) was treated with hydrazine hydrate (0.4 mL) at room temperature and the solution stirred for 3.5 hrs. After removing ethanol in vacuo, the residue was partitioned between CH$_2$Cl$_2$ and water. The aqueous phase was acidified with dilute HCl, and washed with CH₂Cl₂. The aqueous phase was basified with dilute NaOH, and extracted with CH₂Cl₂. The organic extract was dried (MgSO₄), filtered, and concentrated to obtain 50 mg (Yield 54%) of (3-(3-(trifluoromethyl)diaziridin-3-yl)phenyl)methanamine and (3-(3-(trifluoromethyl)-3H-diazirin-3-yl)phenyl)methanamine as a 1:1 mixture; $^1$H NMR (300 MHz, CDCl₃) δ ppm: 3.85 (2 H, s) 3.88 (2 H, s) 7.08 (2 H, s) 7.31-7.40 (4 H, m) 7.43-7.50 (1 H, m, J=6.2 Hz) 7.54 (1 H, s); LC/MS m/z 216 (M+H for diazirine) and 218 (M+H for diaziridine).

Intermediates 67-68

To a solution of 2,4-difluorobenzonitrile (10 g, 72 mmol) dissolved in tetrahydrofuran (20 mL), and dimethylformamide (40 mL) was added 1,2,4-triazole sodium salt (6.3 g, 70 mmol) and the mixture stirred at 90° C. for 3 h after which the mixture was filtered and the solvent removed. The resulting residue was adsorbed onto silica gel and intermediates 67 and 68 separated by flash chromatography, eluting with 0% to 30% ethyl acetate/hexanes.

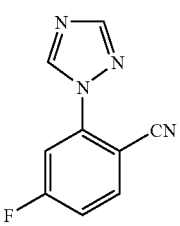

Intermediate 67

4-Fluoro-2-(1H-1,2,4-triazol-1-yl)benzonitrile. Colorless needles (2.46 g, 18% yield) $^1$H NMR (500 MHz, CDCl₃) δ: 8.89 (1H, s), 8.19 (1H, s), 7.85 (1H, dd, J=8.7, 5.6 Hz), 7.60 (1H, dd, J=8.8, 2.4 Hz), 7.28-7.24 (1H, m). LCMS (M+H) calcd for C₉H₆N₄F: 189.05; found: 189.13.

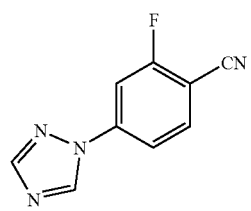

Intermediate 68

4-(1H-1,2,4-Triazol-1-yl)-2-fluorobenzonitrile. White solid (0.746 g, 6% yield) $^1$H NMR (500 MHz, CDCl₃) δ: 8.66 (1H, s), 8.15 (1H, s), 7.79 (1H, dd, J=8.5, 6.7 Hz), 7.69 (1H, dd, J=9.5, 1.8 Hz), 7.65-7.63 (1H, m). LCMS (M+H) calcd for C₉H₆N₄F: 189.05; found: 189.13.

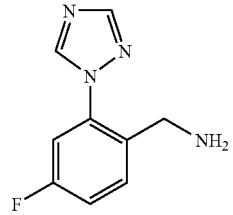

Intermediate 69

(4-Fluoro-2-(1H-1,2,4-triazol-1-yl)phenyl)methanamine hydrochloride). Intermediate 67, 4-fluoro-2-(1H-1,2,4-triazol-1-yl)benzonitrile, (2.46 g, 13.13 mmol) was dissolved in hot ethanol (150 mL). To this was added 1N HCl (15 mL) followed by 10% Pd—C (200 mg). The mixture was treated with H₂ at 55 psi for 4 h in a Parr shaker then filtered over Celite and the solvent removed under reduced pressure. The resulting residue was partitioned between ethyl acetate and water. The aqueous phase was separated and lyophilized to afford the title compound as a white powder (2.96 g, 99% yield). $^1$H NMR (500 MHz, CD₃OD) δ ppm: 9.51 (1H, s), 8.63 (1H, s), 7.85 (1H, dd, J=8.5, 5.8 Hz), 7.68 (1H, dd, J=8.8, 2.4 Hz), 7.49 (1H, td, J=8.3, 2.4 Hz), 4.20 (2H, s). LCMS (M+H) calcd for C₉H₁₀N₄F: 193.08; found: 193.16.

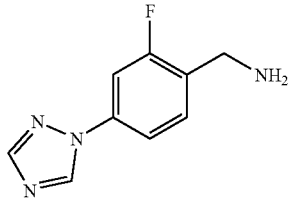

Intermediate 70

(2-Fluoro-4-(1H-1,2, 4-triazol-1-yl)phenyl)methanamine hydrochloride. The title compound can be prepared from intermediate 68 according to the method described for the synthesis of intermediate 69. White powder (79% yield). $^1$H NMR (500 MHz, CD₃OD) δ ppm: 9.25 (1H, s), 8.46 (1H, s), 7.80 (1H, dd, J=8.6, 5.8 Hz), 7.64 (1H, dd, J=8.8, 2.4 Hz), 7.44 (1H, td, J=8.3, 2.6 Hz), 4.17 (2H, s). LCMS (M+H) calcd for C₉H₁₀N₄F: 193.08; found: 193.16.

Intermediates 71-74

Intermediates 71-74 were prepared using the procedure described for the synthesis of intermediate 67-70.

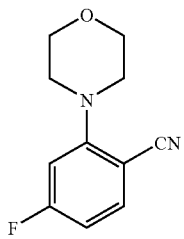

Intermediate 71

4-Fluoro-2-morpholinobenzonitrile $^1$H NMR (500 MHz, CDCl₃) δ ppm: 7.55 (1H, dd, J=8.5, 6.4 Hz), 6.71 (1H, td, J=8.1, 2.3 Hz), 6.67 (1H, dd, J=11.0, 2.4 Hz), 3.88 (4H, t, J=4.6 Hz), 3.22 (4H, t, J=4.6 Hz). LCMS (M+H) calcd for C₁₁H₁₂N₂OF: 207.09; found: 207.19.

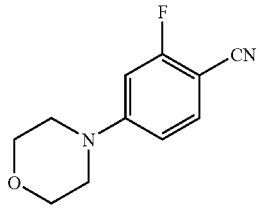

Intermediate 72

4-Morpholino-2-fluorobenzonitrile. ¹H NMR (500 MHz, CDCl₃) δ ppm: 7.42 (1H, dd, J=8.8, 7.6 Hz), 6.63 (1H, dd, J=8.8, 2.4 Hz), 6.56 (1H, dd, J=12.8, 2.4 Hz), 3.84 (4H, t, J=4.9 Hz), 3.28 (4H, t, J=4.9 Hz). LCMS (M+H) calcd for C₁₁H₁₂N₂OF: 207.09; found: 207.19.

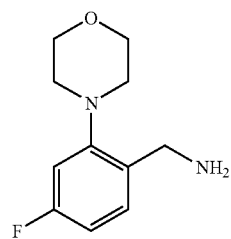

Intermediate 73

(4-Fluoro-2-morpholinophenyl)methanamine hydrochloride. ¹H NMR (500 MHz, CDCl₃) δ ppm: 7.54 (1H, t, J=7.3 Hz), 7.20 (1H, dd, J=10.5, 2.0 Hz), 7.05-7.02 (1H, m), 4.28 (2H, s), 3.93 (4H, bs), 3.03 (4H, bs). LCMS (M+H) calcd for C₁₁H₁₆N₂OF: 211.12; found: 211.23.

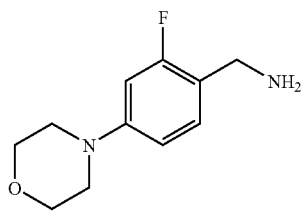

Intermediate 74

(2-Fluoro-4-morpholinophenyl)methanamine hydrochloride. ¹H NMR (500 MHz, CD₃OD) δ ppm: 7.73 (1H, t, J=8.2 Hz), 7.62 (1H, d, J=7.6 Hz), 7.58 (1H, d, J=8.2 Hz), 4.26 (2H, s), 4.11 (4H, t, J=4.4 Hz), 3.65 (4H, t, J=4.4 Hz). LCMS (M+H) calcd for C₁₁H₁₆N₂OF: 211.12; found: 211.23.

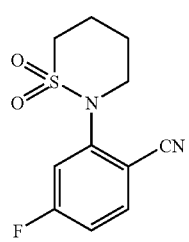

Intermediate 75

4-Fluoro-2-(1,1-dioxo-1λ⁶-[1,2]thiazinan-2-yl)benzonitrile. To a mixture of 2,4-difluorobenzonitrile (10.0 g, 72 mmol) and 1,1-dioxo-1λ6-[1,2]thiazin-2-ane (8.84 g, 65.4 mmol) in 1:1 tetrahydrofuran/dimethylformamide (40 mL) was added potassium carbonate (9.0 g, 65.4 mmol). The mixture was stirred at 90° C. for 18 h then filtered and concentrated. The residue was purified by flash chromatography (SiO₂) eluting with 10%-50% ethyl acetate/hexanes followed by recrystallization from hot ethyl acetate/hexane to give the title compound as white needles (0.537 g, 3% yield). ¹H NMR (500 MHz, CD₃OD) δ ppm: 7.70 (1H, dd, J=8.8, 5.8 Hz), 7.30 (1H, dd, J=8.8, 2.4 Hz), 7.15-7.12 (1H, m), 3.27 (2H, t, J=5.3 Hz), 3.33 (2H, t, J=6.1 Hz), 2.40-2.35 (2H, m), 2.05-2.01 (2H, m). LCMS (M+H) calcd for C₁₁H₁₆N₂OF: 255.06; found: 255.19.

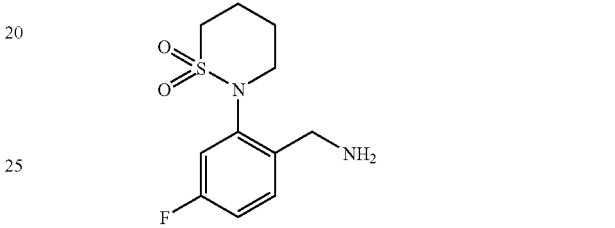

Intermediate 76

(4-Fluoro-2-(1,1-dioxo-1λ⁶-[1,2]thiazinan-2-yl)phenyl)methanamine hydrochloride. Intermediate 75, 4-fluoro-2-(1,1-dioxo-1λ⁶-[1,2]thiazinan-2-yl)benzonitrile (1.37 g, 5.4 mmol) was dissolved in ethanol (120 mL). To this was added 1N HCl (20 mL) and a catalytic amount of 10% Pd—C. The mixture was shaken under hydrogen at 55 psi for 4 h then filtered through Celite and concentrated to give the title compound as white solid (1.58 g, 100% yield). ¹H-NMR (300 MHz, CD₃OD) δ ppm: 7.61 (1H, dd, J=8.4, 6.2 Hz), 7.38 (1H, dd, J=9.3, 2.7 Hz), 7.28 (1H, td, J=8.2, 2.7 Hz), 7.26 (2H, dd, J=21.4, 13.7 Hz), 3.93-3.84 (1H, m) 3.50-3.41 (3H, m), 2.40-2.31 (2H, m), 2.04-1.96 (2H, m). LCMS [M+H]⁺ calcd for C₁₁H₁₆N₂O₆FS: 259.087; found: 259.24.

Intermediates 77-78

To a solution of 1H-1,2,3-triazole (3.5 g, 50.7 mmol) in tetrahydrofuran (10 mL) and dimethylformamide (20 mL) was added, portionwise, NaH (1.3 g, 51 mmol, 95%). The mixture was stirred at room temp for 30 min. 2,4-Difluorobenzonitrile (7.6 g, 55 mmol) was added and the mixture stirred at 85° C. for 3 h. The white mixture was concentrated and purified by flash chromatography eluting with 0% to 10% ethyl acetate/hexanes to give intermediates 77 and 78.

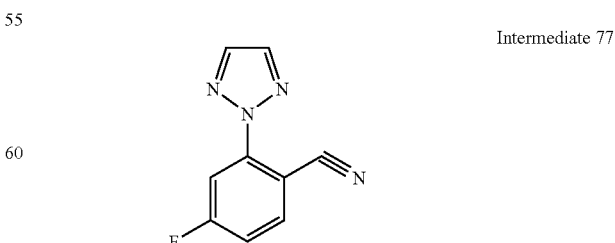

Intermediate 77

4-Fluoro-2-1,2,3-triazol-2-yl-benzonitrile. White needles (0.34 g, 3% yield). 1H-NMR (300 MHz, CDCl₃) δ ppm: 7.92

(2H, s), 7.88-7.79 (2H, m), 7.19-7.12 (1H, m). LCMS [M+H]+ calcd for $C_9H_6N_4F$: 189.05; found: 189.12.

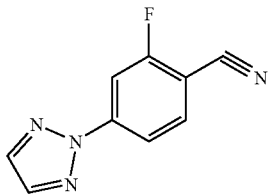

Intermediate 78

2-Fluoro-4-1,2,3-triazol-2-yl-benzonitrile. White solid (0.097 g, 1% yield). $^1$H-NMR (300 MHz, CDCl$_3$) δ ppm: 8.03-7.95 (2H, m), 7.86 (2H, s), 7.74-7.69 (1H, m).

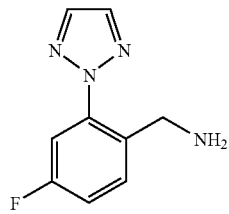

Intermediate 79

4-Fluoro-2-1,2,3-triazol-2-yl-benzylamine hydrochloride. Intermediate 77, 4-fluoro-2-1,2,3-triazol-2-yl-benzonitrile, (0.34 g, 1.8 mmol) was dissolved in ethanol (50 mL). 1N HCl (10 mL) was added along with a catalytic amount of 10%-Pd—C. The mixture was shaken under H$_2$ at 55 psi for 4 h after which it was filtered through Celite and concentrated to give the title compound as the corresponding HCl salt. Yellow solid (0.402 g, 98% yield). $^1$H-NMR (500 MHz, CD$_3$OD) δ ppm: 8.13 (2H, s), 7.87 (1H, dd, J=4.9, 2.6 Hz), 7.73 (1H, dd, J=4.9, 2.6 Hz), 7.34 (1H, td, J=8.2, 2.7 Hz), 4.35 (2H, s). LCMS [M+H]$^+$ calcd for $C_9H_{10}N_4F$: 193.08; found: 193.16.

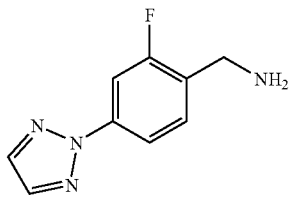

Intermediate 80

(2-Fluoro-4-(2H-1,2,3-triazol-2-yl)phenyl)methanamine: The title compound can be prepared from intermediate 78, 2-fluoro-4-1,2,3-triazol-2-yl-benzonitrile, according to the procedure provide for intermediate 79. $^1$H-NMR (300 MHz, CD$_3$OD) δ ppm: 8.05-7.96 (2H, m), 8.00 (2H, s), 7.68 (1H, t, J=8.2 Hz), 4.26 (2H, s). LCMS [M+H]$^+$ calcd for $C_9H_{10}N_4F$: 193.08; found: 193.14.

Intermediates 81-84

A solution of 2,4-difluorobenzonitrile (7.07 g, 50.8 mmol) and 3-methyl-1H-1,2,4-triazole (4.22 g, 50.8 mmol) in N,N-dimethylformamide (45 ml) was treated with powdered anhydrous potassium carbonate (10 g) and the resulting mixture stirred at 22° C. for 18 h. The solid was then filtered and the filtrate concentrated in vacuo. The residue was diluted with ethyl acetate, washed with water and brine, then dried over anhydrous magnesium sulfate and concentrated. The resulting mixture was purified by a combination of chromatography on silica gel (elution gradient of ethyl acetate in hexane) and reversed phase silica gel to yield intermediates 81-84.

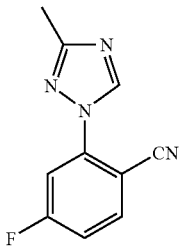

Intermediate 81

4Fluoro-2-(3-methyl-1H-1,2,4-triazol-1-yl)benzonitrile. White crystals (ethyl acetate-hexane); mp 117-118° C. $^1$HNMR 400 MHz (CDCl$_3$) δ ppm: 2.54 (3H, s, CH$_3$), 7.24 (1H, m, CH), 7.62 (1H, dd, J=2.5 Hz and J=9.1 Hz, CH), 7.84 (1H, dd, J=5.6 Hz and J=8.6 Hz, CH), 8.82 (1H, s, CH). Anal. Calcd for $C_{10}H_7FN_4$: C, 59.40; H, 3.49; N, 27.71; Found: C, 59.25; H, 3.32; N, 27.81.

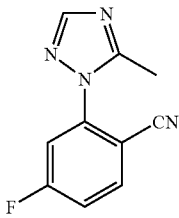

Intermediate 82

4-Fluoro-2-(5-methyl-1H-1,2,4-triazol-1-yl)benzonitrile. White crystals (ethyl acetate-hexane); mp 120-121° C. $^1$HNMR 400 MHz (CDCl$_3$) δ ppm: 2.56 (3H, s, CH$_3$), 7.30 (1H, dd, J=2.5 Hz and J=8.1 Hz, CH), 7.39 (1H, m, CH), 7.91 (1H, dd, J=5.5 Hz and J=8.6 Hz, CH), 8.06 (1H, s, CH). Anal. Calcd for $C_{10}H_7FN_4$: C, 59.40; H, 3.49; N, 27.71; Found: C, 59.35; H, 3.70; N, 27.77.

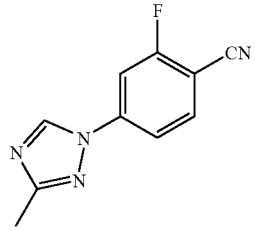

Intermediate 83

2-Fluoro-4-(3-methyl-1H-1,2,4-triazol-1-yl)benzonitrile. White crystals (ethyl acetate-hexane); mp 133-134° C. $^1$HNMR 400 MHz (CDCl$_3$) δ ppm: 2.52 (3H, s, CH$_3$), 7.61 (1H, dd, J=2 Hz and J=9.1 Hz, CH), 7.67 (1H, dd, J=2 Hz and J=9.6 Hz, CH), 7.79 (1H, dd, J=6.5 Hz and J=8.6 Hz, CH), 8.56 (1H, s, CH). Anal. Calcd for $C_{10}H_7FN_4$: C, 59.40; H, 3.49; N, 27.71; Found: C, 59.42; H, 3.24, N, 28.41.

Intermediate 84

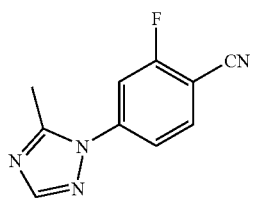

2-Fluoro-4-(5-methyl-1H-1,2,4-triazol-1-yl)benzonitrile. White crystals (ethyl acetate-hexane); mp 89-90° C., $^1$HNMR 400 MHz (CDCl$_3$) δ ppm: 2.69 (3H, s, CH$_3$), 7.49-7.55 (2H, m, 2×CH), 7.83 (1H, dd, J=6.8 Hz and J=8.8 Hz, CH), 8.00 (1H, s, CH). Anal. Calcd for C$_{10}$H$_7$FN$_4$: C, 59.40; H, 3.49; N, 27.71; Found: C, 59.17; H, 3.22; N, 28.01.

Intermediate 85

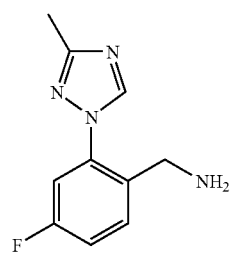

(4-Fluoro-2-(3-methyl-1H-1,2,4-triazol-1-yl)phenyl) methanamine hydrochloride salt. Hydrogenation of intermediate 81, 4-fluoro-2-(3-methyl-1H-1,2,4-triazol-1-yl)benzonitrile, (0.680 g, 3.36 mmol) gave 0.720 g (88% yield) of the title hydrochloride salt as a white solid. $^1$HNMR 400 MHz (DMSO-d$_6$) δ ppm: 2.40 (3H, s, CH$_3$), 4.02 (2H, m, NCH$_2$), 7.50 (1H, m, CH), 7.62 (1H, dd, J=2.8 Hz and J=9.3 Hz, CH), 7.84 (1H, dd, J=6.1 Hz and J=9.1 Hz, CH), 9.00 (1H, s, CH). HRMS (ESI$^+$) calculated for C$_{10}$H$_{12}$FN$_4$ [M+H$^+$]: 207.1046; found: 207.1047.

Intermediate 86

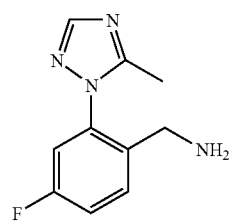

(4-Fluoro-2-(5-methyl-1H-1,2,4-triazol-1-yl)phenyl) methanamine hydrochloride salt. Hydrogenation of intermediate 82, 4-fluoro-2-(5-methyl-1H-1,2,4-triazol-1-yl)benzonitrile, (0.244 g, 1.20 mmol) gave 0.290 g (100% yield) of the title hydrochloride salt as a white solid. $^1$HNMR 400 MHz (DMSO-d$_6$) δ ppm: 2.42 (3H, s, CH$_3$), 3.78 (2H, m, NCH$_2$), 7.58 (1H, m, CH), 7.67 (1H, dd, J=2.8 Hz and J=9.3 Hz, CH), 7.90 (1H, dd, J=6.0 Hz and J=8.6 Hz, CH), 8.22 (1H, s, CH). HRMS (ESI$^+$) calculated for C$_{10}$H$_{12}$FN$_4$ [M+H$^+$]: 207.1046; found: 207.1041.

Intermediate 87

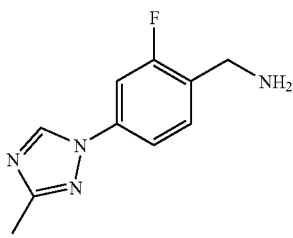

(2-Fluoro-4-(3-methyl-1H-1,2,4-triazol-1-yl)phenyl) methanamine hydrochloride salt. Hydrogenation of intermediate 83, 2-fluoro-4-(3-methyl-1H-1,2,4-triazol-1-yl)benzonitrile, (0.220 g, 1.09 mmol) gave 0.260 g (98% yield) of the title hydrochloride salt as a white solid. $^1$HNMR 400 MHz (DMSO-d$_6$) δ ppm: 2.38 (3H, s, CH$_3$), 4.09 (2H, m, NCH$_2$), 7.75-7.8 (2H, m, 2×CH), 7.83 (1H, dd, J=2 Hz and J=9 Hz, CH), 9.29 (1H, s, CH). MS (ESI$^+$) m/e 207 [M+H$^+$].

Intermediate 88

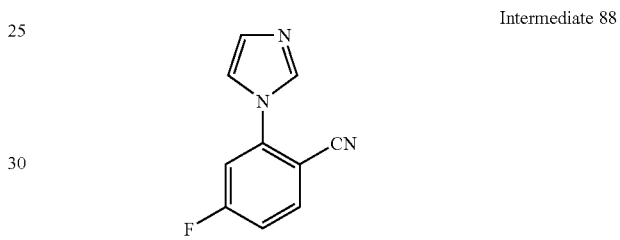

4-Fluoro-2-imidazol-1-yl-benzonitrile. To a solution of imidazole (4.45 g, 65.4 mmol) in tetrahydrofuran (30 mL) and dimethylformamide (10 mL) was added potassium carbonate (9.95 g, 72 mmol) and the mixture was stirred for 30 min at room temp. To this was added 2,4-difluorobenzonitrile (10.0 g, 72 mmol) and the mixture stirred at 90° C. for 3 h then at room temp for 2 days. The mixture was filtered and concentrated and the residue was purified by flash chromatography (SiO$_2$) eluting with 20% to 70% ethyl acetate/hexane to give the title compound as white needles (1.1 g, 9% yield). $^1$H-NMR (500 MHz, CDCl$_3$) δ ppm: 7.94 (1H, s), 7.84 (1H, dd, J=8.7, 5.6 Hz), 7.37 (1H, t, J=8.7, 5.6 Hz), 7.37 (1H, t, J=1.4 Hz), 7.29 (1H, t, J=1.1 Hz), 7.27-7.21 (2H, m). LCMS [M+H]$^+$ calcd for C$_{10}$H$_7$N$_3$F: 188.058; found: 188.12.

Intermediate 89

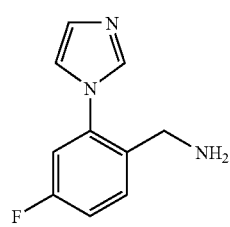

(4-Fluoro-2-(1H-imidazo-1-yl)phenyl)methanamine)hydrochloride. The title compound can be prepared from intermediate 88, 4-fluoro-2-imidazol-1-yl-benzonitrile, according to the method provided for intermediate 79. Yellow solid, $^1$H-NMR (500 MHz, CD$_3$OD) δ ppm: 9.39 (1H, s), 7.98 (1H, d, J=1.5 Hz), 7.92-7.89 (2H, m), 7.63-7.59 (2H, m), 4.11 (2H, s). LCMS [M+H]+ calcd for C10H11N3F: 192.09; found: 192.15.

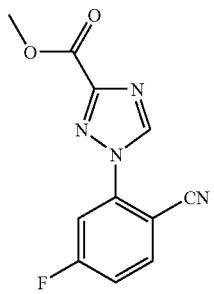

Intermediate 90

1-(2-Cyano-5-fluoro-phenyl)-1H-1,2,4-triazole-3-carboxylic acid methyl ester. To a solution of methyl 1H-1,2,4-triazole-3-carboxylate (27 g, 215 mmol) in dimethylformamide (170 mL) was added sodium hydride (5.53 g, 95%, 217 mmol) and the mixture was stirred for 30 min. Added to this was 2,4-difluorobenzylnitrile (30 g, 217 mmol) and the resulting mixture stirred at room temp for 60 h. The mixture was diluted with water and filtered to remove solids. The solution was extracted with ethyl acetate and the organic phase was washed with water (3×'s) and brine, then dried (Na2SO4) and concentrated. The resulting residue was purified by flash chromatography (SiO2) eluting with 30% tetrahydrofuran/20% CH2Cl2/50% hexane to give the title compound as white needles (5.34 g, 10% yield). 1H-NMR (300 MHz, CDCl3) δ ppm: 8.92 (1H, s), 7.85 (1H, dd, J=8.8, 5.5 Hz), 7.67 (1H, dd, J=8.8, 2,6 Hz), 7.34-7.27 (1H, m), 40.3 (3H, s). LCMS [M+H]+ calcd for C11H8N4FO2: 247.06; found: 247.11.

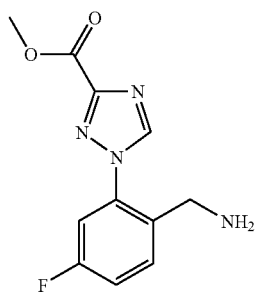

Intermediate 91

Methyl 1-(2-(aminomethyl)-5-fluorophenyl)-1H-1,2,4-triazole-3-carboxylate. The title compound can be prepared from intermediate 90, 1-(2-cyano-5-fluoro-phenyl)-1H-1,2,4-triazole-3-carboxylic acid methyl ester 1H-NMR (300 MHz, CD3OD) δ ppm: 9.15 (1H, s), 7.80 (1H, dd, J=8.8, 5.9 Hz), 7.71 (1H, dd, J=8.8, 2.6 Hz), 7.46 (1 H, td J=8.2, 2.6 Hz), 4.19 (2H, s), 4.03 (3H, s). LCMS [M+H]+ calcd for C11H12N4O2: 251.09; found: 251.17.

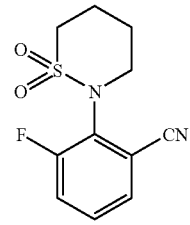

Intermediate 92

3-Fluoro-2-(1,1-dioxo-1λ6-[1,2]thiazinan-2-yl)benzonitrile. To a solution of 1,1-dioxo-1λ6-[1,2]thiazin-2-ane (1.90 g, 14.4 mmol) dissolved in tetrahydrofuran (8 mL) and dimethylformamide (2 mL) was added sodium hydride (0.36 g, 95%, 14.4 mmol) and the mixture stirred for 20 min. To this was added 2,3-difluorobenzonitrile (2.0 g, 14.4 mmol) and the mixture stirred at 90° C. for 2 h. The mixture was partitioned between ethyl acetate and water. The organic phase was washed with water and brine then concentrated. The solid residue was triturated with 1:1 ethyl acetate/hexane to give the title compound as a pale brown solid (0.47 g, 13% yield). 1H-NMR (500 MHz, CDCl3) δ ppm: 7.47-7.45 (1H, m), 7.32-7.36 (2H, m), 4.08-4.02 (1H, m), 3.57 (1H, td, J=13.0, 3,7 Hz), 3.40-3.34 (1H, m), 3.32-3.27 (1H, m), 2.44-2.32 (2HF, m), 2.04-1.97 (2H, m), 1.90-1.84 (1H, m). LCMS [M+H]+ calcd for C11H12N2FO2S: 255.28; found: 255.13.

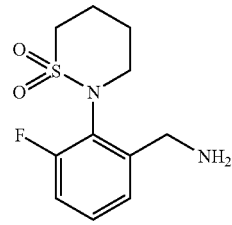

Intermediate 93

3-Fluoro-2-(1,1-dioxo-1λ6-[1,2]thiazinan-2-yl)benzylamine hydrochloride. The title compound can be prepared from intermediate 92, 3-fluoro-2-(1,1-dioxo-1λ6-[1,2]thiazinan-2-yl)benzonitrile according to the procedure provided for intermediate 79. White solid, 1H-NMR (500 MHz, CD3OD) δ ppm: 7.56-7.52 (1H, m), 7.40-7.34 (2H, m), 4.31 (2H, s), 3.98-3.93 (1H, m), 3.68-3.64 (1H, m), 3.42-3.39 (2H, m), 2.42-2.37 (2H, m), 2.03-1.92 (2H, m). LCMS [M+H]+ calcd for C11H16N2O2FS: 259.09; found: 259.18.

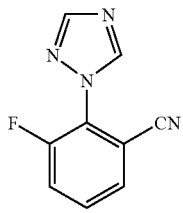

Intermediate 94

3-Fluoro-2-1,2,4-triazol-1-yl-benzonitrile. A mixture of 2,3-difluorobenzylnitrile (2.27 g, 16.3 mmol) and triazole sodium salt (1.33 g, 14.8 mmol) in tetrahydrofuran (5 mL) and dimethylformamide (10 mL) was stirred at 85° C. for 4 h. After concentration, the residue was purified by flash chromatography (SiO$_2$) eluting with 25%-50% ethyl acetate/hexane. The isolated product was recrystallized from hot ethyl acetate/hexane to give the title compound as white needles (1.51 g, 54% yield). $^1$H-NMR (500 MHz, CDCl$_3$) δ ppm: 8.50 (1H, d, J=2.4 Hz), 8.25 (1H, s), 7.69-7.67 (1H, m), 7.60-7.57 (2H, m). LCMS [M+H]$^+$ calcd for C$_9$H$_6$N$_4$F: 189.16; found: 189.14.

Intermediate 95

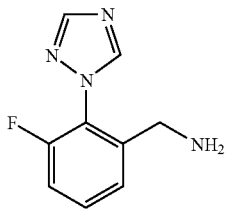

(3-Fluoro-2-(1H-1,2,4-triazol-1-yl)phenyl)methanamine. The title compound can be prepared from intermediate 94, 3-fluoro-2-1,2,4-triazol-1-yl-benzonitrile. $^1$H-NMR (500 MHz, CD$_3$OD) δ ppm: 9.61 (1H, d, J=2.9 Hz), 8.79 (1H, s), 7.82-7.74 (1H, m), 7.67-7.57 (2H, m), 4.14-4.13 (2H, m). LCMS [M+H]$^+$ calcd for C$_9$H$_{10}$N$_4$F: 193.08; found: 193.16.

Intermediate 96

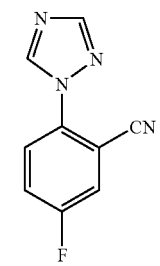

5-Fluoro-2-(1H-1,2,4-triazol-1-yl)benzonitrile. A suspension of 2,5-diflurobenzonitrile (4.5 g, 32.35 mmol) and 1,2,4-triazole sodium salt (3.6 g, 40 mmol) in dimethylformamide (40 mL) was heated at 80° C. for 15 h. The reaction mixture was then cooled, diluted with CH$_2$Cl$_2$ (200 mL), washed with water (3×30 mL) and brine (30 mL), then dried (Na$_2$SO$_4$), filtered and concentrated to give a white solid which was purified by flash column chromatography (SiO$_2$) using 1:1 to 3:1 ethyl acetate/Hexanes to afford the title compound (2.98 g, 49% yield) as a white powder. $^1$H NMR (500 MHz, CDCl$_3$) δ: 8.70 (1H, s), 8.18 (1H, s), 7.76 (1H, dd, J=9.0, 4.8 Hz), 7.55 (1H, dd, J=7.3, 2.8 Hz), 7.51-7.47 (1H, m). LCMS (M+H) calcd for C$_9$H$_6$FN$_4$: 189.17; found: 189.10.

Intermediate 97

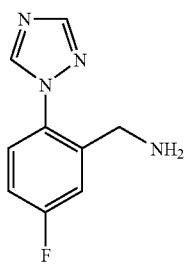

(5-Fluoro-2-(1H-1,2,4-triazol-1-yl)phenyl)methanamine hydrochloride. A solution of intermediate 96, 5-fluoro-2-(1H-1,2,4-triazol-1-yl)benzonitrile (2.94 g, 15.59 mmol) in ethanol (100 mL) and 1N HCl (50 mL) was degassed by bubbling N$_2$. Then, 10%Pd/C was added, the flask evacuated and vented to H$_2$ three times and left on a Parr shaker under a H$_2$ atmosphere (40 psi). After 6 h, the reaction mixture was filtered, concentrated and the aqueous solution lyophilized to afford the title compound (4.07 g, 98%) as a white powder. LCMS (M+H) calcd for C$_9$H10FN$_4$: 193.09; found: 193.15.

Intermediate 98

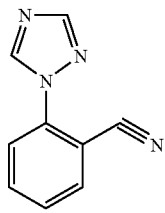

2-(1H-1,2,4-Triazol-1-yl)benzonitrile. A suspension of 2-fluorobenzylnitrile (3.0 g, 25 mmol) and 1,2,4-triazole sodium salt (2.4 g, 27 mmol) were stirred in tetrahydrofuran (7 mL) and dimethylformamide (14 mL) at 95° C. for 18 h. After cooling and concentrating, the product was crystallized from hot CH$_2$Cl$_2$/hexane (1:1) to give the title compound as a white solid (4.25 g, 100% yield). $^1$H-NMR (300 MHz, CDCl$_3$) δ ppm: 8.74 (1H, s), 8.16 (1H, s), 7.82 (1H, dd, J=4.9,1.3 Hz), 7.77-7.25 (2H, m), 7.57-7.51 (1H, m). LCMS [M+H]$^+$ calcd for C$_9$H$_7$N$_4$: 171.06; found: 171.12.

Intermediate 99

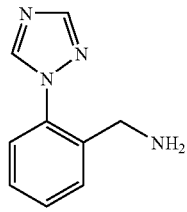

(2-(1H-1,2,4-Triazol-1-yl)phenyl)methanamine hydrochloride. Intermediate 98, 2-(1H-1,2,4-triazol-1-yl)benzonitrile (4.25 g, 25 mmol) was dissolved in ethanol (50 mL) and 1N HCl (25 mL). 10% Pd—C (1 g) was added and the mixture shaken under H$_2$ for 2 h at 50 psi. After filtration through Celite and concentration, the residue was triturated with diethyl ether and the title compound was collected as a white solid. (3.94 g, 75% yield). $^1$H-NMR (300 MHz, CD$_3$OD) δ ppm: 9.01 (1H, s), 8.32 (1H, s), 7.78-7.64 (4H, m), 4.15 (2H, s). LCMS [M+H]$^+$ calcd for C$_9$H$_{11}$N$_4$: 175.09; found: 175.17.

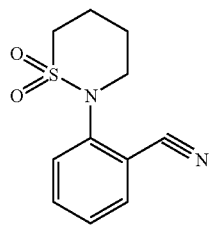

Intermediate 100

2-(1,1-Dioxo-1λ$^6$-[1,2]thiazinan-2-yl)benzonitrile. Added to a solution of 1,1-dioxo[1,2]thiazinane (3.37 g, 25 mmol) in dimethylformamide (35 mL) was sodium hydride (0.675 g, 25 mmol, 95%) and the mixture stirred at room temperature for 15 min. 2-Fluorobenzonitrile (3.37 mL, 31.3 mmol) was added and the mixture stirred at 80° C. for 18 h. The mixture was cooled, diluted with water and extracted with ethyl acetate. The organic phase was washed with water and brine, then dried (Na$_2$SO$_4$) and concentrated. The residue was purified by flash chromatography (SiO$_2$) eluting with 10%-100% ethyl acetate/hexane. The isolated solid was recrystallized from hot ethyl acetate/hexane (2:1) to give the title compound as white crystals (4.15 g, 70% yield). $^1$H-NMR (300 MHz, CDCl$_3$) δ ppm: 7.70 (1H, dd, J=7.7,1.1 Hz), 7.64-7.53 (2H, m), 7.41 (1H, td, J=7.3, 1.6 Hz), 3.72 (2H, t, J=5.5 Hz), 3.32 (2H, t, J=6.0 Hz), 2.40-2.32 (2H, m), 2.05-1.97 (2H, m). LCMS [M+H]$^+$ calcd for C$_{11}$H$_{12}$N$_2$O$_2$S: 237.06; found: 237.10.

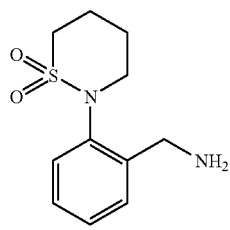

Intermediate 101

2-(1,1-Dioxo-1λ$^6$-[1,2]thiazinan-2-yl)benzylamine hydrochloride. Intermediate 100, 2-(1,1-dioxo-1λ$^6$-[1,2]thiazinan-2-yl)benzonitrile, (2.63 g, 11.14 mmol) was dissolved in ethanol (150 mL) and 1N HCl (13 mL). Added to this was 10% Pd—C (0.5 g) and the mixture shaken under H$_2$ at 55 psi for 24 h. Filtration through Celite followed by concentration gave the title compound as a white solid (2.93 g, 95% yield). $^1$H-NMR (300 MHz, CD$_3$OD) δ ppm: 7.61-7.47 (4H, m), 4.30 (2H, q, J=13.7 Hz), 3.96-3.87 (1H, m), 3.49-3.36 (3H, m), 2.40-2.31 (2H, m) 2.05-1.96 (2H, m). LCMS [M+H]$^+$ calcd for C$_{11}$H$_{17}$N$_2$SO$_2$: 241.10; found: 241.10.

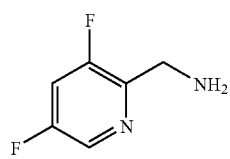

Intermediate 102

(3,5-Difluoropyridin-2-yl)methanamine hydrochloride. A mixture of 3,5-difluoropicolinonitrile (1.4 g, 10 mmol), conc. HCl (12 ml) and 10% Pd—C (200 mg) in 1:1 ethanol/tetrahydrofuran was shaken under a hydrogen atmosphere (50 psi) for 5 h. The reaction mixture was filtered and the ethanol removed in vacuo. The remaining solution was lyophilized to afford an off-white solid (2.16 g, 100% yield). LCMS (M+H) calcd for C$_6$H$_7$F$_2$N$_2$: 145.06; found: 145.12.

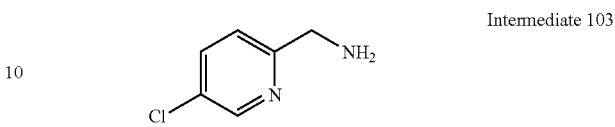

Intermediate 103

(5-Chloropyridin-2-yl)methanamine. A solution of 5-chloropicolinonitrile (3.8 g, 27.43 mmol), conc. HCl (3 mL) and 10% Pd—C (1.0 g) in ethanol (100 mL) was shaken under a hydrogen atmosphere (40 psi) for 2 h. The reaction mixture was filtered, concentrated and the resulting residue taken up in satd NaHCO$_3$ (50 mL) and extracted with CH$_2$Cl$_2$ (4×25 mL). The combined CH$_2$Cl$_2$ layers were dried (Na$_2$SO$_4$), filtered and concentrated to give the title compound as a yellow oil (2.0 g, 51% yield). LCMS (M+H) calcd for C$_6$H$_8$ClN$_2$: 143.04; found: 143.07. $^1$HNMR (500 MHz, CDCl$_3$) δ ppm: 8.56-8.51 (1H, br d), 7.66-7.60 (1H, m), 7.28-7.14 (1H, m), 3.97 (2H, s), 1.72 (2H, s).

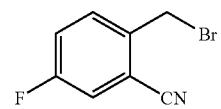

Intermediate 104

2-(Bromomethyl)-5-fluorobenzonitrile. N$_2$ was passed through a mixture of 5-fluoro-2-methylbenzonitrile (28.51 g, 211 mmol), NBS (41.31 g, 232 mmol) and AIBN (2.5 g, 15 mmol) in CCl$_4$ (845 mL) for 10 min after which the reaction was heated at reflux for 8 h. After standing at room temperature overnight, the reaction mixture was filtered and the filter cake washed with CCl$_4$ (500 mL). The combined filtrate was evaporated to give a yellow oil. Flash chromatography (SiO$_2$) using 5-25% ethyl acetate/Hexanes as eluent afforded the title compound (29.74 g, 66% yield) as a pale yellow oil. $^1$H NMR (500 MHz, CDCl$_3$) δ: 7.55 (1H, dd, J=8.6, 5.2 Hz), 7.37 (1H, dd, J=7.9, 2.8 Hz), 7.32-7.28 (1H, m), 4.61 (2H, s).

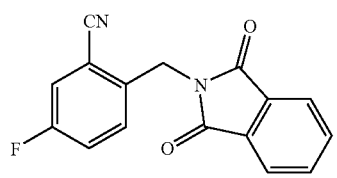

Intermediate 105

2-((1,3-Dioxoisoindolin-2-yl)methyl)-5-fluorobenzonitrile. To a stirred solution of intermediate 104, 2-(bromomethyl)-5-fluorobenzonitrile (29.72 g, 139 mmol) and phthalimide (32.69 g, 222 mmol) in dimethylformamide (300 mL) was added Cs$_2$CO$_3$ (67.87 g, 208 mmol). After stirring vigorously for 1 h, the reaction mixture was poured into water (1.2 L). The precipitated product was filtered, washed with water (600 mL) and methanol (150 mL) to give a white solid. The solid was taken up into 1L of water/methanol (2:1) to which was added K$_2$CO$_3$ (12 g) and the mixture stirred at 40° C. After 30 min., the mixture was cooled and filtered. The filter cake was washed with water (500 mL), and dried under vacuum to afford the title compound (38.91 g, 94% yield) as a white powder. $^1$H NMR (500 MHz, CDCl$_3$) δ: 7.89 (2H, dd, J=5.5, 3.1 HZ), 7.76 (5.5, 3.1 Hz), 7.41 (1H, dd, J=8.6, 5.2 Hz), 7.38 (1H, dd, J=7.9, 2.8 Hz), 7.24 (1H, td, J=8.2, 2.8 Hz), 5.06 (2H, s). LCMS (M+H) calcd for C$_{16}$H$_{10}$FN$_2$O$_2$: 281.07; found: 281.15.

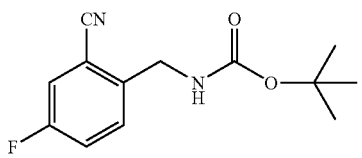

Intermediate 106 tert-Butyl 2-cyano-4-fluorobenzylcarbamate. A suspension of intermediate 105, 2-((1,3-dioxoisoindolin-2-yl)methyl)-5-fluorobenzonitrile, (5.6 g, 20 mmol) in dimethylformamide (20 mL) was warmed until it was dissolved. To this was added tetrahydrofuran (100 mL) and the mixture placed in a pre-heated (70° C.) oil bath. Hydrazine monohydrate was added to this and the reaction stirred for 8 h. The resulting white slurry was left at ambient temperature overnight. To this slurry was added di-tert-butyldicarbonate (6.55 g, 30 mmol) and the mixture stirred for 6 h at room temperature. The reaction mixture was diluted with ether (100 mL), filtered and the filtrate treated with activated carbon at 40° C. After filtration and concentration the crude product was purified by flash chromatography, using 20-30% ethyl acetate/Hexanes as eluent, to provide the title compound (2.88 g, 58% yield) as a light yellow powder. $^1$H NMR (500 MHz, CDCl$_3$) δ: 9.46 (1H, br s), 7.61 (1H, dd, J=7.9, 2.1 Hz), 7.34 (1H, dd, J=8.2, 4.6 Hz), 7.22 (1H, td, J=8.6, 2.4 Hz), 4.71 (2H, s), 1.59 (9H, s). LCMS (M+H) calcd for C$_{13}$H$_{16}$FN$_2$O$_2$: 251.12; found: 251.22.

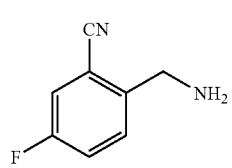

Intermediate 107

2-(Aminomethyl)-5-fluorobenzonitrile trifluoroacetic acid salt. A round-bottom flask was charged with intermediate 106, tert-butyl 2-cyano-4-fluorobenzylcarbamate, (1.9 g, 7.591 mmol) then treated with trifluoroacetic acid (20 ml) at room temperature. After 1 h, the reaction mixture was concentrated to give a yellow oil which was dissolved in CHCl$_3$ and re-concentrated to afford the title compound (2.01 g, 100% yield) as a pale yellow solid. LCMS (M+H) calcd for C$_8$H$_8$FN$_2$: 151.07; found: 151.08.

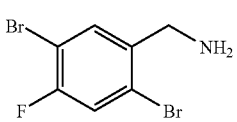

Intermediate 108

(2,5-Dibromo-4-fluorophenyl)methanamine. A solution of 2,5-dibromo-4-fluorobenzyl bromide (0.350 g, 1 mmol) in 7M NH$_3$/MeOH was heated in a sealed tube at 100° C. for 2 h. The reaction mixture was cooled and concentrated to give a white solid which was dissolved in CH$_2$Cl$_2$ and treated with Et$_3$N (1 mL) then concentrated. The resulting residue was triturated with ethyl acetate (25 mL), filtered and concentrated to give the title compound (0.291 g) as a pale yellow oil. HRMS (M+H) calcd for C$_7$H$_7$Br$_2$FN: 283.94; found: 283.93.

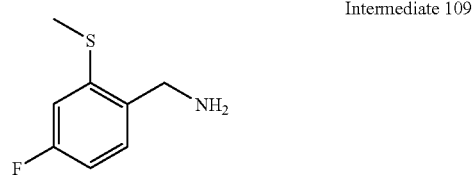

Intermediate 109

4-Fluoro-2-methylsulfanyl-benzylamine. Under N$_2$, 4-fluoro-2-(methylthio)benzonitrile (1.67 g, 0.1 mol) was dissolved in 20 mL tetrahydrofuran and treated with 10 mL 2M BH$_3$.Me$_2$S. This was heated at 60° C. for 2 hrs. Heating was discontinued and 5 mL MeOH was cautiously added, followed by the cautious addition of 4 mL 6N HCl. Additional H$_2$O (20 mL) was added followed by ethyl acetate. The layers were separated. The aqueous layer was made basic with 1N NaOH and extracted with CH$_2$Cl$_2$. The extracts were dried (MgSO$_4$), filtered, concentrated and dried in vacuo to give 1.3 g of the title compound as a solid (Yield=76%). $^1$H NMR (500 MHz, CDCl$_3$) δ ppm: 7.20-7.31 (1 H, m) 6.90 (1 H, dd, J=2.4 Hz) 6.75-6.86 (1 H, m) 3.86 (2 H, s) 2.47 (3 H, s); LC/MS m/z 172.

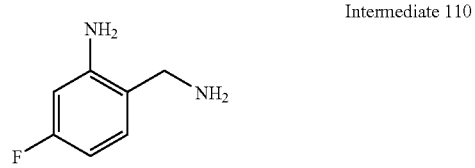

Intermediate 110

2-(Aminomethyl)-5-fluorobenzenamine hydrochloride. 2-Amino-4-fluorobenzonitrile (Fritz Hunziker et al. Eur. J. Med. Chem. 1981, 16, 391) (0.300 g, 1.68 mmol), was dissolved in acetic anhydride (5 mL) and the solution was stirred at 23° C. for 18 h. An additional portion of acetic anhydride (3 mL) was added to dissolve the N-(2-cyano-5-fluorophenyl)acetamide. Then palladium (10% on charcoal) (25 mg) was added and the mixture was agitated under H$_2$ (34 psi) for 72 h. The Pd—C was removed by filtration on Celite and the filtrate concentrated in vacuo to afford a bis-acetamide: LCMS (M+H)$^+$ m/z 225. This was heated at reflux with HCl (6N, 10 mL) for 30 min. The acid was removed under reduced pressure to give a solid which was crystallized from MeOH-ether to afford the title compound (0.120 g, 51% yield). $^1$H NMR (400 MHz, MeOD) δ ppm: 7.51 (1H, m), 6.96(2H, m), 4.20 (2H, s).

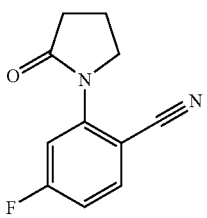

Intermediate 111

4-Fluoro-2-(2-oxopyrrolidin-1-yl)benzonitrile. A 48 mL pressure vessel containing 2-bromo-4-fluorobenzonitrile (1.00 g, 5.00 mmol), 2-pyrrolidinone (0.46 mL, 6.00 mmol), $Cs_2CO_3$ (2.28 g, 7.0 mmol) and 9,9-dimethyl-4,5-bis(diphenylphosphino)xanthene (xantphos) (0.231 g, 0.40 mmol) in dioxane (6 mL) was degassed with argon for 15 min. $Pd_2dba_3$ was introduced and the reaction mixture heated at 105° C. for 48 h. The mixture was cooled, diluted with ethyl acetate or dioxane, and then filtered through Celite. The resulting mixture was concentrated in vacuo and subjected to column chromatography on silica gel with hexanes:ethyl acetate (3:7) gradient as the eluent to afford the title compound as a white solid (0.887 g, 87% yield): $^1$H NMR (400 MHz, $CDCl_3$) δ ppm: 7.69 (1H, dd, J=5.8, 8.6 Hz), 7.22 (1H, dd, J=2.5, 9.6 Hz), 7.07 (1H, ddd, J=2.5, 7.6, 8.6 Hz), 3.96 (2H, t, J=7.0 Hz), 2.62 (2H, t, J=8.1 Hz), 2.30-2.22 (2H, m); LCMS ($^+$ESI, M+H$^+$) m/z 205.

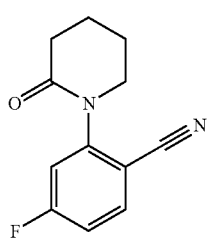

Intermediate 112

4-Fluoro-2-(2-oxopiperidin-1-yl)benzonitrile. The title compound can be prepared according to the procedure provided for intermediate 111 $^1$H NMR (400 MHz, $CDCl_3$) δ ppm: 7.71 (1H, dd, J=5.7, 8.7 Hz), 7.14-7.06 (1H, m), 7.08 (1H, dd, J=2.4, 9.0 Hz), 3.65 (2H, t, J=5.7 Hz), 2.60 (2H, t, J=6.3 Hz), 2.05-1.95 (4H, m); LCMS ($^+$ESI, M+H$^+$) m/z 219.

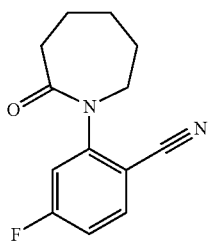

Intermediate 113

4-Fluoro-2-(2-oxoazepan-1-yl)benzonitrile. The title compound can be prepared according to the procedure provided for intermediate 111. $^1$H NMR (400 MHz, $CDCl_3$) δ ppm: 7.68 (1H, dd, J=5.8, 8.6 Hz), 7.08 (1H, ddd, J=2.5, 7.6, 8.6 Hz), 7.01 (1H, dd, J=2.5, 9.0 Hz), 3.77-3.76 (2H, m), 2.75-2.72 (2H, m), 1.91-1.86 (6H, m); LCMS ($^+$ESI, M+H$^+$) m/z 233.

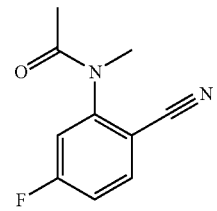

Intermediate 114

N-(2-Cyano-5-fluorophenyl)-N-methylacetamide. The title compound can be prepared according to the procedure provided for intermediate 111 $^1$H NMR (400 MHz, $CDCl_3$) δ ppm: 7.79-7.75 (1H, m), 7.32-7.19 (1H, m), 7.10-7.07 (1H, m), 3.42 (0.6H, brs), 3.30 (2.4H, s), 2.32 (0.6H, brs), 1.91 (2.4H, s); LCMS ($^+$ESI, M+H$^+$) m/z 193; HPLC: 94% (220 nm).

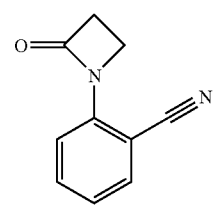

Intermediate 115

2-(2-Oxoazetidin-1-yl)benzonitrile. The title compound can be prepared according to the procedure provided for intermediate 111. $^1$H NMR (400 MHz, DMSO-$d_6$) δ ppm: 8.02 (1H, d, J=8.4 Hz), 7.76 (1H, dd, J=1.5, 7.8 Hz), 7.69-7.65 (1H, m), 7.23 (1H, s), 4.04 (2H, t, J=4.8 Hz), 3.16 (2H, t, J=4.8 Hz). LCMS ($^+$ESI, M+H$^+$) m/z 173.

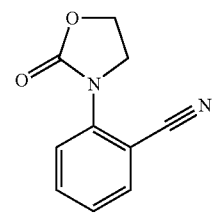

Intermediate 116

2-(2-Oxooxazolidin-3-yl)benzonitrile. The title compound can be prepared according to the procedure provided for intermediate 111. $^1$H NMR (400 MHz, $CDCl_3$) δ ppm: 7.71 (1H, dd, J=1.5, 7.6 Hz), 7.68-7.63 (1H, m), 7.58 (1H, d, J=7.6 Hz), 7.38 (1H, dt, J=1.3, 7.6 Hz), 4.57 (2H, t, J=7.8 Hz), 4.21 (2H, t, J=7.8 Hz); LCMS ($^+$ESI, M+H$^+$) m/z 189.

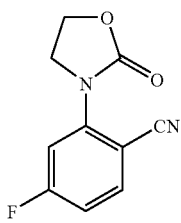

Intermediate 117

4-Fluoro-2-(2-oxooxazolidin-3-yl)benzonitrile. A 48 mL pressure vessel containing 2-bromo-4-fluorobenzonitrile (1.00 g, 5.00 mmol), 2-oxazolidone (0.390 g, 4.50 mmol), $K_2CO_3$ (0.970 g, 7.0 mmol) and xantphos (0.231 g, 0.40 mmol) in dioxane (10 mL) was degassed with argon for 15 min. $Pd_2dba_3$ (0.140 g, 0.15 mmol) was introduced and then the reaction mixture was heated at 70° C. for 18 h. The mixture was cooled, diluted with dioxane, and then filtered through Celite. The resulting mixture was concentrated in vacuo and subjected to column chromatography on silica gel with hexanes:ethyl acetate (1:1) to (3:7) gradient as the eluent to afford the title compound as a white solid (0.460 g, 50% yield): $^1$H NMR (400 MHz, $CDCl_3$) δ ppm: 7.73 (1H, dd, J=5.8, 8.6 Hz), 7.43 (1H, dd, J=2.5, 9.6 Hz), 7.11 (1H, ddd, J=2.5, 7.5, 8.7 Hz), 4.60 (2H, t, J=7.1 Hz), 4.29 (2H, t, J=7.1 HJz); LCMS ($^+$ESI, M+H$^+$) m/z 207.

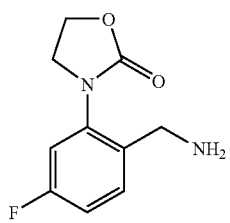

Intermediate 118

3-(2-(Aminomethyl)-5-fluorophenyl)oxazolidin-2-one hydrochloride. $^1$H NMR (400 MHz, MeOD) δ ppm: 7.73 (1H, dd, J=6.0, 8.6 Hz), 7.43 (1H, dd, J=2.5, 9.5 Hz), 7.11 (1H, ddd, J=2.5, 7.5, 8.6 Hz), 4.64 (2H, t, J=7.7 Hz), 4.17 (2H, t, J=7.7 Hz), 4.14 (2H, s); LCMS ($^+$ESI, M+H$^+$) m/z 211.

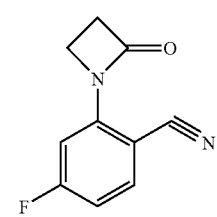

Intermediate 119

4-Fluoro-2-(2-oxoazetidin-1-yl)benzonitrile. The title compound can be prepared according to the procedure provided for intermediate 117 $^1$H NMR (400 MHz, $CDCl_3$) δ ppm: 8.06 (1H, dd, J=10.7, 2.6 Hz), 7.58 (1H, dd, J=8.6, 6.3 Hz), 7.87 (1H, td, J8.6, 2.5 Hz), 4.25 (2H, t, J=5.0 Hz), 3.26 (2H, t, J=5.0 Hz); LCMS ($^+$ESI, M+H$^+$) m/z 191.

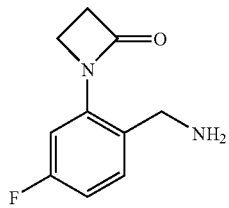

Intermediate 120

1-(2-(Aminomethyl)-5-fluorophenyl)azetidin-2-one hydrochloride. $^1$H NMR (400 MHz, $DMSO/D_2O$) δ ppm: 7.54 (1H, dd, (t), J=8.6 Hz), 7.25 (1H, dd, J=10.8, 2.5 Hz), 7.17 (1H, td, J=8.6, 2.5 Hz), 4.12 (2H, s), 3.79 (2H, t, J=4.6 Hz), 3.09 (2H, t, J=4.6 Hz); LCMS ($^+$ESI, M+H$^+$) m/z 195.

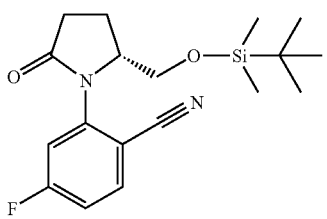

Intermediate 121

(R)-2-(2-((tert-Butyldimethylsilyloxy)methyl)-5-oxopyrrolidin-1-yl)-4-fluorobenzonitrile. The title compound can be prepared according to the procedure provided for intermediate 111. $^1$H NMR (400 MHz, $CDCl_3$) δ ppm: 7.68 (1H, dd, J=5.8, 8.8 Hz), 7.19 (1H, dd, J=2.5, 9.1 Hz), 7.11-7.07 (1H, m), 4.46-4.42 (1H, m). 3.55(2H, d, J=3.3 Hz), 2.72-2.52 (2H, m), 2.43-2.33 (1H, m), 2.09-2.01 (1H, m), 0.81 (9H, s), −0.04 (3H, s), −0.07 (3H, s); LCMS ($^+$ESI, M+H$^+$) m/z 349.

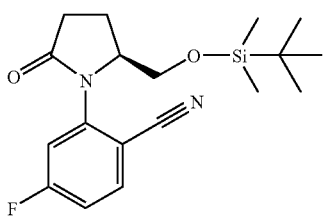

Intermediate 122

(S)-2-(2-((tert-Butyldimethylsilyloxy)methyl)-5-oxopyrrolidin-1-yl)-4-fluorobenzonitrile. The title compound can be prepared according to the procedure provided for intermediate 111. $^1$H NMR (400 MHz, $CDCl_3$) δ ppm: 7.68 (1 H, dd, J=5.8, 8.6 Hz), 7.19 (1H, dd, J=2.5, 9.4 Hz), 7.11-7.07 (1H, m), 4.46-4.43 (1H, m), 3.55(2H, d, J=3.3 Hz), 2.72-2.52 (2H, m), 2.43-2.33 (1H, m), 2.09-2.01 (1H, m), 0.81 (9H, s), −0.04 (3H, s), −0.07 (3H, s); LCMS ($^+$ESI, M+H$^+$) m/z 349.

Intermediate 123

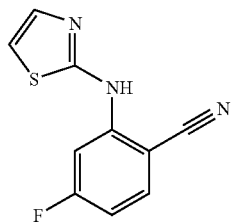

4-Fluoro-2-(thiazol-2-ylamino)benzonitrile. The title compound can be prepared according to the procedure provided for intermediate 111. $^1$H NMR (400 MHz, DMSO-d$_6$) δ ppm: 9.21 (1H, s), 8.39-8.35 (1H, m), 7.97 (1H, d, J=5.0 Hz), 7.23-7.13 (3H, m); LCMS ($^+$ESI, M+H$^+$) m/z 220.

Intermediate 124

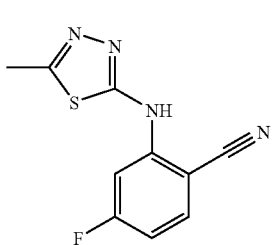

4-Fluoro-2-(5-methyl-1,3,4-thiadiazol-2-ylamino)benzonitrile. The title compound can be prepared according to the procedure provided for intermediate 111. $^1$H NMR (400 MHz, DMSO-d$_6$) δ ppm: 8.30 (1H, dd, J=6.5, 8.8 Hz), 7.96 (1H, s), 7.26-7.19 (2H, m), 2.64 (3H, s); LCMS ($^+$ESI, M+H$^+$) m/z 235.

Intermediate 125

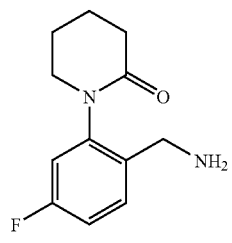

1-(2-(Aminomethyl)-5-fluorophenyl)piperidin-2-one hydrochloride salt. To a stirred solution of intermediate 112, 4-fluoro-2-(2-oxopiperidin-1-yl)benzonitrile (150 mg, 0.69 mmol) in H$_2$O (10 mL) was added ethanol (10 mL) 10% palladium on charcoal (50 mg) and 1N HCl (2.1 mL, 20.6 mmol). The reaction was shaken in a Parr system under H$_2$ (40 psi) for 1 h. Then the Pd/C catalyst was removed by filtration on Celite and the filtrate was concentrated in vacuo to yield a solid. Toluene (2×50 mL) was added to the solid and the solution was evaporated in vacuo. LCMS (M+H)$^+$ m/z 170.

Intermediate 126

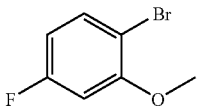

1-Bromo-4-fluoro-2-methoxybenzene. To a mixture of 2-bromo-5-fluorophenol (10 g, 50.8 mmol) and iodomethane (11.2 g, 78.7 mmol) in dimethylformamide (100 mL) was added potassium carbonate (10.9 g, 79 mmol) and the mixture stirred at room temperature for 3 hrs. The mixture was diluted with water (100 mL) and extracted with ether (50 mL×3). The combined extracts were washed with brine, dried over anhydrous magnesium sulfate, and concentrated in vacuo to obtain 11.3 g of 1-bromo-4-fluoro-2-methoxybenzene as an amber colored oil.

Intermediate 127

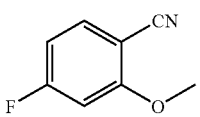

4-Fluoro-2-methoxybenzonitrile. To a solution of intermediate 126, 1-bromo-4-fluoro-2-methoxybenzene (9.0 g) in N-methylpyrrolidone (100 mL, Sure Seal; Aldrich) was added CuCN (6.6 g, 73.7 mmol, 1.8 eq.; Aldrich), and the mixture stirred at 180° C. under anhydrous nitrogen for 5.5 hrs. After cooling, 14% aqueous NH$_4$OH (330 mL) was added and stirring continued for 45 min at room temperature. The mixture was extracted with ether (100 mL×3), and the combined extracts washed sequentially with dilute aqueous NH$_4$OH, dilute HCl and brine, then dried (MgSO$_4$), and concentrated to provide the title compound (5.2 g, Yield 85% in 2 steps) as a white solid: $^1$H NMR (CDCl$_3$, 500 MHz) δ ppm: 3.91 (3H, s, OMe), 6.69 (1H, dd, J=2.3 Hz, J=10.5 Hz, Ar—H), 6.72 (1H, dt, J=2.5 Hz, J=J=8.0 Hz, Ar—H), 7.55 (1H, dd, J=6.5 Hz, J=8.5 Hz, Ar—H); $^{13}$C NMR (CDCl$_3$, 125.8 Hz) δ ppm: 56.49, 98.16, 100.06, 100.27, 108.31, 108.50, 115.83 135.37, 135.46, 163.25, 163.34 165.47, 167.50. An analytical sample was obtained by trituration with ether: Anal. calcd for C$_8$H$_6$FNO: C, 63.57; H, 4.00; N, 9.26; found: C, 63.36; H, 3.91; N, 9.16.

Intermediate 128

4-Fluoro-2-methoxybenzylamine hydrochloride. To a mixture of intermediate 127, 4-fluoro-2-methoxybenzonitrile, (800 mg, 5.3 mmol) and conc.HCl (0.53 mL, 6.36 mmol, 1.2 eq.) in ethanol (20 mL) was added 10% Pd—C (100 mg; Aldrich), and the mixture hydrogenated at 1 atm hydrogen for 15 hrs at room temperature. To this mixture was added an additional amount of conc.HCl (1 mL) and 10% Pd—C (200 mg) and the reaction allowed to continue for another 40 hrs. The mixture was filtered through Celite and the filtrate concentrated in vacuo to dryness. The residue was triturated with ether to provide the title compound (895 mg, Yield 88%) as a white powder: $^1$H NMR (CDCl$_3$, 500 MHz) δ ppm: 3.84 (3H, s, OMe), 3.91 (2H, d, J=5.5 Hz, N—CH$_2$), 6.81 (1H, dt, J=2.5 Hz, J=8.5 Hz, Ar—H), 6.99 (1H, dd, J=2.5 Hz, J=11.3 Hz, Ar—H), 7.47 (1H, dd, J=7 Hz, J=8.5 Hz, Ar—H); $^{13}$C NMR (CDCl$_3$, 125.8 Hz) δ ppm: 36.76, 56.03, 99.30, 99.51 106.28, 106.45, 117.93, 117.95, 131.60, 131.69, 158.56, 158.64, 162.28, 164.22. HRMS (ESI) calcd for C$_8$H$_{11}$FNO (M+H) 156.0825, found 156.0830.

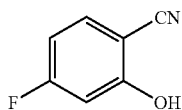

Intermediate 129

4-Fluoro-2-hydroxybenzonitrile. A mixture of intermediate 127, 4-fluoro-2-methoxybenzonitrile, (4.53 g, 30 mmol;) and AlCl$_3$ (5.0 g, 37.6 mmol; Aldrich) in anhydrous toluene (30 mL) was stirred at approximately 130° C. for 18 hrs. After cooling, ice water (~50 mL)was added and the resulting mixture extracted with ether (20 mL×2). The combined extracts were washed sequentially with water and brine, then dried (MgSO$_4$), and concentrated in vacuo to provide the title compound (3.90 g, 28.5 mmol, Yield 95%) as a white solid: $^1$H NMR (DMSO-d6, 300 MHz) δ ppm: 6.74-6.84 (2H, m, Ar-Hs), 7.71 (1H, dd, J=7 Hz, J=8.5 Hz, Ar—H), 11.64 (1H, s, OH); $^{13}$C NMR (DMSO-d6, 75.5 Hz) δ ppm: 95.13 102.45, 102.78, 106.53, 106.83 115.53, 134.68, 134.84, 161.41, 161.58, 163.00, 166.35. HRMS (ESI-) calcd for C$_7$H$_3$NOF (M–H) 136.0199, found 136.0199.

Intermediate 130

4-Fluoro-2-(2-morpholino-2-oxoethoxy)benzonitrile. To a solution of intermediate 129, 4-fluoro-2-hydroxybenzonitrile, (685 mg, 5 mmol) in dimethylformamide (8 mL, Sure Seal; Aldrich) was added NaH (200 mg, 5 mmol; 60% oil dispersion; Aldrich), and the mixture stirred for 5 min under an anhydrous nitrogen atmosphere. To this was added 4-(2-chloroacetyl)morpholine (900 mg, 5.5 mmol, 1.1 eq.; Avocado Organics), and stirring continued at room temperature for 21 hrs. The reaction was quenched by careful addition of water (30 mL). The resulting mixture was extracted with CH$_2$Cl$_2$ (25 mL×2). The combined extracts were washed with brine, dried (MgSO$_4$) and concentrated. The residue was triturated to obtain 1.10 g (4.17 mmol, Yield 83%) of the title compound as a white solid: $^1$H NMR (CDCl$_3$, 500 MHz) δ ppm: 3.63 (2H, t, J=4 Hz, NCH$_2$), 3.67 (1H, m, OCH), 3.72 (1H, m, OCH), 4.86 (2H, s, OCH$_2$), 6.80-6.86 (2H, m, Ar-Hs), 7.61 (1H, dd, J=8.5 Hz, 6.1 Hz, Ar—H); $^{13}$C NMR (CDCl$_3$, 125.77 Hz) δ ppm: 42.63, 46.04, 66.80, 68.33, 98.45, 98.47, 101.57, 101.79, 109.56, 109.74, 115.42, 135.48, 135.57, 161.26, 161.35, 114.79, 165.23, 167.28. HRMS calcd for C$_{13}$H$_{14}$N$_2$O$_3$F (M+H) 265.0988, found 265.0998.

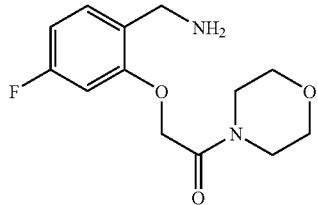

Intermediate 131

2-(2-(Aminomethyl)-5-fluorophenoxy)-1-morpholinoethanone hydrochloride. A solution of intermediate 130, 4-fluoro-2-(2-morpholino-2-oxoethoxy)benzonitrile, (500 mg, 1.89 mmol) in warm ethanol (30 mL) and ethyl acetate (30 mL) was mixed with conc.HCl (0.32 mL, 3.78 mmol, 2 eq.). To this was added 10% Pd—C (100 mg; Aldrich), and the mixture was hydrogenated at 1 atm of hydrogen for 20 hrs at room temperature. To this mixture was added an additional amount of 10% Pd—C (50 mg) and stirring continued for another 7 hrs. The mixture was filtered through Celite and the filtrate concentrated in vacuo to dryness. The residue was triturated with ethyl acetate, then with ethanol to obtain the title compound (168 mg, Yield 29%) as an off-white powder: $^1$H NMR (CD$_3$OD, 500 MHz) δ ppm: 3.55 (2H, t, J=5 Hz, NCH$_2$), 3.62 (2H, t, J=5 Hz, NCH$_2$), 3.70 (2H, t, J=5 Hz, OCH$_2$), 3.75 (2H, t, J=5 Hz, OCH$_2$), 4.17 (2H, s, NCH$_2$), 5.17 (2H, s, OCH$_2$), 6.82 (1H, dt, J=2.5, 8.5 Hz, Ar—H), 7.05 (1H, dd, J=2.5, 10.5 Hz, Ar—H), 7.43 (1H, dd, J=6.5, 8.5 Hz, Ar—H); $^{13}$C NMR (CD$_3$OD, 125.77 Hz) δ ppm: 39.40, 42.49, 44.97, 66.11, 66.46, 66.59, 101.38, 101.59, 108.40, 108.57, 118.40, 132.53, 132.62, 158.43, 158.52, 63.87, 165.83, 168.27. HRMS (ESI) calcd for C$_{13}$H$_{18}$N$_2$O$_3$F (M+H) 269.1301, found 269.1301.

Intermediate 132

Dimethyl-carbamic acid 2-cyano-5-fluoro-phenyl ester. Under N$_2$, a stirred solution of intermediate 129, 4-fluoro-2-hydroxybenzonitrile (685 mg, 5.00 mmol), dimethylcarbamoyl chloride, and triethylamine (606 mg, 6 mmol) in dichloroethane (10 mL) was heated at reflux for 20 hrs. The cooled mixture was diluted with dichloroethane (10 mL) washed with water, and brine. The organic layer was separated, dried (Na$_2$SO$_4$), concentrated, and the residue purified by column chromatography (SiO$_2$, 5% ethyl acetate-CH$_2$Cl$_2$) to provide 700 mg (Yield 67%) of the title compound as a white crystalline solid: $^1$H NMR (CDCl$_3$, 500 MHz) δ ppm: 3.03 (3H, s, NMe), 3.15 (3H, s, NMe), 6.99 (1H, dt, J=2.5 Hz, 8.5 Hz, Ar—H), 7.23 (1H, dd, J=2.5 Hz, 9.5 Hz, Ar—H), 7.61 (1H, dd, J=9 Hz, 6 Hz, Ar—H); $^{13}$C NMR (CDCl$_3$, 125.77 Hz) δ ppm: 36.76, 37.06, 102.84, 102.86, 111.59, 111.79, 113.24, 113.42, 114.99, 134.36, 134.45, 152.54, 155.06, 155.16, 164.26, 166.31. HRMS (ESI) calcd for C$_{10}$H$_{10}$N$_2$O$_2$F (M+H) 209.0726, found 209.0722.

Intermediate 133

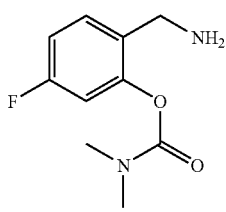

Dimethyl-carbamic acid 2-aminomethyl-5-fluoro-phenyl ester hydrochloride. To a solution of intermediate 132, dimethyl-carbamic acid 2-cyano-5-fluoro-phenyl ester, (340 mg, 1.63 mmol) in ethyl acetate (20 mL) and ethanol (20 mL), was added conc.HCl (0.4 mL) and 10% Pd—C (100 mg) and the mixture hydrogenated in a Parr Shaker at 55 psi of hydrogen for 20 hrs. The reaction mixture was filtered through Celite, and the filtrate concentrated in vacuo to give an oil which was partitioned between ethyl acetate (10 mL) and water (10 mL). After separation, the aqueous phase was washed with additional ethyl acetate (5 mL). The combined extracts were concentrated in vacuo to dryness. The residual oil was triturated with ether to provide 145 mg (Yield 38%) of the title compound, as a tan powder: $^1$H NMR (CD$_3$OD, 500 MHz) δ ppm: 3.06 (3H, s, NMe), 3.21 (3H, s, NMe), 4.11 (2H, s, NCH$_2$), 7.13 (2H, m, Ar-Hs), 7.60 (1H, m, Ar—H); $^{13}$C NMR (CD$_3$OD, 125.77 Hz) δ ppm: 36.03, 36.25 37.58, 110.79, 110.99, 113.26, 113.43, 122.32, 132.18, 132.25, 151.55, 154.72, 162.69, 164.67. HRMS (ESI) calcd for C$_{10}$H$_{13}$N$_2$O$_2$F (M+H) 213.1039, found 213.1039.

Intermediate 134

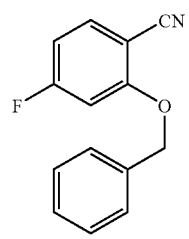

2-(Benzyloxy)-4-fluorobenzonitrile. Benzyl alcohol (13 mL, 125 mmol) was slowly added to a stirred suspension of NaH (95%, 2.86 g, 113 mmol) in toluene (200 mL) at room temperature. After 30 min, 2,4-difluorobenzonitrile (15.3 g, 110 mmol; Aldrich) was added all at once and stirring continued overnight (18 h). After this, the reaction mixture was washed with water (2×25 mL) and brine (25 ml). The organic layer was dried (Na$_2$SO$_4$), filtered and concentrated to give a white slurry which was triturated with hexanes and filtered to afford the title compound as a white solid (20.34 g, 81% yield). $^1$H NMR (500 MHz, CDCl$_3$): 7.59-7.55 (1H, m), 7.45-7.34 (5H, m), 6.75-6.71 (2H, m), 5.19 (2H, s); $^{13}$C NMR (125.76 MHz, DMSO-d6) δ ppm: 71.16, 98.75, 101.54, 101.75, 108.66, 108.84, 115.83, 127.16, 128.58, 128.94, 135.03, 135.44, 135.54, 162.22, 162.31, 165.26, 167.29. LCMS calcd for C$_{14}$H$_{11}$FNO: 228.2; found: 228.0.

Intermediate 135

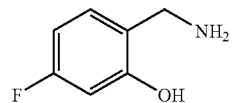

2-Hydroxy-4-fluoro-benzylamine hydrochloride. A solution of intermediate 134, 2-(benzyloxy)-4-fluorobenzonitrile, (9.03 g, 39.7 mmol) in ethanol (100 mL) and ethyl acetate (100 mL) was stirred with 10% palladium on carbon (1.67 g,) and concentrated hydrochloric acid (12 mL, 144 mmol) under a hydrogen atmosphere (60 psi) for four days. The catalyst was removed by filtration through Celite, and the filtrate was concentrated. The crude product was triturated with ether and the resulting solid collected by filtration to give the title compound (5.24 g, 74% yield) as a pale orange solid. $^1$H NMR (500 MHz, DMSO-D6) δ ppm: 10.81 (1 H, s), 8.18 (3 H, s), 7.36 (1 H, t, J=7.3 Hz), 6.79 (1 H, dd, J=10.8, 2.6 Hz), 6.66 (1 H, dt, J=8.5, 2.3 Hz), 3.90 (2 H, d, J=5.2 Hz).

Intermediate 136

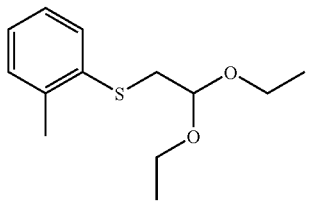

(2,2-Diethoxyethyl)(o-tolyl)sulfane. In ethanol (50 mL) was dissolved sodium metal (1.6 g, 66 mmol) at 23° C. 2-Methylbenzenethiol (8.1 mL, 68 mmol) was slowly added to this solution, followed by bromoacetaldehyde diethylacetal (9.50 mL, 63 mmol). The reaction mixture was stirred at reflux for 18 h. The solvent was then evaporated in vacuo and the residue was washed with H$_2$O (100 mL) and extracted with ether (100 mL). The organic solution was dried (MgSO$_4$), concentrated in vacuo and purified by distillation to afford the title compound (13.48 g, 82% yield): $^1$H NMR (400 MHz, CDCl$_3$) δ ppm: 7.33 (1H, d, J=7.9 Hz), 7.16-7.08 (3H, m), 4.65 (1H, t, J=5.6 Hz), 3.66 (2H, q, J=7.0 Hz), 3.55 (2H, q, J=7.0 Hz), 3.09 (2H, d, J=5.6 Hz), 2.38 (3H, s), 1.20 (6H, t, J=7.0 Hz). LCMS (M+H)$^+$ m/z 241 (t=2.65min.).

Intermediate 137

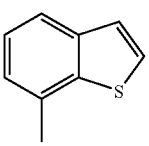

7-Methylbenzo[b]thiophene. To a solution of intermediate 136, (2,2-diethoxyethyl)(o-tolyl)sulfane (0.58 g, 2.41 mmol) in chlorobenzene (20 mL) was added polyphosphoric acid. The reaction mixture was stirred at reflux for 18 h. Water (100 mL) was then added and the organic material was extracted with CH$_2$Cl$_2$ (2×50 mL). The organic solution was dried (MgSO$_4$) and concentrated in vacuo to afford 335 mg (94% yield) of the title compound: $^1$H NMR (400 MHz, CDCl$_3$) δ: 7.68 (1H, d, J=7.8 Hz), 7.43 (1H, d, J=5.4 Hz), 7.36 (1H, d, J=5.4 Hz), 7.30 (1H, dd, J=7.8, 7.1 Hz), 7.14 (1H, d, J=7.1 Hz), 2.58 (3H, s); LCMS (M+H)⁺ m/z 148.

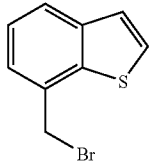

Intermediate 138

7-(Bromomethyl)benzo[b]thiophene. To a solution of intermediate 137, 7-methylbenzo[b]thiophene (1.0 g, 6.5 mmol) in CCl₄ (20 mL) was added benzoyl peroxide (1.1 g, 4.54 mmol) followed by portionwise addition of NBS (1.15 g, 6.5 mmol). The reaction mixture stirred at reflux while irradiating with a 250 W lamp. The reaction mixture was stirred at reflux for 3 h. The solution was cooled, filtered and the solvent evaporated in vacuo. The residue was subjected to column chromatography on silica gel with hexanes as the eluent to afford the title compound (0.570 g, 33% yield): ¹H NMR (400 MHz, CDCl₃) δ: 7.80 (1H, dd, J=7.8, 1.7 Hz), 7.49 (1H, d, J=5.4 Hz), 7.40-7.33 (3H, m), 4.78 (2H, s). LCMS (M+H)⁺ m/z 209.

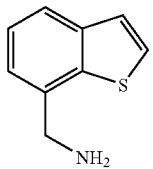

Intermediate 139

Benzo[b]thiophen-7-ylmethanamine hydrochloride. To intermediate 138, 7-(bromomethyl)benzo[b]thiophene (0.20 g, 0.96 mmol) was added a methanolic solution saturated with ammonia (30 mL). The reaction mixture was heated in a steal bomb at 70° C. for 18 h. The solvent was evaporated in vacuo and the residue was dissolved in MeOH (10 mL). HCl (1M in ethanol, 1 mL) was added to the solution and the solvents were removed in vacuo to afford the title compound (0.177 g, 99% yield); LCMS (M+H)⁺ m/z 164.

Intermediates 140-148

The synthesis of intermediates 140-148 provides representative procedures for the synthesis of other compounds in the invention.

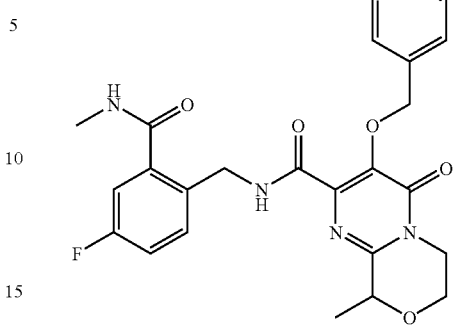

Intermediate 140

N-{4-Fluoro-2-(methylcarbamoyl)benzyl}-3-benzyloxy-9-methyl-4-oxo-4,6,7,9-tetrahydropyrimido[2,1-c][1,4]oxazine-2-carboxamide. A mixture of intermediate 27, 3-benzyloxy-9-methyl-4-oxo-4,6,7,9-tetrahydropyrimido[2,1-c][1,4]oxazine-2-carboxylic acid (0.172 g, 0.54 mmol) and intermediate 39, 2-(aminomethyl)-5-fluoro-N-methylbenzamide trifluoroacetate salt (0.177 g, 0.60 mmol) in dichloromethane (10 ml) was treated at 22° C. with triethylamine (0.17 ml, 1.22 mmol) followed by benzotriazole-1-yloxy-tris-pyrrolidino-phosphonium hexafluorophosphate (Py-BOP) (0.340 g, 0.65 mmol). After 3 h, the reaction mixture was diluted with ethyl acetate, washed with saturated sodium bicarbonate and brine then dried over anhydrous magnesium sulfate. Evaporation of the solvent followed by chromatography of the residue on silica gel (elution gradient ethyl acetate 50-100% in toluene) gave 0.260 g (100% yield) of the title amide as a white solid. ¹HNMR 400 MHz (CDCl₃) δ (ppm): 1.70 (3H, d, J=6.6 Hz, CH₃), 3.01 (3H, d, J=4.7 Hz, NCH₃), 3.89 (2H, m, CH₂), 4.14 (1H, m, CH), 4.29 (1H, m, CH), 4.53 (2H, d, J=6.7 Hz, NCH₂), 4.69 (1H, q, J=6.6 Hz, OCH), 5.35 (2H, s, OCH₂), 6.69 (1H, broad q, NH), 7.09 (1H, m, aromatic), 7.16 (1H, m, aromatic), 7.32 (3H, m, aromatics), 7.42 (1H, m, aromatic), 7.47 (2H, m, aromatics), 8.61 (1H, broad t, NH). HRMS (ESI⁺) calculated for C₂₅H₂₆FN₄O₅ [M+H⁺]: 481.1887: found: 481.1884.

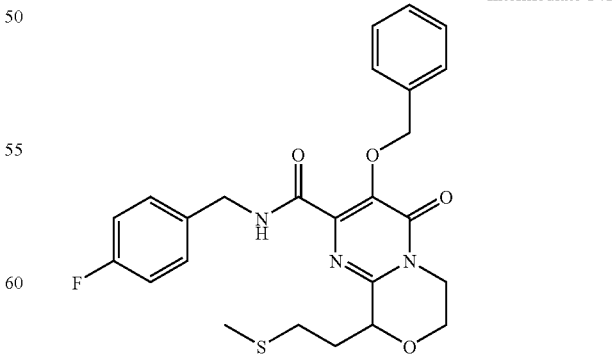

Intermediate 141

N-(4-fluorobenzyl)-3-(benzyloxy)-9-(2-(methylthio) ethyl)-4-oxo-4, 6,7,9-tetrahydropyrimido[2,1-c][1,4]oxazine-2-carboxamide. A solution of intermediate 22 (82 mg, 0.22 mmol) and O-(7-azabenzotriazol-1-yl)-N,N,N',N'-tetramethyluronium hexafluorophosphate (HATU) (152 mg, 0.4 mmol) in 1 mL dimethylformamide was stirred for 20 min under N₂. 4-Fluorobenzylamine (38 mg, 0.3 mmol) was then added and stirring continued for 16 hrs. The dimethylformamide was evaporated under reduced pressure and the remaining residue dissolved in CH₂Cl₂. The resulting solution was washed with dil HCl. The solvent was removed under reduced pressure and the crude product purified by chromatography (SiO₂, ethyl acetate) to provide the title compound (70 mg, Yield=66%). LC/MS m/e 484 (M+H).

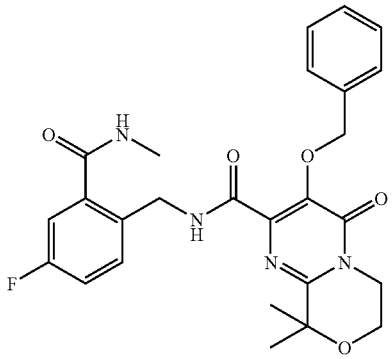

Intermediate 143

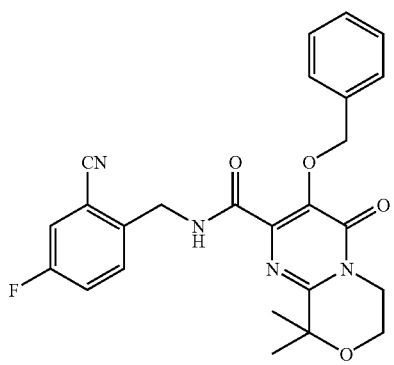

Intermediate 142

3-(Benzyloxy)-2-(6-fluoro-1-oxoisoindoline-2-carbonyl)-9,9-dimethyl-6,7-dihydropyrimido[2,1-c][1,4]oxazin-4(9H)-one. To a stirred suspension of intermediate 27, 3-(benzyloxy)-9,9-dimethyl-4-oxo-4,6,7,9-tetrahydropyrimido-[2,1-c][1,4]oxazine-2-carboxylic acid, (1.65 g, 5 mmol) in CH₂Cl₂ (15 mL) was added a catalytic amount of dimethylformamide and 10 mL of a 2 M oxalylchloride in CH₂Cl₂. After 30 min., the resulting clear yellow solution was concentrated to afford a light brown solid. This solid was dissolved in CH₂Cl₂ (50 mL) and added to a stirred mixture of intermediate 107, 2-(aminomethyl)-5-fluorobenzonitrile trifluoroacetic acid salt, (1.77 g, 5.97 mmol) and diethylisopropylamine (2.6 mL, 15 mmol) in CH₂Cl₂ (100 mL). After 1 h, the clear brown reaction mixture was concentrated and the resulting residue dissolved in ethyl acetate (200 mL) then washed sequentially with water (25 mL), 1N HCl (25 mL), water (25 mL) and brine (25 mL). The combined aqueous layers were extracted with CH₂Cl₂ (3×50 mL). The combined organic phases were dried (Na₂SO₄), filtered, concentrated and purified by flash chromatography (SiO₂), using 30-50% ethyl acetate/Hexanes as eluent to afford the title compound (0.331 g, 14% yield) as a yellow powder. ¹H NMR (500 MHz, CDCl₃) δ: 7.48-7.45 (1H, m), 7.88 (2H, d, J=7.9 Hz), 7.30 (2H, d, J=7.0 Hz), 7.12 (2H, t, J=7.6 Hz), 7.05-7.01 (1H, m), 5.22 (2H, s), 4.77 (2H, s), 4.06 (4H, s), 1.59 (6H, s). HRMS (M+H) calcd for $C_{25}H_{23}FN_3O_5$: 464.1622; found: 464.1628.

N-(4-Fluoro-2-(methylcarbamoyl)benzyl)-3-(benzyloxy)-9,9-dimethyl-4-oxo-4,6,7,9-tetrahydropyrimido[2,1-c][1,4]oxazine-2-carboxamide. A 25 mL round-bottom flask was charged with intermediate 27, 3-(benzyloxy)-9,9-dimethyl-4-oxo-4,6,7,9-tetrahydropyrimido-[2,1-c][1,4]oxazine-2-carboxylic acid, (0.991 g, 3.0 mmol), intermediate 39, 2-(aminomethyl)-5-fluoro-N-methylbenzamide trifluoroacetic acid salt (1.185 g, 4.0 mmol), 4-dimethylaminopyridine (DMAP, 1.1 g, 9.0 mmol) and O-(7-azabenzotriazol-1-yl)-N,N,N',N'-tetramethyluronium hexafluorophosphate (HATU, 1.722 g, 4.5 mmol). Dimethylformamide (20 mL) was added and the mixture stirred for 1 h at ambient temperature. After this, the reaction mixture was diluted with ethyl acetate (100 mL) then washed with water (3×25 mL) and brine (25 mL). The organic layer was dried (Na₂SO₄), filtered, concentrated and purified by flash chromatography (SiO₂), eluting with hexanes/ethyl acetate (1:1 to 1:3) followed by ethyl acetate, to afford the title compound as an off-white solid (1.48 g, 100% yield). ¹H NMR (500 MHz, CDCl₃) δ ppm: 8.49 (1H, t, J=6.1 Hz), 7.48-7.46 (2H, m), 7.43 (1H, dd, J=8.5, 5.5 Hz), 7.31-7.27 (3H, m), 7.12 (1H, dd, J=8.9, 2.7 Hz), 7.05 (1H, td, J=8.2, 2.7 Hz), 6.52 (1H, br s), 5.26 (2H, s), 4.53 (2H, d, J=6.4 Hz), 4.01 (2H, t, J=4.9 Hz), 3.96 (2H, t, J=4.9 Hz), 2.97 (3H, d, J=4.9 Hz), 1.62 (6H, s). HRMS (M+H) calcd for $C_{26}H_{28}FN_4O_5$: 495.2044; found: 495.2032.

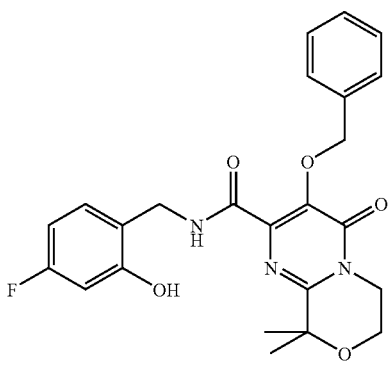

Intermediate 144

N-(4-Fluoro-2-hydroxybenzyl)-3-(benzyloxy)-9,9-dimethyl-4-oxo-4,6,7,9-tetrahydropyrimido[2,1-c][1,4]oxazine-2-carboxamide. A solution of intermediate 27, 3-(benzyloxy)-9,9-dimethyl-4-oxo-4,6,7,9-tetrahydropyrimido-[2,1-c][1,4]oxazine-2-carboxylic acid, (1.50 g, 4.54 mmol) and HATU (2.07 g, 5.45 mmol) in anhydrous dimethylformamide was stirred for 20 minutes under a nitrogen atmosphere at room temperature. To the solution was added intermediate 135, 2-hydroxy-4-fluoro-benzylamine hydrochloride, (1.05 g, 5.9 mmol) followed by DMAP (1.39 g, 11.4 mmol), and the reaction mixture stirred at 60° C. for 90 minutes. The solvent was removed in vacuo and the crude residue purified by flash column chromatography (SiO$_2$), eluting with 40%-60% ethyl acetate in hexanes to give the title compound (1.31 g, 64% yield) as a solid. $^1$H NMR (500 MHz, CDCl$_3$) δ ppm: 9.69 (1H, br s), 8.18 (1H, t, J=6.3 Hz), 7.44 (2H, dd, J=6.6, 2.6 Hz), 7.30-7.35 (3H, m), 7.00 (1H, dd, J=8.2, 6.7 Hz), 6.68 (1H, dd, J=10.4, 2.4 Hz), 6.54 (1H, dt, J=8.2, 2.4 Hz), 5.29 (2H, s), 4.36 (2H, d, J=6.7 Hz), 3.97-4.05 (4H, m), 1.61 (6H, s).

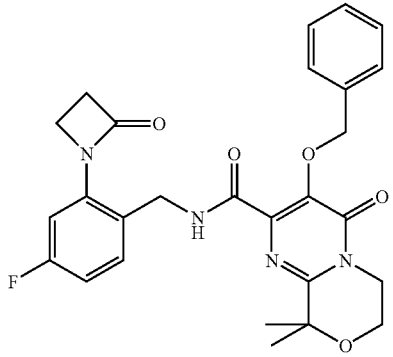

Intermediate 146

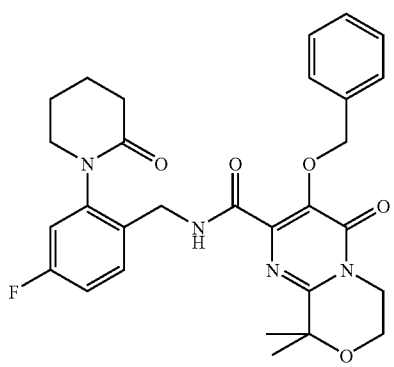

Intermediate 145

N-(4-Fluoro-2-(2-oxopiperidin-1-yl)benzyl)-3-(benzyloxy)-9,9-dimethyl-4-oxo-4,6,7,9-tetrahydropyrimido[2,1-c][1,4]oxazin-4(9H)-one. To intermediate 27, 3-(benzyloxy)-9,9-dimethyl-4-oxo-4,6,7,9-tetrahydropyrimido[2,1-c][1,4]oxazine-2-carboxylic acid, (80 mg, 0.242 mmol) in CH$_3$CN/dimethylformamide (5 mL:1 mL:) was added intermediate 125, 1-(2-(aminomethyl)-5-fluorophenyl)piperidin-2-one hydrochloride salt, (69 mg, 0.266 mmol), benzotriazole-1-yloxy-tris-pyrrolidino-phosphonium hexafluorophosphate (PyBOP) (139 mg, 0.266 mmol) and diisopropylethylamine (169 μL, 0.968 mmol). The reaction mixture was stirred at 23° C. for 3 h. The solvents were then removed in vacuo and an aqueous solution of HCl (1N, 25 mL) was added. This was extracted with ethyl acetate (3×25 mL). The combined organic fractions were dried (MgSO$_4$), filtered and concentrated in vacuo. The crude material was purified on a Biotage system using a silica gel column with Hexanes/ethyl acetate (1:1) to (1:5) as eluent to afford 114 mg (88% yield) of the title compound. $^1$HNMR 400 MHz (DMSO) δ ppm: 8.73 (1H, dd, (t), J=6.0 Hz), 7.46 (2H, m), 7.35 (4H, m), 7.18 (1H, dd, J=9.8, 3.0 Hz) 7.0 (1H, m); 5.10 (2H, s), 4.43 (1H, dd, J=15.0, 7.08 Hz), 4.06 (1H, dd, J=15.0, 5.56), 4.02 (2H, t, J=5.0 Hz), 3.90 (2H, t, J=5.0 Hz), 3.64 (1H, m), 3.44 (1H, m), 2.45 (1H, m), 2.35 (1H, m), 1.86 (4H, m), 1.56 (6H, s). LCMS (M+H)$^+$ m/z 535.

N-(4-Fluoro-2-(2-oxoazetidin-1-yl)benzyl)-3-(benzyloxy)-9,9-dimethyl-4-oxo-4,6,7,9-tetrahydropyrimido[2,1-c][1,4]oxazine-2-carboxamide. To a solution of intermediate 27, 3-(benzyloxy)-9,9-dimethyl-4-oxo-4,6,7,9-tetrahydropyrimido[2,1-c][1,4]oxazine-2-carboxylic acid, (0.142 g, 0.430 mmol) in CH$_3$CN: dimethylformamide (30 mL:5 mL) was added intermediate 120, 1-(2-(aminomethyl)-5-fluorophenyl)azetidin-2-one hydrochloride, (0.100 g, 0.43 mmol), (benzotriazole-1-yloxy)tris(dimethylamino)phosphonium hexafluorophosphate (0.207 g, 0.470 mmol) and diisopropylethylamine (280 μL, 1.72 mmol). The reaction mixture was stirred at 23° C. for 18 h. The solvents were removed in vacuo and 1N HCl (50 mL) added. This was extracted with ethyl acetate (2×50 mL). The combined organic extracts were dried (MgSO$_4$), filtered and concentrated in vacuo. The residue was purified on a Biotage system using a silica gel column with ethyl acetate as eluent to afford the title compound (0.157 g, 72% yield). $^1$H NMR (400 MHz, MeOD) δ ppm: 7.88 (1H, d, J=8.3 Hz), 7.76 (1H, d, J=8.0Hz), 7.58-7.30 (4H, m), 7.10 (1H, dd, J=10.2, 2.5 Hz), 6.90 (1H, m), 5.20 (2H, s), 4.55 (2H, s), 4.04 (2H, m), 3.96 (2H, m), 3.78 (2H, t, J=4.2 Hz), 3.10 (2H, t, J=4.2 Hz), 1.58 (6H, s); LCMS (M+H)$^+$ m/z 506.

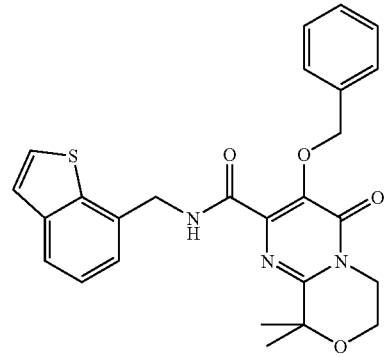

Intermediate 147

N-(Benzo[b]thiophen-7-ylmethyl)-3-(benzyloxy)-9,9-dimethyl-4-oxo-4,6,7,9-tetrahydropyrimido[2,1-c][1,4]oxazine-2-carboxamide. To a solution of intermediate 27, 3-(benzyloxy)-9,9-dimethyl-4-oxo-4,6,7,9-tetrahydropyrimido[2,1-c][1,4]oxazine-2-carboxylic acid (0.200 g, 0.60 mmol) in CH$_3$CN:dimethylformamide (30 mL:5 mL) was added intermediate 139, benzo[b]thiophen-7-ylmethanamine hydrochloride (0.069 g, 0.266 mmol), benzotriazole-1-yloxy-tris-pyrrolidino-phosphonium hexafluorophosphate (PyBOP) (0.347 g, 0.670 mmol) and diisopropylethylamine (420 µL, 2.40 mmol). The reaction mixture was stirred at 23° C. for 60 h. The solvents were then removed in vacuo and 1N HCl (50 mL) added. This was extracted with ethyl acetate (2×50 mL). The combined organic extracts were dried (MgSO$_4$), filtered and concentrated in vacuo. The residue was purified on a Biotage system using a silica gel column with hexane:ethyl acetate (1:1) to (1:5) gradient as eluent to afford the title compound (0.279 g, 87% yield): $^1$H NMR (400 MHz, DMSO-d$_6$) δ: 9.11 (1H, dd, J=5.6 Hz), 7.81 (1H, m), 7.77 (1H, d, J=5.6 Hz), 7.52 (1H, d, J=5.6 Hz), 7.48-7.26 (6H, m), 5.09 (2H, s), 4.67 (2H, d, J=5.2 Hz), 4.04 (2H, m), 3.90 (2H, m), 1.58 (6H, s). LCMS (M+H)$^+$ m/z 476.

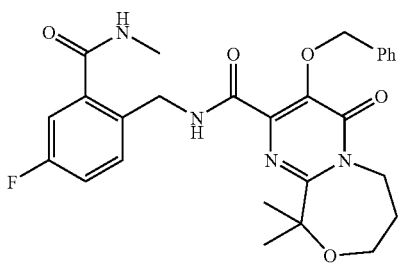

Intermediate 148

N-(4-Fluoro-2-(methylcarbamoyl)benzyl)-3-(benzyloxy)-10,10-dimethyl-4-oxo-6,7,8,10-tetrahydro-4H-pyrimido[2,1-c][1,4]oxazepine-2-carboxamide. A solution of intermediate 35, 3-(benzyloxy)-10,10-dimethyl-4-oxo-6,7,8,10-tetrahydro-4H-pyrimido[2,1-c][1,4]oxazepine-2-carboxylic acid in anhydrous dimethylformamide (4 mL) was treated with HATU (0.278 g, 0.70 mmol) and stirred for 10 minutes. The reaction mixture was treated with 2-(aminomethyl)-5-fluoro-N-methylbenzamide trifluoroacetic acid salt (0.24 g, 0.8 mmol), followed by dimethylaminopyridine (0.121 g, 0.97 mmol), then stirred for 4 hours at 60° C. Following this, the solvent was removed in vacuo and the remaining residue dissolved in ethyl acetate (15 mL) and washed with 1.0 N HCl (15 mL). The organic layer was dried (sodium sulfate), filtered, and concentrated to dryness. The crude product was purified by flash column chromatography (SiO$_2$), eluting with ethyl acetate. Fractions containing the product were pooled, concentrated to dryness and triturated with ether to provide 0.366 g of the title compound as a white glassy solid. $^1$H NMR (500 MHz, d$_6$-acetone) δ ppm: 8.71-8.82 (1H, m), 7.84-7.95 (1H, br), 7.47-7.62 (4H, m), 7.27-7.40 (5H, m), 7.20 (1H, dt, J=8.5, 2.7 Hz), 5.15-5.21 (2H, br, s), 4.48-4.60 (4H, m), 2.96 (2H, s), 2.94 (2H, s), 1.62-1.64 (6H, s).

Intermediates 149-174

Intermediates 149-174 were prepared according to the coupling procedures described for intermediates 140-148.

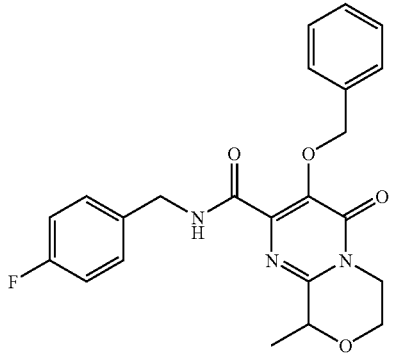

Intermediate 149

N-(4-Fluorobenzyl)-3-(benzyloxy)-9-methyl-4-oxo-4,6,7,9-tetrahydropyrimido[2,1-c][1,4]oxazine-2-carboxamide. The title compound can be prepared from intermediate 16, 3-benzyloxy-9-methyl-4-oxo-4,6,7,9-tetrahydropyrimido[2,1-c][1,4]oxazine-2-carboxylic acid and 4-fluorobenzylamine. $^1$HNMR 400 MHz (CDCl$_3$) δ (ppm): 1.67 (3H, d, J=6.6 Hz, CH$_3$), 3.91 (2H, m, CH$_2$), 4.12-4.35 (2H, m, CH$_2$), 4.52 (2H, d, J=5.9 Hz, NCH$_2$), 4.70 (1H, q, J=6.6 Hz, OCH), 5.33 (2H, s, OCH$_2$), 7.02 (2H, m, aromatics), 7.25 (2H, m, aromatics), 7.35 (3H, m, aromatics), 7.47 (2H, m, aromatics), 7.71 (1H, broad t, NH).

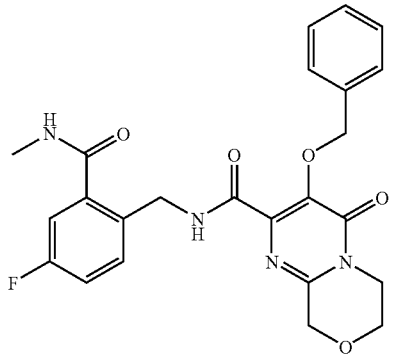

Intermediate 150

N-(4-Fluoro-2-(methylcarbamoyl)benzyl)-3-(benzyloxy)-4-oxo-4,6,7,9-tetrahydropyrimido[2,1-c][1,4]oxazine-2-carboxamide. The title compound can be prepared from intermediate 7,3-(benzyloxy)-4-oxo-4,6,7,9-tetrahydropyrimido[2,1-c][1,4]oxazine-2-carboxylic acid and intermediate 39, 2-(aminomethyl)-5-fluoro-N-methylbenzamide. White crystals; mp 189-190° C. (ethyl acetate). $^1$HNMR 400 MHz (CDCl$_3$) δ (ppm): 3.01 (3H, d, J=4.5 Hz, NCH$_3$), 4.00 (2H, m, CH$_2$), 4.08 (1H, m, CH), 4.50 (2H, d, J=6.6 Hz, NCH$_2$), 4.71 (2H, s, OCH$_2$), 5.38 (2H, s, OCH$_2$), 6.88 (1H, broad q, NH), 7.07 (1H, m, aromatic), 7.16 (1H, dd, J=2.5 Hz and J=8.6 Hz, aromatic), 7.30-7.44 (6H, m, aromatics), 8.55 (1H, broad t, NH). Anal. Calcd for C$_{24}$H$_{23}$FN$_4$O$_5$: C, 61.80; H, 4.97; N, 12.01. Found: C, 61.84; H, 4.82; N, 12.00.

Intermediate 151

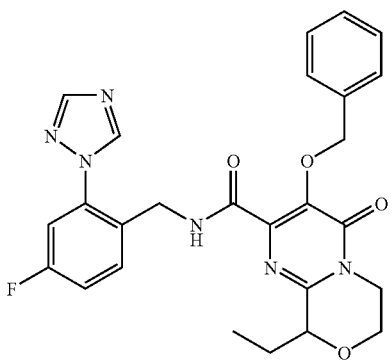

N-(4-Fluoro-2-(1H-1,2,4-triazol-1-yl)benzyl)-3-(benzyloxy)-9-ethyl-4-oxo-4,6,7,9-tetrahydropyrimido[2,1-c][1,4]oxazine-2-carboxamide. The title compound can be prepared from 3-(benzyloxy)-9-ethyl-4-oxo-4,6,7,9-tetrahydropyrimido[2,1-c][1,4]oxazine-2-carboxylic acid which was synthesized using the method described for the synthesis or intermediates 7 and 16, and intermediate 69, (4-fluoro-2-(1H-1,2,4-triazol-1-yl)phenyl)methanamine. White needles; mp 155-157° C. (ethyl acetate). $^1$HNMR 400 MHz (CDCl$_3$) δ (ppm): 1.03 (3H, t, J=7.5 Hz, CH$_3$), 1.97-2.02 (1H, m, CH), 2.29-2.32 (1H, m, CH), 3.83-3.88 (2H, m, CH$_2$), 4.15-4.31 (2H, m, CH$_2$), 4.44 (2H, m, CH$_2$), 4.53 (1H, m, CH), 5.34 (2H, s, OCH$_2$), 7.08 (1H, dd, J=2.5 Hz and J=8.6 Hz, aromatic), 7.20 (1H, m, aromatic), 7.29-7.31 (3H, m, aromatics), 7.47 (2H, m, aromatics), 7.74 (1H, dd, J=6.1 Hz and J=8.6 Hz, aromatic), 8.02 (1H, s, CH), 8.41 (1H, s, CH), 8.55 (1H, broad t, NH). Anal. Calcd for C$_{26}$H$_{25}$FN$_6$O$_4$: C, 61.89; H, 4.99; N, 16.65. Found: C, 61.67; H, 5.13; N, 16.61.

Intermediate 152

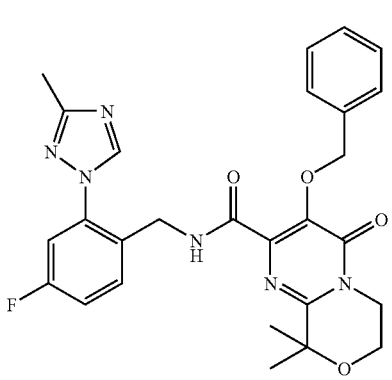

N-(4-Fluoro-2-(3-methyl-1H-1,2,4-triazol-1-yl)benzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and intermediate 85, (4-fluoro-2-(3-methyl-1H-1,2,4-triazol-1-yl)phenyl)methanamine. White crystals; mp 203° C. (ethyl acetate). $^1$HNMR 400 MHz (CDCl$_3$) δ (ppm): 1.65 (6H, s, 2×CH$_3$), 2.50 (3H, s, CH$_3$), 4.03 (4H, m, 2×CH$_2$), 4.46 (2H, d, J=6.6 Hz, NCH$_2$), 5.31 (2H, s, OCH$_2$), 7.06 (1H, dd, J=3 Hz and J=8.6 Hz, aromatic), 7.16 (1H, m, aromatic), 7.30-7.34 (3H, m, aromatics), 7.50 (2H, m, aromatics), 7.74 (1H, dd, J=6.0 Hz and J=8.6 Hz, aromatic), 8.28 (1H, s, CH), 8.45 (1H, broad t, NH). Anal. Calcd for C$_{27}$H$_{27}$FN$_6$O$_4$: C, 62.54; H, 5.25; N, 16.21. Found: C, 62.48; H, 5.31; N, 16.29.

Intermediate 153

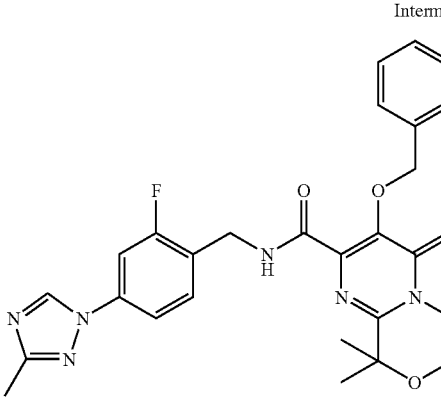

N-(2-Fluoro-4-(3-methyl-1H-1,2,4-triazol-1-yl)benzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and intermediate 87, (2-fluoro-4-(3-methyl-1H-1,2,4-triazol-1-yl)phenyl)methanamine. White crystals; mp 183-185° C. (ethyl acetate). $^1$HNMR 400 MHz (CDCl$_3$) δ (ppm): 1.65 (6H, s, 2×CH$_3$), 2.52 (3H, s, CH$_3$), 4.05 (4H, m, 2×CH$_2$), 4.64 (2H, d, J=6.1 Hz, NCH$_2$), 5.33 (2H, s, OCH$_2$), 7.29-7.55 (8H, m, aromatics), 7.84 (1H, broad t, NH), 8.45 (1H, s, CH). Anal. Calcd for C$_{27}$H$_{27}$FN$_6$O$_4$: C, 62.54; H, 5.25; N, 16.21. Found: C, 62.41; H, 5.40; N, 16.23.

Intermediate 154

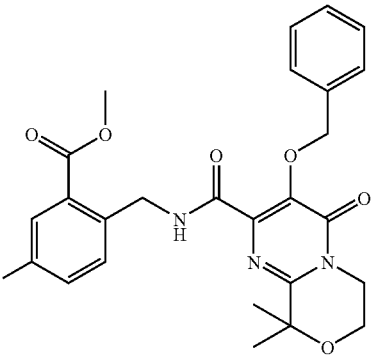

Methyl 2-((3-(benzyloxy)-9,9-dimethyl-4-oxo-4,6,7,9-tetrahydropyrimido[2,1-c][1,4]oxazine-2-carboxamido)methyl)-5-fluorobenzoate. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and intermediate 38, methyl 2-(aminomethyl)-5-fluorobenzoate. $^1$H NMR (CDCl$_3$, 500 MHz) δ ppm: 1.61 (6H, s, gem-Me), 3.88 (3H, s, OMe), 3.97 (2H, t, J=5.5 Hz, CH$_2$), 4.02 (2H, t, J=5.5 Hz, CH$_2$), 4.73 (2H, d, J=6.7 Hz, NCH$_2$), 5.25 (2H, s, OCH$_2$), 7.19 (1H, dt, J=3, 8.5 Hz, Ar—H), 7.27-7.31 (3H, m, Ar-Hs), 7.48-7.50 (2H, m, Ar-Hs), 7.61 (1H, dd, J=5.5, 8.5 Hz, Ar—H), 7.66 (1H, dd, J=3, 9.5 Hz, Ar—H). LC/MS m/z 496 (M+H).

Intermediate 155

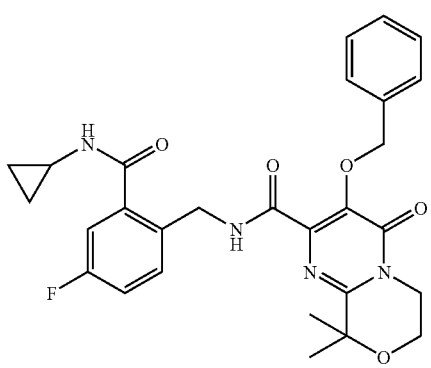

N-(2-(Cyclopropylcarbamoyl)-4-fluorobenzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and intermediate 40, 2-(aminomethyl)-N-cyclopropyl-5-fluorobenzamide. LC/MS m/z 521 (M+H).

Intermediate 156

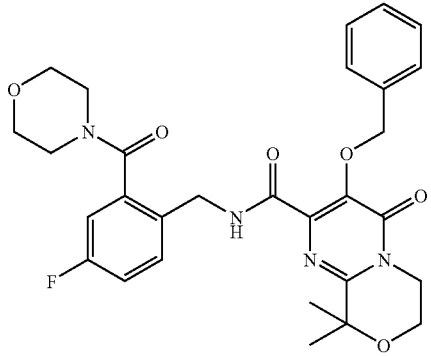

N-(4-Fluoro-2-(morpholine-4-carbonyl)benzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and intermediate 44, (2-(aminomethyl)-5-fluorophenyl)(morpholino)methanone. $^1$H NMR (CDCl$_3$, 500 MHz) δ ppm: 1.59 (6H, s), 3.29 (2H, brs), 3.57 (2H, m), 3.74 (4H, s), 3.98 (4H, m), 5.26 (2H, s), 6.88 (1H, dd, J=8.2, 2.7 Hz), 7.03 (1H, dt, J=8.5, 2.5 Hz), 7.24-7.33 (3H, m), 7.42 (2 H, dd, J=8.6, 5.3 Hz), 7.47 (2H, dd, J=7.5, 2.0 Hz), 8.18 (1H, t, J=6.4 Hz); LC/MS m/z 551 (M+H).

Intermediate 157

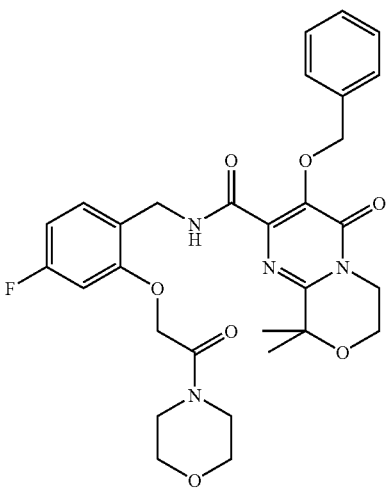

N-(4-Fluoro-2-(2-morpholino-2-oxoethoxy)benzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and intermediate 131, 2-(2-(aminomethyl)-5-fluorophenoxy)-1-morpholinoethanone.
$^1$H NMR (CDCl$_3$, 500 MHz) δ ppm: 1.59 (6H, s, gem-Me), 3.38, 3.54 (4H, br, NCH$_2$), 3.62 (4H, m, OCH$_2$), 3.96 (2H, m, NCH$_2$), 4.01 (2H, m, OCH$_2$), 4.55 (2H, s, OCH$_2$), 4.55 (2H, d, J4.3 Hz, NCH$_2$), 5.17 (2H, s, OCH$_2$), 6.53 (1H, dd, J=10, 2.1 Hz, Ar—H), 6.63 (1H, dt, J=2.5, 8 Hz, Ar—H), 7.23-7.26 (1H, m, Ar—H), 7.28-7.30 (3H, m, Ar-Hs), 7.42-7.44 (2H, m, Ar-Hs), 8.00 (1H, t, J=5.5 Hz, NH); $^{13}$C NMR (CDCl$_3$, 125.77 Hz) δ ppm: 27.74, 38.76, 42.30, 42.98, 45.38, 58.06, 66.55, 66.78, 66.91, 74.72, 76.27, 100.40, 100.61, 108.07, 108.23, 122.56, 128.37, 128.49, 128.84, 130.88, 130.96, 139.69, 141.36, 141.98, 156.70, 157.02, 157.10, 159.58, 162.04, 163.99, 162.86, 165.79. HRMS (ESI) calcd for C$_{30}$H$_{34}$N$_4$O$_7$F (M+H) 581.2412, found 581.2393.

Intermediate 158

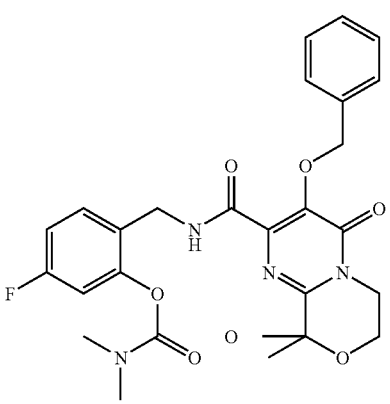

Dimethyl-carbamic acid 2-{[(3-benzyloxy-9,9-dimethyl-4-oxo-4,6,7,9-tetrahydro-pyrimido[2,1]-c[1,4]oxazine-2-carbonyl)-amino]-methyl}-5-fluoro-phenyl ester. The title compound can be prepared from intermediate 27, 3-(benzyloxy)-9,9-dimethyl-4-oxo-4,6,7,9-tetrahydropyrimido-[2,1- c][1,4]oxazine-2-carboxylic acid and intermediate 133, 2-(aminomethyl)-5-fluorophenyl dimethylcarbamate. $^1$H NMR (CDCl$_3$, 500 MHz) δ ppm: 1.58 (6H, s, gem-Me), 2.92, 3.05 (2s, NMe), 3.96 (2H, m, NCH$_2$), 4.00 (2H, m, OCH$_2$), 4.48 (2H, d, J=5.5 Hz, NCH$_2$), 5.26 (2H, s, OCH$_2$), 6.84 (1H, dd, J=2.5 Hz, 9 Hz, Ar—H), 6.87 (1H, dt, J=2.5 Hz, 8 Hz, Ar—H), 7.25-7.33 (4H, m, Ar-Hs), 7.53 (2H, d, J=~7 Hz, Ar-Hs), 7.78-(1H, brt, J=5 Hz, NH); $^{13}$C NMR (CDCl$_3$, 125.77 Hz) δ ppm: 27.68, 36.61, 36.89, 37.97, 42.97, 58.06, 74.73, 76.23, 110.58, 110.77, 113.06, 113.23, 126.55, 126.58, 128.31, 128.45, 128.91, 131.23, 131.31, 136.76, 140.70, 142.00, 150.60, 150.69, 154.50, 156.30, 159.79, 161.40, 163.37, 162.43. HRMS (ESI) calcd for C$_{27}$H$_{30}$N$_4$O$_6$F (M+H) 525.2149, found 525.2163.

Intermediate 159

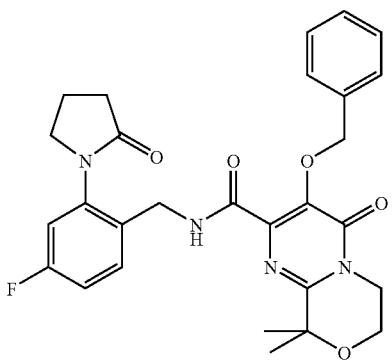

N-(4-Fluoro-2-(2-oxopyrrolidin-1-yl)benzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and 1-(2-(aminomethyl)-5-fluorophenyl)pyrrolidin-2-one, derived from reduction of intermediate 111, 4-fluoro-2-(2-oxopyrrolidin-1-yl)benzonitrile. $^1$HNMR 400 MHz (MeOD) δ ppm: 7.44 (3H, m), 7.33 (3H, m), 7.11 (1H, dd, J=9.2, 3.0 Hz) 7.03 (1H, m), 5.21 (2H, s), 4.43 (2H, s), 4.08 (2H, t, J=5.0 Hz), 3.98 (2H, t, J=5.0 Hz), 3.85 (2H, t, J=7.1 Hz), 2.58 (2H, t, J=8.0 Hz), 2.23 (2H, m), 1.61 (6H, s). LCMS (M+H)$^+$ m/z 521.

Intermediate 160

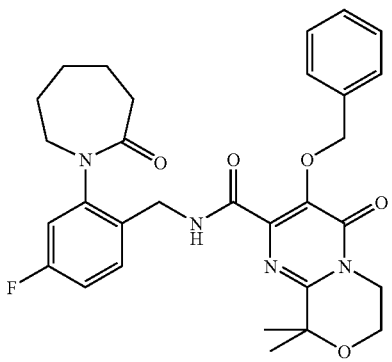

N-(4-Fluoro-2-(2-oxoazepan-1-yl)benzyl)-3-(benzyloxy)-9,9-dimethyl-4-oxo-4,6,7,9-tetrahydropyrimido[2,1-c][1,4]oxazine-2 carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and 1-(2-(aminomethyl)-5-fluorophenyl)azepan-2-one, derived from reduction of intermediate 113, 4-fluoro-2-(2-oxoazepan-1-yl)benzonitrile. $^1$HNMR 400 MHz (DMSO) δ ppm: 8.80 (1H, dd, (t), J=6.0 Hz), 7.46 (2H, m), 7.36 (4H, m), 7.08 (1H, dd, J=9.8, 2.8 Hz), 7.0 (1H, m), 5.09 (2H, s), 4.43 (1H, dd, J=15.2, 7.1 Hz), 4.06 (1H, dd, J=15.2, 5.0 Hz), 4.02 (2H, t, J=5.0 Hz), 3.90 (2H, t, J=5.0 Hz), 3.77 (1H, m), 3.51 (1H, m), 2.70 (1H, m), 2.51 (2H, m), 1.76 (6H, m), 1.56 (6H, s). LCMS (M+H)$^+$ m/z 549.

Intermediate 161

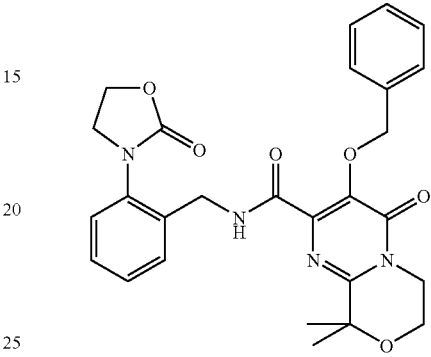

N-(2-(2-Oxooxazolidin-3-yl)benzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and 3-(2-(aminomethyl)phenyl)oxazolidin-2-one, derived from reduction of intermediate 116, 2-(2-oxoxazolidin-3-yl)benzonitrile. $^1$H NMR (400 MHz, DMSO-d$_6$) δ ppm: 8.90 (1H, t, J=6.0 Hz), 7.58-7.32 (7H, m), 7.22 (1H, t, J=7.5 Hz), 5.08 (2H, s), 4.48 (2H, t, J=7.8 Hz), 4.44 (2H, d, J=6.0 Hz), 4.06-3.97 (4H, m), 3.88 (2H, m), 1.56 (6H, s); LCMS (M+H)$^+$ m/z 505.

Intermediate 162

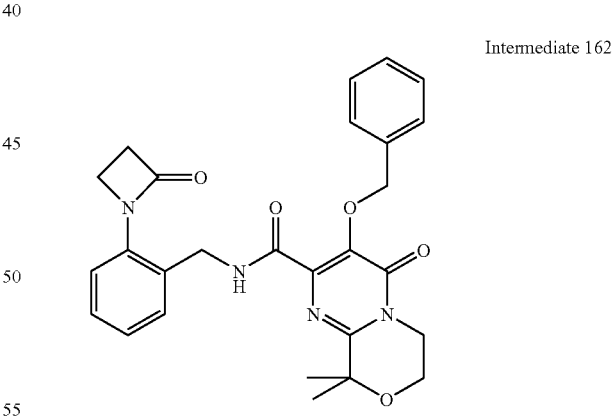

N-(2-(2-Oxoazetidin-1-yl)benzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and 1-(2-(aminomethyl)phenyl)azetidin-2-one, derived from reduction of intermediate 115, 2-(2-oxoazetidin-1-yl)benzonitrile. $^1$H NMR (400 MHz, CDCl$_3$) δ ppm: 8.67 (1H, brt, J=6.3 Hz), 7.60 (1H, dd, J=1.3, 7.6 Hz), 7.53-7.50 (1H, dd, m), 7.34-7.24 (5H, m), 7.18 (1H, ddd(dt), J=1.2, 7.4 Hz), 7.10 (1H, dd, J=1.2, 8.0 Hz), 5.27 (2H, s), 4.60 (2H, d, J=6.3

Hz), 4.01-3.95 (4H, m), 3.71 (2H, t, J=4.5 Hz), 3.10 (2H, t, J=4.5 Hz), 1.60 (6H, s); LCMS (+ESI, M+H+) m/z 489.

Intermediate 163

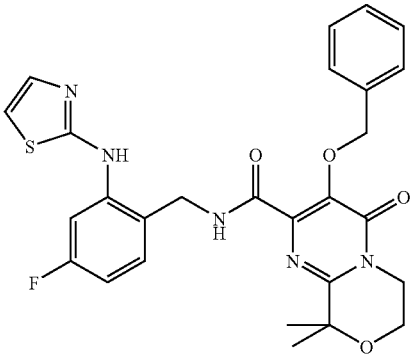

N-(4-Fluoro-2-(thiazol-2-ylamino)benzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and N-(2-(aminomethyl)-5-fluorophenyl)thiazol-2-amine, derived from reduction of intermediate 123, 4-fluoro-2-(thiazol-2-ylamino)benzonitrile. $^1$H NMR (400 MHz, DMSO-d6) δ ppm: 9.92 (1H, s), 9.10 (1H, t, J=6.3 Hz), 8.19 (1H, dd, J=2.8, 12.3 Hz), 7.41-7.38 (2H, m), 7.32-7.28 (5H, m), 6.99 (1H, d, J=3.8 Hz), 6.71 (1H, ddd(dt), J=2.8, 8.3), 5.05 (2H, s), 4.45 (2H, d, J=6.3 Hz), 4.01-3.98 (2H, m), 3.88-3.85 (2H, m), 1.54 (6H, s) LCMS (+ESI, M+H+) m/z 536.

Intermediate 164

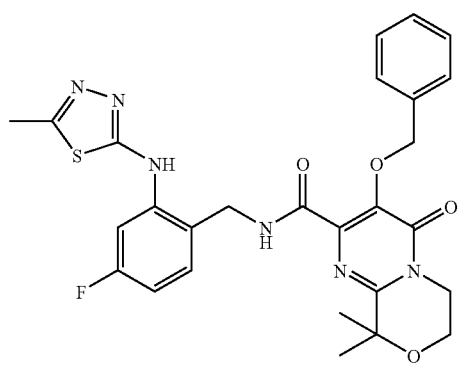

N-(4-Fluoro-2-(5-methyl-1,3,4-thiadiazol-2-ylamino)benzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and N-(2-(aminomethyl)-5-fluorophenyl)-5-methyl-1,3,4-thiadiazol-2-amine, derived from reduction of intermediate 124, 4-fluoro-2-(5-methyl-1,3,4-thiadiazol-2-ylamino)benzonitrile. LCMS (+ESI, M+H+) m/z 551.

Intermediate 165

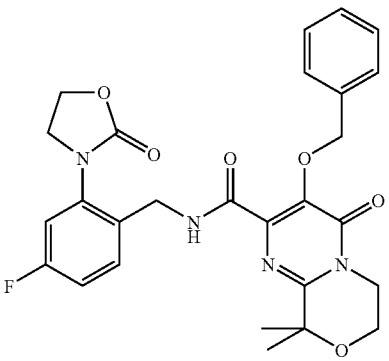

N-(4-Fluoro-2-(2-oxooxazolidin-3-yl)benzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and 3-(2-(aminomethyl)-5-fluorophenyl)oxazolidin-2-one, derived from reduction of intermediate 117, 4-fluoro-2-(2-oxooxazolidin-3-yl)benzonitrile. $^1$H NMR (400 MHz, MeOD) δ ppm: 9.48 (1H, dd, J=8.6, 6.5 Hz), 7.41 (2H, m), 7.32 (3H, m), 7.22 (1H, dd, J=9.6, 2.5 Hz), 7.08 (1H, td, J=8.6, 2.7 Hz), 5.21 (2H, s), 4.57 (2H, t, J=7.7 Hz), 4.50 (2H, s), 4.07 (4H, m), 3.99 (2H, m), 1.61 (6H, s). LCMS (M+H)+ m/z 523.

Intermediate 166

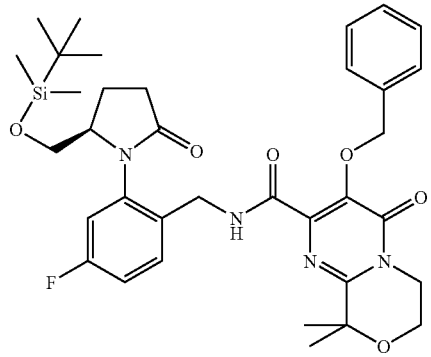

(R)-N-(2-(2-(((tert-Butyldimethylsilyloxy)methyl)-5-oxopyrrolidin-1-yl)-4-fluorobenzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and (S)-1-(2-(aminomethyl)-5-fluorophenyl)-5-((tert-butyldimethylsilyloxy)methyl)pyrrolidin-2-one, derived from reduction of intermediate 122, (R)-2-(2-(((tert-butyldimethylsilyloxy)methyl)-5-oxopyrrolidin-1-yl)-4-fluorobenzonitrile $^1$HNMR 400 MHz (DMSO) δ ppm: 8.82 (1H, broad s), 7.47 (2H, m), 7.35 (4H, m), 7.00 (1H, broad s), 5.09 (2H, s), 4.60-4.10 (3H, m), 4.02 (3H, m), 3.88 (2H, m), 3.53 (2H, broad s), 2.42-2.35 (2H, m), 1.94 (1H, m), 1.56 (3H, s), 1.55 (3H, s), 0.82 (9H, broad s), −0.01 (6H, s). LCMS (M+H)+ m/z 665.

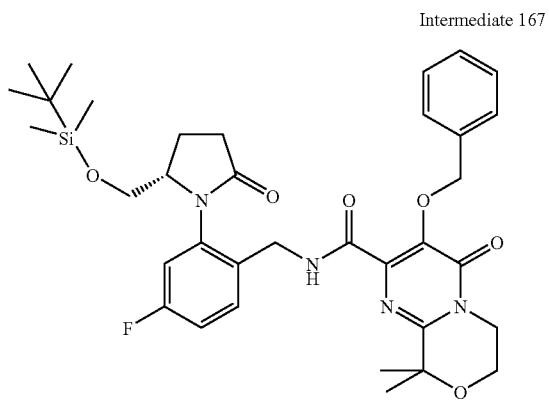

Intermediate 167

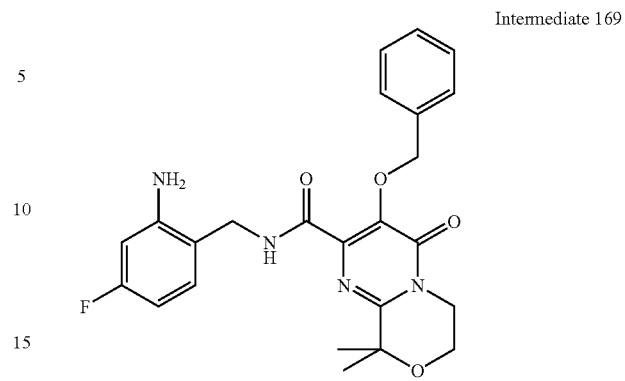

Intermediate 169

(S)-N-(2-(2-(((tert-Butyldimethylsilyloxy)methyl)-5-oxopyrrolidin-1-yl)-4-fluorobenzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and (S)-1-(2-(aminomethyl)-5-fluorophenyl)-5-((tert-butyldimethylsilyloxy)methyl)pyrrolidin-2-one, derived from reduction of intermediate 121, (R)-2-(2-(((tert-butyldimethylsilyloxy)methyl)-5-oxopyrrolidin-1-yl)-4-fluorobenzonitrile. $^1$HNMR 400 MHz (DMSO) δ ppm: 8.82 (1H, broad s), 7.52-7.33 (7H, m), 7.02 (1H, broad s), 5.60 (2H, s), 4.60-4.20 (2H, m), 4.02 (3H, t, J=5.0 Hz), 3.89 (3H, t, 5.0 Hz), 3.53 (2H, broad s), 2.51 (2H, s), 2.44-2.26 (2H, m), 1.94 (1H, broad s), 1.57 (3H, s), 1.55 (3H, s), 0.82 (9H, broad s), −0.02 (6H, s). LCMS (M+H)$^+$ m/z 665.

N-(2-Amino-4-fluorobenzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid 2-(aminomethyl)-5-fluorobenzenamine. $^1$HNMR 400 MHz (MeOD) δ ppm: $^1$HNMR 400 MHz (MeOD) δ ppm: 7.36 (2H, m), 7.30 (3H, m), 7.10 (1H, dd, J=8.3, 6.5 Hz), 6.47 (1H, dd, J=11.1, 2.5Hz), 6.32 (1H, ddd, (dt), J=8.6, 2.5Hz), 5.19 (2H, s), 4.40 (2H, s), 4.07 (2H, t, J=5.0 Hz), 3.99 (2H, t, J=5.0 Hz), 1.61 (6H, s). LCMS (M+H)$^+$ m/z 453.

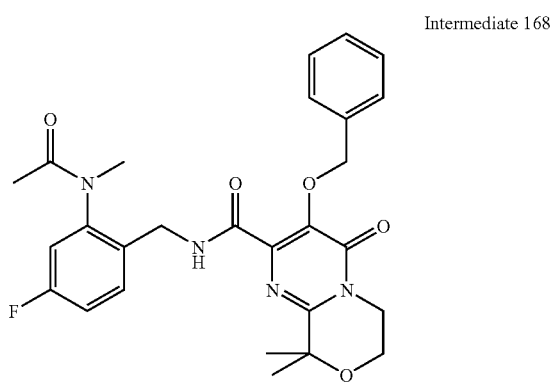

Intermediate 168

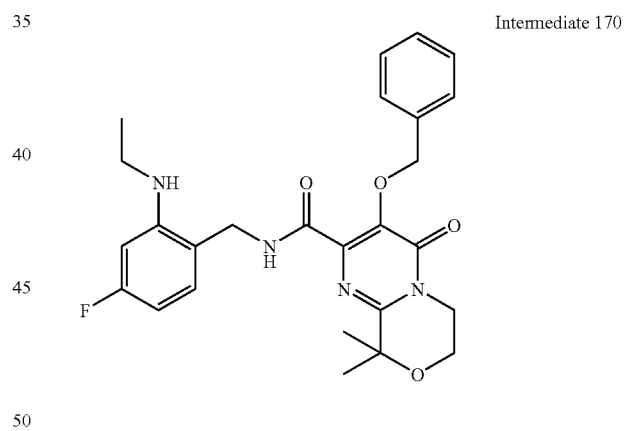

Intermediate 170

N-(4-Fluoro-2-(N-methylacetamido)benzyl)-3-(benzyloxy)-9,9-dimethyl-4-oxo-4,6,7,9-tetrahydropyrimido[2,1-c][1,4]oxazine-2-carboxamide. The title compound can be prepared from intermedite 27, 3-(benzyloxy)-9,9-dimethyl-4-oxo-4,6,7,9-tetrahydropyrimido-[2,1-c][1,4]oxazine-2-carboxylic acid N-(2-(aminomethyl)-5-fluorophenyl)-N-methylacetamide, derived from reduction of intermediate 114, N-(2-cyano-5-fluorophenyl)-N-methylacetamide. $^1$HNMR 400 MHz (MeOD) δ ppm: 7.49-7.33 (6H, m), 7.15-7.06 (2H, m), 5.22 (2H, s), 4.41 (2H, d, J=2.4 Hz), 4.09 (2H, t, J=5.1 Hz), 4.01 (2H, t, J=5.1 Hz), 3.25 (0.4H, s), 3.22 (2.6H, s), 1.85 (3H, s), 1.63 (6H, s). LCMS (M+H)$^+$ m/z 509.

N-(2-(Ethylamino)-4-fluorobenzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and 2-(aminomethyl)-N-ethyl-5-fluorobenzenamine. $^1$HNMR 400 MHz (CDCl$_3$) δ (ppm): 1.27 (3H, t, J=7.1 Hz, CH$_3$), 1.63 (6H, s, 2×CH$_3$), 3.10 (2H, q, J=7.1 Hz, CH$_2$), 4.04 (4H, m, 2×CH$_2$), 4.45 (2H, d, J=6.6 Hz, NCH$_2$), 5.27 (2H, s, OCH$_2$), 6.28 (1H, broad s, aromatic), 6.31 (1H, m, aromatic), 6.98 (1H, m, aromatic), 7.3-7.38 (3H, m, aromatics), 7.49 (2H, m, aromatics), 7.54 (1H, broad t, NH). HRMS (ESI$^+$) calculated for C$_{26}$H$_{30}$FN$_4$O$_4$ [M+H+]: 481.225 1: found: 481.2254.

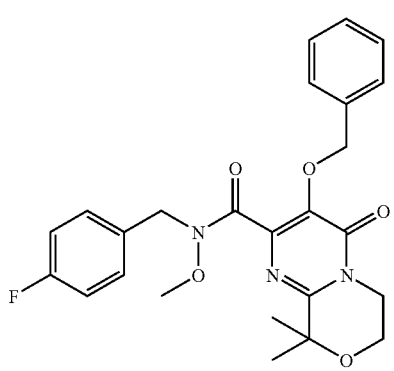

Intermediate 171

N-(4-Fluorobenzyl)-3-(benzyloxy)-N-methoxy-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and (4-fluorophenyl)-N-methoxymethanamine. White crystals; mp 141° C. (ethyl acetate-hexane). $^1$HNMR 400 MHz (CDCl$_3$) δ (ppm): 1.66 (6H, s, 2×CH$_3$), 3.59 (3H, s, OCH$_3$), 4.07 (4H, m, 2×CH$_2$), 4.90 (2H, s, NCH$_2$), 5.20 (2H, s, OCH$_2$), 6.81 (2H, m, aromatics), 7.26-7.30 (3H, m, aromatics), 7.36 (2H, m, aromatics), 7.44 (2H, m, aromatics). HRMS (ESI$^+$) calculated for C$_{25}$H$_{27}$FN$_3$O$_5$ [M+H$^+$]: 468.1935: found: 468.1916.

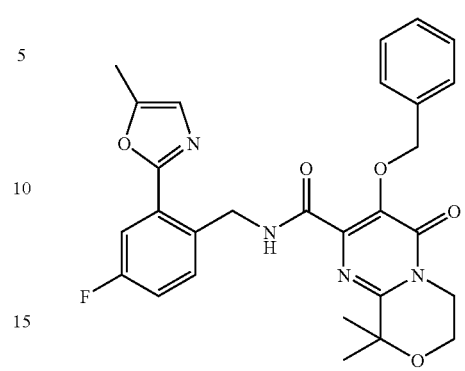

Intermediate 173

N-(4-Fluoro-2-(5-methyloxazol-2-yl)benzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and (4-fluoro-2-(5-methyloxazol-2-yl)phenyl)methanamine. White crystals; mp 186° C. (ethyl acetate-hexane). $^1$HNMR 400 MHz (CDCl$_3$) δ (ppm): 1.61 (6H, s, 2×CH$_3$), 2.43 (3H, s, CH$_3$), 4.02 (4H, m, 2×CH$_2$), 4.80 (2H, d, J=6.3 Hz, NCH$_2$), 5.25 (2H, OCH$_2$), 6.82 (1H, s, CH), 7.11 (1H, m, aromatic), 7.29-7.34 (3H, m, aromatics), 7.52 (2H, m, aromatics), 7.65 (1H, dd, J=2.5 Hz and J=9.6 Hz, aromatic), 7.69 (1H, dd, J=6.1 Hz and J=8.6 Hz, aromatic), 9.32 (1H, broad t, NH). HRMS (ESI$^+$) calculated for C$_{28}$H$_{28}$FN$_4$O$_5$ [M+H$^+$]: 519.2044: found: 519.2024.

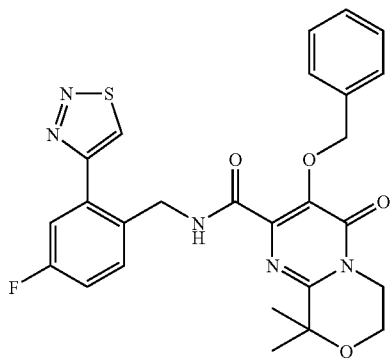

Intermediate 172

N-(4-Fluoro-2-(1,2,3-thiadiazol-4-yl)benzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and (4-fluoro-2-(1,2,3-thiadiazol-4-yl)phenyl)methanamine. $^1$HNMR 400 MHz (CDCl$_3$) δ (ppm): 1.66 (6H, s, 2×CH$_3$), 4.02 (4H, m, 2×CH$_2$), 4.57 (2H, d, J=6.6 Hz, NCH$_2$), 5.32 (2H, s, OCH$_2$), 7.18 (1H, m, aromatic), 7.27-7.34 (4H, m, aromatics), 7.54 (2H, m, aromatics), 7.74 (1 H, dd, J=6.2 Hz and J=8.6 Hz, aromatic), 8.71 (1 H, s, CH), 8.80 (1H, broad t, NH). HRMS (ESI$^+$) calculated for C$_{26}$H$_{25}$FN$_5$O$_4$S [M+H$^+$]: 522.1611: found: 522.1601.

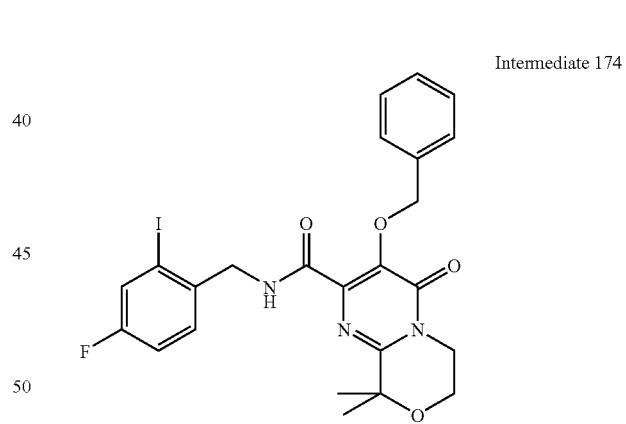

Intermediate 174

N-(4-Fluoro-2-iodobenzyl)-3-(benzyloxy)-9,9-dimethyl-4-oxo-4,6,7,9-tetrahydropyrimido[2,1-c][1,4]oxazine-2-carboxamide. The title compound can be prepared from intermediate 27, 3-(benzyloxy)-9,9-dimethyl-4-oxo-4,6,7,9-tetrahydropyrimido-[2,1-c][1,4]oxazine-2-carboxylic acid and (4-fluoro-2-iodophenyl)methanamine. White solid. $^1$HNMR 400 MHz (CDCl$_3$) δ ppm: 1.66 (6H, s, 2×CH$_3$), 4.04 (4H, m, 2×CH$_2$), 4.57 (2H, d, J=6.6 Hz, NCH$_2$), 7.05 (1H, m aromatic), 7.3-7.38 (3H, m, aromatics), 7.42 (1H, dd, J=6.1 Hz and J=8.6 Hz, aromatic), 7.53 (2H, m, aromatics), 7.56 (1H, dd, J=2.6 Hz and J=8.0 Hz, aromatic), 8.05 (1 H, broad t, NH). HRMS (ESI$^+$) calculated for C$_{24}$H$_{24}$FIN$_3$O$_4$ [M+H$^+$]: 564.0796; found: 564.0809.

Intermediate 175

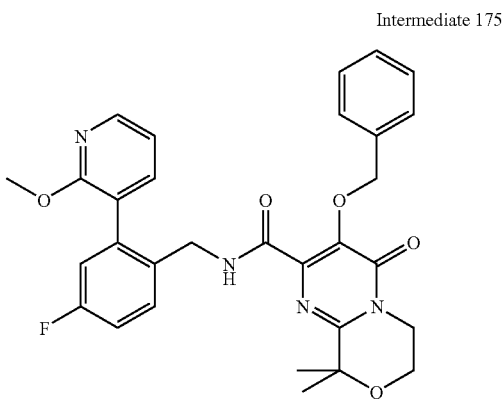

N-(4-Fluoro-2-(2-methoxypyridin-3-yl)benzyl)-3-(benzyloxy)-9,9-dimethyl-4-oxo-4,6,7,9-tetrahydropyrimido[2,1-c][1,4]oxazine-2-carboxamide. Intermediate 174, N-(4-fluoro-2-iodobenzyl)-3-(benzyloxy)-9,9-dimethyl-4-oxo-4,6,7,9-tetrahydropyrimido[2,1-c][1,4]oxazine-2-carboxamide (0.350 g, 0.62 mmol) in a mixture of acetonitrile (12 ml) and water (12 ml) was treated with 2-methoxypyridin-3-ylboronic acid (0.190 g, 1.24 mmol), sodium carbonate (0.20 g, 1.88 mmol) and tetrakis(triphenylphosphine)palladium(0) (0.15 g). The reaction mixture was degassed, flushed with argon and heated at 90° C. for 30 min. The reaction mixture was then diluted with ethyl acetate, washed with water and brine, dried over anhydrous magnesium sulfate and concentrated. Chromatography of the residue on silica gel (elution gradient of ethyl acetate in hexane) gave 0.245 g (72% yield) of the title material as a white solid. $^1$HNMR 400 MHz (CDCl$_3$) δ ppm: 1.63 (6H, s, 2×CH$_3$), 3.89 (3H, s, OCH$_3$), 4.04 (4H, m, 2×CH$_2$), 4.37 (2H, broad, NCH$_2$), 5.26 (2H, s, OCH$_2$), 6.93 (1H,dd, J=2.5 Hz and J=9 Hz, aromatic), 7.0 (1H,dd, J=5 Hz and J=7 Hz, aromatic), 7.06 (1H, m, aromatic), 7.3-7.5 (8H, m, aromatics and NH), 8.24 (1H, m, aromatic). HRMS (ESI$^+$) calculated for C$_{30}$H$_{30}$FN$_4$O$_5$ [M+H$^+$]: 545.2200; found: 545.2184.

Intermediate 176

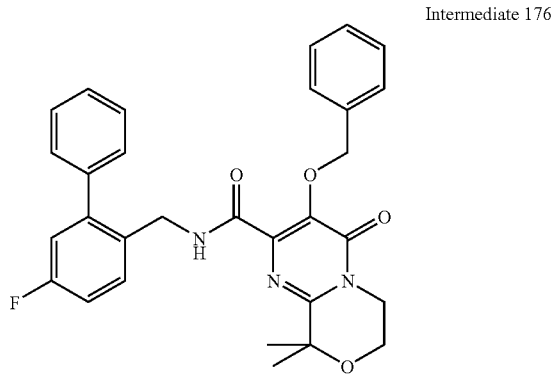

N-(4-Fluoro-2-phenyl-benzyl)-3-(benzyloxy)-9,9-dimethyl-4-oxo-4,6,7,9-tetrahydropyrimido[2,1-c][1,4]oxazine-2-carboxamide. Intermediate 174, N-(4-Fluoro-2-iodobenzyl)-3-(benzyloxy)-9,9-dimethyl-4-oxo-4,6,7,9-tetrahydropyrimido[2,1-c][1,4]oxazine-2-carboxamide (0.150 g, 0.266 mmol) in a mixture of acetonitrile (10 ml) and water (10 ml) was treated with phenylboronic acid (0.042 g, 0.35 mmol), sodium carbonate (0.062 g, 0.58 mmol) and tetrakis(triphenylphosphine)palladium(0) (0.070 g). The reaction mixture was degassed, flushed with argon and heated at 90° C. for 30 min. The reaction mixture was then diluted with ethyl acetate, washed with water and brine, dried over anhydrous magnesium sulfate and concentrated. Chromatography of the residue on silica gel (elution gradient of ethyl acetate in hexane) gave 0.124 g (91% yield) of the title material as a light yellow solid. $^1$HNMR 400 MHz (CDCl$_3$) δ ppm: 1.61 (6H, s, 2×CH$_3$), 4.03 (4H, m, 2×CH$_2$), 4.49 (2H, d, J=6.1 Hz, NCH$_2$), 7.02 (2H, m, aromatics), 7.29-7.51 (12H, m, aromatics and NH). HRMS (ESI$^+$) calculated for C$_{30}$H$_{29}$FN$_3$O$_4$ [M+H$^+$]: 514.2142; found: 514.2137.

Inrermediate 177

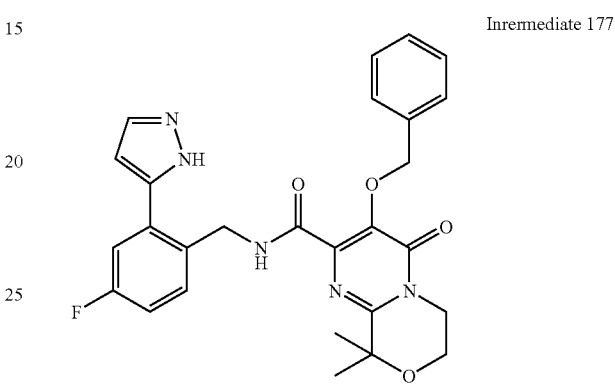

N-(4-Fluoro-2-(1H-pyrazol-5-yl)benzyl)-3-(benzyloxy)-9,9-dimethyl-4-oxo-4,6,7,9-tetrahydropyrimido[2,1-c][1,4]oxazine-2-carboxamide. Intermediate 174, N-(4-fluoro-2-iodobenzyl)-3-(benzyloxy)-9,9-dimethyl-4-oxo-4,6,7,9-tetrahydropyrimido[2,1-c][1,4]oxazine-2-carboxamide (0.150 g, 0.27 mmol) was reacted with 1H-pyrazol-5-ylboronic acid (0.060 g, 0.54 mmol), sodium carbonate (0.085 g, 0.81 mmol) and tetrakis(triphenylphosphine)palladium(0) (0.070 g) to give 0.085 g (62% yield) of the title material as a white solid after chromatography on silica gel. $^1$HNMR 400 MHz (CDCl$_3$) δ (ppm): 1.63 (6H, s, 2×CH$_3$), 4.03 (4H, m, 2×CH$_2$), 4.65 (2H, d, J=6.5 Hz, NCH$_2$), 5.25 (2H, s, OCH$_2$), 6.54 (1H, d, J=2.5 Hz, CH), 7.03 (1H, m, aromatic), 7.25 (1H, dd, J=2.5 Hz and J=9.8 Hz, aromatic), 7.35 (3H, m, aromatics), 7.53 (2H, m, aromatics), 7.56 (1H, d, J=2.5 Hz, CH), 7.60 (1H, dd, J=6.1 Hz and J=8.6 Hz, aromatic), 8.96 (1H, broad t, NH). HRMS (ESI$^+$) calculated for C$_{27}$H$_{27}$FN$_5$O$_4$ [M+H$^+$]: 504.2047: found: 504.2068.

Inrermediate 178

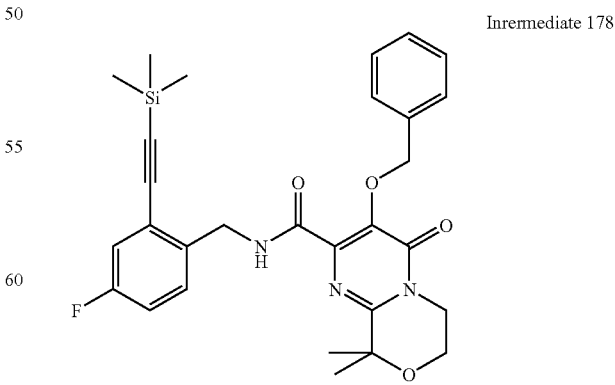

N-(4-Fluoro-2-(2-(trimethylsilyl)ethynyl)benzyl)-3-(benzyloxy)-9,9-dimethyl-4-oxo-4,6,7,9-tetrahydropyrimido[2, 1-c][1,4]oxazine-2-carboxamide. A solution of intermediate 174, N-(4-fluoro-2-iodobenzyl)-3-(benzyloxy)-9,9-dimethyl-4-oxo-4,6,7,9-tetrahydropyrimido[2,1-c][1,4]oxazine-2-carboxamide (0.277 g, 0.49 mmol) in a mixture of N,N-dimethylformamide (3 ml) and piperidine (1.2 ml) was treated under argon with dichlorobis(triphenylphosphine)palladium(II) (0.020 g), triphenylphosphine (0.010 g), copper (1) iodide (0.010 g) followed by (trimethylsilyl)acetylene (0.21 ml, 1.47 mmol). The resulting mixture was sealed and heated at 50° C. for one hour. The reaction mixture was then diluted with ethyl acetate, washed with water and brine, dried over anhydrous magnesium sulfate and concentrated under reduced pressure. Chromatography of the residue on silica gel (elution gradient of ethyl acetate in hexane) gave 0.164 g (63% yield) of the title material as a light yellow solid. $^1$HNMR 400 MHz (CDCl$_3$) δ ppm: 0.27 (9H, s, SiCH$_3$), 1.64 (6H, s, 2×CH$_3$), 4.04 (4H, m, 2×CH$_2$), 4.71 (2H, d, J=6.1 Hz, NCH$_2$), 5.32 (2H, s, OCH$_2$), 6.99 (1H, m, aromatic), 7.19 (1H,dd, J=2.6 Hz and J=9.1 Hz, aromatic), 7.3-7.37 (4H, m, aromatics), 7.48-7.51 (2H, m, aromatics), 7.75 (1H, broad t, NH). HRMS (ESI$^+$) calculated for C$_{29}$H$_{33}$FN$_3$O$_4$Si [M+H$^+$]: 534.2224; found: 534.2229.

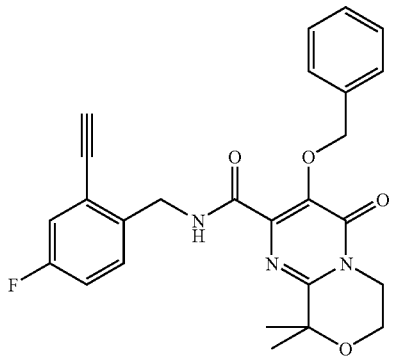

Inrermediate 179

N-(2-Ethynyl-4-fluorobenzyl)-3-(benzyloxy)-9,9-dimethyl-4-oxo-4,6,7,9-tetrahydropyrimido[2,1-c][1,4]oxazine-2-carboxamide. A solution of intermediate 178, N-(4-fluoro-2-(2-(trimethylsilyl)ethynyl)benzyl)-3-(benzyloxy)-9,9-dimethyl-4-oxo-4,6,7,9-tetrahydropyrimido[2,1-c][1,4]oxazine-2-carboxamide (0.150 g, 0.28 mmol) in methanol (5 ml) was treated with potassium carbonate (0.120 g, 0.84 mmol) and the resulting mixture stirred at 22° C. for one hour. The reaction mixture was then diluted with ethyl acetate, washed with water and brine, dried over anhydrous magnesium sulfate and concentrated under reduced pressure to give 0.129 g (100% yield) of the title material as a light yellow solid. $^1$HNMR 400 MHz (CDCl$_3$) δ ppm: 1.64 (6H, s, 2×CH$_3$), 3.31 (1H, s, CH), 4.04 (4H, m, 2×CH$_2$), 4.69 (2H, d, J=6.6 Hz, NCH$_2$), 5.31 (2H, s, OCH$_2$), 7.04 (1H, m, aromatic), 7.21 (1H,dd, J=2.6 Hz and J=9.1 Hz, aromatic), 7.32-7.42 (3H, m, aromatics), 7.40 (1H,dd, J=6.1 Hz and J=8.6 Hz, aromatic), 7.52-7.54 (2H, m, aromatics), 8.00 (1H, broad t, NH). HRMS (ESI$^+$) calculated for C$_{26}$H$_{25}$FN$_3$O$_4$ [M+H]: 462.1829; found: 462.1822.

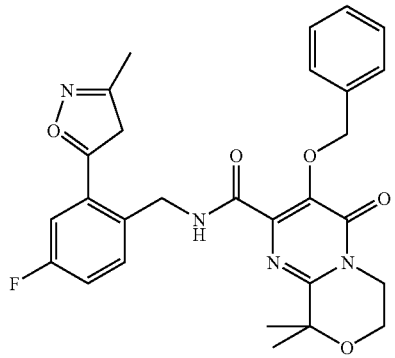

Inrermediate 180

N-(4-Fluoro-2-(3-methylisoxazol-5-yl)benzyl)-3-(benzyloxy)-9,9-dimethyl-4-oxo-4,6,7,9-tetrahydropyrimido[2,1-c][1,4]oxazine-2-carboxamide. A solution of intermediate 179, N-(2-ethynyl-4-fluorobenzyl)-3-(benzyloxy)-9,9-dimethyl-4-oxo-4,6,7,9-tetrahydropyrimido[2,1-c][1,4]oxazine-2-carboxamide (0.150 g, 0.32 mmol) in dimethyl sulfoxide (5 ml) was treated with nitromethane (0.14 ml, 1.92 mmol), 4-(4,6-dimethoxy-1,3,5-triazin-2-yl)-4-methylmorpholinium chloride (DMTMM) (0.241 g, 1.0 mmol) (M. Kunishima et al., Tetrahedron, 55, 1999, 13159-13170) and 4-(dimethylamino)pyridine (DMAP) (0.010 g) and the resulting mixture stirred at 22° C. for 16 h. Identical quantities of nitromethane, DMTMM and DMAP were then added and the mixture was stirred for another 24 h. The reaction mixture was diluted with ethyl acetate, washed with saturated sodium bicarbonate and brine, then dried over anhydrous magnesium sulfate and concentrated under reduced pressure. Chromatography of the residue on silica gel (elution gradient of ethyl acetate in dichloromethane) gave 0.122 g (73% yield) of the title material as a white solid. $^1$HNMR 400 MHz (CDCl$_3$) δ ppm: 1.62 (6H, s, 2×CH$_3$), 2.39 (3H, s, CH$_3$), 4.04 (4H, m, 2×CH$_2$), 4.69 (2H, d, J=6.1 Hz, NCH$_2$), 5.31 (2H, s, OCH$_2$), 6.36 (1H, m, CH), 7.13 (1H, m, aromatic), 7.30-7.35 (4H, m, aromatics), 7.50-7.53 (2H, m, aromatics), 7.58 (1H,dd, J=5.5 Hz and J=8.6 Hz, aromatic), 8.06 (1H, broad t, NH). HRMS (ESI$^+$) calculated for C$_{28}$H$_{28}$FN$_4$O$_5$ [M+H$^+$]: 519.2044; found: 519.2059.

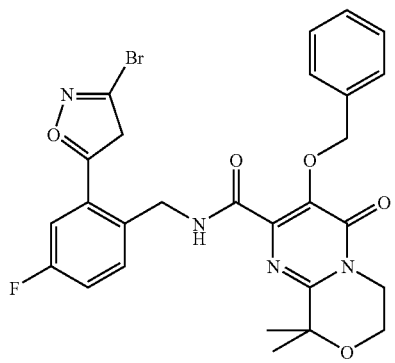

Inrermediate 181

N-(2-(3-Bromoisoxazol-5-yl)-4-fluorobenzyl)-3-(benzyloxy)-9,9-dimethyl-4-oxo-4,6,7,9-tetrahydropyrimido[2,1-c][1,4]oxazine-2-carboxamide. A solution of intermediate 179, N-(2-ethynyl-4-fluorobenzyl)-3-(benzyloxy)-9,9-dimethyl-4-oxo-4,6,7,9-tetrahydropyrimido[2,1-c][1,4]oxazine- 2-carboxamide (0.350 g, 0.76 mmol) in a mixture of ethyl acetate (10 ml) and water (2 ml) was treated with potassium bicarbonate (0.230 g, 2.3 mmol) followed by dibromoformaldoxime (0.354 g, 1.75 mmol) (D. M. Vyas, Y. Chiang and T. W. Doyle, Tetrahedron Letters, 1984, 25, 487-490) and the resulting mixture stirred at 22° C. After 1 h, identical quantities of potassium bicarbonate and dibromoformaldoxime were added and the mixture stirred for another 1.5 h. The reaction mixture was then diluted with ethyl acetate, washed with brine, dried over anhydrous magnesium sulfate and concentrated under reduced pressure. Crystallization of the residue from ether gave 0.300 g (68% yield) of the title material as a white solid. $^1$HNMR 400 MHz (CDCl$_3$) δ ppm: 1.63 (6H, s, 2×CH$_3$), 4.04 (4H, m, 2×CH$_2$), 4.67 (2H, d, J=6.6 Hz, NCH$_2$), 5.32 (2H, OCH$_2$), 6.60 (1H, s, CH), 7.17 (1H, m, aromatic), 7.30-7.36 (4H, m, aromatics), 7.51-7.53 (2H, m, aromatics), 7.60 (1H,dd, J=5.5 Hz and J=8.6 Hz, aromatic), 8.01 (1H, broad t, NH). HRMS (ESI$^+$) calculated for C$_{27}$H$_{25}$BrFN$_4$O$_5$ [M+H$^+$]: 583.0992; found: 583.0986.

Intermediate 182

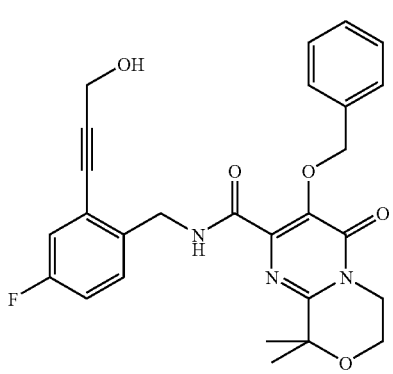

N-(4-Fluoro-2-(3-hydroxyprop-1-ynyl)benzyl)-3-(benzyloxy)-9,9-dimethyl-4-oxo-4,6,7,9-tetrahydropyrimido[2,1-c][1,4]oxazine-2-carboxamide. Reaction of intermediate 174, N-(4-fluoro-2-iodobenzyl)-3-(benzyloxy)-9,9-dimethyl-4-oxo-4,6,7,9-tetrahydropyrimido[2,1-c][1,4]oxazine-2-carboxamide (0.563 g, 1.00 mmol) with propargyl alcohol (0.18 ml, 3.2 mmol) using the conditions described for intermediate 178 gave 0.415 g (85% yield) of the title material as a white solid. $^1$HNMR 400 MHz (CDCl$_3$) δ ppm: 1.64 (6H, s, 2×CH$_3$), 4.04 (4H, m, 2×CH$_2$), 4.39 (2H, d, J=6.6 Hz, CH$_2$), 4.68 (2H, d, J=6.0 Hz, CH$_2$), 5.29 (2H, s, OCH$_2$), 6.99 (1H, m, aromatic), 7.13 (1H,dd, J=2.5 Hz and J=9.1 Hz, aromatic), 7.22 (1H,dd, J=5.6 Hz and J=8.6 Hz, aromatic), 7.33-7.37 (3H, m, aromatics), 7.44-7.47 (2H, m, aromatics), 7.68 (1H, broad t, NH). HRMS (ESI$^+$) calculated for C$_{27}$H$_{27}$FN$_3$O$_5$ [M+H$^+$]: 492.1935; found: 492.1939.

Intermediate 183

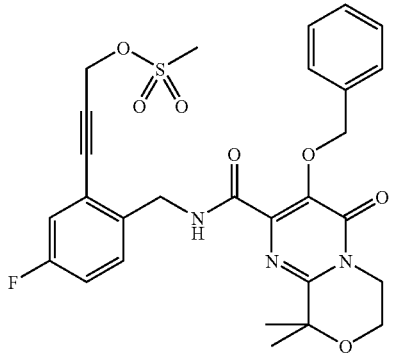

3-[2-((3-(Benzyloxy)-9,9-dimethyl-4-oxo-4,6,7,9-tetrahydropyrimido[2,1-c][1,4]oxazine-2-carboxamido)methyl)-5-fluorophenyl]prop-2-ynyl methanesulfonate. A solution of intermediate 182, N-(4-fluoro-2-(3-hydroxyprop-1-ynyl)benzyl)-3-(benzyloxy)-9,9-dimethyl-4-oxo-4,6,7,9-tetrahydropyrimido[2,1-c][1,4]oxazine-2-carboxamide (0.280 g, 0.57 mmol) and triethylamine (0.12 ml, 0.86 mmol) in dichloromethane (5 ml) was cooled to 0° C., treated drop wise with methanesulfonyl chloride (0.050 ml, 0.64 mmol) and then stirred for 30 min. The reaction mixture was then diluted with ethyl acetate, washed with saturated sodium bicarbonate, brine, dried over anhydrous magnesium sulfate and concentrated under reduced pressure. Chromatography of the residue on silica gel (elution gradient of ethyl acetate in hexane) gave 0.245 g (75% yield) of the title material as a white solid. $^1$ HNMR 400 MHz (CDCl$_3$) δ ppm: 1.65 (6H, s, 2×CH$_3$), 3.10 (3H, s, SCH$_3$), 4.05 (4H, m, 2×CH$_2$), 4.67 (2H, d, J=6.1 Hz, NCH$_2$), 5.03 (2H, s, CH$_2$), 5.29 (2H, s, OCH$_2$), 7.07 (1H, m, aromatic), 7.18 (1H,dd, J=2.5 Hz and J=9.1 Hz, aromatic), 7.32-7.36 (3H, m, aromatics), 7.38 (1H,dd, J=5.5 Hz and J=8.6 Hz, aromatic), 7.49-7.51 (2H, m, aromatics), 7.77 (1H, broad t, NH). MS (ESI$^+$) m/e 570 [M+H$^+$].

Intermediate 184

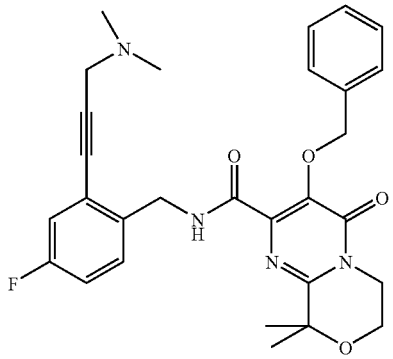

N-(2-(3-(Dimethylamino)prop-1-ynyl)-4-fluorobenzyl)-3-(benzyloxy)-9,9-dimethyl-4-oxo-4,6,7,9-tetrahydropyrimido[2,1-c][1,4]oxazine-2-carboxamide. A solution of intermediate 183, 3-[2-((3-(benzyloxy)-9,9-dimethyl-4-oxo-4,6,7,9-tetrahydropyrimido[2,1-c][1,4]oxazine-2-carboxamido)methyl)-5-fluorophenyl]prop-2-ynyl methanesulfonate (0.100 g, 0.18 mmol) in acetonitrile (5 ml) was treated at 22° C. with 0.3 ml (0.6 mmol) of a 2 M solution of dimethylamine in tetrahydrofuran and the resulting mixture was stirred for 30 min. The reaction mixture was then diluted with ethyl acetate, washed with saturated sodium bicarbonate, brine, then dried over anhydrous magnesium sulfate and concentrated under reduced pressure to give 0.080 g (88% yield) of the title material as a white solid. $^1$HNMR 400 MHz (CDCl$_3$) δ ppm: 1.64 (6H, s, 2×CH$_3$), 2.43 (6H, s, 2×NCH$_3$), 3.58 (2H, broad s, CH$_2$), 4.05 (4H, m, 2×CH$_2$), 4.70 (2H, d, J=6.0 Hz, NCH$_2$), 5.30 (2H, s, OCH$_2$), 7.01 (1H, m, aromatic), 7.18 (1H,dd, J=3 Hz and J=9.1 Hz, aromatic), 7.32-7.38 (4H, m, aromatics), 7.50-7.53 (2H, m, aromatics), 7.79 (1H, broad t, NH). HRMS (ESI$^+$) calculated for C$_{29}$H$_{32}$FN$_4$O$_4$ [M+H$^+$]: 519.2408; found: 519.2407.

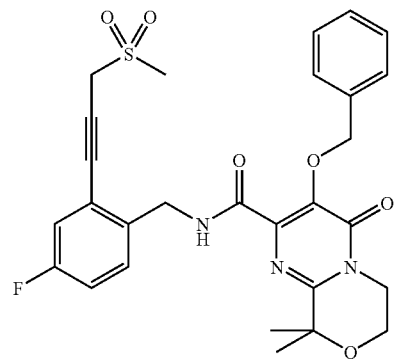

Intermediate 186

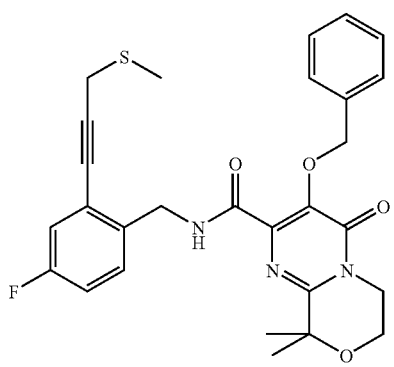

Intermediate 185

N-(4-Fluoro-2-(3-(methylthio)prop-1-ynyl)benzyl)-3-(benzyloxy)-9,9-dimethyl-4-oxo-4,6,7,9-tetrahydropyrimido[2,1-c][1,4]oxazine-2-carboxamide. A solution of intermediate 183, 3-[2-((3-(benzyloxy)-9,9-dimethyl-4-oxo-4,6,7,9-tetrahydropyrimido[2,1-c][1,4]oxazine-2-carboxamido)methyl)-5-fluorophenyl]prop-2-ynyl methanesulfonate (0.160 g, 0.28 mmol) in N,N-dimethylformamide (3 ml) was treated at 0° C. with sodium thiomethoxide (0.026 g, 0.37 mmol) and the resulting mixture stirred for 2 h. The reaction mixture was then diluted with ethyl acetate, washed with saturated sodium bicarbonate and brine, then dried over anhydrous magnesium sulfate and concentrated under reduced pressure. Chromatography of the residue on silica gel (elution gradient of ethyl acetate in hexane) gave 0.114 g (78% yield) of the title material as a white solid. $^1$HNMR 400 MHz (CDCl$_3$) δ ppm: 1.64 (6H, s, 2×CH$_3$), 2.28 (3H, s, SCH$_3$), 3.45 (2H, s, SCH$_2$), 4.05 (4H, m, 2×CH$_2$), 4.69 (2H, d, J=6.1 Hz, NCH$_2$), 5.31 (2H, s, OCH$_2$), 6.98 (1H, m, aromatic), 7.15 (1H,dd, J=3 Hz and J=9.1 Hz, aromatic), 7.32-7.38 (4H, m, aromatics), 7.50-7.53 (2H, m, aromatics), 7.80 (1H, broad t, NH). HRMS (ESI$^+$) calculated for C$_{28}$H$_{29}$FN$_3$O$_4$S [M+H$^+$]: 522.1863; found: 522.1844.

N-(4-Fluoro-2-(3-(methylsufonyl)prop-1-ynyl)benzyl)-3-(benzyloxy)-9,9-dimethyl-4-oxo-4,6,7,9-tetrahydropyrimido[2,1-c][1,4]oxazine-2-carboxamide. A solution of intermediate 185, N-(4-fluoro-2-(3-(methylthio)prop-1-ynyl)benzyl)-3-(benzyloxy)-9,9-dimethyl-4-oxo-4,6,7,9-tetrahydropyrimido[2,1-c][1,4]oxazine-2-carboxamide (0.110 g, 0.21 mmol) in dichloromethane (3 ml) was treated at 0° C. with 3-chloroperoxybenzoic acid (0.120 g of 85%, 0.59 mmol) and the resulting mixture was stirred at 22° C. for 30 min. The reaction mixture was then diluted with ethyl acetate, washed with saturated sodium bicarbonate, brine, then dried over anhydrous magnesium sulfate and concentrated under reduced pressure. Chromatography of the residue on silica gel (elution gradient of ethyl acetate in dichloromethane) gave 0.074 g (64% yield) of the title material as a white solid. $^1$HNMR 400 MHz (CDCl$_3$) δ ppm: 1.64 (6H, s, 2×CH$_3$), 3.03 (3H, s, SCH$_3$), 4.03 (2H, s, SCH$_2$), 4.05 (4H, m, 2×CH$_2$), 4.65 (2H, d, J=6.0 Hz, NCH$_2$), 5.27 (2H, s, OCH$_2$), 7.06 (1H, m, aromatic), 7.17 (1H,dd, J=3 Hz and J=8.6 Hz, aromatic), 7.31-7.38 (6H, m, aromatics), 8.12 (1H, broad t, NH). HRMS (ESI$^+$) calculated for C$_{28}$H$_{29}$FN$_3$O$_6$S [M+H$^+$]: 554.1761; found: 554.1784.

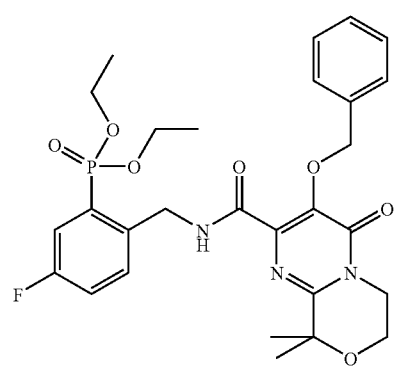

Intermediate 187

Diethyl 2-((3-(benzyloxy)-9,9-dimethyl-4-oxo-4,6,7,9-tetrahydropyrimido[2,1-c][1,4]oxazine-2-carboxamido)methyl)-5-fluorophenylphosphonate. A solution of intermediate 174, N-(4-fluoro-2-iodobenzyl)-3-(benzyloxy)-9,9-dimethyl-4-oxo-4,6,7,9-tetrahydropyrimido[2,1-c][1,4]oxazine-2-carboxamide (0.200 g, 0.35 mmol) and triphenylphosphine (0.020 mg) in ethanol (5 ml) was flushed with argon and then treated with N,N-diisopropylethylamine (0.25 ml, 1.4 mmol), palladium(11) acetate (0.020 g) and diethyl phosphite (0.15 ml, 1.16 mmol). The reaction mixture was then sealed and heated at 80° C. for 18 h. The reaction mixture was then diluted with ethyl acetate, washed with 0.1 N hydrochloric acid, saturated sodium bicarbonate, brine, then dried over anhydrous magnesium sulfate and concentrated. Chromatography of the residue on silica gel (elution gradient of acetonitrile in dichloromethane) gave 0.103 g (51% yield) of the title compound as a white solid. $^1$HNMR 400 MHz (CDCl$_3$) δ ppm: 1.36 (6H, t, J=6.6 Hz, 2×CH$_3$), 1.64 (6H, s, 2×CH$_3$), 4.04 (4H, m, 2×CH$_2$), 4.08-4.22 (4H, m, 2×OCH$_2$), 4.78 (2H, d, J=6.6 Hz, NCH$_2$), 5.29 (2H, s, OCH$_2$), 7.21 (1H, m, aromatic), 7.29-7.34 (3H, m, aromatics), 7.45-7.52 (3H, m, aromatics), 7.65-7.72 (1H, m, aromatic), 8.67 (1H, broad t, NH). HRMS (ESI$^+$) calculated for C$_{28}$H$_{34}$FN$_3$O$_7$P [M+H$^+$]: 574.2118; found: 574.2126.

Intermediate 188

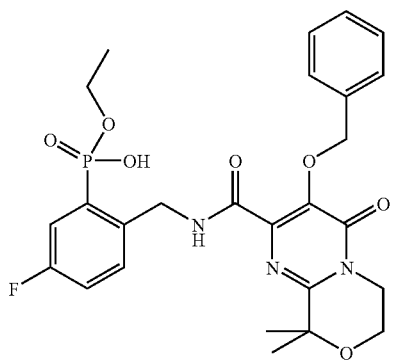

Ethyl hydrogen 2-((3-(benzyloxy)-9,9-dimethyl-4-oxo-4,6,7,9-tetrahydropyrimido[2,1-c][1,4]oxazine-2-carboxamido)methyl)-5-fluorophenylphosphonate. A solution of intermediate 187, diethyl 2-((3-(benzyloxy)-9,9-dimethyl-4-oxo-4,6,7,9-tetrahydropyrimido[2,1-c][1,4]oxazine-2-carboxamido)methyl)-5-fluorophenylphosphonate (0.115 g, 0.20 mmol) in tetrahydrofuran (3 ml)/ethanol (3 mL) was treated with 1N aqueous sodium hydroxide (1.0 ml, 1.0 mmol) and the resulting mixture heated at 45° C. for 2 h. The reaction mixture was then diluted with ethyl acetate, washed with 0.1 N hydrochloric acid, brine, dried over anhydrous magnesium sulfate and concentrated. The residue was purified on a Shimadzu automated preparative HPLC system (column YMC Pack C-18, 5μ, 20×250 mm, elution gradient acetonitrile-water 0.1% trifluoroacetic acid) to give 0.070 g (64% yield) of the title material as a clear oil. $^1$HNMR 400 MHz (CDCl$_3$) δ ppm: 1.37 (3H, t, J=7.1 Hz, CH$_3$), 1.62 (6H, s, 2×CH$_3$), 4.04 (4H, m, 2×CH$_2$), 4.18 (2H, m, OCH$_2$), 4.75 (2H, broad d, J=5 Hz, NCH$_2$), 5.32 (2H, s, OCH$_2$), 7.21 (1H, m, aromatic), 7.30-7.33 (3H, m, aromatics), 7.38-7.40 (2H, m, aromatics), 7.47-7.52 (1H, m, aromatic), 7.56-7.63 (1H, m, aromatic), 8.56 (1H, broad t, NH). HRMS (ESI$^+$) calculated for C$_{26}$H$_{30}$FN$_3$O$_7$P [M+H$^+$]: 546.1805; found: 546.1786.

Intermediate 189

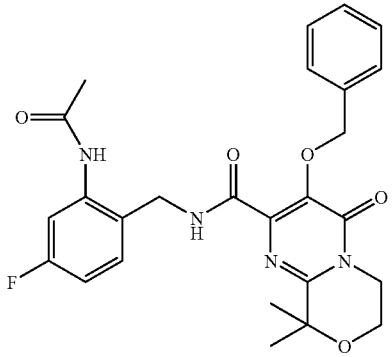

N-(2-Acetamido-4-fluorobenzyl)-3-(benzyloxy)-9,9-dimethyl-4-oxo-4,6,7,9-tetrahydropyrimido[2,1-c][1,4]oxazine-2-carboxamide. To a solution of intermediate 169, N-(2-amino-4-fluorobenzyl)-3-(benzyloxy)-9,9-dimethyl-4-oxo-4,6,7,9-tetrahydropyrimido[2,1-c][1,4]oxazine-2-carboxamide (0.033 g, 0.073 mmol) in dry tetrahydrofuran (10 mL) was added acetyl chloride (5.7 μL, 0.08 mmol) and diisopropylethylamine (38 μL, 0.22 mmol). The reaction mixture was stirred at 23° C. for 3 h. NaHCO$_3$ (0.25 M, 20 mL) was then added and the organic material extracted with ethyl acetate (3×25 mL). The organic extracts were combined, dried (MgSO$_4$) and concentrated in vacuo. The residue was purified on a Biotage system using a silica gel column with ethyl acetate:Hex (1:2 to 2:1) as eluent to afford the title compound (0.025 g, 69% yield). $^1$HNMR 400 MHz (MeOD) δ (ppm): 7.66 (1H, dd, J=10.5, 2.8 Hz), 7.43-7.25 (6H, m), 6.87 (1H, ddd, (dt), J=8.8, 2.6 Hz), 5.19 (2H, s), 4.47 (2H, m), 4.08 (2H, t, J=4.9 Hz), 3.99 (2H, t, J=4.9 Hz), 2.19 (3H, s), 1.62 (6H, s). LCMS (M+H)$^+$ m/z 495.

Intermediate 190

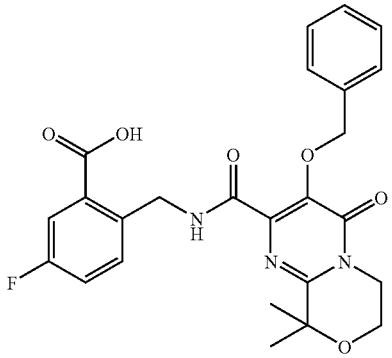

2-((3-(Benzyloxy)-9,9-dimethyl-4-oxo-4,6,7,9-tetrahydropyrimido[2,1-c][1,4]oxazine-2-carboxamido)methyl)-5-fluorobenzoic acid. To a suspension of intermediate 154, methyl 2-((3(benzyloxy)-9,9-dimethyl-4-oxo-4,6,7,9-tetrahydropyrimido[2,1-c][1,4]oxazine-2-carboxamido)methyl)-5-fluorobenzoate. (500 mg, 1.01 mmol) in MeOH (10 mL) and CH$_3$CN (5 mL) was added 1N NaOH (2 mL) and the mixture stirred at room temperature for 2 hrs. The mixture was concentrated in vacuo and the residue purified by reverse phase column chromatography (YMC, C-18 ODS, 10-25% CH$_3$CN/H$_2$O) to provide 90 mg (Yield 19%) of the title compound as an off-white powder: LC/MS m/Z 482 (M+H).

Intermediate 191

N-(2-((2-Aminoethyl)carbamoyl)-4-fluorobenzyl)-3-(benzyloxy)-9,9-dimethyl-4-oxo-4,6,7,9-tetrahydropyrimido[2,1-c][1,4]oxazine-2-carboxamide. A mixture of intermediate 190, 2-((3-(benzyloxy)-9,9-dimethyl-4-oxo-4,6,7,9-tetrahydropyrimido[2,1-c][1,4]oxazine-2-carboxamido)methyl)-5-fluorobenzoic acid, (59 mg, 0.12 mmol) and O-(7-azabenzotriazol-1-yl)-N,N,N',N'-tetramethyluronium hexafluorophosphate, HATU (76 mg, 0.2 mmol; Aldrich) in DMF (1 mL) was stirred for 20 min. To this mixture was added ethanolamine (20 mg, 0.3 mmol) and the stirring continued overnight. The mixture was concentrated in vacuo, dissolved in CH$_2$Cl$_2$, washed with water then dried (MgSO$_4$), filtered, and concentrated to provide 55 mg (Yield 87%) of the title compound: LC/MS m/z 525 (M+H).

Intermediate 192

(R)-N-(4-Fluoro-2-(2-(hydroxymethyl)-5-oxopyrrolidin-1-yl)benzyl)-3-(benzyloxy)-9,9-dimethyl-4-oxo-4,6,7,9-tetrahydropyrimido[2,1-c][1,4]oxazine-2-carboxamide. To a stirred solution of intermediate 166, (R)-N-(2-(2-((tert-butyldimethylsilyloxy)methyl)-5-oxopyrrolidin-1-yl)-4-fluorobenzyl)-3-(benzyloxy)-9,9-dimethyl-4-oxo-4,6,7,9-tetrahydropyrimido[2,1-c][1,4]oxazine-2-carboxamide (0.10 g, 0.150 mmol) in tetrahydrofuran (5 mL) at 23° C. was added a solution of tetrabutylammonium fluoride (1M in tetrahydrofuran) (180 µL, 0.18 mmol). The reaction mixture was stirred at 23° C. for 3 h. NaHCO$_3$ (1N in H$_2$O, 30 mL) was then added and the organic material was extracted with ethyl acetate (2×25 mL). The combined organic extracts were dried (MgSO$_4$), filtered and concentrated in vacuo. The residue was purified on a Biotage system using a silica gel column with ethyl acetate/Hexanes (1:1) to ethyl acetate 100% as eluent to afford the title compound (0.060 g, 73% yield): $^1$HNMR 400 MHz (MeOD) δ (ppm): 7.55 (1H, dd, (t), 6.6 Hz), 7.43 (2H, m), 7.13 (1H, dd, J=9.5, 2.4 Hz), 7.03 (1H, m), 5.26 (2H, s), 4.57 (1H, m), 4.32 (2H, m), 4.08 (2H, t, J=5.0 Hz), 7.03 (2H, t, J=5.0 Hz), 3.53 (2H, m), 2.69-2.56 (2H, m), 2.38 (1H, m), 2.22 (1H, m), 1.62 (6H, s). LCMS (M+H)$^+$ m/z 551.

Intermediate 193

(R)-(1-(2-((3-(Benzyloxy)-9,9-dimethyl-4-oxo-4,6,7,9-tetrahydropyrimido[2,1-c][1,4]oxazine-2-carboxamido)methyl)-5-fluorophenyl)-5-oxopyrrolidin-2-yl)methyl acetate. To a solution of intermediate 192, (R)-N-(4-fluoro-2-(2-(hydroxymethyl)-5-oxopyrrolidin-1-yl)benzyl)-3-(benzyloxy)-9,9-dimethyl-4-oxo-4,6,7,9-tetrahydropyrimido[2,1-c][1,4]oxazine-2-carboxamide (0.045 g, 0.082 mmol) in tetrahydrofuran (5 mL) was added acetyl chloride (12.8 µL, 0.180 mmol) and diisopropylethylamine (31.4 µL, 0.180 mmol). The reaction mixture was stirred at 23° C. for 4 h. NaHCO$_3$ (1N in H$_2$O, 30 mL) was then added and the organic material was extracted with ethyl acetate (2×25 mL). The combined organic extracts were dried (MgSO$_4$), filtered and concentrated in vacuo. The residue was purified on a Biotage system using a silica gel column with ethyl acetate/Hexanes (1:1) to ethyl acetate 100% as eluent to afford the title compound (0.032 g, 67% yield): $^1$HNMR 400 MHz (MeOD) δ ppm: 7.48 (3H, m), 7.33 (3H, m), 7.16 (1H, m), 7.03 (1H, m), 5.24 (2H, s), 4.60 (1H, m), 4.55 (1H, m), 4.22 (1H, dd, J=12.0, 4.5 Hz), 4.08 (2H, t, J=5.0 Hz), 3.99 (3H, m), 2.62 (2H, m), 2.44 (1H, m), 2.09-1.92 (5H, m), 1.62 (3H, s), 1.61 (3H, s). LCMS (M+H)$^+$ m/z 593.

Intermediate 194

(R)-(1-(2-((3-(Benzyloxy)-9,9-dimethyl-4-oxo-4,6,7,9-tetrahydropyrimido[2,1-c][1,4oxazine-2-carboxamido)methyl)-5-fluorophenyl)-5-oxopyrrolidin-2-yl)methyl methanesulfonate. To a stirred solution of intermediate 192, (R)-N-(4-fluoro-2-(2-(hydroxymethyl)-5-oxopyrrolidin-1-yl)benzyl)-3-(benzyloxy)-9,9-dimethyl-4-oxo-4,6,7,9-tetrahydropyrimido[2,1-c][1,4]oxazine-2-carboxamide (0.160 g, 0.291 mmol) in CH$_2$Cl$_2$ (10 mL) at 0° C. was added triethylamine (81 μL, 0.582 mmol) and methanesulfonyl chloride (27 μL, 0.349 mmol). The reaction mixture was stirred at 23° C. for 4 h. Water (50 mL) was then added and the organic material was extracted with CH$_2$Cl$_2$ (2×50 mL). The combined organic extracts were dried (MgSO$_4$), filtered and concentrated in vacuo to afford the title compound (0.178 g, 98% yield). The crude material was used without further purification for the next step: LCMS (M+H)$^+$ m/z 629.

dimethyl-4-oxo-4,6,7,9-tetrahydropyrimido[2,1-c][1,4]oxazine-2-carboxamide (0.100 g, 0.21 mmol) in dichloroethane (10 mL) was added per-acetic acid (32% in H$_2$O) (1.0 mmol, 200 μL). The reaction mixture was stirred at 23° C. for 48 h. Water (50 mL) was added and the organic material was extracted with CH$_2$Cl$_2$ (2×50 mL). The combined organic extracts were dried (MgSO$_4$), filtered and concentrated in vacuo to afford the title compound (0.106 g, 99% yield): $^1$H NMR (400 MHz, DMSO-d$_6$) δ ppm: 9.11(1H, t, J=6.4 Hz), 7.65 (1H, d, J=6.8 Hz) 7.59-7.29 (9H, m), 5.15 (2H, s). 4.77 (2H, d, J=6.5 Hz), 4.04 (2H, t, J=5.0 Hz), 3.90 (2H, m), 1.59 (6H, s). LCMS (M+H)$^+$ m/z 508.

EXAMPLE 1

Intermediate 195

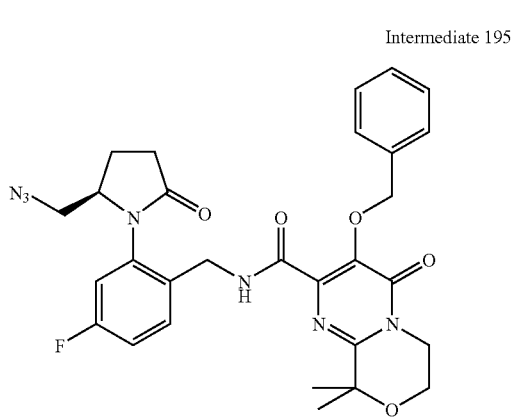

(R)-N-(2-(2-(Azidomethyl)-5-oxopyrrolidin-1-yl)-4-fluorobenzyl)-3-(benzyloxy)-9,9-dimethyl-4-oxo-4,6,7,9-tetrahydropyrimido[2,1-c][1,4]oxazine-2-carboxamide. To a solution of intermediate 194, (R)-(1-(2-((3-(benzyloxy)-9,9-dimethyl-4-oxo-4,6,7,9-tetrahydropyrimido[2,1-c][1,4]oxazine-2-carboxamido)methyl)-5-fluorophenyl)-5-oxopyrrolidin-2-yl)methyl methanesulfonate (0.150 g, 0.239 mmol) in DMF (10 mL) was added sodium azide (0.019 g, 0.287 mmol). The resulting mixture was stirred at 50° C. for 6 h. Water (50 mL) was then added and the organic material was extracted with ethyl acetate (2×50 mL). The combined organic extracts were washed with H$_2$O (50 mL), dried (MgSO$_4$), filtered and concentrated in vacuo to afford the title compound (0.125 g, 91% yield). LCMS (M+H)$^+$ m/z 576.

Intermediate 196

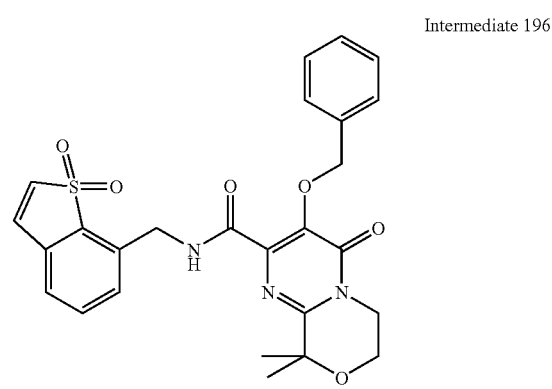

N-(Benzo[b]thiophen-1,1-dione-7-ylmethyl)-3-(benzyloxy)-9,9-dimethyl-4-oxo-4,6,7,9-tetrahydropyrimido[2,1-c][1,4]oxazine-2-carboxamide. To a solution of intermediate 147, N-(benzo[b]thiophen-7-ylmethyl)-3-(benzyloxy)-9,9-

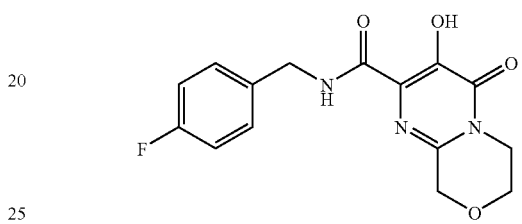

Pyrimido[2,1-c[1,4]oxazine-2-carboxamide, N-[(4-fluorophenyl)methyl]-4,6,7,9-tetrahydro-3-hydroxy-4-oxo-. A mixture of intermediate 7, ethyl 3-hydroxy-4-oxo-4,6,7,9-tetrahydropyrimido[2,1-c][1,4]oxazine-2-carboxylate, (0.036 g, 0.15 mmol) and 4-fluorobenzylamine (0.11 g, 0.87 mmol) in anhydrous ethyl alcohol (5 ml) and N,N-dimethylformamide (2 ml) was heated under reflux for 18 h. The solvent was then evaporated in vacuo and the residue was partitioned between ethyl acetate and 0.1 N hydrochloric acid. The organic phase was washed with water, brine and dried over anhydrous sodium sulfate. Evaporation of the solvent and recrystallization of the resulting solid from ethanol gave 0.023 g (47% yield) of the title amide as white crystals; mp 211° C. (ethyl acetate-hexane). $^1$HNMR 400 MHz (CDCl$_3$) δ ppm: 4.06 (4H, m, 2×CH$_2$), 4.59 (2H, d, J=7.6 Hz, NCH$_2$), 4.61 (2H, s, OCH$_2$), 7.09 (2H, m, aromatics), 7.33 (2H, m, aromatics), 7.84 (1H, broad t, NH), 12.06 (1H, s, OH). MS (ESI$^+$) m/z 320 [M+H$^+$].

EXAMPLE 2

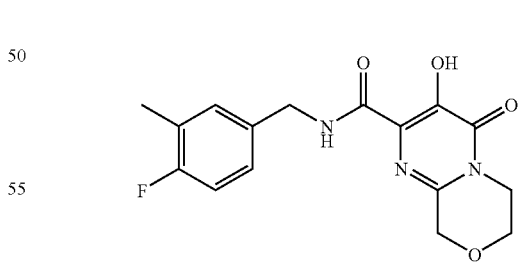

Pyrimido[2,1-c][1,4]oxazine-2-carboxamide, N-[(4-fluoro-3-methylphenyl)methyl]-4,6,7,9-tetrahydro-3-hydroxy-4-oxo-. Reaction of intermediate 7, ethyl 3-hydroxy-4-oxo-4,6,7,9-tetrahydropyrimido[2,1-c][1,4]oxazine-2-carboxylate, (0.100 g, 0.42 mmol) with 4-fluoro-3-methylbenzylamine (0.23 g, 1.66 mmol) as described in the preparation of example 1 gave 0.101 g (73% yield) of the title amide as white crystals; mp 206-208° C. (ethyl acetate).

¹HNMR 400 MHz (CDCl₃) δ ppm: 2.30 (3H, s, CH₃), 4.06 (4H, m, 2×CH₂), 4.55 (2H, d, J=6.1 Hz, NCH₂), 4.60 (2H, s, OCH₂), 7.01 (1H, m, aromatic), 7.14 (2H, m, aromatics), 7.81 (1H, broad t, NH), 12.09 (1H, s, OH). MS (ESI⁺) m/z 334 [M+H⁺].

EXAMPLE 3

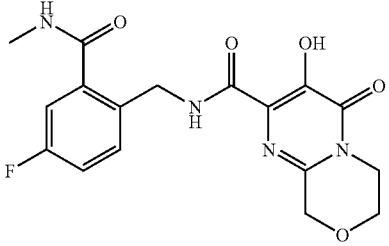

Pyrimido[2,1-c][1,4]oxazine-2-carboxamide, N-[[4-fluoro-2-[(methylamino)carbonyl]phenyl]methyl]-4,6,7,9-tetrahydro-3-hydroxy-4-oxo-. The title compound can be prepared from intermediate 150, N-(4-fluoro-2-(methylcarbamoyl)benzyl)-3-(benzyloxy)-4-oxo-4,6,7,9-tetrahydropyrimido[2,1-c][1,4]oxazine-2-carboxamide.

¹HNMR 400 MHz (DMSO-d₆) δ ppm: 2.79 (3H, d, J=4.5 Hz, NCH₃), 3.83 (2H, m, CH₂), 4.02 (2H, m, CH₂), 4.54 (2H, d, J=6.7 Hz, NCH₂), 4.58 (2H, s, OCH₂), 7.31 (2H, m, aromatics), 7.38 (1H, m, aromatic), 8.54 (1H, broad q, NH), 9.21 (1H, broad t, NH), 12.24 (1H, s, OH). HRMS (ESI⁺) calculated for C₁₇H₁₈FN₄O₅ [M+H⁺]: 377.1261; found: 377.1249.

EXAMPLE 4

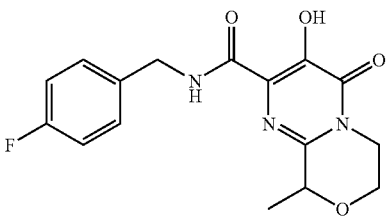

Pyrimido[2,1-c][]1,4]oxazine-2-carboxamide, N-[(4-fluorophenyl)methyl]-4,6,7,9-tetrahydro-3-hydroxy-9-methyl-4-oxo-. Reaction of intermediate 15, ethyl 3-hydroxy-9-methyl-4-oxo-4,6,7,9-tetrahydropyrimido[2,1-c][1,4]oxazine-2-carboxylate (0.050 g, 0.20 mmol) with 4-fluorobenzylamine (0.11 g, 0.87 mmol) as described in the preparation of example 1 gave 0.056 g (84% yield) of the title amide as white crystals; mp 165-167° C. (ethyl acetate-hexane). ¹HNMR 400 MHz (CDCl₃) δ ppm: 1.62 (3H, d, J=7.0 Hz, CH₃), 3.90 (2H, m, CH₂), 4.15-4.32 (2H, m, CH₂), 4.61 (3H, m, NCH₂ and OCH), 7.08 (2H, m, aromatics), 7.34 (2H, m, aromatics), 7.82 (1H, broad t, NH), 12.06 (1H, s, OH). Anal. Calcd for C₁₆H₁₆FN₃O₄: C, 57.65; H, 4.83; N, 12.60. Found: C, 57.44; H, 4.69; N, 12.37.

EXAMPLE 5

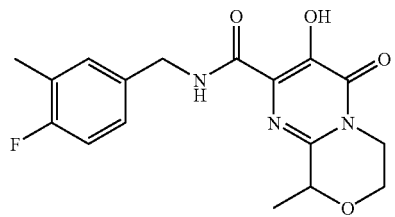

Pyrimido[2,1-c][]1,4]oxazine-2-carboxamide, N-[(4-fluoro-3-methylphenyl)methyl]-4,6,7,9-tetrahydro-3-hydroxy-9-methyl-4-oxo-. Reaction of intermediate 15, ethyl 3-hydroxy-9-methyl-4-oxo-4,6,7,9-tetrahydropyrimido[2,1-c][1,4]oxazine-2-carboxylate, (0.090 g, 0.35 mmol) with 4-fluoro-3-methylbenzylamine (0.180 g, 1.3 mmol) as described in the preparation of example 1 gave 0.068 g (55% yield) of the title amide as white crystals; mp 134° C. (ethyl acetate-hexane). ¹HNMR 400 MHz (CDCl₃) δ ppm: 1.62 (3H, d, J=6.6 Hz, CH₃), 2.30 (3H, s, CH₃), 3.90 (2H, m, CH₂), 4.13-4.32 (2H, m, CH₂), 4.49-4.64 (3H, m, NCH₂ and OCH), 7.01 (1H, m, aromatic), 7.16 (2H, m, aromatics), 7.79 (1H, broad t, NH), 12.09 (1H, s, OH). Anal. Calcd for C₁₇H₁₈FN₃O₄: C, 58.78; H, 5.22; N, 12.09. Found: C, 58.57; H, 5.55; N, 11.90.

EXAMPLE 6

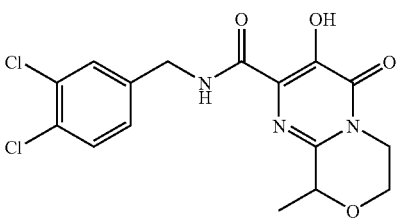

Pyrimido[2,1-c][1,4]oxazine-2-carboxamide, N-[(3,4-dichlorophenyl)methyl]-4,6,7,9-tetrahydro-3-hydroxy-9-methyl-4-oxo-. Reaction of intermediate 15, ethyl 3-hydroxy-9-methyl-4-oxo-4,6,7,9-tetrahydropyrimido[2,1-c][1,4]oxazine-2-carboxylate (0.075 g, 0.29 mmol) with 3,4-dichlorobenzylamine (0.140 g, 0.8 mmol) as described in the preparation of example 1 gave 0.085 g (75% yield) of the title amide as white crystals; mp 192° C. (ethyl acetate-hexane). ¹HNMR 400 MHz (CDCl₃) δ ppm: 1.64 (3H, d, J=6.6 Hz, CH₃), 3.91 (2H, m, CH₂), 4.17-4.32 (2H, m, CH₂), 4.50-4.68 (3H, m, NCH₂ and OCH), 7.20 (1H, dd, J=2.0 Hz and J=8.0 Hz, aromatic), 7.44 (1H, d, J=2.0 Hz, aromatic), 7.46 (1H, d, J=8.0 Hz, aromatic), 7.86 (1H, broad t, NH), 11.92 (1H, s, OH). MS (ESI⁺) m/z 384 [M+H⁺]. Anal. Calcd for C₁₆H₁₅Cl₂N₃O₄: C, 50.02; H, 3.94; N, 10.94. Found: C, 49.40; H, 4.06; N, 10.41.

EXAMPLE 7

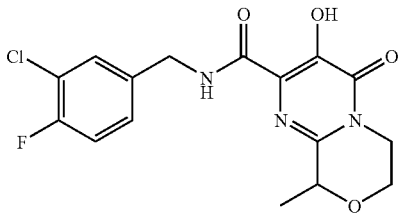

Pyrimido[2,1-c][1,4]oxazine-2-carboxamide, N-[(3-chloro-4-fluorophenyl)methyl]-4,6,7,9-tetrahydro-3-hydroxy-9-methyl-4-oxo-. Reaction of intermediate 15, ethyl 3-hydroxy-9-methyl-4-oxo-4,6,7,9-tetrahydropyrimido[2,1-c][1,4]oxazine-2-carboxylate, (0.075 g, 0.30 mmol) with 3-chloro-4-fluorobenzylamine (0.14 g, 0.88 mmol) as described in the preparation of example 1 gave 0.050 g (46% yield) of the title amide as white crystals; mp 172° C. (ethyl acetate-ether). ¹HNMR 400 MHz (CDCl₃) δ ppm: 1.63 (3H, d, J=6.6 Hz, CH₃), 3.91 (2H, m, CH₂), 4.17-4.32 (2H, m, CH₂), 4.50-4.67 (3H, m, NCH₂ and OCH), 7.16 (1H, m, aromatic), 7.24 (1H, m, aromatic), 7.40 (1H, m, aromatic), 7.85 (1H, broad t, NH), 11.95 (1H, s, OH). Anal. Calcd for C₁₆H₁₅ClFN₃O₄: C, 52.25; H, 4.11; N, 11.42. Found: C, 51.991; H, 4.01; N, 11.09.

EXAMPLE 8

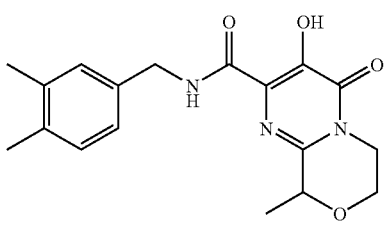

Pyrimido[2,1-c][1,4]oxazine-2-carboxamide, N-[(3,4-dimethylphenyl)methyl]-4,6,7,9-tetrahydro-3-hydroxy-9-methyl-4-oxo-. Reaction of intermediate 15, ethyl 3-hydroxy-9-methyl-4-oxo-4,6,7,9-tetrahydropyrimido[2,1-c][1,4]oxazine-2-carboxylate, (0.075 g, 0.30 mmol) with 3,4-dimethylbenzylamine (0.15 g, 1.1 mmol) as described in the preparation of example 1 gave 0.033 g (33% yield) of the title amide as a white solid. ¹HNMR 400 MHz (CDCl₃) δ ppm: 1.61 (3H, d, J=6.6 Hz, CH₃), 2.28 (3H, s, CH₃), 2.29 (3H, s, CH₃), 3.90 (2H, m, CH₂), 4.16-4.30 (2H, m, CH₂), 4.50-4.65 (3H, m, NCH₂ and OCH), 7.08-7.17 (3H, m, aromatics), 7.78 (1H, broad t, NH), 12.17 (1H, s, OH). MS (ESI⁺) m/z 344 [M+H⁺].

EXAMPLE 9

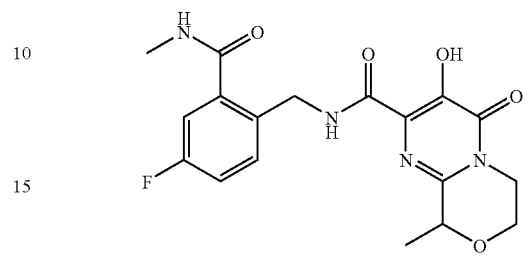

Pyrimido[2,1-c][]1,4]oxazine-2-carboxamide, N-[[4-fluoro-2-[(methylamino)carbonyl]phenyl]methyl]-4,6,7,9-tetrahydro-3-hydroxy-9-methyl-4-oxo-. A solution of intermediate 140, N-(4-fluoro-2-(methylcarbamoyl)benzyl)-3-benzyloxy-9-methyl-4-oxo-4,6,7,9-tetrahydropyrimido[2,1-c][1,4]oxazine-2-carboxamide, (0.268 g, 0.56 mmol) in a mixture of ethyl acetate (25 ml) and ethanol (25 ml) was hydrogenated under 1 atm of hydrogen at 25° C. over 10% palladium on activated carbon (0.09 g) for 2.5 h to give 0.121 g (56% yield) of the title ester as a white solid. ¹HNMR 400 MHz (DMSO-d₆) δ ppm: 1.57 (3H, d, J=6.7 Hz, CH₃), 2.79 (3H, d, J=4.6 Hz, NCH₃), 3.70 (1H, m, CH), 3.87 (1H, m, CH), 3.98 (1H, m CH), 4.15 (1H, m, CH), 4.55 (2H, m, NCH₂), 4.62 (1H, q, J=6.6 Hz, OCH), 7.25-7.44 (3H, m, aromatics), 8.59 (1H, broad q, NH), 9.39 (1H, broad, NH), 12.18 (1H, s, OH). HRMS (ESI⁺) calculated for C₁₈H₂₀FN₄O₅ [M+H⁺]: 391.1418; found: 391.1431.

EXAMPLES 10-14

Examples 10-14 can be prepared from ethyl 9-ethyl-3-hydroxy-4-oxo-4,6,7,9-tetrahydropyrimido[2,1-c][1,4]oxazine-2-carboxylate and the indicated amines according to the method described for the synthesis of example 1. Ethyl 9-ethyl-3-hydroxy-4-oxo-4,6,7,9-tetrahydropyrimido[2,1-c][1,4]oxazine-2-carboxylate was prepared according to the method used to prepare intermediate 15.

EXAMPLE 10

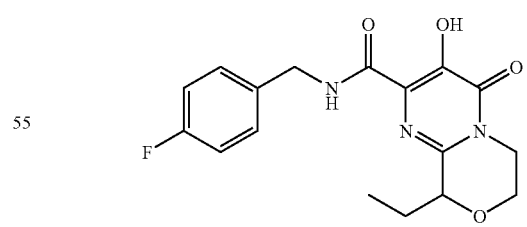

Pyrimido[2,1-c][1,4]oxazine-2-carboxamide, 9-ethyl-N-[(4-fluorophenyl)methyl]-4,6,7,9-tetrahydro-3-hydroxy-4-oxo-. The title compound can be prepared from 4-fluorobenzylamine. ¹HNMR 400 MHz (CDCl₃) δ ppm: 1.02 (3H, t, J=7.3 Hz, CH₃), 1.93 (1H, m, CH), 2.15 (1H, m, CH), 3.88 (2H, m, CH₂), 4.2-4.29 (2H, m, CH₂), 4.46 (1H, m, CH), 4.53-4.69 (2H, m, CH₂), 7.06 (2H, m, aromatics), 7.34 (2H, m, aromatics), 7.82 (1H, broad t, NH), 12.05 (1H, s, OH). HRMS (ESI+) calculated for $C_{17}H_{19}FN_3O_4$ [M+H+]: 348.1360; found: 348.1355.

EXAMPLE 11

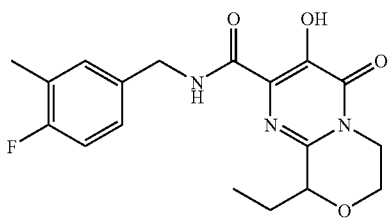

Pyrimido[2,1-c][1,4]oxazine-2-carboxamide, 9-ethyl-N-[(4-fluoro-3-methylphenyl)methyl]-4,6,7,9-tetrahydro-3-hydroxy-4-oxo-. The title compound can be prepared from (4-fluoro-3-methylphenyl)methanamine. $^1$HNMR 400 MHz (CDCl$_3$) δ ppm: 1.01 (3H, t, J=7.4 Hz, CH$_3$), 1.91 (1H, m, CH), 2.16 (1H, m, CH), 2.30 (3H, s, CH$_3$), 3.87 (2H, m, CH$_2$), 4.2-4.30 (2H, m, CH$_2$), 4.46 (1H, m, CH), 4.48-4.65 (2H, m, CH$_2$), 7.01 (1H, m, aromatic), 7.14 (2H, m, aromatics), 7.81 (1H, broad t, NH), 12.07 (1H, s, OH). Anal. Calcd for $C_{18}H_{20}FN_3O_4$: C, 59.82; H, 5.57; N, 11.62; Found: C, 59.53; H, 5.86; N, 11.42.

EXAMPLE 12

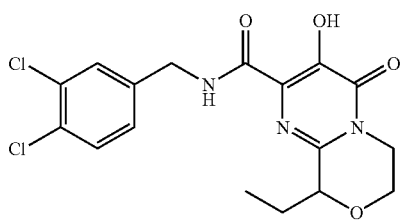

Pyrimido[2,1-c][1,4]oxazine-2-carboxamide, N-[(3,4-dichlorophenyl)methyl]-9-ethyl-4,6,7,9-tetrahydro-3-hydroxy-4-oxo-. The title compound can be prepared from (3,4-dichlorophenyl)methanamine. $^1$HNMR 400 MHz (CDCl$_3$) δ ppm: 1.00 (3H, t, J=7.3 Hz, CH$_3$), 1.91 (1H, m, CH), 2.15 (1H, m, CH), 3.85 (2H, m, CH$_2$), 4.19-4.28 (2H, m, CH$_2$), 4.45 (1H, m, CH), 4.48-4.66 (2H, m, CH$_2$), 7.19 (1H, m, aromatic), 7.43 (2H, m, aromatics), 7.84 (1H, broad t, NH), 11.88 (1H, s, OH). Anal. Calcd for $C_{17}H_{17}Cl_2N_3O_4$: C, 51.27; H, 4.30; N, 10.55; Found: C, 51.16; H, 4.21; N, 10.34.

EXAMPLE 13

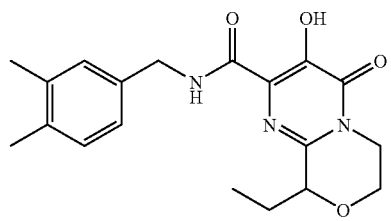

Pyrimido[2,1-c][1,4]oxazine-2-carboxamide, N-[(3,4-dimethylphenyl)methyl]-9-ethyl-4,6,7,9-tetrahydro-3-hydroxy-4-oxo-. The title compound can be prepared from (3,4-dimethylphenyl)methanamine. $^1$HNMR 400 MHz (CDCl$_3$) δ ppm: 0.98 (3H, t, J=7.3 Hz, CH$_3$), 1.87 (1H, m, CH), 2.12 (1H, m, CH), 2.26 (3H, s, CH$_3$), 2.27 (3H, s, CH$_3$), 3.83 (2H, m, CH$_2$), 4.17-4.26 (2H, m, CH$_2$), 4.41 (1H, m, CH), 4.45-4.64 (2H, m, CH$_2$), 7.05-7.24 (3H, m, aromatics), 7.75 (1H, broad t, NH), 12.13 (1H, s, OH). Anal. Calcd for $C_{19}H_{23}N_3O_4$: C, 63.85; H, 6.49; N, 11.76; Found: C, 63.55; H, 6.48; N, 11.74.

EXAMPLE 14

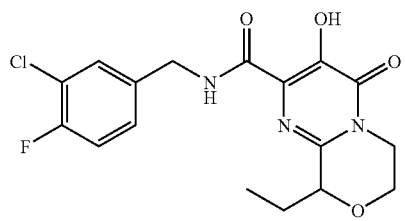

Pyrimido[2,1-c][1,4]oxazine-2-carboxamide, N-[(3-chloro-4-fluorophenyl)methyl]-9-ethyl-4,6,7,9-tetrahydro-3-hydroxy-4-oxo-. The title compound can be prepared from (3-chloro-4-fluorophenyl)methanamine. $^1$HNMR 400 MHz (CDCl$_3$) δ ppm: 1.03 (3H, t, J=7.3 Hz, CH$_3$), 1.92 (1H, m, CH), 2.17 (1H, m, CH), 3.88 (2H, m, CH$_2$), 4.18-4.32 (2H, m, CH$_2$), 4.46 (1H, m, CH), 4.5-4.68 (2H, m, CH$_2$), 7.16 (1H, m, aromatic), 7.24 (1H, m, aromatic), 7.40 (1H, m, aromatic), 7.84 (1H, broad t, NH), 11.93 (1H, s, OH). Anal. Calcd for $C_{17}H_{17}ClFN_3O_4$: C, 53.48; H, 4.48; N, 11.00; Found: C, 53.25; H, 4.49; N, 10.79.

EXAMPLES 15-16

Examples 15-16 can be prepared from 3-(benzyloxy)-9-ethyl-4-oxo-4,6,7,9-tetrahydropyrimido[2,1-c][1,4]oxazine-2-carboxylic acid and the indicated amines according to the methods described for the synthesis of intermediate 140 and example 9. 3-(Benzyloxy)-9-ethyl-4-oxo-4,6,7,9-tetrahydropyrimido[2,1-c][1,4]oxazine-2-carboxylic acid was prepared according to the method used to prepare intermediate 16.

EXAMPLE 15

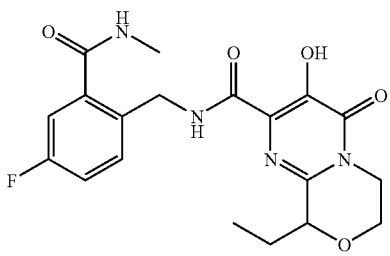

Pyrimido[2,1-c][1,4]oxazine-2-carboxamide, 9-ethyl-N-[[4-fluoro-2-[(methylamino)carbonyl]phenyl]methyl]-4,6,7,9-tetrahydro-3-hydroxy-4-oxo-. The title compound can be prepared from intermediate 39. $^1$HNMR 400 MHz (CDCl$_3$) δ ppm: 1.03 (3H, t, J=7.3 Hz, CH$_3$), 1.98 (1H, m, CH), 2.28 (1H, m, CH), 3.06 (3H, d, J=4.5 Hz, NCH$_3$), 3.86 (2H, m, CH$_2$), 4.14-4.29 (2H, m, CH$_2$), 4.48 (1H, m, CH), 4.60 (2H, m, CH$_2$), 6.2 (1H, broad, NH), 7.14-7.21 (2H, m, aromatics), 7.54 (1H, m, aromatic), 8.85 (1H, broad t, NH), 12.1 (1H, s, OH). HRMS (ESI$^+$) calculated for C$_{19}$H$_{22}$FN$_4$O$_5$ [M+H$^+$]: 405.1574; found: 405.1579.

EXAMPLE 16

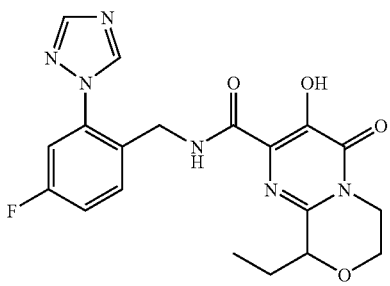

Pyrimido[2,1-c][1,4]oxazine-2-carboxamide, 9-ethyl-N-[[4-fluoro-2-(1H-1,2,4-triazol-1-yl)phenyl]methyl]-4,6,7,9-tetrahydro-3-hydroxy-4-oxo-. The title compound can be prepared from intermediate 151, N-(4-fluoro-2-(1H-1,2,4-triazol-1-yl)benzyl)-3-(benzyloxy)-9-ethyl-4-oxo-4,6,7,9-tetrahydropyrimido[2,1-c][1,4]oxazine-2-carboxamide, according to a procedure similar to that described in example 9. $^1$HNMR 400 MHz (DMSO-d$_6$) δ ppm: 0.94 (3H, t, J=7.5 Hz, CH$_3$), 1.88 (1H, m, CH), 2.27 (1H, m, CH), 3.68 (1H, m, CH), 3.87 (1H, m, CH), 4.0 (1H, m, CH), 4.19 (1H, m, CH), 4.36-4.49 (3H, m, CH$_2$ and CH), 7.43 (1H, m, aromatic), 7.56 (2H, m, aromatics), 8.32 (1H, m, CH), 9.05 (1H, m, CH), 9.3 (1H, broad t, NH), 12.04 (1H, s, OH). HRMS (ESI$^+$) calculated for C$_{19}$H$_{20}$FN$_6$O$_4$ [M+H$^+$]: 415.1530; found: 415.1515.

EXAMPLES 17-18

Examples 17-18 can be prepared from ethy3-hydroxy-9-isopropyl-4-oxo-4,6,7,9-tetrahydropyrimido[2,1-c][1,4]oxazine-2-carboxylate and the indicated amines according to the method described for the synthesis of example 1. Ethy3-hydroxy-9-isopropyl-4-oxo-4,6,7,9-tetrahydropyrimido[2,1-c][1,4]oxazine-2-carboxylate can be prepared according to the method used to prepare intermediate 15.

EXAMPLE 17

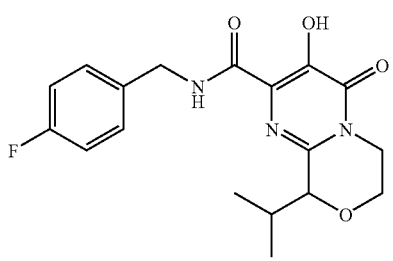

Pyrimido[2,1-c][1,4]oxazine-2-carboxamide, N-[(4-fluorophenyl)methyl]-4,6,7,9-tetrahydro-3-hydroxy-9-(1-methylethyl)-4-oxo-. The title compound can be prepared from 4-fluorobenzylamine. $^1$HNMR 400 MHz (CDCl$_3$) δ ppm: 0.80 (3H, d, J=6.7 Hz, CH$_3$), 1.13 (3H, d, J=7.1 Hz, CH$_3$), 2.54 (1H, m, CH), 3.77 (2H, m, CH$_2$), 4.3 (2H, m, CH$_2$), 4.40 (1H, d, J=2.5 Hz, CH), 4.50-4.72 (2H, m, CH$_2$), 7.09 (2H, m, aromatics), 7.34 (2H, m, aromatics), 7.82 (1H, broad t, NH), 12.04 (1H, s, OH). Anal. Calcd for C$_{18}$H$_{20}$FN$_3$O$_4$: C, 59.82; H, 5.57; N, 11.62; Found: C, 59.22; H, 5.81; N, 11.50.

EXAMPLE 18

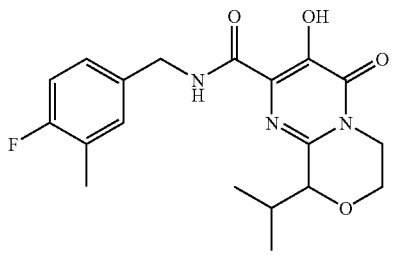

Pyrimido[2,1-c][1,4]oxazine-2-carboxamide, N-[(4-fluoro-3-methylphenyl)methyl]-4,6,7,9-tetrahydro-3-hydroxy-9-(1-methylethyl)-4-oxo-. The title compound can be prepared from (4-fluoro-3-methylphenyl)methanamine. $^1$HNMR 400 MHz (CDCl$_3$) δ ppm: 0.80 (3H, d, J=6.6 Hz, CH$_3$), 1.13 (3H, d, J=7.1 Hz, CH$_3$), 2.30 (3H, s, CH$_3$), 2.54 (1H, m, CH), 3.77 (2H, m, CH$_2$), 4.3 (2H, m, CH$_2$), 4.40 (1H, broad s, CH), 4.46-4.68 (2H, m, CH$_2$), 7.02 (1H, m, aromatic), 7.17 (2H, m, aromatics), 7.80 (1H, broad t, NH), 12.07

(1H, s, OH). HRMS (ESI⁺) calculated for C₁₉H₂₃FN₃O₄ [M+H⁺]: 376.1673; found: 376.1671.

EXAMPLE 19

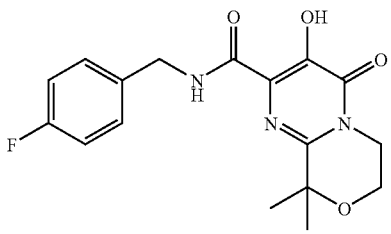

Pyrimido[2,1-c[]1,4]oxazine-2-carboxamide, N-[(4-fluorophenyl)methyl]-4,6,7,9-tetrahydro-3-hydroxy-9,9-dimethyl-4-oxo-. To a solution of intermediate 25, ethy3-hydroxy-9,9-dimethyl-4-oxo-4,6,7,9-tetrahydropyrimido[2,1-c][1,4]oxazine-2-carboxylate, (3.0 g, 11.19 mmol) in DMF (20 mL) and ethano(10 mL) was added triethylamine (1.55 mL) followed by 4-fluorobenzylamine (3.82 mL, 33.57 mmol). The mixture was stirred at 90° C. for 2 h and then concentrated. The resultant oiwas partitioned between ethyacetate (50 mL) and 1N aqueous HC(35 mL). The aqueous layer was back-extracted with ethyacetate (20 mL) and the organic layers were combined and washed with H₂O (4×20 mL) and brine then dried (Na₂SO₄) and concentrated. The brown residue was triturated with ether and the solids filtered and washed with ether. The pale brown solids were recrystallized from 95:5 MeOH/H₂O to give the title compound as colorless needles (3.18 g, 82% yield). ¹H NMR (500 MHz, CDCl₃) δ ppm: 11.96 (1H, s), 7.77 (1H, brs), 7.30 (2H, dd, J=8.4, 5.3 Hz), 7.04 (2H, t, J=8.7 Hz), 4.57 (2H, d, J=6.1 Hz), 4.01 (4H, s), 1.56 (6H, s) HRMS (M+H) calcd for C₁₇H₁₉FN₃O₄: 348.13597; found: 348.1365. Anal calcd for C₁₇H₁₈FN₃O₄: C, 58.78; H, 5.22; N, 12.09. Found: C, 58.38; H, 5.23; N, 11.80.

EXAMPLE 20

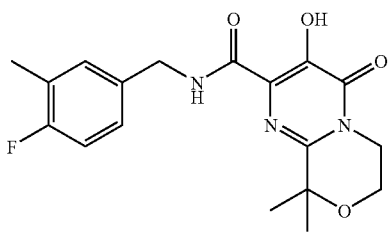

Pyrimido[2,1-c][1,4]oxazine-2-carboxamide, N-[(4-fluoro-3-methylphenyl)methyl]-4,6,7,9-tetrahydro-3-hydroxy-9,9-dimethyl-4-oxo-. A DMF solution of intermediate 25, ethy3-hydroxy-9,9-dimethyl-4-oxo-4,6,7,9-tetrahydropyrimido[2,1-c][1,4]oxazine-2-carboxylate, (4 mL, 1 mmol), Et₃N (0.14 mL, 1 mmol) and 3-methyl-4-fluorobenzylamine (0.418 g, 3 mmol) was heated at 90° C. for 5 h. The reaction mixture was cooled and the product isolated by reverse phase preparative HPLC using MeOH/H₂O-0.1% CF₃CO₂H as eluent. The fractions containing the desired material were combined and concentrated to afford the title compound as a yellow powder (0.19 g, 52% yield). ¹H NMR (500 MHz, CDCl₃) δ ppm: 11.99 (1H, s), 7.73 (1H, s), 7.14 (1H, d, J=7.3 Hz), 7.12-7.09 (1H, m), 6.98 (1H, t, J=9.0 Hz), 4.54 (2H, d, J=6.4 Hz), 4.01 (4H, s), 2.27 (3H, s), 1.56 (6H, s). HRMS (M+H) calcd for C₁₈H₂₁FN₃O₄: 362.1516; found: 362.1509. Anal calcd for C₁₈H₂₀FN₃O₄+0.07H₂O: C, 59.26; H, 5.55; N, 11.48. Found: C, 58.88; H, 11.34.

EXAMPLES 21-41

Examples 21-41 can be prepared from intermediate 25, ethy3-hydroxy-9,9-dimethyl-4-oxo-4,6,7,9-tetrahydropyrimido[2,1-c][1,4]oxazine-2-carboxylate, and the indicated amines according to the method described for the synthesis of examples 1, 19 and 20.

EXAMPLE 21

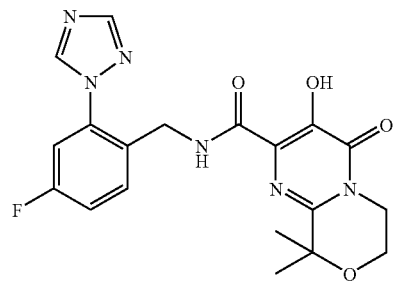

Pyrimido[2,1-c][1,4]oxazine-2-carboxamide, N-[[4-fluoro-2-(1H-1,2,4-triazol-1-yl)phenyl]methyl]-4,6,7,9-tetrahydro-3-hydroxy-9,9-dimethyl-4-oxo-. The title compound can be prepared from intermediate 69. Solid, ¹H NMR (500 MHz, DMSO-d₆) δ ppm: 11.93 (1H, s), 9.29 (1H, t, J=6.2 Hz), 9.05 (1H, s), 8.32 (1H, s), 7.57-7.53 (2H, m), 7.43 (1H, td, J=7.9, 1.7 Hz), 4.44 (2H, d, J=6.1 Hz), 3.98 (2H, t, J=4.9 Hz), 3.83 (2H, t, J=4.9 Hz), 1.56 (6H, s). HRMS (M+H) calcd for C₁₉H₂₀N₆O₄F: 415.15302; found: 415.1520. Anal Calcd for C₁₉H₁₉N₆O₄F: C, 55.07; H, 4.62; N, 20.28; F, 4.58; found: C, 54.95; H, 4.67; N, 20.27; F, 4.56.

EXAMPLE 22

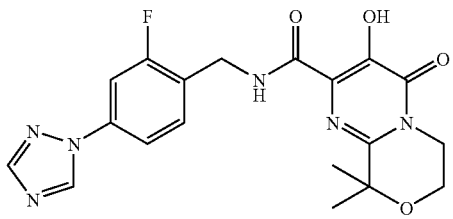

Pyrimido[2,1-c][1,4]oxazine-2-carboxamide, N-[[2-fluoro-4-(1H-1,2,4-triazol-1-yl)phenyl]methyl]-4,6,7,9-tetrahydro-3-hydroxy-9,9-dimethyl-4-oxo-. The title compound can be prepared from intermediate 70. Solid, ¹H NMR (500 MHz, DMSO-d₆) δ ppm: 12.07 (1H, s), 9.46 (1H, bs), 9.33 (1H, s), 8.26 (1H, s), 7.81 (1H, dd, J=11.1, 2.0 Hz), 7.73 (1H, dd, J=8.2, 1.8 Hz), 7.52 (1H, t, J=8.2 Hz), 4.59 (2H, d, J=6.1 Hz), 3.98 (2H, t, J=5.0 Hz), 3.84 (2H, t, J=5.0 Hz), 1.58 (6H, s). HRMS (M+H) calcd for C₁₉H₂₀N₆O₄F: 415.15302;

found: 415.1520. Anal calcd for $C_{19}H_{19}N_6O_4F+1.25 H_2O$: C, 52.23; H, 4.96; N, 19.23; F, 4.35; found: C, 52.29; H 4.66; N, 19.23; F, 4.35.

EXAMPLE 23

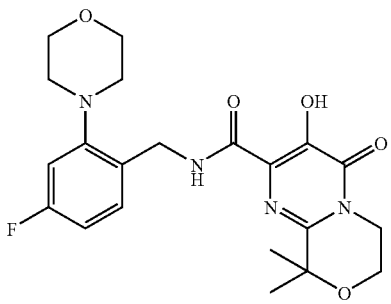

Pyrimido[2,1-c][1,4]oxazine-2-carboxamide, N-[[4-fluoro-2-(4-morpholinyl)phenyl]methyl]-4,6,7,9-tetrahydro-3-hydroxy-9,9-dimethyl-4-oxo-. The title compound can be prepared from intermediate 73. Solid, $^1$H NMR (500 MHz, CDCl$_3$) δ ppm: 12.09 (1H, s), 7.91 (1H, brs), 7.31-7.28 (1H, m), 6.90 (1H, dd, J=10.4, 2.4 Hz), 6.84 (1H, td, J=8.1, 2.4 Hz), 4.66 (2H, d, J=6.4 Hz), 4.02 (4H, s), 3.89-3.87 (4H, m), 2.94-2.92 (4H, m), 1.59 (6H, s). HRMS (M−H) calcd for $C_{21}H_{24}N_4O_5F$: 431.17307; found: 431.1719. Anal calcd for $C_{21}H_{25}N_4O_5F$: C, 58.32; H, 5.82; N, 12.95; F, 4.39; found: C, 58.13; H, 5.81; N, 12.79; F, 4.33.

EXAMPLE 24

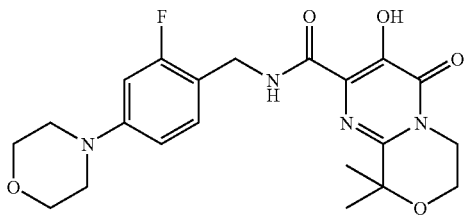

Pyrimido[2,1-c][1,4]oxazine-2-carboxamide, N-[[2-fluoro-4-(4-morpholinyl)phenyl]methyl]-4,6,7,9-tetrahydro-3-hydroxy-9,9-dimethyl-4-oxo-. The title compound can be prepared from intermediate 74. $^1$H NMR (500 MHz, CDCl$_3$) δ ppm: 12.01 (1H, s), 7.80 (1H, brs), 7.28-7.24 (1H, m), 6.66 (1H, d, J=8.5 Hz), 6.61 (1H, dd, J=13.4, 1.8 Hz), 4.56 (2H, d, J=6.1 Hz), 4.01 (4H, s), 3.85-3.84 (4H, m), 3.17-3.15 (4H, m), 1.60 (6H, s). HRMS (M−H) calcd for $C_{21}H_{24}N_4O_5F$: 431.17307; found: 431.1729. Anal calcd for $C_{21}H_{25}N_4O_5F$: C, 58.32; H, 5.82; N, 12.95; F, 4.39; found: C, 58.23; H, 5.73; N, 12.82; F, 4.21.

EXAMPLE 25

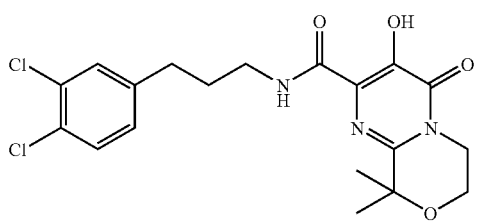

Pyrimido[2,1-c][1,4]oxazine-2-carboxamide, N-[3-(3,4-dichlorophenyl)propyl]-4,6,7,9-tetrahydro-3-hydroxy-9,9-dimethyl-4-oxo-. The title compound can be prepared from 3-(3,4-dichlorophenyl)propan-1-amine. $^1$H NMR (500 MHz, CDCl$_3$) δ ppm: 12.05 (1H, s), 7.46 (1H, brs), 7.35 (1H, d, J=8.2 Hz), 7.28 (1H, d, J=2.1 Hz), 7.04 (1H, dd, J=8.2, 2.1 Hz), 4.02 (4H, s), 3.46 (2H, q, J=6.9 Hz), 2.67 (2H, t, J=7.6 Hz), 1.95 (2H, m), 1.59 (6H, s). HRMS (M+H) calcd for $C_{19}H_{22}N_3O_4Cl_2$: 426.09875; found: 426.0996. Anal calcd for $C_{19}H_{21}N_3O_4Cl_2$: C, 53.53; H, 4.96; N, 9.85; Cl, 16.63; found: C, 53.57; H, 4.96; N, 9.76; Cl, 16.63.

EXAMPLE 26

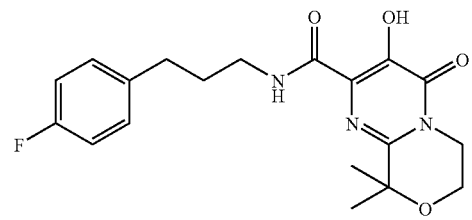

Pyrimido[2,1-c][1,4oxazine-2-carboxamide, N-[3-(4-fluorophenyl)propyl]-4,6,7,9-tetrahydro-3-hydroxy-9,9-dimethyl-4-oxo-. The title compound can be prepared from 3-(4-fluorophenyl)propan-1-amine. $^1$H NMR (500 MHz, CDCl$_3$) δ ppm: 12.09 (1H, s), 7.15 (2H, dd, J=8.2, 5.5 Hz), 6.97 (2H, t, J=8.5 Hz), 4.02 (4H, s), 3.44 (2H, q, J=13.9, 6.9 Hz), 2.68 (2H, t, J=7.6 Hz), 1.98-1.92 (2H, m), 1.62 (6H, s). HRMS (M+H) calcd for $C_{19}H_{23}N_3O_4F$: 376.16727; found:

376.1687. Anal calcd for $C_{19}H_{22}N_3O_4F$: C, 60.79; H, 5.90; N, 11.19; F, 5.06; found: C, 60.70; H, 5.87; N, 11.14; F, 4.92.

EXAMPLE 27

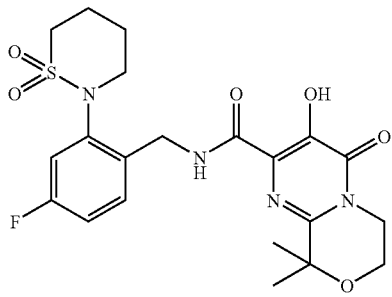

Pyrimido[2,1-c][1,4]oxazine-2-carboxamide, N-[[4-fluoro-2-(tetrahydro-1,1-dioxido-2H-1,2-thiazin-2-yl)phenyl]methyl]-4,6,7,9-tetrahydro-3-hydroxy-9,9-dimethyl-4-oxo-. The title compound can be prepared from intermediate 76. $^1$H NMR (500 MHz, CDCl$_3$) δ ppm: 12.07 (1H, s), 8.31 (1H, d, J=6.44 Hz), 7.46 (1H, dd, J=8.5, 6.4 Hz), 7.19 (1H, dd, J=9.0, 2.6 Hz), 7.08 (1H, td, J=8.2, 2.7 Hz), 4.92 (1H, dd, J=14.0, 8.8 Hz), 4.37 (1H, dd, J=14.0, 3.4 Hz), 4.02-3.97 (2H, m), 3.99 (2H, s), 3.87-3.82 (1H, m), 3.45-3.41 (1H, m), 3.30-3.20 (2H, m), 2.46-2.32 (2H, m), 2.00-1.88 (2H, m), 1.57 (3H, s), 1.53 (3H, s). HRMS (M−H) calcd for $C_{21}H_{26}N_4O_6FS$: 481.15572; found: 481.1570. Anal calcd for $C_{21}H_{25}N_4O_6FS$: C, 52.49; H, 5.24; N, 11.66; F, 3.95; S, 6.67; found: C, 52.29; H, 5.37; N, 11.40; F, 3.91; S, 6.70.

EXAMPLE 28

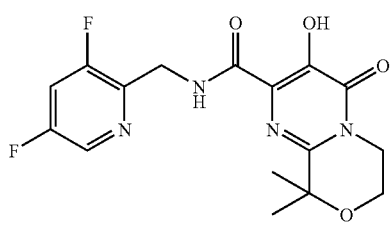

Pyrimido[2,1-c][1,4]oxazine-2-carboxamide, N-[(3,5-difluoro-2-pyridinyl)methyl]-4,6,7,9-tetrahydro-3-hydroxy-9,9-dimethyl-4-oxo-. The title compound can be prepared from intermediate 102. $^1$H NMR (500 MHz, CDCl$_3$) δ ppm: 11.86 (1H, s), 8.58 (1H, brs), 8.33 (1H, d, J=2.4 Hz), 7.27-7.24 (1H, m), 4.76 (2H, d, J=5.2 Hz), 4.03 (4H, s), 1.63 (6H, s). HRMS (M+H) calcd for $C_{16}H_{17}F_2N_4O_4$: 367.1218; found: 367.1230.

EXAMPLE 29

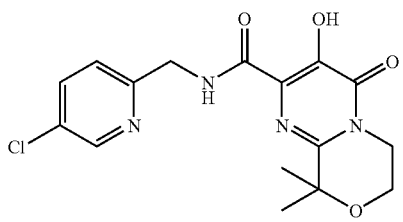

N-((5-Chloropyridin-2-yl)methyl)-3-hydroxy-9,9-dimethyl-4-oxo-4,6,7,9-tetrahydropyrimido[2,1-c][1,4]oxazine-2-carboxamide. The title compound can be prepared from intermediate 103. $^1$H NMR (500 MHz, CDCl$_3$) δ ppm: 11.80 (1H, brs), 8.64 (1H, brs), 8.57 (1H, d, J=2.4 Hz), 7.78 (1H, dd, J=8.6, 2.4 Hz), 7.44 (1H, d, J=8.6 Hz), 4.72 (2H, d, J=6.1 Hz), 4.02 (4H, s), 1.61 (6H, s). HRMS (M+H) calcd for $C_{17}H_{18}ClN_4O_4$: 365.1017; found: 365.1028. Anal calcd for $C_{16}H_{17}ClN_4O_4 \cdot 0.25H_2O \cdot 0.5\ CF_3CO_2H$: C, 47.90; H, 4.26; N, 13.14, Cl, 8.32; found: C, 47.88; H, 3.98; N, 12.94, Cl, 8.57.

EXAMPLE 30

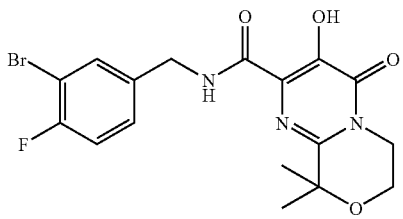

Pyrimido[2,1-c][1,4]oxazine-2-carboxamide, N-[(3-bromo-4-fluorophenyl)methyl]-4,6,7,9-tetrahydro-3-hydroxy-9,9-dimethyl-4-oxo-. The title compound can be prepared from (3-bromo-4-fluorophenyl)methanamine Off white solid, $^1$H-NMR (500 MHz, CDCl$_3$) δ ppm: 11.88 (1H, s), 7.76-7.84 (1H, br), 7.53 (1H, dd, J=6.3, 2.0 Hz), 7.26-7.29 (H, m), 7.07-7.14 (1H, m), 4.57 (2H, d, J=6.4 Hz), 4.02 (4H, s), 1.58 (6H, s). $^{13}$C-NMR (126 MHz, CDCl$_3$) δ ppm: 168.41, 157.79, 151.99, 146.52, 134.91, 132.89, 128.44, 128.39, 125.30, 117.04, 116.86, 77.69, 75.84, 58.21, 43.22, 41.98, 28.11. HRMS [M+H]⁺ calcd for $C_{17}H_{18}N_3O_4FBr$: 426.04648; found: 426.0468.

EXAMPLE 31

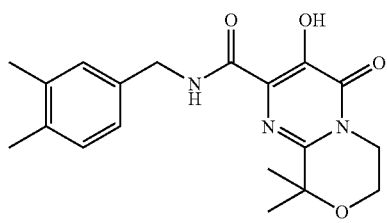

Pyrimido[2,1-c][1,4]oxazine-2-carboxamide, N-[(3,4-dimethylphenyl)methyl]-4,6,7,9-tetrahydro-3-hydroxy-9,9-dimethyl-4-oxo-. The title compound can be prepared from (3,4-dimethylphenyl)methanamine Off white solid, ¹H-NMR (500 MHz, CDCl₃) δ ppm: 7.74 (1H), 7.04-7.15 (3H, m), 4.56 (2H, d, J=5.8 Hz), 4.00-4.07 (4H, m), 2.27 (3H, s), 2.26 (3H, s), 1.57 (6H, s). ¹³C-NMR (126 MHz, CDCl₃) δ ppm: 167.92, 158.58, 151.61, 146.22, 137.37, 136.47, 134.53, 130.23, 129.11, 126.12, 125.12, 75.93, 58.10, 43.42, 43.00, 28.04, 19.85, 19.53. HRMS [M+H]⁺ calcd for $C_{19}H_{24}N_3O_4$: 358.17669; found: 358.1783.

EXAMPLE 32

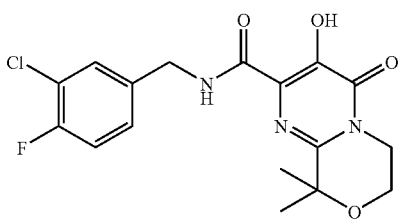

Pyrimido[2,-c][1,4]oxazine-2-carboxamide, N-[(3-chloro-4-fluorophenyl)methyl]-4,6,7,9-tetrahydro-3-hydroxy-9,9-dimethyl-4-oxo-. The title compound can be prepared from (3-chloro-4-fluorophenyl)methanamine. Off white solid, ¹H-NMR (500 MHz, CDCl₃) δ ppm: 11.88 (1H, br s), 7.80 (1H, t, J=5.5 Hz), 7.38 (1H, dd, J=6.7, 2.1 Hz), 7.19-7.23 (1H, m), 7.13 (1H, t, J=8.5 Hz), 4.57 (2H, d, J=6.4 Hz), 4.02 (4H, s), 1.58 (6H, s). ¹³C-NMR (126 MHz, CDCl₃) δ ppm: 168.41, 157.82, 151.99, 146.52, 134.54, 130.02, 127.58, 127.52, 125.32, 121.61, 117.18, 117.01, 75.84, 58.21, 43.23, 42.08, 28.11. HRMS [M+H]⁺ calcd for $C_{17}H_{18}N_3O_4FCl$: 382.09644; found: 382.0980.

EXAMPLE 33

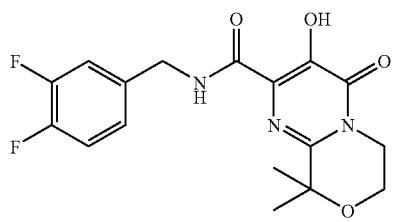

Pyrimido[2,1-c][1,4]oxazine-2-carboxamide, N-[(3,4-difluorophenyl)methyl]-4,6,7,9-tetrahydro-3-hydroxy-9,9-dimethyl-4-oxo-. The title compound can be prepared from (3,4-difluorophenyl)methanamine. Light brown solid, ¹H-NMR (500 MHz, CDCl₃) δ ppm: 7.77 (1H), 7.30-7.36 (2H, m), 7.27 (1H, s), 4.59 (2H, d, J=6.4 Hz), 4.01-4.06 (4H, m), 1.58 (6H, s). ¹³C-NMR (126 MHz, CDCl₃) δ ppm: 168.22, 158.36, 151.98, 151.17, 146.35, 134.33, 125.74, 123.70, 123.67, 117.87, 117.73, 116.88, 116.73, 75.90, 58.13, 43.42, 42.28, 28.06. HRMS [M+H]⁺ calcd for $C_{17}H_{18}N_3O_4F_2$: 366.12655; found: 366.1269.

EXAMPLE 34

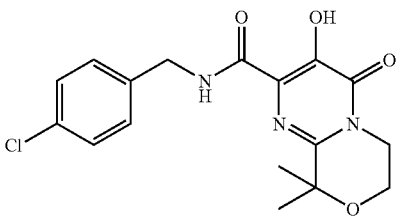

Pyrimido[2,1-c][]1,4]oxazine-2-carboxamide, N-[(4-chlorophenyl)methyl]-4,6,7,9-tetrahydro-3-hydroxy-9,9-dimethyl-4-oxo-. The title compound can be prepared from (4-chlorophenyl)methanamine. Pale pink solid. ¹H-NMR (500 MHz, CDCl₃) δ ppm: 7.77 (1H, br), 7.33-7.35 (2H, m), 7.25-7.28 (2H, m), 4.59 (2H, d, J=6.4 Hz), 4.04 (4H, ddd, J=14.0, 7.9, 2.7 Hz), 1.58 (6H, s). ¹³C-NMR (126 MHz, CDCl₃) δ ppm: 168.12, 158.48, 151.87, 146.28, 135.72, 133.98, 129.92, 129.18, 129.09, 125.90, 75.92, 58.12, 43.45, 42.61, 28.06. HRMS [M+H]+ calcd for C17H19N3O4Cl: 364.10642; found: 364.1060.

EXAMPLE 35

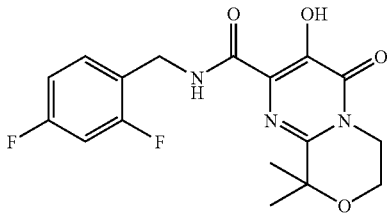

Pyrimido[2,1-c][1,4]oxazine-2-carboxamide, N-[(2,4-difluorophenyl)methyl]-4,6,7,9-tetrahydro-3-hydroxy-9,9-dimethyl-4-oxo-. The title compound can be prepared from (2,4-difluorophenyl)methanamine. Off white solid, 1H-NMR (500 MHz, CDCl3) δ ppm: 7.86 (1H, t, J=5.6 Hz), 7.34-7.40 (1H, m), 6.83-6.90 (2H, m), 4.62 (2H, d, J=6.4 Hz), 4.01-4.06 (4H, m), 1.59 (6H, s). 13C-NMR (126 MHz, CDCl3) δ ppm: 168.09, 158.43, 151.81, 146.22, 131.30, 131.25, 131.22, 131.18, 125.87, 120.37, 120.34, 111.85, 111.82, 111.68, 111.65, 104.47, 104.27, 104.07, 75.94, 58.12, 43.43, 37.00, 28.07. HRMS [M+H]+ calcd for C17H18N3O4F2: 366.12655; found: 366.1281.

EXAMPLE 36

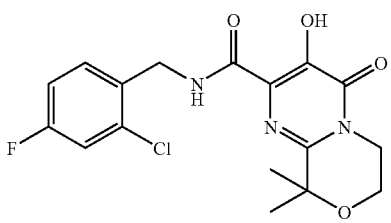

Pyrimido[2,1-c][1,4]oxazine-2-carboxamide, N-[(2-chloro-4-fluorophenyl)methyl]-4,6,7,9-tetrahydro-3-hydroxy-9,9-dimethyl-4-oxo-. The title compound can be prepared from (2-chloro-4-fluorophenyl)methanamine. Off white solid, 1H-NMR (500 MHz, CDCl3) δ ppm: 8.05 (1H, br), 7.41 (1H, dd, J=8.4, 6.0 Hz), 7.17 (1H, dd, J=8.2, 2.4 Hz), 6.99 (1H, td, J=8.2, 2.7 Hz), 4.66 (2H, d, J=6.4 Hz), 4.04 (4H, s), 1.60 (6H, s). 13C-NMR (126 MHz, CDCl3) δ ppm: 167.88, 163.30, 161.31, 158.70, 151.77, 146.08, 134.55, 134.47, 131.65, 131.58, 130.70, 130.67, 126.12, 117.48, 117.28, 114.68, 114.51, 109.67, 75.99, 58.10, 43.51, 40.82, 28.08. HRMS [M+H]+ calcd for C17H18N3O4FCl: 382.09644; found: 382.0987.

EXAMPLE 37

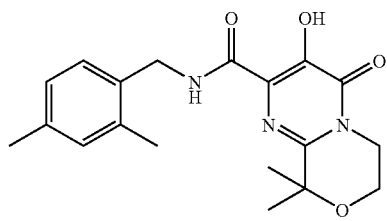

Pyrimido[2,1-c][1,4]oxazine-2-carboxamide, N-[(2,4-dimethylphenyl)methyl]-4,6,7,9-tetrahydro-3-hydroxy-9,9-dimethyl-4-oxo-. The title compound can be prepared from (2,4-dimethylphenyl)methanamine. Off white solid, 1H-NMR (500 MHz, CDCl3) δ ppm: 12.08 (1H, brs), 7.63 (1H, br), 7.15 (1H, d, J=7.6 Hz), 7.00-7.05 (2H, m), 4.57 (2H, d, J=5.8 Hz), 4.01 (4H, s), 2.32 (3H, s), 2.32 (3H, s), 1.55 (6H, s). 13C-NMR (126 MHz, CDCl3) δ ppm: 167.97, 157.98, 151.74, 146.35, 137.95, 136.22, 131.90, 131.67, 128.38, 127.10, 125.64, 75.84, 58.21, 43.21, 41.15, 28.07, 21.11, 19.13. HRMS [M+H]+ calcd for C19H24N3O4: 358.17669; found: 358.1771.

EXAMPLE 38

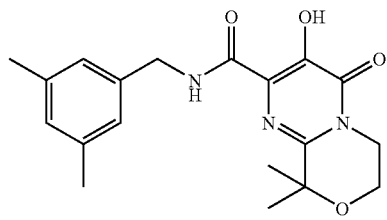

Pyrimido[2,1-c][1,4]oxazine-2-carboxamide, N-[(3,5-dimethylphenyl)methyl]-4,6,7,9-tetrahydro-3-hydroxy-9,9-dimethyl-4-oxo-. The title compound can be prepared from (3,5-dimethylphenyl)methanamine. Off white solid, 1H-NMR (500 MHz, CDCl3) δ ppm: 12.09 (1H, s), 7.72-7.80 (1H, br), 6.95 (1H, s), 6.94 (2H, s), 4.55 (2H, d, J=6.4 Hz), 4.00-4.04 (4H, s), 2.32 (6H, s), 1.57 (6H, s). 13C-NMR (126 MHz, CDCl3) δ ppm: 168.19, 157.89, 151.73, 146.44, 138.71, 137.25, 129.58, 125.61, 125.48, 75.86, 58.23, 43.18, 43.06, 28.08, 21.38. HRMS [M+H]+ calcd for C19H24N3O4: 358.17669; found: 358.1758.

EXAMPLE 39

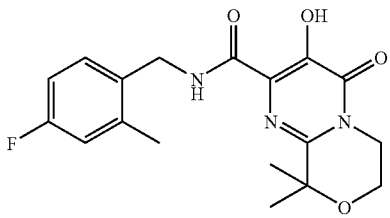

Pyrimido[2,1-c][1,4]oxazine-2-carboxamide, N-[(4-fluoro-2-methylphenyl)methyl]-4,6,7,9-tetrahydro-3-hydroxy-9,9-dimethyl-4-oxo-. The title compound can be prepared from (4-fluoro-2-methylphenyl)methanamine. Off white solid, $^1$H-NMR (500 MHz, CDCl$_3$) δ ppm: 11.97 (1H, s), 7.64 (1H, br), 7.23 (1H, dd, J=8.2, 5.8 Hz), 6.87-6.94 (2H, m), 4.57 (2H, d, J=6.1 Hz), 4.02 (4H, s), 2.36 (3H, s), 1.56 (6H, s). $^{13}$C-NMR (126 MHz, CDCl$_3$) δ ppm: 168.07, 163.40, 161.44, 157.82, 151.86, 146.43, 138.81, 138.75, 130.78, 130.75, 129.97, 129.90, 125.42, 117.69, 117.52, 113.20, 113.03, 75.81, 58.23, 43.21, 40.71, 28.09, 19.32. HRMS [M+H]+ calcd for C18H21N3O4F: 362.15162; found: 362.1521.

EXAMPLE 40

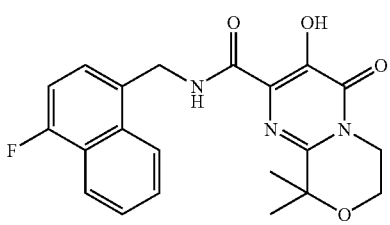

Pyrimido[2,1-c][1,4]oxazine-2-carboxamide, N-[(4-fluoro-1-naphthalenyl)methyl]-4,6,7,9-tetrahydro-3-hydroxy-9,9-dimethyl-4-oxo-. The title compound can be prepared from intermediate 37. White solid. $^1$H-NMR (500 MHz, CDCl$_3$) δ ppm: 12.00 (1H, s), 8.15-8.20 (1H, m), 8.05 (1H, d, J=8.2 Hz), 7.73 (1H, br), 7.58-7.65 (2H, m), 7.43 (1H, dd, J=7.8, 5.3 Hz), 7.12 (1H, dd, J=10.1, 7.9 Hz), 5.02 (2H, d, J=6.1 Hz), 3.99 (4H, ddd, J=13.8, 8.0, 2.9 Hz), 1.49 (6H, s). $^{13}$C-NMR (126 MHz, CDCl$_3$) δ ppm: 168.01, 160.13, 158.12, 157.77, 151.87, 146.51, 132.72, 132.68, 128.59, 128.56, 127.86, 126.54, 126.46, 125.42, 124.45, 123.23, 121.65, 121.60, 109.00, 108.84, 75.76, 58.21, 43.14, 40.86, 27.99. HRMS [M+H]+ calcd for C21H21N3O4F: 398.15162; found: 398.1536.

EXAMPLE 41

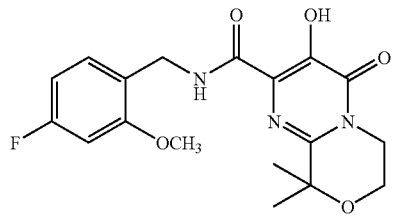

Pyrimido[2,1-c][1,4]oxazine-2-carboxamide, N-[(4-fluoro-2-methoxyphenyl)methyl]-4,6,7,9-tetrahydro-3-hydroxy-9,9-dimethyl-4-oxo-. The title compound can be prepared from (4-fluoro-2-methoxyphenyl)methanamine. HRMS [M+H]+ calcd for C18H2FN3O5: 378.1465; found: 378.1480. Light yellow crystals; $^1$H NMR (CDCl$_3$, 500 MHz) δ ppm: 1.58 (6H. s, gem-di-Me), 3.88 (3H, s, OMe), 4.00 (4H, s, CH$_2$), 4.53 (2H, d, J=6.5 Hz, CH$_2$), 6.61-6.64 (2H, m, Ar—Hs), 7.24 (1H, m, Ar—Hs); $^{13}$C NMR (CDCl$_3$, 125.8 Hz) δ ppm: 28.03 (CH$_3$), 38.79 (CH$_2$), 43.09 (CH$_2$), 55.72 (CH$_3$), 58.27 (CH$_2$), 75.78 (C), 99.15, 99.35 (d, J=27 Hz, CH), 106.97, 107.14 (d, J=21 Hz, CH), 121.17, 121.20 (d, J=3.8 Hz, C), 125.75 (C), 130.44, 130.51 (d, J=9.6 Hz, CH), 146.26 (C), 151.50 (C), 157.87 (C=O), 158.77, 158.83 (d, J=9.6 Hz, C), 162.63, 164.48 (d, J=234 Hz, CF), 167.81 (C=O); HRMS (ESI) calcd for C18H21FN3O5 (M+H) 378.1465, found 378.1480; UV (MeOH) λmax 219 nm (ε 1.66×10$^4$), 245 (ε 9.69×10$^3$), 305 (ε 7.70×10$^3$); Anal. Calcd for C18H20FN3O5.0.2H2O: C, 55.95; H, 5.48; N, 10.88; found C, 55.99; H, 5.11; N, 10.63.

EXAMPLES 42-43

Examples 42-43 can be prepared from intermediate 31, ethy9,9-diethyl-3-hydroxy-4-oxo-4,6,7,9-tetrahydropyrimido[2,1-c][1,4]oxazine-2-carboxylate and the indicated amines according to the methods described for examples 1, 19 and 20.

EXAMPLE 42

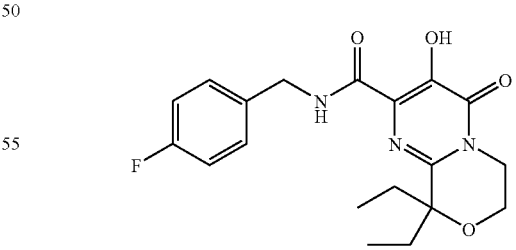

Pyrimido[2,1-c[]1,4]oxazine-2-carboxamide, 9,9-diethyl-N-[(4-fluorophenyl)methyl]-4,6,7,9-tetrahydro-3-hydroxy-4-oxo-. The title compound can be prepared from 4-fluorobenzylamine. $^1$H NMR (500 MHz, CDCl$_3$) δ ppm: 11.96 (1H, br), 7.76 (1H, br), 7.30 (2H, m), 7.06 (2H, m), 4.58 (2H, d, J=6.4 Hz), 4.00 (4H, m), 1.93 (2H, m), 1.86 (2H, m), 0.86 (6H, t, J=7.3 Hz). $^{13}$C NMR (500 MHz, CDCl$_3$) δ ppm:

168.36, 163.46, 157.87, 151.61, 143.23, 133.14, 129.50, 125.58, 115.99, 115.82, 80.89, 58.46, 43.13, 42.50, 31.36, 7.79. HRMS [M+H]+ calcd for C19H23N3O4F: 376.16727; found: 376.1675.

EXAMPLE 43

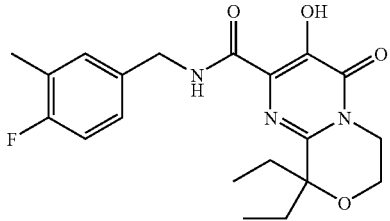

Pyrimido[2,1-c][1,4]oxazine-2-carboxamide, 9,9-diethyl-N-[(4-fluoro-3-methylphenyl)methyl]-4,6,7,9-tetrahydro-3-hydroxy-4-oxo-). The title compound can be prepared from 3-methyl, 4-fluorobenzylamine. $^1$H NMR (500 MHz, CDCl$_3$) δ ppm: 11.99 (1H, br), 7.74 (1H, br), 7.15-7.09 (2H, m), 6.99 (1H, m), 4.54 (2H, d, J=6.1 Hz), 4.00, (4H, m), 2.27 (1H, s), 1.93 (2H, m), 1.86 (2H, m), 0.84 (6H, t, J=7.3 Hz). $^{13}$C NMR (126 MHz, CDCl$_3$) δ ppm: 168.32, 161.97, 160.02, 157.84, 151.56, 146.23, 132.83, 130.96, 126.64, 125.59, 115.38, 80.88, 58.48, 43.11, 42.52, 31.36, 14.66, 7.79. HRMS [M+H]+ calcd for C20H25N3O4F: 390.18292; found: 390.1835.

EXAMPLES 44-45

Examples 44-45 can be prepared from intermediate 36, 3-hydroxy-10,10-dimethyl-4-oxo-6,7,8,10-tetrahydro-4H-pyrimido[2,1-c][1,4]oxazepine-2-carboxylate and the indicated amines according to the methods described for examples 1, 19 and 20.

EXAMPLE 44

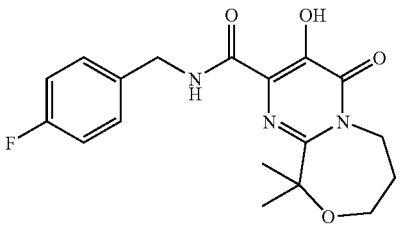

6H-Pyrimido[2,1-c][1,4]oxazepine-2-carboxamide, N-[(4-fluorophenyl)methyl]-4,7,8,10-tetrahydro-3-hydroxy-10,10-dimethyl-4-oxo-. The title compound can be prepared from 4-fluorobenzylamine $^1$H NMR (500 MHz, CDCl$_3$) δ ppm: 11.97 (1H, s), 7.72 (1H, br), 7.31 (1H, d, J=8.5 Hz), 7.30 (1H, d, J=8.5 Hz), 7.05 (1H, t, J=8.5 Hz), 4.58 (2H, d, J=6.4 Hz), 4.57 (2H, br), 3.67 (2H, t, J=6.4 Hz), 1.95 (2H, p, J=6.1 Hz), 1.57 (6H, s). $^{13}$C NMR (126 MHz, CDCl$_3$) δ ppm: 168.32, 163.45, 161.49, 158.20, 153.63, 147.44, 133.17, 129.50, 129.43, 124.70, 115.97, 115.81, 82.29, 60.87, 42.47, 38.68, 27.82, 27.30. HRMS [M+H]+ calcd for C18H21N3O4F: 362.15162; found: 362.1530.

EXAMPLE 45

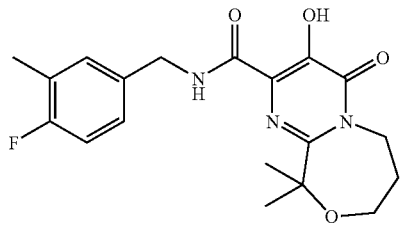

6H-Pyrimido[2,1-c][1,4]oxazepine-2-carboxamide, N-[(4-fluoro-3-methylphenyl)methyl]-4,7,8,10-tetrahydro-3-hydroxy-10,10-dimethyl-4-oxo-. The title compound can be prepared from 3-methyl, 4-fluorobenzylamine. $^1$H NMR (500 MHz, CDCl$_3$) δ ppm: 12.00 (1H, s), 7.70 (1H, br), 7.14 (1H, m), 7.1 (1H, m), 6.98 (1H, t, J=8.9 Hz), 4.56 (2H, br), 4.54 (2H, d, J=6.4 Hz), 3.68 (2H, t, J=6.4 Hz), 2.27 (3H, s), 1.95 (2H, p, J=6.1 Hz), 1.57 (6H, s). $^{13}$C NMR (126 MHz, CDCl$_3$) δ ppm: 168.26, 164.98, 160.02, 158.22, 153.59, 147.44, 132.82, 130.97, 126.58, 125.46, 124.75, 115.38, 82.30, 60.87, 42.51, 38.68, 27.83, 27.31, 14.66. HRMS [M+H]+ calcd for C19H23N3O4F: 376.16727; found: 376.1686.

EXAMPLES 46-51

Examples 46-52 can be prepared from the indicated intermediates according to the method provide for example 46.

EXAMPLE 46

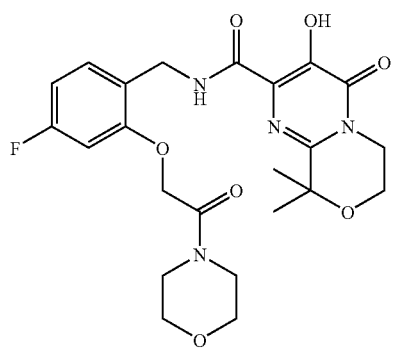

Pyrimido[2,1-c][1,4]oxazine-2-carboxamide, N-[[4-fluoro-2-[2-(4-morpholinyl)-2-oxoethoxy]phenyl]methyl]-4,6,7,9-tetrahydro-3-hydroxy-9,9-dimethyl-4-oxo-. A solution of intermediate 157, 3-benzyloxy-9,9-dimethyl-4-oxo-4,6,7,9-tetrahydro-pyrimido[2,1-c][1,4]oxazine-2-carboxylic acid 4-fluoro-2-(2-morpholin-4-yl-2-oxo-ethoxy)-benzylamide, (187 mg, 0.32 mmol) in trifluoroacetic acid (2 mL) was stirred at room temperature for 2.5 hrs, after which the mixture was concentrated in vacuo to dryness. The residual oil was crystallized from 95% ethanol to provide 120 mg (0.25 mmol, Yield 77%) of the title compound as a white crystalline powder: $^1$H NMR (CDCl$_3$, 500 MHz) δ ppm: 1.57 (6H, s, Me), 3.51, 3.64 (4H, brs, NCH₂), 3.70 (4H, m, OCH₂), 3.99 (4H, s, NCH₂, OCH₂), 4.60 (2H, d, J=6 Hz, NCH₂), 4.76 (2H, s, OCH₂), 6.59 (1H, dd, J=10, 2.5 Hz, Ar—H), 6.63 (1H, dt, J=2.5, 8 Hz, Ar—H), 7.29 (1H, dd, J=6.5, 8.5 Hz, Ar—H), 8.25 (1H, t, J=6 Hz, NH), 12.2 (br, OH). $^{13}$C NMR (CDCl₃, 125.77 Hz) δ ppm: 27.93 (CH₃), 38.44 (NCH₂), 42.39 (NCH₂), 43.14 (NCH₂), 45.31 (NCH₂), 58.19 (OCH₂), 66.40 (OCH₂), 66.59 66.86 (OCH₂), 75.94 (C), 100.26, 100.46 (d, J=26 Hz, CH), 108.19, 108.36 (d, J=21 Hz, CH), 122.03, 122.06 (d, J=3 Hz, C), 125.84 (C), 131.06, 131.14 (d, J=11 Hz, CH), 146.37 (C), 151.46 (C), 157.06, 157.14 (d, J=11 Hz, C), 157.96 (C=O), 162.25, 164.21 (d, J=248 Hz, CF), 165.47 (C=O), 168.23 (C=O); HRMS calcd for C₂₃H₂₈N₄O₇F (M+H) 491.1942, found 491.1958; UV (MeOH) λmax 249 nm (ε 7.84×10³), 290 nm (ε 3.06×10³), 303 nm (ε 2.2×10³); Anal. Calcd for C₂₃H₂₇N₄O₇F.1.7H₂O: C, 53.01; H, 5.88; N, 10.75; found C, 52.53; H, 5.37; N, 10.48.

EXAMPLE 47

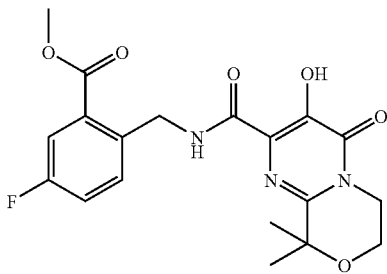

Benzoic acid, 5-fluoro-2-[[[(4,6,7,9-tetrahydro-3-hydroxy-9,9-dimethyl-4-oxopyrimido[2,1-c][1,4]oxazin-2-yl)carbonyl]amino]methyl]-, methyl ester. The title compound can be prepared from intermediate 154, methyl 2-((3-(benzyloxy)-9,9-dimethyl-4-oxo-4,6,7,9-tetrahydropyrimido[2,1-c][1,4]oxazine-2-carboxamido)methyl)-5-fluorobenzoate. White solid; $^1$H NMR (300 MHz, CDCl₃) δ ppm: 11.94 (1H, br s), 8.76 (1H, t, J=6.77 Hz), 7.69 (1H, dd, J=9.2, 2.9 Hz), 7.53 (1H, dd, J=8.4, 5.5 Hz), 7.15-7.22 (1H, m), 4.71 (2H, d, J=7.0 Hz), 3.97 (4H, s), 3.89-3.94 (3H, m), 1.56 (6H, s); HRMS (ESI) calcd for C₁₉H₂₀FN₄O₆ (M+H) 406.1414, found 406.1432.

EXAMPLE 48

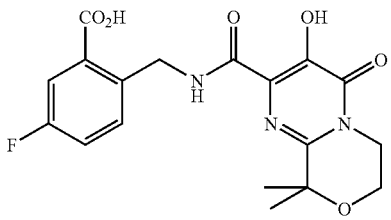

Benzoic acid, 5-fluoro-2-[[[(4,6,7,9-tetrahydro-3-hydroxy-9,9-dimethyl-4-oxopyrimido[2,1-c][1,4]oxazin-2-yl)carbonyl]amino]methyl]-. The title compound can be prepared from intermediate 190, 2-((3-(benzyloxy)-9,9-dimethyl-4-oxo-4,6,7,9-tetrahydropyrimido[2,1-c][1,4]oxazine-2-carboxamido)methyl)-5-fluorobenzoic acid. White-solid; $^1$H NMR (500 MHz, CDCl₃) δ ppm: 11.92 (1H, br s), 8.68 (1H, t, J=6.4 Hz), 7.80 (1H, dd, J=8.7, 2.6 Hz), 7.60 (1H, dd, J=8.5, 5.5 Hz), 7.30 (1H, dt, J=8.1, 2.8 Hz), 4.78 (2H, d, J=6.7 Hz), 4.00 (4H, s), 1.58 (6H, s); HRMS (ESI) calcd for C₁₈H₁₈FN₃O₆ (M+H) 392.1258, found 392.1250.

EXAMPLE 49

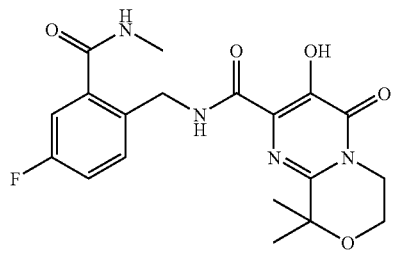

Pyrimido[2,1-c][1,4]oxazine-2-carboxamide, N-[[4-fluoro-2-[(methylamino)carbonyl]phenyl]methyl]-4,6,7,9-tetrahydro-3-hydroxy-9,9-dimethyl-4-oxo-. The title compound can be prepared from intermediate 143, N-(4-fluoro-2-(methylcarbamoyl)benzyl)-3-(benzyloxy)-9,9-dimethyl-4-oxo-4,6,7,9-tetrahydropyrimido[2,1-c][1,4]oxazine-2-carboxamide. $^1$H NMR (500 MHz, DMSO-d₆) δ ppm: 11.97 (1H, br s), 9.46 (1H, br s), 8.55-8.51 (1H, m), 7.40-7.38 (1H, m), 7.32-7.27 (2H, m), 4.56 (2H, d, J=6.1 Hz), 3.97 (2H, t, J=4.9 Hz), 3.82 (2H, t, J=4.9 Hz), 2.80 (3H, d, J=4.6 Hz), 1.55 (6H, s). HRMS (M+H) calcd for C₁₉H₂₂FN₄O₅: 405.1574; found: 405.1588.

EXAMPLE 50

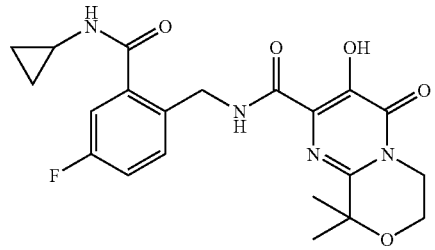

Pyrimido[2,1-c][1,4]oxazine-2-carboxamide, N-[[2-[(cyclopropylamino)carbonyl]-4-fluorophenyl]methyl]-4,6,7,9-tetrahydro-3-hydroxy-9,9-dimethyl-4-oxo-. The title compound can be prepared from intermediate 155, N-(2-(cyclopropylcarbamoyl)-4-fluorobenzyl)-3-(benzyloxy)-9,9-dimethyl-4-oxo-4,6,7,9-tetrahydropyrimido[2,1-c][1,4]oxazine-2-carboxamide. White solid; $^1$H NMR (300 MHz, CDCl₃) δ ppm: 11.98 (1H, br s), 8.84 (1H, t, J=7.32 Hz), 7.48 (1H, dd, J=9.0, 5.3 Hz), 7.05-7.16 (2H, m), 6.20-6.31 (1H, br s), 4.56 (2 H, d, J=6.6 Hz), 3.92-4.02 (4H, m), 2.90 (1H, dt, J=7.1, 3.3 Hz), 1.59 (6H, s), 0.88 (2H, q, J=6.6 Hz), 0.57-0.66 (2H, m); HRMS (ESI) calcd for $C_{21}H_{23}FN_4O_5$ (M+H) 431.1731, found 431.1734.

EXAMPLE 51

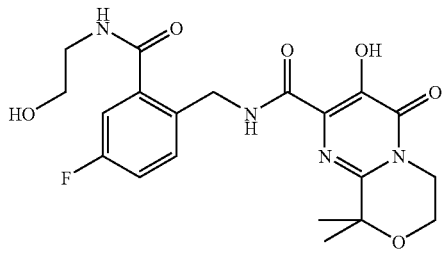

Pyrimido[2,1-c][1,4]oxazine-2-carboxamide, N-[[4-fluoro-2-[[(2-hydroxyethyl)amino]carbonyl]phenyl]methyl]-4,6,7,9-tetrahydro-3-hydroxy-9,9-dimethyl-4-oxo-. The title compound can be prepared from intermediate 191, N-(2-((2-aminoethyl)carbamoyl)-4-fluorobenzyl)-3-(benzyloxy)-9,9-dimethyl-4-oxo-4,6,7,9-tetrahydropyrimido[2,1-c][1,4]oxazine-2-carboxamide. $^1$H NMR (500 MHz, CDCl$_3$) δ ppm: 11.98 (1H, br s), 8.88 (1H, t, J=6.0 Hz), 7.51 (1H, dd, J=8.2, 5.5 Hz), 7.21 (1H, dd, J=8.5, 2.8 Hz), 7.14 (1H, dt, J=8.3, 2.6 Hz), 6.57-6.63 (1H, m), 4.58 (2H, d, J=6.7 Hz), 4.00 (4H, s), 3.87 (2H, t, J=5.1 Hz), 3.63-3.68 (2H, m), 1.60 (6H, s); HRMS (ESI) calcd for $C_{20}H_{23}FN_4O_6$(M+H) 435.1680, found 435.1700.

EXAMPLE 52

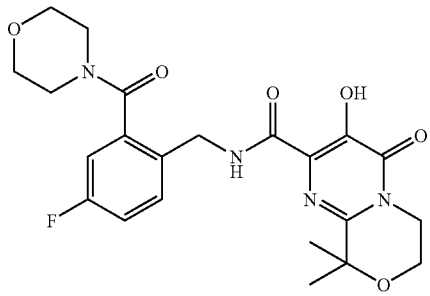

Pyrimido[2,1-c][1,4]oxazine-2-carboxamide, N-[[4-fluoro-2-(4-morpholinylcarbonyl)phenyl]methyl]-4,6,7,9-tetrahydro-3-hydroxy-9,9-dimethyl-4-oxo-. The title compound can be prepared from intermediate 156, N-(4-fluoro-2-(morpholine-4-carbonyl)benzyl)-3-(benzyloxy)-9,9-dimethyl-4-oxo-4,6,7,9-tetrahydropyrimido[2,1-c][1,4]oxazine-2-carboxamide. White solid; $^1$H NMR (500 MHz, CDCl$_3$) δ ppm: 11.94 (1H, s), 8.46 (1H, t, J=5.5 Hz), 7.47 (1H, dd, J=8.5, 5.5 Hz), 7.10 (1H, dt, J=8.4, 2.4 Hz), 6.94 (1H, dd, J=8.2, 2.4 Hz), 4.00 (4H, s), 3.79-3.88 (2H, br), 3.78 (2H, br), 3.61 (2H, br), 3.31-3.40 (2H, br), 1.61 (6H, s); HRMS (ESI) calcd for $C_{22}H_{25}FN_4O_6$(M+H) 461.1836, found 461.1852.

EXAMPLES 53-60

Examples 53-60 can be prepared from intermediate 25, ethyl 3-hydroxy-9,9-dimethyl-4-oxo-4,6,7,9-tetrahydropyrimido[2,1-c][1,4]oxazine-2-carboxylate and the indicated amines according to the method described for the synthesis of examples 1, 19 and 20.

EXAMPLE 53

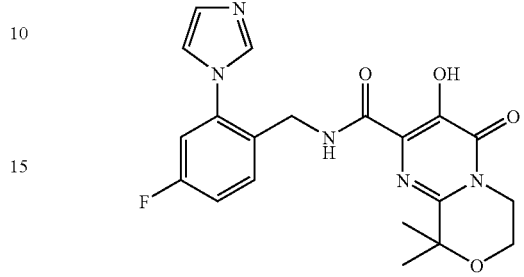

Pyrimido[2,1-c][1,4]oxazine-2-carboxamide, N-[[4-fluoro-2-(1H-imidazol-1-yl)phenyl]methyl]-4,6,7,9-tetrahydro-3-hydroxy-9,9-dimethyl-4-oxo-. The title compound can be prepared from intermediate 89. $^1$H-NMR (500 MHz, CDCl$_3$) δ ppm: 11.66 (1H, bs), 8.07 (1H, s), 7.74 (1H, t, J=5.5 Hz), 7.57 (1H, dd, J=8.7, 5.9 Hz), 7.35 (1H, s), 7.25-7.21 (2H, m), 7.08 (1H, dd, J=8.2, 2.4 Hz), 4.42 (2H, d, J=6.4 Hz), 4.01 (4H, s), 1.59 (6H, s). HRMS [M+H]$^+$ calcd for $C_{20}H_{21}N_5O_4F$: 414.15777; found: 414.1563. Anal calcd for $C_{20}H_{20}N_5O_4F.0.25$ H$_2$O: C, 57.48; H, 4.94; N, 16.76; F, 4.55; found: C, 57.77; H, 4.89; N, 16.29; F, 4.48.

EXAMPLE 54

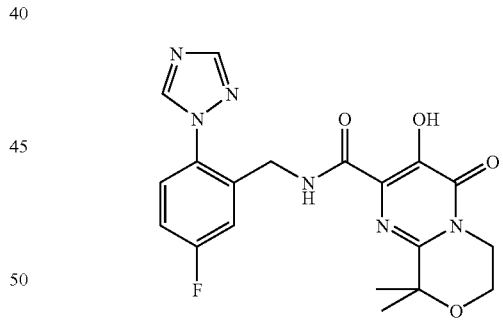

Pyrimido[2,1-c][1,4]oxazine-2-carboxamide, N-[[5-fluoro-2-(1H-1,2,4-triazol-1-yl)phenyl]methyl]-4,6,7,9-tetrahydro-3-hydroxy-9,9-dimethyl-4-oxo-e. The title compound can be prepared from intermediate 97. $^1$H NMR (500 MHz, CDCl$_3$) δ ppm: 11.82 (1H, s), 8.70 (1H, t, J=6.5 Hz), 8.39 (1H, s), 8.17 (1H, s), 7.40 (1H, dd, J=8.6, 2.7 Hz), 7.34 (1H, dd, J=8.9, 4.9 Hz), 7.17-7.13 (1H, m), 4.44 (2H, d, J=6.7 Hz), 4.01 (4H, s), 1.62 (6H, s). HRMS (M+H) calcd for $C_{19}H_{20}FN_6O_4$: 415.1530; found: 415.1544. Anal calcd for $C_{19}H_{19}FN_6O_4$: C, 55.07; H, 4.62; N, 20.28; F, 4.58; found: C, 54.83; H, 4.51; N, 19.89; F, 4.56.

EXAMPLE 55

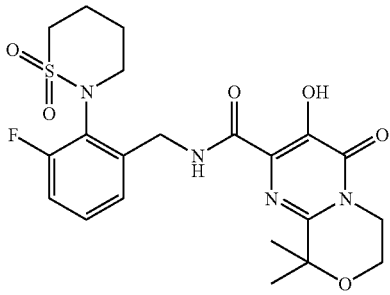

Pyrimido[2,1-c][1,4]oxazine-2-carboxamide, N-[[3-fluoro-2-(tetrahydro-1,1-dioxido-2H-1,2-thiazin-2-yl)phenyl]methyl]-4,6,7,9-tetrahydro-3-hydroxy-9,9-dimethyl-4-oxo-. The title compound can be prepared from intermediate 93. White solid. 36% yield. $^1$H-NMR (500 MHz, CDCl$_3$) δ ppm: 11.96 (1H, s), 8.42-8.39 (2H, m), 7.14-7.11 (1H, m), 4.97 (1H, dd J=14.3, 8.8 Hz), 4.37 (1H, dd, J=14.3, 4.0 Hz), 4.00 (4H, s), 3.86-3.80 (1H, m), 3.75-3.70 (1H, m), 3.34-3.24 (2H, m), 2.44-2.39 (2H, m), 2.08-2.00 (1H, m), 1.83-1.77 (1H, m), 1.60 (3H, s), 1.57 (3H, s). HRMS [M+H]$^+$ calcd for $C_{21}H_{26}N_4O_6FS$: 481.15572; found: 481.1559. Anal calcd for $C_{21}H_{25}N_4O_6FS$: C, 52.49; H, 5.24; N, 11.66; S, 6.67; F, 3.95; found: C, 52.43; H, 5.21; N, 11.61; S, 6.56; F, 4.16.

EXAMPLE 56

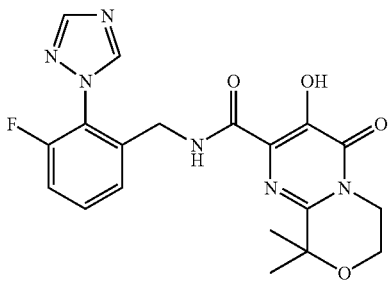

Pyrimido[2,1-c][1,4]oxazine-2-carboxamide, N-[[3-fluoro-2-(1H-1,2,4-triazol-1-yl)phenyl]methyl]-4,6,7,9-tetrahydro-3-hydroxy-9,9-dimethyl-4-oxo-. The title compound can be prepared from intermediate 95. White solid. $^1$H-NMR (500 MHz, CDCl$_3$) δ ppm: 11.86 (1H, s), 8.76 (1H, brs), 8.46 (1H, d, J=3.0 Hz), 8.22 (1H, s), 7.48-7.47 (2H, m), 7.29-7.26 (1H, m), 4.44 (2H, d, J=6.7 Hz), 4.01 (4H, s), 1.63 (6H, s). HRMS [M+H]$^+$ calcd for $C_{19}H_{20}N_6O_4F$: 415.15302; found: 415.1541. Anal calcd for $C_{19}H_{19}N_6O_4F$: C, 55.07; H, 4.62; N, 20.28; F, 4.58; found: C, 55.18; H, 4.42; N, 20.17; F, 4.51.

EXAMPLE 57

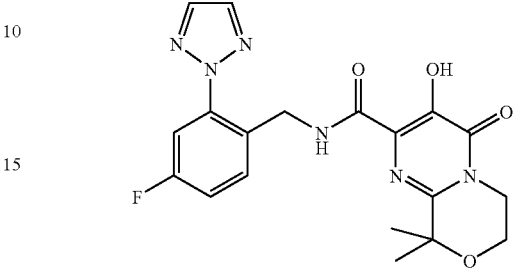

Pyrimido[2,1-c][1,4]oxazine-2-carboxamide, N-[[4-fluoro-2-(2H-1,2,3-triazol-2-yl)phenyl]methyl]-4,6,7,9-tetrahydro-3-hydroxy-9,9-dimethyl-4-oxo-. The title compound can be prepared from intermediate 77. Pale orange solid. $^1$H-NMR (300 MHz, CDCl$_3$) δ ppm: 11.99 (1H, s), 8.99 (1H, t, J=6.4 Hz), 7.91 (2H, s), 7.65-7.58 (2H, m), 7.10 (1H, td, J=8.1, 2.6 Hz), 4.61 (2H, d, J=7.0 Hz), 3.97 (4H, s), 1.55 (6H, s). HRMS [M−H]$^-$ calcd for $C_{19}H_{18}N_6O_4F$: 413.13736; found: 413.1354. Anal calcd for $C_{19}H_{17}N_6O_4F$: C, 55.07; H, 4.62; N, 20.28; F, 4.58; found: C, 54.94; H, 4.78; N, 20.32; F, 4.53.

EXAMPLE 58

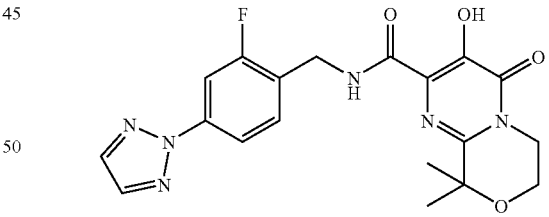

Pyrimido[2,1-c][1,4]oxazine-2-carboxamide, N-[[2-fluoro-4-(2H-1,2,3-triazol-2-yl)phenyl]methyl]-4,6,7,9-tetrahydro-3-hydroxy-9,9-dimethyl-4-oxo-. The title compound can be prepared from intermediate 77. Pale brown solid $^1$H-NMR (300 MHz, CDCl$_3$) δ ppm: 11.85 (1H, s), 7.88-7.82 (3H, m), 7.79 (2H, s), 7.47 (1H, t, J=8.3 Hz), 4.67 (2H, d, J=6.2 Hz), 3.99 (4H, s), 1.56 (6H, s). HRMS [M+H]$^+$ calcd for $C_{19}H_{20}N_6O_4F$: 415.15302; found: 415.1513. Anal calcd for C₁₉H₁₉N₆O₄F: C, 55.07; H, 4.62; N, 20.28; F, 4.58; found: C, 54.94; H, 4.76; N, 19.94; F, 4.26.

EXAMPLE 59

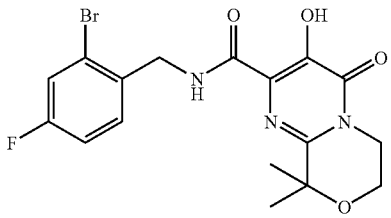

Pyrimido[2,1-c][1,4]oxazine-2-carboxamide, N-[(2-bromo-4-fluorophenyl)methyl]-4,6,7,9-tetrahydro-3-hydroxy-9,9-dimethyl-4-oxo-. The title compound can be prepared from (2-bromo-4-fluorophenyl)methanamine. White needles. ¹H-NMR (300 MHz, CDCl₃) δ ppm: 11.78 (1H, s), 8.08 (1H, t, J=6.0 Hz), 7.39 (1H, dd, J=8.8, 5.8 Hz), 7.31 (1H, dd, J=8.0, 2,6 Hz), 7.01 (1H, dt, J=8.2, 2.6 Hz), 4.61 (2H, d, J=6.6 Hz), 3.99 (4H, s), 1.56 (6H, s). HRMS [M+H]⁺ calcd for C₁₇H₁₈N₃O₄FBr: 426.04648; found: 426.0465.

EXAMPLE 60

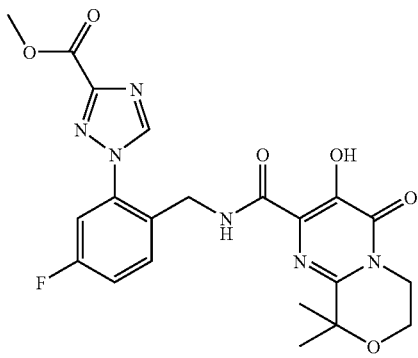

1H-1,2,4-Triazole-3-carboxylic acid, 1-[5-fluoro-2-[[[(4,6,7,9-tetrahydro-3-hydroxy-9,9-dimethyl-4-oxopyrimido[2,1-c][1,4]oxazin-2-yl)carbonyl]amino]methyl]phenyl]-, methyl este. The title compound can be prepared from intermediate 91. White solid. ¹H-NMR (300 MHz, CDCl₃) δ ppm: 11.90 (1H, s), 8.49 (1H, s), 8.36 (1H, t, J=6.2 Hz), 7.72 (1H, dd, J=8.8, 5.9 Hz), 7.26-7.20 (1H, m), 7.14 (1H, dd, J=8.4, 2,6 Hz), 4.49 (2H, d, J=6.6 Hz), 4.01 (3H, s), 3.98 (4H, s), 1.58 (6H, s). HRMS [M+H]⁺ calcd for C₂₁H₂₂N₆O₆F: 473.1585; found: 473.1563. Anal calcd for C₂₁H₂₁N₆O₆F.0.5 H₂O: C, 52.39; H, 4.61; N, 17.46; F, 3.95; found: C, 52.14; H, 4.70; N, 17.41; F, 4.12.

EXAMPLE 61

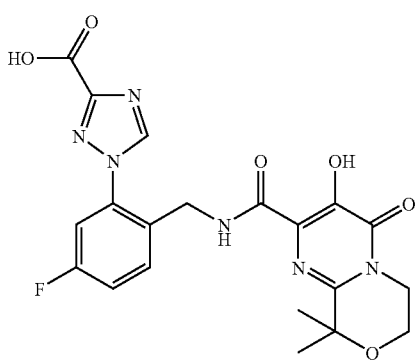

1H-1,2,4-Triazole-3-carboxylic acid, 1-[5-fluoro-2-[[[(4,6,7,9-tetrahydro-3-hydroxy-9,9-dimethyl-4-oxopyrimido[2,1-c][1,4]oxazin-2-yl)carbonyl]amino]methyl]phenyl]-. To a solution of example 60, 1H-1,2,4-triazole-3-carboxylic acid, 1-[5-fluoro-2-[[[(4,6,7,9-tetrahydro-3-hydroxy-9,9-dimethyl-4-oxopyrimido[2,1-c][1,4]oxazin-2-yl)carbonyl]amino]methyl]phenyl]-, methyl ester, (2.156 g, 4.6 mmol) in tetrahydrofuran (200 mL) and water (50 mL) at 0° C. was added lithium hydroxide monohydrate (0.58 g, 13.8 mmol). The mixture was stirred at 0° C. 2 h and at room temp for 1 h. The resulting solution was partitioned between ethyl acetate and water. The aqueous phase was acidified with 1 N HCl and extracted with ethyl acetate and CH₂Cl₂. The organic extracts were combined, dried (Na₂SO₄) and concentrated to give the title compound as a white solid (2.05 g, 97% yield). ¹H-NMR (300 MHz, CDCl₃) δ ppm: 11.91 (1H, bs), 8.55 (1H, s), 8.43 (1H, t, J=6.6 Hz), 7.77 (1H, dd, J=8.8, 5.9 Hz), 7.28-7.23 (1H, m), 7.16 (1H, dd, J=8.0, 2.6 Hz), 4.47 (2H, d, J=6.9 Hz), 3.98 (4H, s), 1.59 (6H, s). HRMS [M+H]⁺ calcd for C₂₀H₂₀N₆O₆F: 459.14285; found: 459.1442.

EXAMPLES 62-72

Examples 62-72 can be prepared from intermediate 61, 1H-1,2,4-triazole-3-carboxylic acid, 1-[5-fluoro-2-[[[(4,6,7,9-tetrahydro-3-hydroxy-9,9-dimethyl-4-oxopyrimido[2,1-c]

[1,4]oxazin-2-yl)carbonyl]amino]methyl]phenyl]-, according to the method and describe for the synthesis of example 62.

EXAMPLE 62

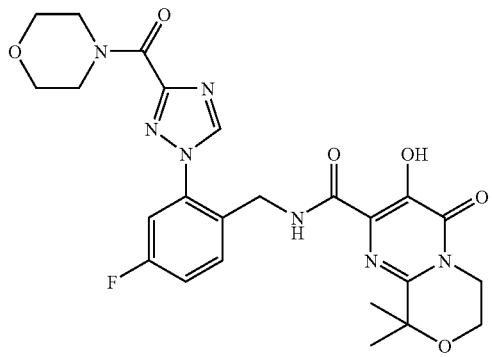

Pyrimido[2,1-c][1,4]oxazine-2-carboxamide, N-[[4-fluoro-2-[3-(4-morpholinylcarbonyl)-1H-1,2,4-triazol-1-yl]phenyl]methyl]-4,6,7,9-tetrahydro-3-hydroxy-9,9-dimethyl-4-oxo-. To a solution of example 61, 1H-1,2,4-triazole-3-carboxylic acid, 1-[5-fluoro-2-[[[(4,6,7,9-tetrahydro-3-hydroxy-9,9-dimethyl-4-oxopyrimido[2,1-c][1,4]oxazin-2-yl)carbonyl]amino]methyl]phenyl]-, (0.0259 g, 0.057 mmol) in DMF (2 mL), at 0° C., was added O-(7-azabenzotriazol-1-yl)-N,N,N$^1$,N$^1$-tetramethyluronium hexafluorophosphate (0.044 g, 0.115 mmol). The solution was stirred at 0° C. for 10 min before adding morpholine (0.025 mL, 0.285 mmol) after which it was stirred at room temp for 2 h. Purification by reverse phase preparative HPLC chromatography (YMC Combiprep ODS-A, 30 mm×50 mm, MeOH/H$_2$O/0.1% CF$_3$CO$_2$H) gave the title compound as a white solid (0.015 g, 50% yield). $^1$H-NMR (500 MHz, CDCl$_3$) δ ppm: 8.50 (1H, t, J=6.9 Hz), 8.45 (1H, s), 7.69 (1H, dd, J=8.7, 5.9 Hz), 7.22 (1H, td, J=8.2, 2,3 Hz), 7.13 (1H, dd, J=8.2, 2.4 Hz), 4.49 (2H, s), 3.98 (4H, s), 3.88-3.72 (8H, m), 1.57 (6H, s). HRMS [M+H]$^+$ calcd for C$_{24}$H$_{27}$N$_7$O$_6$F: 528.20069; found: 528.2025.

EXAMPLE 63

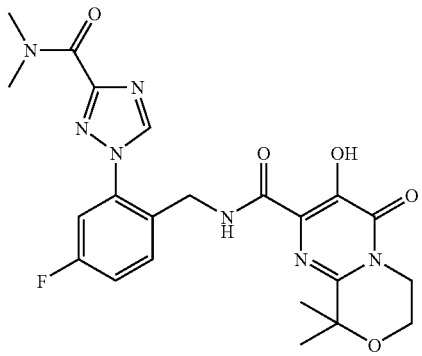

Pyrimido[2,1-c][1,4]oxazine-2-carboxamide, N-[[2-[3-[(dimethylamino)carbonyl]-1H-1,2,4-triazol-1-yl]-4-fluorophenyl]methyl]-4,6,7,9-tetrahydro-3-hydroxy-9,9-dimethyl-4-oxo-. Pale purple solid. $^1$H-NMR (300 MHz, CDCl$_3$) δ ppm: 8.51-8.45 (2H, m), 7.70 (1H, dd, J=8.4, 5.9 Hz), 7.24-7.18 (1H, m), 7.12 (1H, dd, J=8.2, 2.4 Hz), 4.47 (2H, d, J=6.9 Hz), 3.97 (4H, s), 3.24 (3H, s), 3.15 (3H, s), 1.54 (6H, s). HRMS [M+H]$^+$ calcd for C$_{22}$H$_{25}$N$_7$O$_5$F: 486.19013; found: 486.1887.

EXAMPLE 64

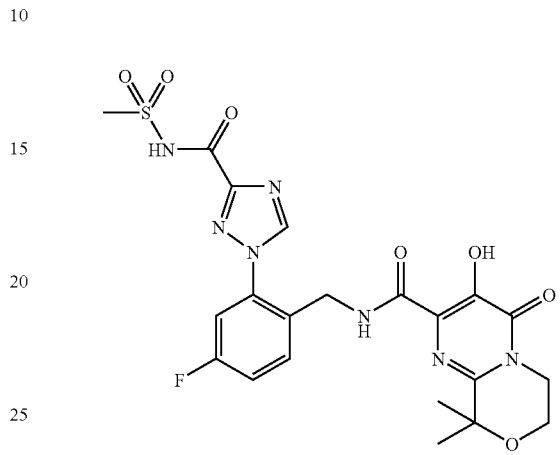

Pyrimido[2,1-c][1,4]oxazine-2-carboxamide, N-[[4-fluoro-2-[3-[[(methylsulfonyl)amino]carbonyl]-1H-1,2,4-triazol-1-yl]phenyl]methyl]-4,6,7,9-tetrahydro-3-hydroxy-9,9-dimethyl-4-oxo-. White solid. $^1$H-NMR (300 MHz, CDCl$_3$) δ ppm: 8.52 (1H, s), 8.36 (1H, t, J=6.8 Hz), 7.70 (1H, dd, J=8.6, 5.7 Hz), 7.26-7.19 (1H, m), 7.13 (1H, dd, J=8.4, 2.6 Hz), 4.46 (2H, d, J=7.0 Hz), 3.95 (4H, s), 3.39 (4H, s), 1.57 (6H, s). HRMS [M+H]$^+$ calcd for C$_{21}$H$_{23}$N$_7$O$_7$FS: 536.1364; found: 536.1376. Anal calcd for C$_{21}$H$_{22}$N$_7$O$_7$FS.0.07CF$_3$CO$_2$H: C, 46.72; H, 4.09; N, 18.04; F, 4.23; found: C, 46.42; H, 3.91; N, 17.70; F, 4.17.

EXAMPLE 65

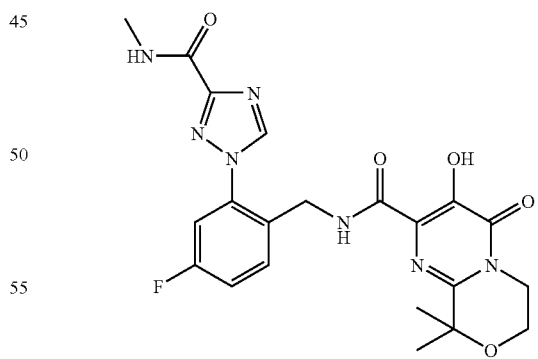

Pyrimido[2,1-c][1,4]oxazine-2-carboxamide, 4,6,7,9-tetrahydro-3-hydroxy-N-[(1R)-2-hydroxy-1-phenylethyl]-9,9-dimethyl-4-oxo-. White solid. $^1$H-NMR (300 MHz, CDCl$_3$) δ ppm: 8.43 (1H, s), 8.20 (1H, t, J=6.0 Hz), 7.64 (1H, dd, J=8.8, 5.9 Hz), 7.42-7.40 (1H, m), 7.26-7.19 (1H, m), 7.11 (1H, dd, J=8.0, 2.6 Hz), 4.53 (2H, d, J=6.6 Hz), 3.99 (4H, s), 3.06 (3H, d, J=4.7 Hz), 1.56 (6H, s). HRMS [M+H]$^+$ calcd for C$_{21}$H$_{23}$N$_7$O$_5$F: 472.1745; found: 472.1741. Anal calcd for $C_{21}H_{22}N_7O_5F$: C, 53.50; H, 4.70; N, 20.79; F, 4.03; found: C, 53.22; H, 4.51; N, 20.70; F, 4.01.

EXAMPLE 66

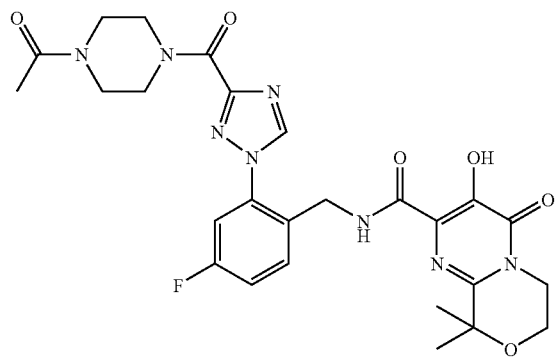

Pyrimido[2,1-c][1,4]oxazine-2-carboxamide, N-[[2-[3-[(4-acetyl-1-piperazinyl)carbonyl]-1H-1,2,4-triazol-1-yl]-4-fluorophenyl]methyl]-4,6,7,9-tetrahydro-3-hydroxy-9,9-dimethyl-4-oxo-. White solid. $^1$H-NMR (300 MHz, CDCl$_3$) δ ppm: 8.46 (1H, s), 8.36 (1H, t, J=5.7 Hz), 7.68 (1H, dd, J=8.6, 5.7 Hz), 7.27-7.21 (1H, m), 7.14 (1H, dd, J=8.2, 2.7 Hz), 4.48 (2H, d, J=6.6 Hz), 3.98 (4H, s), 3.94-3.61 (8H, m), 2.13 (3H, s), 1.55 (6H, s). HRMS [M+H]$^+$ calcd for $C_{26}H_{30}N_8O_6F$: 569.2272; found: 569.2269. Anal calcd for $C_{26}H_{29}N_8O_6F$.0.8 H$_2$O: C, 53.57; H, 5.29; N, 19.22; F, 3.26; found: C, 53.48; H, 4.95; N, 19.21; F, 3.21.

EXAMPLE 67

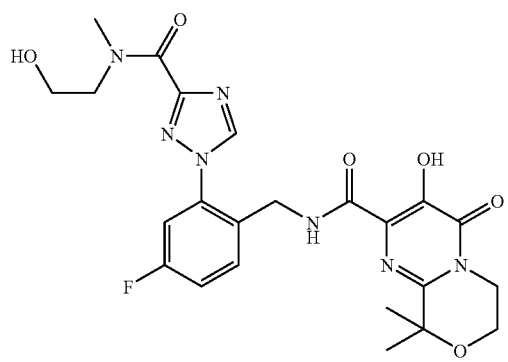

Pyrimido[2,1-c][1,4]oxazine-2-carboxamide, N-[[4-fluoro-2-[3-[[(2-hydroxyethyl)methylamino]carbonyl]-1H-1,2,4-triazol-1-yl]phenyl]methyl]-4,6,7,9-tetrahydro-3-hydroxy-9,9-dimethyl-4-oxo-. White solid. $^1$H-NMR (300 MHz, CDCl$_3$) δ ppm: 8.54 (1H, t, J=7.3 Hz), 8.44 (1H, s), 7.66 (1H, dd, J=8.8, 5.8 Hz), 7.21-7.09 (2H, m), 4.44 (2H, d, J=4.4 Hz), 3.93 (4H, s), 3.86-3.78 (2H, m), 3.70-3.65 (2H, m), 3.13 (3H, s), 1.94 (1H, bs), 1.55 (6H, s). HRMS [M+H]$^+$ calcd for $C_{23}H_{27}N_7O_6F$: 516.2007; found: 516.2011. Anal calcd for $C_{23}H_{26}N_7O_6F$: C, 53.59; H, 5.08; N, 19.02; F, 3.68; found: C, 53.31; H, 5.06; N, 18.80; F, 3.60.

EXAMPLE 68

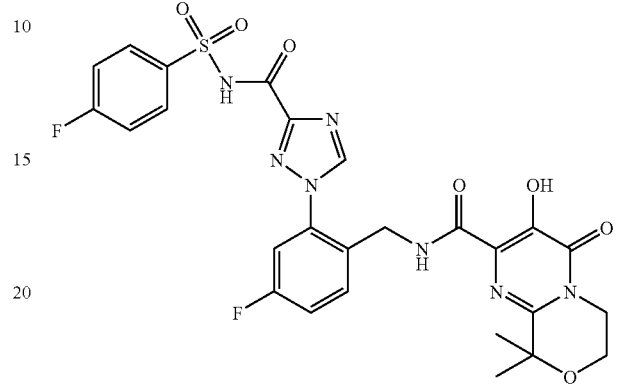

Pyrimido[2,1-c][1,4]oxazine-2-carboxamide, N-[[4-fluoro-2-[3-[[[(4-fluorophenyl)sulfonyl]amino]carbonyl]-1H-1,2,4-triazol-1-yl]phenyl]methyl]-4,6,7,9-tetrahydro-3-hydroxy-9,9-dimethyl-4-oxo-. White solid. $^1$H-NMR (300 MHz, CDCl$_3$) δ ppm: 8.47 (1H, s), 8.18-8.13 (2H, m), 7.68 (1H, dd, J=8.8, 5.9 Hz), 7.24-7.16 (3H, m), 7.08 (1H, dd, J=8.0, 2.6 Hz), 4.39 (2H, s), 3.96 (4H, s), 1.55 (6H, s). HRMS [M+H]$^+$ calcd for $C_{26}H_{24}N_7O_7F_2S$: 616.1426; found: 616.1426. Anal calcd for $C_{26}H_{23}N_7O_7F_2S$: C, 50.73; H, 3.76; N, 15.92; F, 6.17; found: C, 50.49; H, 3.66; N, 15.98; F, 6.12.

EXAMPLE 69

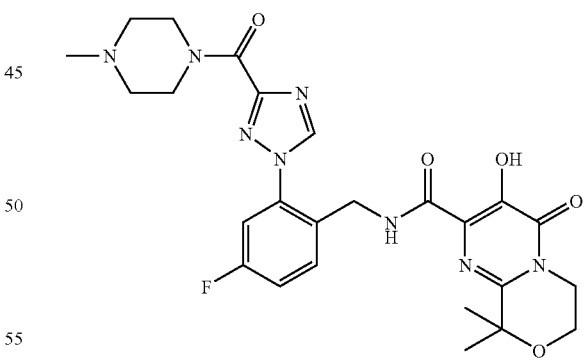

Pyrimido[2,1-c][1,4]oxazine-2-carboxamide, N-[[4-fluoro-2-[3-[(4-methyl-1-piperazinyl)carbonyl]-1H-1,2,4-triazol-1-yl]phenyl]methyl]-4,6,7,9-tetrahydro-3-hydroxy-9,9-dimethyl-4-oxo-. Pale brown foam. $^1$H-NMR (300 MHz, CDCl$_3$) δ ppm: 8.43 (1H, s), 8.29 (1H, t, J=6.8 Hz), 7.63 (1H, dd, J=8.4, 5.9 Hz), 7.25-7.19 (1H, m), 7.11 (1H, dd, J=8.0, 2.6 Hz), 4.46 (2H, d, J=6.6 Hz), 3.95 (4H, s), 3.30 (4H, bs), 2.86 (3H, s), 1.91 (4H, bs), 1.53 (6H, s). HRMS [M+H]$^+$ calcd for $C_{25}H_{30}N_8O_5F$: 541.2323; found: 541.2341. Anal calcd for $C_{25}H_{29}N_8O_5F \cdot 0.5 CF_3CO_2H \cdot 0.5\ H_2O$: C, 46.67; H, 4.41; N, 15.55; F, 14.50; found: C, 46.86; H, 4.44; N, 15.67; F, 14.48.

EXAMPLE 70

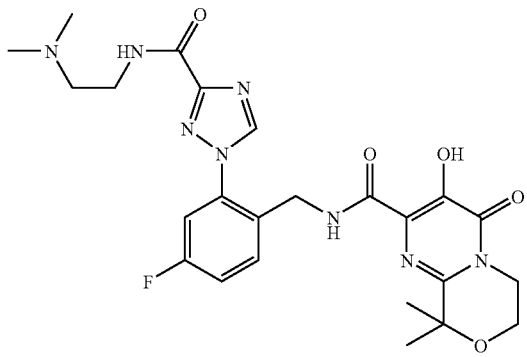

Pyrimido[2,1-c][1,4]oxazine-2-carboxamide, N-[[2-[3-[[[2-(dimethylamino)ethyl]amino]carbonyl]-1H-1,2,4-triazol-1-yl]-4-fluorophenyl]methyl]-4,6,7,9-tetrahydro-3-hydroxy-9,9-dimethyl-4-oxo-. Pale brown foam. $^1$H-NMR (300 MHz, CDCl$_3$) δ ppm: 8.39 (1H, s), 7.58 (1H, dd, J=8.6, 5.7 Hz), 7.23-7.14 (1H, m), 7.09 (1H, dd, J=8.4, 2.6 Hz), 4.50 (2H, s), 3.95 (4H, s), 3.84 (2H, t, J=5.5 Hz), 3.34 (2H, t, J=6.0 Hz), 2.89 (6H, s), 1.55 (6H, s). HRMS [M+H]$^+$ calcd for $C_{24}H_{30}N_8O_5F$: 529.2323; found: 529.2315.

EXAMPLE 71

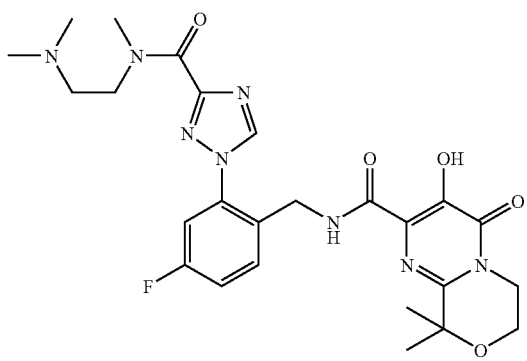

Pyrimido[2,1-c][1,4]oxazine-2-carboxamide, N-[[2-[3-[[[2-(dimethylamino)ethyl]methylamino]carbonyl]-1H-1,2,4-triazol-1-yl]-4-fluorophenyl]methyl]-4,6,7,9-tetrahydro-3-hydroxy-9,9-dimethyl-4-oxo-. Pale brown foam. $^1$H-NMR (300 MHz, CDCl$_3$) δ ppm: 8.44 (1H, s), 8.21 (1H, t, J=6.5 Hz), 7.67-7.58 (1H, m), 7.24-7.09 (2H, m), 4.48-4.45 (2H, m), 3.95 (4H, s), 3.94-3.89 (2H, m), 3.37-3.33 (2H, m), 2.91 (6H, s), 2.88 (3H, s), 1.56 (6H, s). HRMS [M+H]$^+$ calcd for $C_{25}H_{32}N_8O_5F$: 543.2480; found: 543.2491. Anal calcd for $C_{25}H_{31}N_8O_5F \cdot CF_3CO_2H$: C, 45.20; H, 4.32; N, 14.54; F, 17.26; found: C, 45.13; H, 4.14; N, 14.74; F, 17.01.

EXAMPLE 72

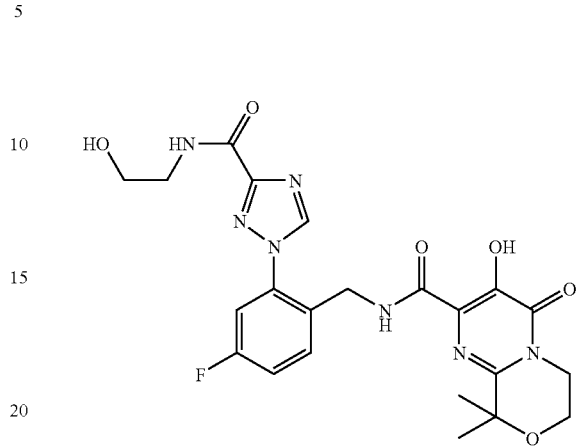

Pyrimido[2,1-c][1,4]oxazine-2-carboxamide, N-[[4-fluoro-2-[3-[[(2-hydroxyethyl)amino]carbonyl]-1H-1,2,4-triazol-1-yl]phenyl]methyl]-4,6,7,9-tetrahydro-3-hydroxy-9,9-dimethyl-4-oxo-. White solid. $^1$H-NMR (300 MHz, CDCl$_3$) δ ppm: 8.41 (1H, s), 8.32 (1H, t, J=6.2 Hz), 7.63 (1H, dd, J=8.4, 5.9 Hz), 7.20 (1H, dt, J=8.4, 2.6 Hz), 7.11 (1H, dd, J=8.4, 2.6 Hz), 4.52-4.50 (2H, m), 3.95 (4H, s), 3.78 (2H, t, J=5.1 Hz), 3.59 (2H, t, J=5.1 Hz), 1.56 (6H, s). HRMS [M+H]$^+$ calcd for $C_{22}H_{25}N_7O_6F$: 502.1850; found: 502.1850.

EXAMPLE 73

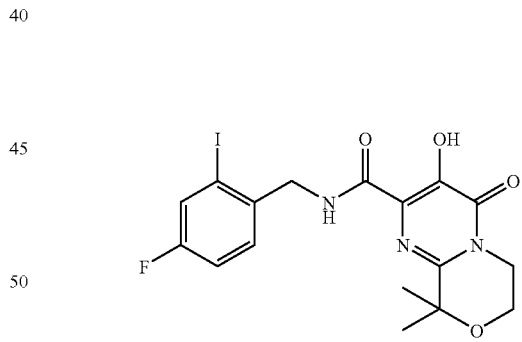

Pyrimido[2,1-c][1,4]oxazine-2-carboxamide, N-[(4-fluoro-2-iodophenyl)methyl]-4,6,7,9-tetrahydro-3-hydroxy-9,9-dimethyl-4-oxo-. The title compound can be prepared from intermediate 174, N-(4-fluoro-2-iodobenzyl)-3-(benzyloxy)-9,9-dimethyl-4-oxo-4,6,7,9-tetrahydropyrimido[2,1-c][1,4]oxazine-2-carboxamide. $^1$HNMR 400 MHz (CDCl$_3$) δ ppm: 1.63 (6H, s, 2×CH$_3$), 4.05 (4H, s, 2×CH$_2$), 4.63 (2H, d, J=7.1 Hz, NCH$_2$), 7.11 (1H, m, aromatic), 7.42 (1H, dd, J=5.6 Hz and J=8.6 Hz, aromatic), 7.62 (1H, dd, J=2.5 Hz and J=8.1

Hz, aromatic), 8.20 (1H, broad t, NH), 11.82 (1H, s, OH). HRMS (ESI⁺) calculated for $C_{17}H_{18}FIN_3O_4$ [M+H⁺]: 474.0326; found: 474.0328.

EXAMPLES 74-77

Examples 74-77 can be prepared from the indicated intermediates by hydrogenolysis or trifluoroacetic acid mediated hydrolysis.

EXAMPLE 74

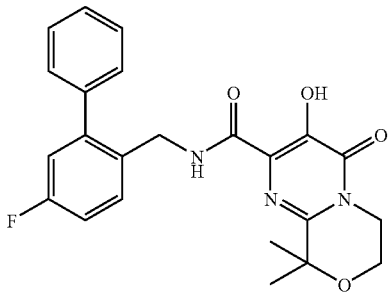

Pyrimido[2,1-c][1,4]oxazine-2-carboxamide, N-[(5-fluoro[1,1'-biphenyl]-2-yl)methyl]-4,6,7,9-tetrahydro-3-hydroxy-9,9-dimethyl-4-oxo-. The title compound can be prepared from intermediate 176, N-(4-fluoro-2-phenyl-benzyl)-3-(benzyloxy)-9,9-dimethyl-4-oxo-4,6,7,9-tetrahydropyrimido[2,1-c][1,4]oxazine-2-carboxamide. ¹HNMR 400 MHz (CDCl₃) δ ppm: 1.56 (6H, s, 2×CH₃), 4.03 (4H, s, 2×CH₂), 4.56 (2H, d, J=6.0 Hz, NCH₂), 7.03 (1H, dd, J=2.5 Hz and J=9.3 Hz, aromatic), 7.09 (1H, m, aromatic), 7.36 (2H, m, aromatics), 7.42-7.51 (5H, m, aromatics and NH), 11.96 (1H, s, OH). HRMS (ESI⁺) calculated for $C_{23}H_{23}FN_3O_4$ [M+H⁺]: 424.1673; found: 424.1675.

EXAMPLE 75

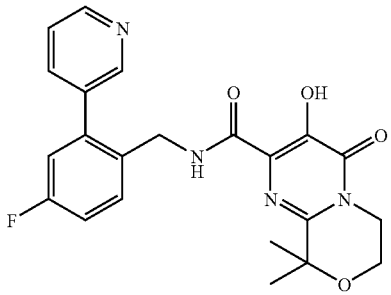

Pyrimido[2,1-c][1,4]oxazine-2-carboxamide, N-[[4-fluoro-2-(3-pyridinyl)phenyl]methyl]-4,6,7,9-tetrahydro-3-hydroxy-9,9-dimethyl-4-oxo-. ¹HNMR 400 MHz (CDCl₃) δ ppm: 1.57 (6H, s, 2×CH₃), 4.04 (4H, s, 2×CH₂), 4.55 (2H, d, J=6.1 Hz, NCH₂), 7.04 (1H, dd, J=2.5 Hz and J=9.1 Hz, aromatic), 7.16 (1H, m, aromatic), 7.43 (1H, m, aromatic), 7.49 (1H, dd, J=5.6 Hz and J=8.6 Hz, aromatic), 7.52 (1H, broad t, NH), 7.71 (1H, m, aromatic), 8.63 (1H, m, aromatic), 8.70 (1H, m, aromatic), 11.84 (1H, s, OH). HRMS (ESI⁺) calculated for $C_{22}H_{22}FN_4O_4$ [M+H⁺]: 425.1625; found: 425.1616.

EXAMPLE 76

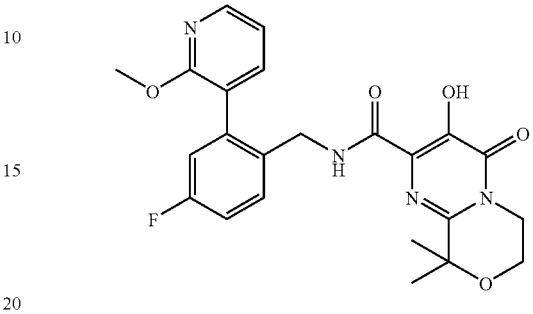

Pyrimido[2,1-c][1,4]oxazine-2-carboxamide, N-[[4-fluoro-2-(2-methoxy-3-pyridinyl)phenyl]methyl]-4,6,7,9-tetrahydro-3-hydroxy-9,9-dimethyl-4-oxo-. Hydrogenolysis of intermediate 175, N-(4-fluoro-2-(2-methoxypyridin-3-yl)benzyl)-3-(benzyloxy)-9,9-dimethyl-4-oxo-4,6,7,9-tetrahydropyrimido[2,1-c][1,4]oxazine-2-carboxamide gave the title material as a white solid; mp 227° C. ¹HNMR 400 MHz (CDCl₃) δ ppm: 1.58 (6H, s, 2×CH₃), 3.99 (3H, s, OCH₃), 4.04 (4H, s, 2×CH₂), 4.43 (2H, broad, NCH₂), 6.97 (1H, dd, J=2.5 Hz and J=8.5 Hz, aromatic), 7.03 (1H, dd, J=5.0 Hz and J=8.5 Hz, aromatic), 7.12 (1H, m, aromatic), 7.45 (1H, dd, J=4.5 Hz and J=8.6 Hz, aromatic), 7.53 (1H, dd, J=2.0 Hz and J=7.1 Hz, aromatic), 7.57 (1H, broad t, NH), 8.28 (1H, dd, J=2.5 Hz and J=5.0 Hz, aromatic), 12.03 (1H, s, OH). HRMS (ESI⁺) calculated for $C_{23}H_{24}FN_4O_5$ [M+H⁺]: 455.1731; found: 455.1737.

EXAMPLE 77

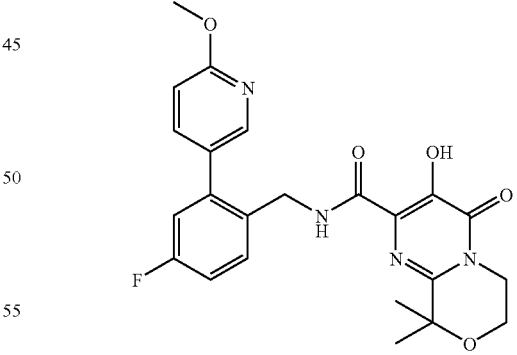

Pyrimido[2,1-c][1,4]oxazine-2-carboxamide, N-[[4-fluoro-2-(6-methoxy-3-pyridinyl)phenyl]methyl]-4,6,7,9-tetrahydro-3-hydroxy-9,9-dimethyl-4-oxo. ¹HNMR 400 MHz (CDCl₃) δ ppm: 1.58 (6H, s, 2×CH₃), 4.02 (3H, s, OCH₃), 4.04 (4H, s, 2×CH₂), 4.55 (2H, d, J=6.1 Hz, NCH₂), 6.87 (1H, d, J=9.0 Hz, aromatic), 7.01 (1H, dd, J=2.0 Hz and J=9.0 Hz, aromatic), 7.12 (1H, m, aromatic), 7.46 (1H, dd, J=5.5 Hz and J=8.6 Hz, aromatic), 7.55 (1H, broad t, NH), 7.60 (1H, dd, J=2.0 Hz and J=8.6 Hz, aromatic), 8.17 (1H, d, J=2.0 Hz, aromatic), 11.89 (1H, s, OH). HRMS (ESI+) calculated for $C_{23}H_{24}FN_4O_5$ [M+H+]: 455.1731; found: 455.1717.

EXAMPLES 78-80

Examples 78-80 can be prepared from the indicated intermediates according to the method described for example 78.

EXAMPLE 78

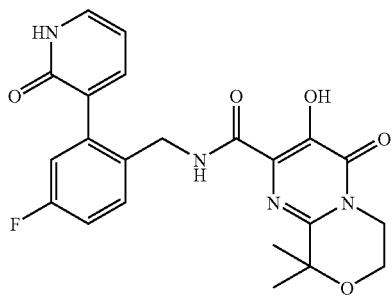

Pyrimido[2,1-c][1,4]oxazine-2-carboxamide, N-[[2-(1,2-dihydro-2-oxo-3-pyridinyl)-4-fluorophenyl]methyl]-4,6,7,9-tetrahydro-3-hydroxy-9,9-dimethyl-4-oxo-. A solution of intermediate 175, N-(4-fluoro-2-(2-methoxypyridin-3-yl)benzyl)-3-(benzyloxy)-9,9-dimethyl-4-oxo-4,6,7,9-tetrahydropyrimido[2,1-c][1,4]oxazine-2-carboxamide, (0.125 g, 0.23 mmol) in acetonitrile (5 ml) was treated with sodium iodide (0.090 g, 0.6 mmol) and chlorotrimethylsilane (0.45 ml, 3.5 mmol), sealed in a pressure resistant vessel and heated at 80° C. for 1.5 h. The mixture was diluted with ethyl acetate washed with water and brine then dried over anhydrous magnesium sulfate. Filtration and removal of solvent provided the title compound. $^1$HNMR 400 MHz (CDCl$_3$) δ ppm: 1.60 (6H, s, 2×CH$_3$), 4.03 (4H, s, 2×CH$_2$), 4.5 (2H, broad, NCH$_2$), 6.47 (1H, m, aromatic), 6.95 (1H, dd, J=2 Hz and J=9 Hz, aromatic), 7.12 (1H, m, aromatic), 7.45 (1H, dd, J=2 Hz and J=7 Hz, aromatic), 7.50 (1H, dd, J=6 Hz and J=9 Hz, aromatic), 7.53 (1H, dd, J=2 Hz and J=7 Hz, aromatic), 8.64 (1H, broad t, NH). HRMS (ESI+) calculated for $C_{22}H_{22}FN_4O_5$ [M+H+]: 441.1574; found: 441.1585.

EXAMPLE 79

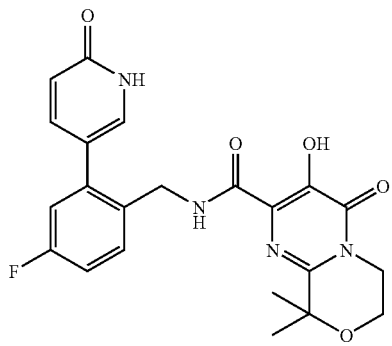

Pyrimido[2,1-c][1,4]oxazine-2-carboxamide, N-[[2-(1,6-dihydro-6-oxo-3-pyridinyl)-4-fluorophenyl]methyl]-4,6,7,9-tetrahydro-3-hydroxy-9,9-dimethyl-4-oxo-. The title compound can be prepared from example 77. $^1$HNMR 400 MHz (CDCl$_3$) δ ppm: 1.59 (6H, s, 2×CH$_3$), 4.02 (3H, s, OCH$_3$), 4.05 (4H, s, 2×CH$_2$), 4.55 (2H, d, J=6.6 Hz, NCH$_2$), 6.95 (1H, d, J=9.0 Hz, aromatic), 7.00 (1H, dd, J=2.6 Hz and J=9.0 Hz, aromatic), 7.17 (1H, m, aromatic), 7.46 (1H, dd, J=5.5 Hz and J=8.6 Hz, aromatic), 7.63 (1H, d, J=2.6 Hz, aromatic), 7.71 (1H, broad t, NH), 7.79 (1H, dd, J=2.6 Hz and J=9.1 Hz, aromatic). HRMS (ESI+) calculated for $C_{22}H_{22}FN_4O_5$ [M+H+]: 441.1574; found: 441.1570.

EXAMPLE 80

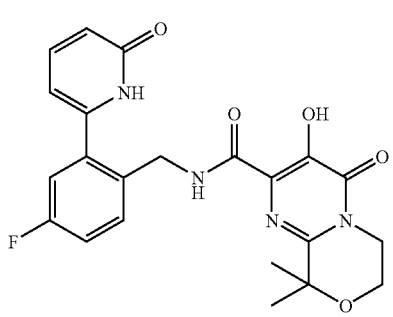

Pyrimido[2,1-c][1,4]oxazine-2-carboxamide, N-[[2-(1,6-dihydro-6-oxo-2-pyridinyl)-4-fluorophenyl]methyl]-4,6,7,9-tetrahydro-3-hydroxy-9,9-dimethyl-4-oxo-. The title compound can be prepared from N-(4-fluoro-2-(6-methoxypyridin-2-yl)benzyl)-3-(benzyloxy)-9,9-dimethyl-4-oxo-4,6,7,9-tetrahydropyrimido[2,1-c][1,4]oxazine-2-carboxamide, which can be prepared according to the methods described for the synthesis of intermediate 175. $^1$HNMR 400 MHz (CDCl$_3$) δ (ppm): 1.62 (6H, s, 2×CH$_3$), 4.04 (4H, s, 2×CH$_2$), 4.60 (2H, d, J=7.0 Hz, NCH$_2$), 6.38 (1H, d, J=7.0 Hz, aromatic), 6.68 (1H, d, J=9.0 Hz, aromatic), 7.14 (1H, dd, J=2.5 Hz and J=9.1 Hz, aromatic), 7.23 (1H, m, aromatic), 7.50 (1H, dd, J=5.6 Hz and J=8.6 Hz, aromatic), 7.58 (1H, dd, J=7.0 Hz and J=9.0 Hz, aromatic), 8.15 (1H, broad t, NH).

EXAMPLES 81-93

Examples 81-93 can be prepared from the indicated intermediates by hydrogenolysis or trifluoroacetic acid mediated hydrolysis.

EXAMPLE 81

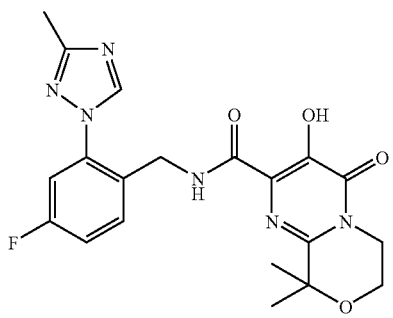

Pyrimido[2,1-c][1,4]oxazine-2-carboxamide, N-[[4-fluoro-2-(3-methyl-1H-1,2,4-triazol-1-yl)phenyl]methyl]-4,6,7,9-tetrahydro-3-hydroxy-9,9-dimethyl-4-oxo-. The title compound can be prepared from intermediate 152, N-(4-fluoro-2-(3-methyl-1H-1,2,4-triazol-1-yl)benzyl)-3-(benzyloxy)-9,9-dimethyl-4-oxo-4,6,7,9-tetrahydropyrimido[2,1-c][1,4]oxazine-2-carboxamide $^1$HNMR 400 MHz (CDCl$_3$) δ ppm: 1.64 (6H, s, 2×CH$_3$), 2.59 (3H, s, CH$_3$), 4.04 (4H, s, 2×CH$_2$), 4.50 (2H, d, J=7.1 Hz, NCH$_2$), 7.1 (1H, dd, J=2.5 Hz and J=8.6 Hz, aromatic), 7.20 (1H, m, aromatic), 7.72 (1H, dd, J=6.0 Hz and J=8.6 Hz, aromatic), 8.34 (1H, s, CH), 8.80 (1H, broad t, NH), 12.11 (1H, s, OH). HRMS (ESI$^+$) calculated for C$_{20}$H$_{22}$FN$_6$O$_4$ [M+H$^+$]: 429.1687; found: 429.1675.

EXAMPLE 82

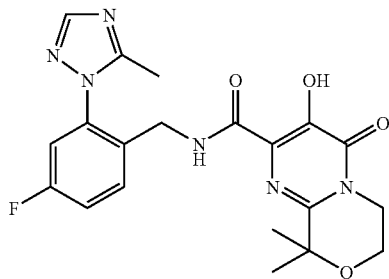

Pyrimido[2,1-c][1,4]oxazine-2-carboxamide, N-[[4-fluoro-2-(5-methyl-1H-1,2,4-triazol-1-yl)phenyl]methyl]-4,6,7,9-tetrahydro-3-hydroxy-9,9-dimethyl-4-oxo-. $^1$HNMR 400 MHz (CDCl$_3$) δ ppm: 1.66 (6H, s, 2×CH$_3$), 2.50 (3H, s, CH$_3$), 4.04 (4H, s, 2×CH$_2$), 4.32 (2H, d, J=7.0 Hz, NCH$_2$), 7.05 (1H, dd, J=2.5 Hz and J=8.1 Hz, aromatic), 7.27 (1H, m, aromatic), 7.70 (1H, dd, J=6.1 Hz and J=8.6 Hz, aromatic), 8.04 (1H, s, CH), 8.61 (1H, broad t, NH), 11.90 (1H, s, OH). HRMS (ESI$^+$) calculated for C$_{20}$H$_{22}$FN$_6$O$_4$ [M+H$^+$]: 429.1687; found: 429.1688.

EXAMPLE 83

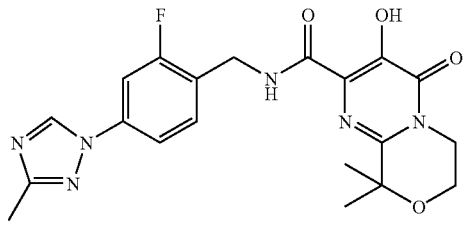

Pyrimido[2,1-c][1,4]oxazine-2-carboxamide, N-[[2-fluoro-4-(3-methyl-1H-1,2,4-triazol-1-yl)phenyl]methyl]-4,6,7,9-tetrahydro-3-hydroxy-9,9-dimethyl-4-oxo-. The title compound can be prepared from intermediate 153, N-(2-fluoro-4-(3-methyl-1H-1,2,4-triazol-1-yl)benzyl)-3-(benzyloxy)-9,9-dimethyl-4-oxo-4,6,7,9-tetrahydropyrimido[2,1-c][1,4]oxazine-2-carboxamide. $^1$HNMR 400 MHz (CDCl$_3$) δ ppm: 1.61 (6H, s, 2×CH$_3$), 2.51 (3H, s, CH$_3$), 4.05 (4H, s, 2×CH$_2$), 4.72 (2H, d, J=6.6 Hz, NCH$_2$), 7.44-7.55 (3H, m, aromatics), 7.94 (1H, broad t, NH), 8.46 (1H, s, CH), 11.86 (1H, s, OH). HRMS (ESI$^+$) calculated for C$_{20}$H$_{22}$FN$_6$O$_4$ [M+H$^+$]: 429.1687; found: 429.1695.

EXAMPLE 84

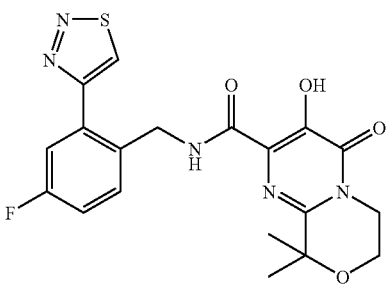

Pyrimido[2,1-c][1,4]oxazine-2-carboxamide, N-[[4-fluoro-2-(1,2,3-thiadiazol-4-yl)phenyl]methyl]-4,6,7,9-tetrahydro-3-hydroxy-9,9-dimethyl-4-oxo-. The title compound can be prepared from intermediate 172, N-(4-fluoro-2-(1,2,3-thiadiazol-4-yl)benzyl)-3-(benzyloxy)-9,9-dimethyl-4-oxo-4,6,7,9-tetrahydropyrimido[2,1-c][1,4]oxazine-2-carboxamide. $^1$HNMR 400 MHz (DMSO-d$_6$) δ ppm: 1.54 (6H, s, 2×CH$_3$), 3.83 (2H, broad t, CH$_2$), 3.96 (2H, broad t, CH$_2$), 4.61 (2H, d, J=6.7 Hz, NCH$_2$), 7.39 (1H, m, aromatic), 7.55 (1H, m, aromatic), 7.62 (1H, m, aromatic), 9.41 (1H, broad t, NH), 9.63 (1H, s, CH), 12.0 (1H, s, OH). HRMS (ESI$^+$) calculated for C$_{19}$H$_{19}$FN$_5$O$_4$S [M+H$^+$]: 432.1142; found: 432.1124.

EXAMPLE 85

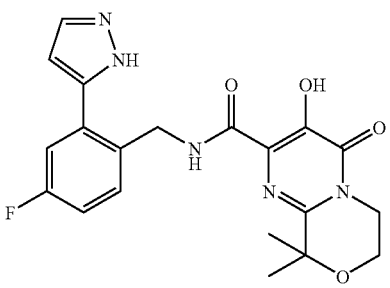

Pyrimido[2,1-c][1,4]oxazine-2-carboxamide, N-[[4-fluoro-2-(1H-pyrazol-5-yl)phenyl]methyl]-4,6,7,9-tetrahydro-3-hydroxy-9,9-dimethyl-4-oxo-. The title compound can be prepared from intermediate 177, N-(4-fluoro-2-(1H-pyrazol-5-yl)benzyl)-3-(benzyloxy)-9,9-dimethyl-4-oxo-4,6,7,9-tetrahydropyrimido[2,1-c][1,4]oxazine-2-carboxamide. $^1$HNMR 400 MHz (CDCl$_3$) δ ppm: 1.59 (6H, s, 2×CH$_3$), 4.03 (4H, s, 2×CH$_2$), 4.67 (2H, d, J=6.6 Hz, NCH$_2$), 6.65 (1H, d, J=2.5 Hz, CH), 7.07 (1H, m, aromatic), 7.31 (1H, dd, J=2.5 Hz and J=9.8 Hz, aromatic), 7.56 (1H, dd, J=5.8 Hz and J=8.3 Hz, aromatic), 7.75 (1H, d, J=2.5 Hz, CH), 9.22 (1H, broad t, NH), 10.33 (1H, broad, NH), 12.2 (1H, s, OH). HRMS (ESI+) calculated for $C_{20}H_{21}FN_5O_4$ [M+H+]: 414.1578; found: 414.1560.

EXAMPLE 86

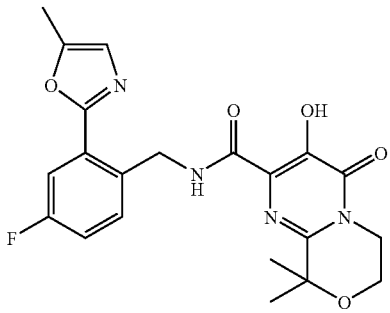

Pyrimido[2,1-c][1,4]oxazine-2-carboxamide, N-[[4-fluoro-2-(5-methyl-2-oxazolyl)phenyl]methyl]-4,6,7,9-tetrahydro-3-hydroxy-9,9-dimethyl-4-oxo-. The title compound can be prepared from intermediate 173, N-(4-fluoro-2-(5-methyloxazol-2-yl)benzyl)-3-(benzyloxy)-9,9-dimethyl-4-oxo-4,6,7,9-tetrahydropyrimido[2,1-c][1,4]oxazine-2-carboxamide. $^1$HNMR 400 MHz (CDCl$_3$) δ ppm: 1.58 (6H, s, 2×CH$_3$), 2.48 (3H, s, CH$_3$), 4.01 (4H, s, 2×CH$_2$), 4.77 (2H, d, J=7.0 Hz, NCH$_2$), 6.96 (1H, s, CH), 7.13 (1H, m, aromatic), 7.61 (1H, dd, J=5.8 Hz and J=8.3 Hz, aromatic), 7.70 (1H, dd, J=3.2 Hz and J=9.6 Hz, aromatic), 9.76 (1H, broad t, NH), 12.15 (1H, s, OH). HRMS (ESI+) calculated for $C_{21}H_{22}FN_4O_5$ [M+H+]: 429.1574; found: 429.1564.

EXAMPLE 87

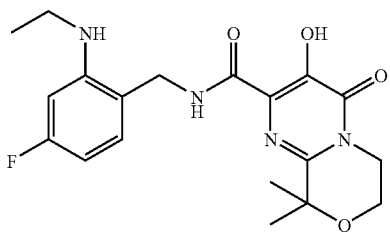

Pyrimido[2,1-c][1,4]oxazine-2-carboxamide, N-[[2-(ethylamino)-4-fluorophenyl]methyl]-4,6,7,9-tetrahydro-3-hydroxy-9,9-dimethyl-4-oxo-. The title compound can be prepared from intermediate 170, N-(2-(ethylamino)-4-fluorobenzyl)-3-(benzyloxy)-9,9-dimethyl-4-oxo-4,6,7,9-tetrahydropyrimido[2,1-c][1,4]oxazine-2-carboxamide. $^1$HNMR 400 MHz (CDCl$_3$) δ ppm: 1.30 (3H, t, J=7.3 Hz, CH$_3$), 1.59 (6H, s, 2×CH$_3$), 3.12 (2H, m, CH$_2$), 4.04 (4H, s, 2×CH$_2$), 4.52 (2H, d, J=6.6 Hz, NCH$_2$), 5.09 (1H, broad, NH), 6.3-6.37 (2H, m, aromatics), 7.10 (1H, dd, J=6.6 Hz and J=8.1 Hz, aromatic), 7.67 (1H, broad t, NH), 11.93 (1H, s, OH). HRMS (ESI+) calculated for $C_{19}H_{24}FN_4O_4$ [M+H+]: 391.1782; found: 391.1774.

EXAMPLE 88

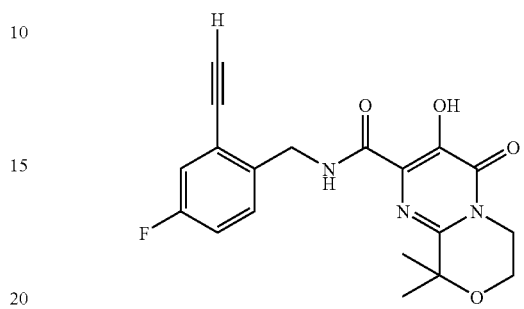

Pyrimido[2,1-c][1,4]oxazine-2-carboxamide, N-[(2-ethynyl-4-fluorophenyl)methyl]-4,6,7,9-tetrahydro-3-hydroxy-9,9-dimethyl-4-oxo-. The title compound can be prepared from intermediate 179, N-(2-ethynyl-4-fluorobenzyl)-3-(benzyloxy)-9,9-dimethyl-4-oxo-4,6,7,9-tetrahydropyrimido[2,1-c][1,4]oxazine-2-carboxamide. $^1$HNMR 400 MHz (CDCl$_3$) δ ppm: 1.61 (6H, s, 2×CH$_3$), 3.46 (1H, s, CH), 4.04 (4H, s, 2×CH$_2$), 4.73 (2H, d, J=6.5 Hz, NCH$_2$), 7.1 (1H, m, aromatic), 7.26 (1H, dd, J=2.5 Hz and J=8.5 Hz, aromatic), 7.40 (1H, dd, J=5.6 Hz and J=8.6 Hz, aromatic), 8.18 (1H, broad t, NH), 11.92 (1H, s, OH). HRMS (ESI+) calculated for $C_{19}H_{19}FN_3O_4$ [M+H+]: 372.1360; found: 372.1345.

EXAMPLE 89

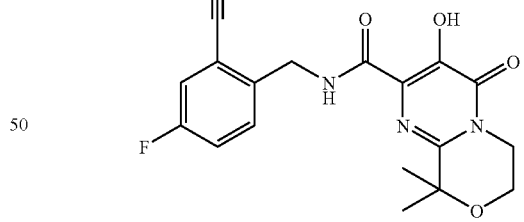

Pyrimido[2,1-c][1,4]oxazine-2-carboxamide, N-[[4-fluoro-2-(3-hydroxy-1-propynyl)phenyl]methyl]-4,6,7,9-tetrahydro-3-hydroxy-9,9-dimethyl-4-oxo-. The title compound can be prepared from intermediate 182, N-(4-fluoro-2-(3-hydroxyprop-1-ynyl)benzyl)-3-(benzyloxy)-9,9-dimethyl-4-oxo-4,6,7,9-tetrahydropyrimido[2,1-c][1,4]oxazine-2-carboxamide. $^1$HNMR 400 MHz (CDCl$_3$) δ ppm: 1.60 (6H, s, 2×CH$_3$), 4.04 (4H, s, 2×CH$_2$), 4.55 (2H, broad d, CH$_2$), 4.73 (2H, d, J=6.6 Hz, NCH$_2$), 7.07 (1H, m, aromatic), 7.20 (1H, dd, J=2.5 Hz and J=9.1 Hz, aromatic), 7.38 (1H, dd, J=5.3 Hz and J=8.3 Hz, aromatic), 7.95 (1H, broad t, NH),

EXAMPLE 90

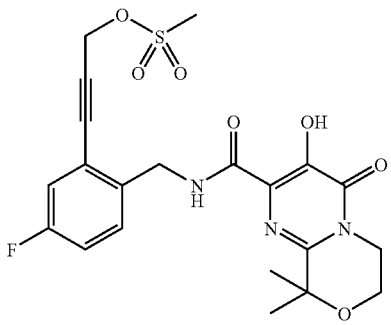

Pyrimido[2,1-c][1,4]oxazine-2-carboxamide, N-[[4-fluoro-2-[3-[(methylsulfonyl)oxy]-1-propynyl]phenyl]methyl]-4,6,7,9-tetrahydro-3-hydroxy-9,9-dimethyl-4-oxo-. The title compound can be prepared from intermediate 183, 3-[2-((3-(benzyloxy)-9,9-dimethyl-4-oxo-4,6,7,9-tetrahydropyrimido[2,1-c][1,4]oxazine-2-carboxamido)methyl)-5-fluorophenyl]prop-2-ynyl methanesulfonate. $^1$HNMR 400 MHz (CDCl$_3$) δ ppm: 1.62 (6H, s, 2×CH$_3$), 3.16 (3H, s, CH$_3$), 4.05 (4H, s, 2×CH$_2$), 4.72 (2H, d, J=6.0 Hz, NCH$_2$), 5.12 (2H, s, OCH$_2$), 7.12 (1H, m, aromatic), 7.21 (1H, dd, J=2.6 Hz and J=8.6 Hz, aromatic), 7.45 (1H, dd, J=5.1 Hz and J=8.6 Hz, aromatic), 8.03 (1H, broad t, NH).

EXAMPLE 91

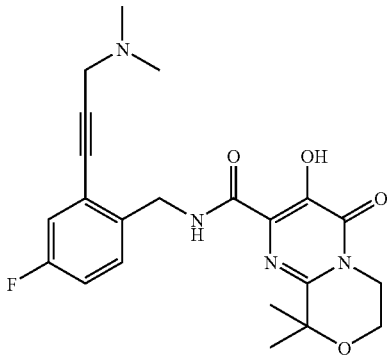

Pyrimido[2,1-c][1,4]oxazine-2-carboxamide, N-[[2-[3-(dimethylamino)-1-propynyl]-4-fluorophenyl]methyl]-4,6,7,9-tetrahydro-3-hydroxy-9,9-dimethyl-4-oxo-. The title compound can be prepared from intermediate 184, N-(2-(3-(dimethylamino)prop-1-ynyl)-4-fluorobenzyl)-3-(benzyloxy)-9,9-dimethyl-4-oxo-4,6,7,9-tetrahydropyrimido[2,1-c][1,4]oxazine-2-carboxamide. The title compound was isolated as a trifluoroacetic acid salt. $^1$HNMR 400 MHz (CDCl$_3$) δ ppm: 1.62 (6H, s, 2×CH$_3$), 3.03 (6H, s, 2×CH$_3$), 4.06 (4H, s, 2×CH$_2$), 4.23 (2H, s, NCH$_2$), 4.75 (2H, d, J=6.0 Hz, NCH$_2$), 7.16 (1H, m, aromatic), 7.24 (1H, dd, J=2.5 Hz and J=8.6 Hz, aromatic), 7.42 (1H, dd, J=5.6 Hz and J=8.6 Hz, aromatic), 8.04 (1H, broad t, NH). HRMS (ESI$^+$) calculated for C$_{22}$H$_{26}$FN$_4$O$_4$ [M+H$^+$]: 429.1938; found: 429.1917.

EXAMPLE 92

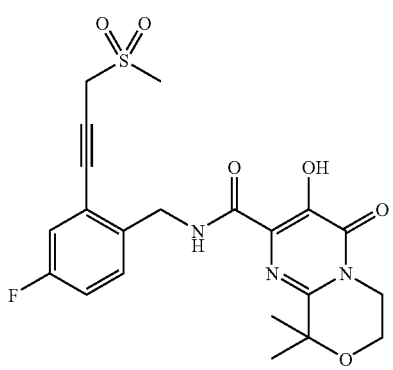

Pyrimido[2,1-c][1,4]oxazine-2-carboxamide, N-[[4-fluoro-2-[3-(methylsulfonyl)-1-propynyl]phenyl]methyl]-4,6,7,9-tetrahydro-3-hydroxy-9,9-dimethyl-4-oxo-. The title compound can be prepared from intermediate 186, N-(4-fluoro-2-(3-(methylsulfonyl)prop-1-ynyl)benzyl)-3-(benzyloxy)-9,9-dimethyl-4-oxo-4,6,7,9-tetrahydropyrimido[2,1-c][1,4]oxazine-2-carboxamide. $^1$HNMR 400 MHz (CDCl$_3$) δ ppm: 1.63 (6H, s, 2×CH$_3$), 3.16 (3H, s, SCH$_3$), 4.04 (4H, s, 2×CH$_2$), 4.17 (2H, s, SCH$_2$), 4.70 (2H, d, J=6.0 Hz, NCH$_2$), 7.12 (1H, m, aromatic), 7.21 (1H, dd, J=2.5 Hz and J=8.6 Hz, aromatic), 7.49 (1H, dd, J=5.6 Hz and J=8.6 Hz, aromatic), 8.16 (1H, broad t, NH)., 11.99 (1H, s, OH). HRMS (ESI$^+$) calculated for C$_{21}$H$_{23}$FN$_3$O$_6$S [M+H$^+$]: 464.1292; found: 464.1271.

EXAMPLE 93

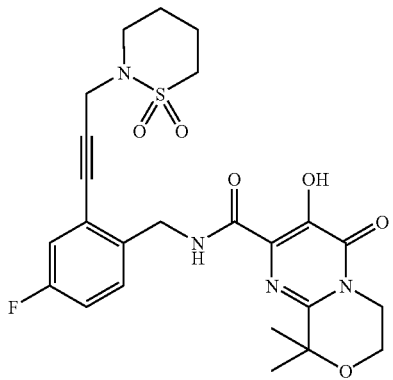

Pyrimido[2,1-c][1,4]oxazine-2-carboxamide, N-[[4-fluoro-2-[3-(tetrahydro-1,1-dioxido-2H-1,2-thiazin-2-yl)-1-propynyl]phenyl]methyl]-4,6,7,9-tetrahydro-3-hydroxy-9,9-dimethyl-4-oxo-. $^1$HNMR 400 MHz (CDCl$_3$) δ ppm: 1.63 (6H, s, 2×CH$_3$), 1.86 (2H, m, CH$_2$), 2.28 (2H, m, CH$_2$), 3.11 (2H, m, CH$_2$), 3.53 (2H, m, CH$_2$), 4.05 (4H, s, 2×CH$_2$), 4.27 (2H, s, NCH$_2$), 4.73 (2H, d, J=6.0 Hz, NCH$_2$), 7.07 (1H, m, aromatic), 7.17 (1H, dd, J=2.5 Hz and J=8.6 Hz, aromatic), 7.47 (1H, dd, J=5.6 Hz and J=8.6 Hz, aromatic), 8.12 (1H, broad t, NH).

EXAMPLE 94

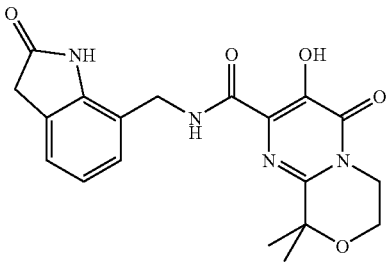

Pyrimido[2,1-c][1,4]oxazine-2-carboxamide, 4,6,7,9-tetrahydro-3-hydroxy-9,9-dimethyl-4-oxo-N-[2-(phenylsulfonyl)ethyl]-. The title compound can be prepared from intermediate 25, ethyl 3-hydroxy-9,9-dimethyl-4-oxo-4,6,7,9-tetrahydropyrimido[2,1-c][1,4]oxazine-2-carboxylate and 7-(aminomethyl)indolin-2-one according to the methods described for examples 1, 19 and 20. $^1$H NMR (500 MHz, DMSO-$d_6$) δ ppm: 1.58 (s, 6), 3.50 (s, 2), 3.83 (m, 2), 3.97 (m, 2), 4.42 (d, 2), 6.9-7.13 (overlapping m, 3). Anal calcd $C_{19}H_{20}N_4O_5$: C, 59.36; H, 5.24; N, 14.57. Found: C, 59.61; H, 5.43; N, 14.46.

EXAMPLE 95

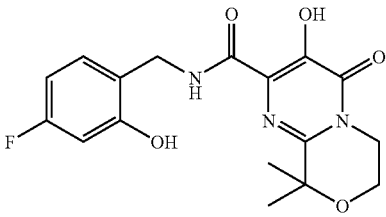

Pyrimido[2,1-c][1,4]oxazine-2-carboxamide, N-[(4-fluoro-2-hydroxyphenyl)methyl]-4,6,7,9-tetrahydro-3-hydroxy-9,9-dimethyl-4-oxo-. A solution of intermediate 144, N-(4-fluoro-2-hydroxybenzyl)-3-(benzyloxy)-9,9-dimethyl-4-oxo-4,6,7,9-tetrahydropyrimido[2,1-c][1,4]oxazine-2-carboxamide, (0.070 g, 0.154 mmol) in dichloromethane (3 mL) and trifluoroacetic acid (3 mL) was stirred for 2 hours. The solvent was then removed in vacuo and the resulting residue dissolved in ethyl acetate. The ethyl acetate solution was washed with 1.0 N HCl (10 mL), dried over sodium sulfate, then filtered. Solvent was removed by rotary evaporator and the crude product purified by reverse phase preparative HPLC, (C18, 30%-40% $CH_3CN/H_2O$-0.1% $CF_3CO_2H$). Fractions containing product were concentrated by rotary evaporator and the resulting aqueous suspension extracted with ethyl acetate (3×50 mL). The combined organic layers were dried (sodium sulfate), filtered, and concentrated to dryness by rotary evaporator. The residue was triturated with ether and dried in vacuo to give the title compound as a white solid. $^1$H NMR (500 MHz, $d_6$-Acetone) δ ppm: 11.96 (2H, s), 9.25 (2H, s), 8.98 (1H, br s), 7.23 (1H, t, J=7.6 Hz), 6.63 (1H, dd, J=8.2, 2.4 Hz), 6.57 (1H, dt, J=8.4, 2.4 Hz), 4.53 (2H, d, J=6.7 Hz), 4.05 (2H, d, J=5.2 Hz), 3.90 (2H, t, J=5.2 Hz), 1.55 (6H, s); HRMS [M+H]$^+$ calcd for $C_{17}H_{19}N_3O_5F$: 364.13088; found: 364.1302.

EXAMPLE 96

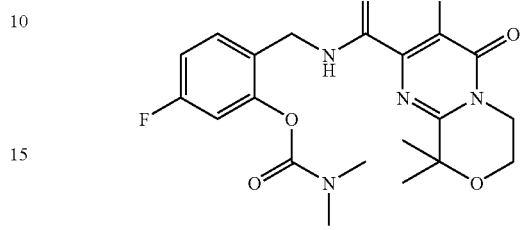

Carbamic acid, dimethyl-, 5-fluoro-2-[[[(4,6,7,9-tetrahydro-3-hydroxy-9,9-dimethyl-4-oxopyrimido[2,1-c][1,4]oxazin-2-yl)carbonyl]amino]methyl]phenyl ester. The title compound can be prepared from intermediate 158, dimethylcarbamic acid 2-{[(3-benzyloxy-9,9-dimethyl-4-oxo-4,6,7,9-tetrahydro-pyrimido[2,1-c][1,4]oxazine-2-carbonyl)-amino]-methyl}-5-fluoro-phenyl ester according to the method described for example 95. White crystalline powder; $^1$H NMR (CDCl$_3$, 500 MHz) δ ppm: 1.56 (6H, s, Me), 2.96, 3.11 (2s, NMe), 3.99 (4H, s, CH$_2$), 4.51 (2H, d, J=6 Hz, NCH$_2$), 6.85 (1H, dd, J=2.5 Hz, 9 Hz, CH), 6.94 (1H, dt, J=2.5 Hz, 8.3 Hz, Ar—H), 7.37 (1H, dd, J=6.5 Hz, 8.5 Hz, Ar—H), 8.05 (1H, brt, J=5 Hz, NH), 12.0 (1H, s, OH); $^{13}$C NMR (CDCl$_3$, 125.77 Hz) δ ppm: 27.90 (CH$_3$), 36.68, 36.92 (2s, NCH$_3$), 37.80 (NCH$_2$), 43.14 (NCH$_2$), 58.20 (OCH$_2$), 75.99 (OC), 110.88, 110.07 (d, J=24 Hz, CH), 113.41, 113.57 (d, J=21 Hz, CH), 125.71 (C), 125.91, 125.94 (d, J=3.6 Hz, C), 131.57, 131.64 (d, J=9.6 Hz, CH), 146.22 (C), 150.83, 150.92 (d, J=11 Hz, C), 151.66 (C), 154.68 (C=O), 157.92 (C=O), 161.70, 163.68 (d, J=249 Hz, CF), 167.86 (C=O); HRMS calcd for $C_{20}H_{24}N_4O_6F$ (M+H) 435.1680, found 435.1695 (δ+3.5 ppm). UV (MeOH): λmax 245 nm (ε 1.05×10$^4$), 306 nm (ε 8.00×10$^3$); Anal. calcd for $C_{20}H_{23}N_4O_6F$; C, 55.30; H, 5.34; N, 12.90: found C, 55.32; H, 5.38; N, 12.77.

EXAMPLE 97

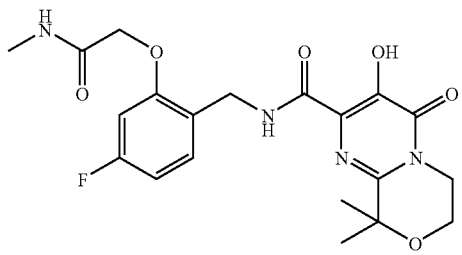

Pyrimido[2,1-c][1,4]oxazine-2-carboxamide, N-[[4-fluoro-2-[2-(methylamino)-2-oxoethoxy]phenyl]methyl]-4,6,7,9-tetrahydro-3-hydroxy-9,9-dimethyl-4-oxo-. A solution of intermediate 144, N-(4-fluoro-2-hydroxybenzyl)-3-(benzyloxy)-9,9-dimethyl-4-oxo-4,6,7,9-tetrahydropyrimido[2,1-c][1,4]oxazine-2-carboxamide (0.150 g, 0.331 mmol) and sodium hydride (0.015 g, 0.37 mmol, 60% oil dispersion) in anhydrous dimethylformamide (4 mL) was stirred for 5 minutes under a nitrogen atmosphere. The reaction mixture was treated with 2-chloro-N-methylacetamide (0.054 g, 0.50 mmol), and stirred for an additional 16 hours. Solvent was removed by rotary evaporator, and the resulting residue purified by short path flash silica gel chromatography (ethyl acetate). The fractions containing product were combined and concentrated to dryness. The residue was dissolved in dichloromethane (5 mL) and trifluoroacetic acid (5 mL) and stirred for 1 hour. Solvent was removed by rotary evaporator and the crude product was triturated with a minimal volume of 95% ethanol. The resulting solid was collected by filtration, and dried under vacuum resulting in 93 mg (0.21 mmol, Yield 65%) of the title compound as a white powder: $^1$H NMR (500 MHz, CDCl$_3$) δ ppm: 11.92 (1H, s), 7.67 (1H, t, J=6.3 Hz), 7.57 (1H, br), 7.30 (1H, dd, J=8.2, 6.4 Hz), 6.74 (1H, dt, J=8.2, 2.3 Hz), 6.60 (1H, dd, J=10.4, 2.4 Hz), 4.68 (2H, d, J=6.7 Hz), 4.45 (2H, s), 4.00 (4H, s), 2.93 (3H, d, J=4.9 Hz), 1.55 (6H, s). $^{13}$C NMR (125.77 MHz, CDCl$_3$) δ ppm: 168.05, 167.44, 164.79, 162.82, 157.71, 156.57, 156.50, 152.14, 146.60, 131.94, 131.86, 125.23, 120.71, 120.68, 108.37, 108.20, 100.76, 100.55, 75.81, 67.46, 58.15, 43.24, 38.19, 28.08, 25.83. HRMS [M+H]$^+$ calcd for C$_{20}$H$_{24}$N$_4$O$_6$F: 435.1680; found: 435.1668.

EXAMPLE 98

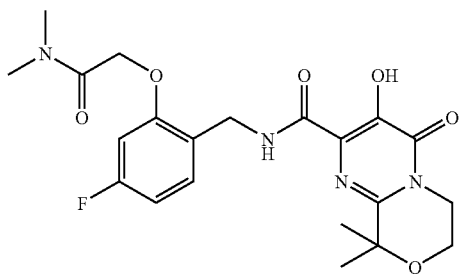

Pyrimido[2,1-c][1,4]oxazine-2-carboxamide, N-[[2-[2-(dimethylamino)-2-oxoethoxy]-4-fluorophenyl]methyl]-4,6,7,9-tetrahydro-3-hydroxy-9,9-dimethyl-4-oxo-. The title compound can be prepared from intermediate 144, N-(4-fluoro-2-hydroxybenzyl)-3-(benzyloxy)-9,9-dimethyl-4-oxo-4,6,7,9-tetrahydropyrimido[2,1-c][1,4]oxazine-2-carboxamide according to the method described for example 97. White powder; $^1$H NMR (500 MHz, CDCl$_3$) δ ppm: 12.25 (1H, br s), 8.36 (1H, t, J=5.65 Hz), 7.31 (1H, dd, J=8.39, 6.56 Hz), 6.67 (1H, dt, J=8.32, 2.29 Hz), 6.57 (1H, dd, J=10.38, 2.14 Hz), 4.76 (2H, s), 4.62 (2H, d, J=6.10 Hz), 4.00 (4H, s), 3.06 (3H, s), 3.01 (3H, s), 1.58 (6H, s). $^{13}$C NMR (125.77 MHz, CDCl$_3$) δ ppm: 168.25, 166.62, 164.23, 162.27, 158.02, 157.39, 151.36, 146.39, 131.25, 131.18, 125.95, 122.23, 122.20, 108.25, 108.08, 100.47, 100.27, 76.03, 66.24, 58.22, 43.15, 38.59, 36.07, 35.77, 27.94. HRMS [M+H]$^+$ calcd for C$_{21}$H$_{26}$N$_4$O$_6$F: 449.18365; found: 449.1837.

EXAMPLE 99

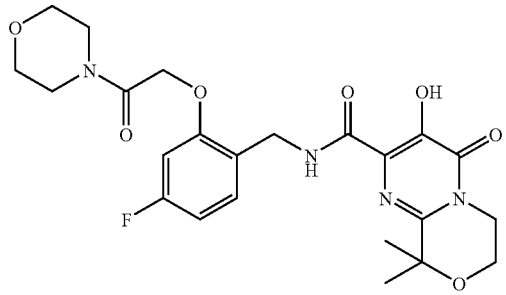

4-Morpholinecarboxylic acid, 5-fluoro-2-[[[(4,6,7,9-tetrahydro-3-hydroxy-9,9-dimethyl-4-oxopyrimido[2,1-c][1,4]oxazin-2-yl)carbonyl]amino]methyl]phenyl ester. The title compound can be prepared from intermediate 144, N-(4-fluoro-2-hydroxybenzyl)-3-(benzyloxy)-9,9-dimethyl-4-oxo-4,6,7,9-tetrahydropyrimido[2,1-c][1,4]oxazine-2-carboxamide according to the method described for example 97. White powder; $^1$H NMR (500 MHz, CDCl$_3$) δ ppm: 12.01 (1H, br s), 7.96 (1H, t, J=5.34 Hz), 7.38 (1H, dd, J=8.39, 6.26 Hz), 6.97 (1H, dt, J=8.24, 2.44 Hz), 6.87 (1H, dd, J=8.85, 2.44 Hz), 4.51 (2H, d, J=6.10 Hz), 4.00 (4H, s), 3.70-3.76 (4H, m), 3.65-3.70 (2H, m), 3.49-3.54 (2H, m), 1.55 (6H, s). $^{13}$C NMR (125.77 MHz, CDCl$_3$) δ ppm: 167.91, 163.68, 157.86, 153.48, 151.71, 150.51, 150.42, 146.31, 131.58, 131.50, 125.83, 125.59, 113.84, 113.67, 111.03, 110.84, 75.93, 66.59, 66.52, 58.22, 45.17, 44.41, 43.16, 37.70, 27.95. HRMS [M+H]$^+$ calcd for C$_{22}$H$_{26}$N$_4$O$_7$F: 477.17856; found: 477.1788.

EXAMPLE 100

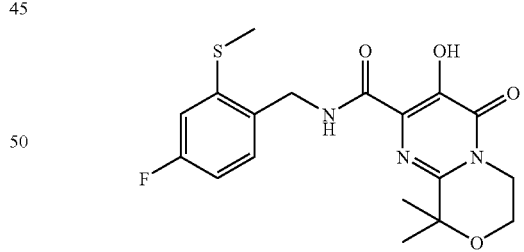

Pyrimido[2,1-c][1,4]oxazine-2-carboxamide, N-[[4-fluoro-2-(methylthio)phenyl]methyl]-4,6,7,9-tetrahydro-3-hydroxy-9,9-dimethyl-4-oxo-. The title compound can be prepared from intermediate 25, ethyl 3-hydroxy-9,9-dimethyl-4-oxo-4,6,7,9-tetrahydropyrimido[2,1-c][1,4]oxazine-2-carboxylate, and (4-fluoro-2-(methylthio)phenyl)methanamine according to the methods described for the synthesis of examples 1, 19 and 20. White solid. $^1$H NMR (300 MHz, CDCl$_3$) δ ppm: 11.88 (1H, br), 8.03 (1H, t, J=6.04 Hz), 7.28 (1H, dd, J=8.42, 5.85 Hz), 6.93 (1H, dd, J=9.51, 2.20 Hz), 6.81 (1H, dt, J=8.23, 2.56 Hz), 4.58 (2H, d, J=6.22 Hz), 3.98

(4H, s), 2.49 (3H, s), 1.55 (6H, s); HRMS (ESI) calcd for $C_{18}H_{21}FN_3O_4S$ (M+H) 394.1237, found 394.1218.

EXAMPLE 101

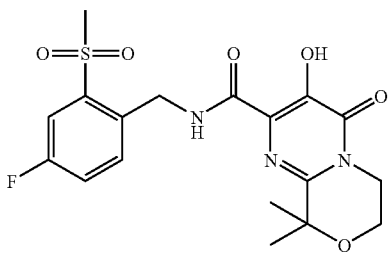

Pyrimido[2,1-c][1,4]oxazine-2-carboxamide, N-[[4-fluoro-2-(methylsulfonyl)phenyl]methyl]-4,6,7,9-tetrahydro-3-hydroxy-9,9-dimethyl-4-oxo-. To a solution of example 100 pyrimido[2,1-c][1,4]oxazine-2-carboxamide, N-[[4-fluoro-2-(methylthio)phenyl]methyl]-4,6,7,9-tetrahydro-3-hydroxy-9,9-dimethyl-4-oxo- (158 mg, 0.4 mmol), in $CH_2Cl_2$ (4 mL) was added 3-chloroperoxybenzoic acid (132 mg, 0.6 mmol; 77%, Aldrich) and the mixture stirred at room temperature for 2 hrs. After removing the solvent in vacuo, the residue was triturated with diethyl ether. The crude powder was purified by reverse phase column chromatography (YMC, ODS, 8% $CH_3CN/H_2O$-0.1% $CF_3CO_2H$) to provide 32 mg (0.075 mmol, Yield 19%) of the title compound as a white powder after trituration with diethyl ether, and 35 mg (0.086 mmol, Yield 21%) of the corresponding sulfoxide. $^1H$ NMR (300 MHz, $CDCl_3$) δ ppm: 11.71 (1 H, s), 8.58 (1 H, t, J=6.04 Hz), 7.73 (1 H, dd, J=8.23, 2.74 Hz), 7.68 (1 H, dd, J=8.42, 5.12 Hz), 7.32 (1 H, dt, J=8.05, 2.93 Hz), 4.79 (2 H, d, J=6.95 Hz), 3.97 (4 H, s), 3.15 (3 H, s), 1.56 (6 H, s); HRMS (ESI) calcd for $C_{18}H_{19}FN_3O_6S$ (M−H) 424.0979, found 424.0973.

EXAMPLE 102

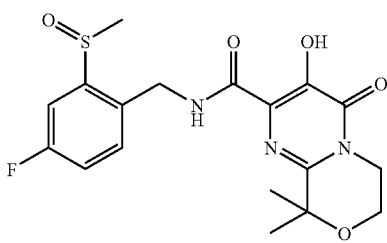

Pyrimido[2,1-c][1,4]oxazine-2-carboxamide, N-[[4-fluoro-2-(methylsulfinyl)phenyl]methyl]-4,6,7,9-tetrahydro-3-hydroxy-9,9-dimethyl-4-oxo. Formed in the reaction described for example 101. $^1H$ NMR (300 MHz, $CDCl_3$) δ ppm: 11.73 (1H, s), 8.19 (1H, t, J=6.59 Hz), 7.54 (1H, dd, J=8.05, 2.93 Hz), 7.47 (1H, dd, J=8.42, 5.12 Hz), 7.16 (1H, dt, J=8.14, 2.74 Hz), 4.57-4.81 (2H, m), 3.99 (4H, s), 2.80 (3H, s), 1.56 (6H, s); HRMS (ESI) calcd for $C_{18}H_{21}FN_3O_5S$ (M−H) 410.1196, found 410.1194.

EXAMPLE 103

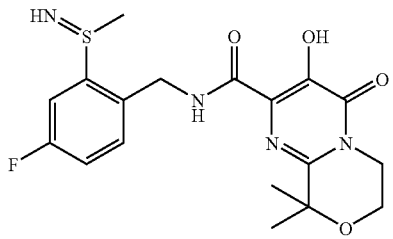

Pyrimido[2,1-c][1,4]oxazine-2-carboxamide, N-[[4-fluoro-2-(S-methylsulfinimidoyl)phenyl]methyl]-4,6,7,9-tetrahydro-3-hydroxy-9,9-dimethyl-4-oxo-. To a solution of example 100, pyrimido[2,1-c][1,4]oxazine-2-carboxamide, N-[[4-fluoro-2-(methylthio)phenyl]methyl]-4,6,7,9-tetrahydro-3-hydroxy-9,9-dimethyl-4-oxo-, (245 mg, 0.75 mmol) in $CH_2Cl_2$ (3 mL) was added tert-butyl azido formate (115 mg, 0.8 mmol; prepared following the procedure described in Organic Synthesis 1979, 50, 9-12) and ferrous chloride ($FeCl_2$, 50 mg) and the resulting mixture stirred for 18 hrs. The mixture was diluted with dichloromethane, washed with water, dried ($MgSO_4$), filtered and concentrated to yield 450 mg of 3-hydroxy-9,9-dimethyl-4-oxo-4,6,7,9-tetrahydro-pyrimido[2,1-c][1,4]oxazine-2-carboxylic acid 4-fluoro-2-(N-tert-butoxycarbonyl-S-methyl)sulfiliminyl-benzylamide as a dark gum; LC/MS m/z 509 (M+H).

A solution of this material, (100 mg) in $CF_3CO_2H$ (1 mL), was stirred for 20 min then concentrated. The residue was purified by C-18 reverse phase HPLC (YMC ODS, 5-10% $CH_3CN/H_2O$-0.1% $CF_3CO_2H$) to provide 15 mg (0.037 mmol, Yield 21%) of the title compound as the corresponding trifluoroacetic acid salt. $^1H$ NMR (300 MHz, DMSO-D6) δ ppm: 11.62 (1 H, s), 9.57 (1 H, t, J=6.0 Hz), 8.11 (1 H, dd, J=8.8, 1.8 Hz), 7.62-7.71 (2 H, m), 4.58-4.82 (2 H, m), 3.97 (2 H, t, J=4.8 Hz), 3.82 (2 H, t, J=4.8 Hz), 3.37 (3 H, s), 1.57 (6 H, s); HRMS (ESI) calcd for $C_{18}H_{22}FN_4O_4S$ (M+H) 409.1346, found 409.1333.

EXAMPLE 104

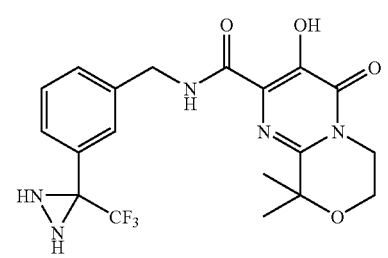

Pyrimido[2,1-c][1,4]oxazine-2-carboxamide, 4,6,7,9-tetrahydro-3-hydroxy-9,9-dimethyl-4-oxo-N-[[3-[3-(trifluoromethyl)-3-diaziridinyl]phenyl]methyl]-. The title compound can be prepared from intermediate 25, ethyl 3-hydroxy-9,9-dimethyl-4-oxo-4,6,7,9-tetrahydropyrimido[2,1-c][1,4]oxazine-2-carboxylate and (4-(diaziridin-3-yl)phenyl)methanamine (formed in the preparation of interme-

EXAMPLE 105

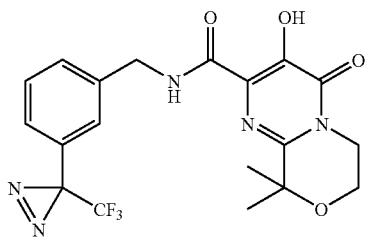

Pyrimido[2,1-c][1,4]oxazine-2-carboxamide, 4,6,7,9-tetrahydro-3-hydroxy-9,9-dimethyl-4-oxo-N-[[3-[3-(trifluoromethyl)-3H-diazirin-3-yl]phenyl]methyl]-. The title compound can be prepared from intermediate 25, ethyl 3-hydroxy-9,9-dimethyl-4-oxo-4,6,7,9-tetrahydropyrimido[2,1-c][1,4]oxazine-2-carboxylate and intermediate 66, (3-(3-(trifluoromethyl)diaziridin-3-yl)phenyl)methanamine, according to the methods described for the synthesis of examples 1, 19 and 20. White solid; $^1$H NMR (300 MHz, CDCl$_3$) δ ppm: 11.86 (1H, s), 7.73-7.84 (1H, m), 7.35-7.40 (2H, m), 7.11-7.17 (1H, m, J=2.9 Hz), 7.08-7.11 (1H, m), 4.60 (2H, d, J=6.2 Hz), 4.00 (4H, s), 1.55 (6H, s); HRMS (ESI) calcd for C$_{19}$H$_{19}$F$_3$N$_5$O$_4$ (M+H) 438.1389, found 438.1371.

EXAMPLE 106

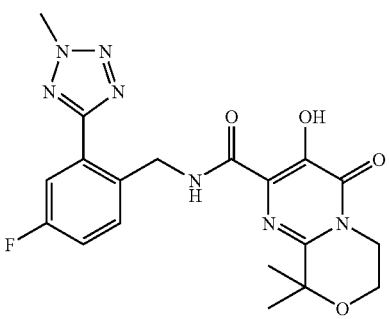

Pyrimido[2,1-c][1,4]oxazine-2-carboxamide, N-[[4-fluoro-2-(2-methyl-2H-tetrazol-5-yl)phenyl]methyl]-4,6,7,9-tetrahydro-3-hydroxy-9,9-dimethyl-4-oxo-. The title compound can be prepared from intermediate 25, ethyl 3-hydroxy-9,9-dimethyl-4-oxo-4,6,7,9-tetrahydropyrimido[2,1-c][1,4]oxazine-2-carboxylate and intermediate 59, (4-fluoro-2-(2-methyl-2H-tetrazol-5-yl)phenyl)methanamine hydrochloride, according to the methods described for the synthesis of examples 1, 19 and 20. (white solid); $^1$H NMR (300 MHz, CDCl$_3$) δ ppm: 12.01 (1H, s), 9.24 (1H, t, J=6.8 Hz), 7.75 (1H, dd, J=9.5, 2.6 Hz), 7.63 (1H, dd, J=8.4, 5.5 Hz), 7.15 (1H, dt, J=8.2, 2.6 Hz), 4.70 (2H, d, J=7.0 Hz), 4.45 (3H, s), 3.96 (4 H, s), 1.53 (6H, s); HRMS (ESI) calcd for C$_{19}$H$_{21}$FN$_7$O$_4$ (M+H) 430.1639, found 430.1649.

EXAMPLE 107

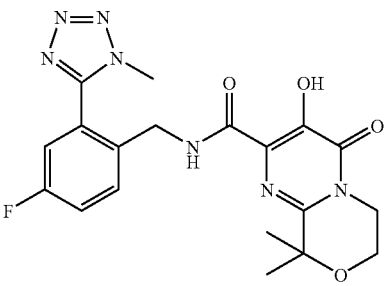

Pyrimido[2,1-c][1,4]oxazine-2-carboxamide, N-[[4-fluoro-2-(1-methyl-1H-tetrazol-5-yl)phenyl]methyl]-4,6,7,9-tetrahydro-3-hydroxy-9,9-dimethyl-4-oxo-. The title compound can be prepared from intermediate 25, ethyl 3-hydroxy-9,9-dimethyl-4-oxo-4,6,7,9-tetrahydropyrimido[2,1-c][1,4]oxazine-2-carboxylate and intermediate 62, (4-fluoro-2-(1-methyl-2H-tetrazol-5-yl)phenyl)methanamine hydrochloride, according to the methods described for the synthesis of examples 1, 19 and 20. Off-white solid; $^1$H NMR (500 MHz, CDCl$_3$) δ ppm: 11.83 (1H, s), 9.17 (1H, t, J=5.8 Hz), 7.75 (1H, dd, J=8.4, 5.7 Hz), 7.30 (1H, t, J=8.2 Hz), 7.14 (1H, d, J=7.9 Hz), 4.43 (2H, d, J=6.7 Hz), 4.14-4.16 (3H, m), 4.00 (4 H, s), 1.67 (6H, s); HRMS (ESI) calcd for C$_{19}$H$_{21}$FN$_7$O$_4$ (M+H) 430.1639, found 430.1619.

EXAMPLES 108-112

Examples 108-112 can be prepared from intermediate 25, ethyl 3-hydroxy-9,9-dimethyl-4-oxo-4,6,7,9-tetrahydropyrimido[2,1-c][1,4]oxazine-2-carboxylate and the indicated amines according to the methods described for the synthesis of examples 1, 19 and 20.

EXAMPLE 108

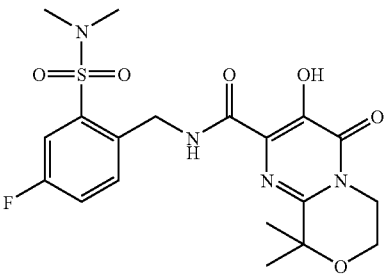

Pyrimido[2,1-c][1,4]oxazine-2-carboxamide, N-[[2-[(dimethylamino)sulfonyl]-4-fluorophenyl]methyl]-4,6,7,9-tetrahydro-3-hydroxy-9,9-dimethyl-4-oxo-. The title compound can be prepared from intermediate 48, 2-(aminomethyl)-5-fluoro-N,N-dimethylbenzenesulfonamide. White solid; $^1$H NMR (500 MHz, CDCl$_3$) δ ppm: 11.83 (1H, s), 8.64 (1H, t, J=6.6 Hz), 7.68 (1H, dd, J=8.6, 5.5 Hz), 7.50 (1H, dd, J=8.2, 2.8 Hz), 7.26-7.30 (1H, m), 4.80 (2H, d, J=7.0 Hz), 3.99 (4H, s), 2.91 (6H, s), 1.58 (6H, s); HRMS (ESI) calcd for $C_{19}H_{24}FN_4O_6S$ (M+H) 455.1401, found 455.1402.

EXAMPLE 109

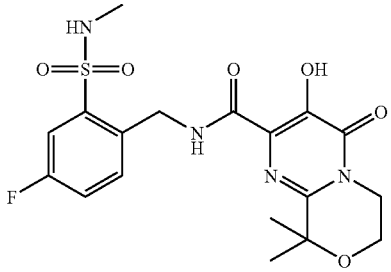

Pyrimido[2,1-c][1,4]oxazine-2-carboxamide, N-[[4-fluoro-2-[(methylamino)sulfonyl]phenyl]methyl]-4,6,7,9-tetrahydro-3-hydroxy-9,9-dimethyl-4-oxo-. The title compound can be prepared from intermediate 52, 2-(aminomethyl)-5-fluoro-N-methylbenzenesulfonamide hydrochloride. Off-white solid; $^1H$ NMR (300 MHz, CDCl$_3$) δ ppm: 11.69 (1H, s), 8.55 (1H, br), 7.58-7.67 (2H, m), 7.24-7.29 (1H, m), 4.87-4.97 (1H, br), 4.82 (2H, d, J=6.2 Hz), 3.97 (4H, s), 2.71 (3H, d, J=4.4 Hz), 1.56 (6H, s); HRMS (ESI) calcd for $C_{18}H_{22}FN_4O_6S$ (M+H) 441.1244, found 441.1237.

EXAMPLE 110

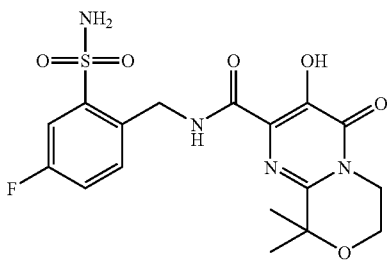

Pyrimido[2,1-c][1,4]oxazine-2-carboxamide, N-[[2-(aminosulfonyl)-4-fluorophenyl]methyl]-4,6,7,9-tetrahydro-3-hydroxy-9,9-dimethyl-4-oxo-. The title compound can be prepared from intermediate 56, 2-(aminomethyl)-5-fluorobenzenesulfonamide hydrochloride. Off-white solid, $^1H$ NMR (300 MHz, DMSO-D6) δ ppm: 11.92 (1H, s), 9.33 (1H, t, J=6.4 Hz), 7.66 (1H, dd, J=8.8, 2.2 Hz), 7.41-7.52 (2H, m), 4.89 (2H, d, J=6.2 Hz), 3.98 (2H, t, J=4.9 Hz), 3.83 (2H, t, J=4.9 Hz), 3.37 (2H, br), 1.55 (6H, s); HRMS (ESI) calcd for $C_{17}H_{20}FN_4O_6S$ (M+H) 427.1088, found 427.1082.

EXAMPLE 111

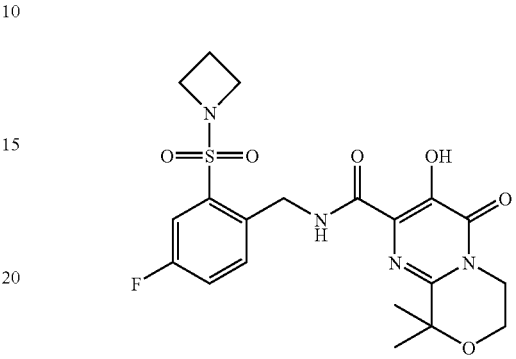

Pyrimido[2,1-c][1,4]oxazine-2-carboxamide, N-[[2-(1-azetidinylsulfonyl)-4-fluorophenyl]methyl]-4,6,7,9-tetrahydro-3-hydroxy-9,9-dimethyl-4-oxo-. The title compound can be prepared from (2-(azetidin-1-ylsulfonyl)-4-fluorophenyl)methanamine, which was synthesized according to the methods used to prepare intermediate 48. White solid, $^1H$ NMR (500 MHz, CDCl$_3$) δ ppm 11.86 (1H, s), 8.57 (1H, t, J=6.3 Hz), 7.65-7.72 (2H, m), 7.26-7.31 (1H, m), 4.82 (2H, d, J=6.7 Hz), 3.99 (4H, s), 3.96 (4H, t, J=7.8 Hz), 2.23-2.32 (2H, m), 1.58 (6H, s); HRMS (ESI) calcd for $C_{20}H_{24}FN_4O_6S$ (M+H) 467.1401, found 467.1398.

EXAMPLE 112

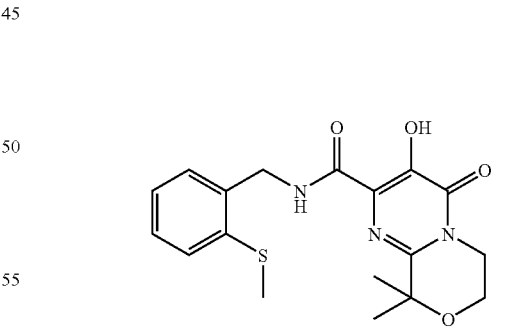

Pyrimido[2,1-c][1,4]oxazine-2-carboxamide, 4,6,7,9-tetrahydro-3-hydroxy-9,9-dimethyl-N-[[2-(methylthio)phenyl]methyl]-4-oxo-. Prepared according to the method described for the synthesis of example 100. White solid, $^1H$ NMR (300 MHz, CDCl$_3$) δ ppm: 1.55 (6H, s), 2.50 (3H, s), 3.98 (4H, s), 4.65 (2H, d, J=6.6 Hz), 7.1-7.4 (3H, m), 8.11 (1H, t, J=5.9 Hz), 11.94 (1H, s); LC/MS m/z 376 (M+H).

EXAMPLE 113

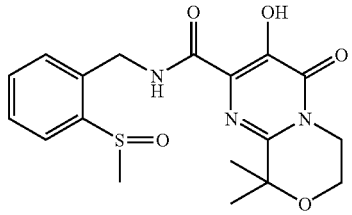

Pyrimido[2,1-c][1,4]oxazine-2-carboxamide, 4,6,7,9-tetrahydro-3-hydroxy-9,9-dimethyl-N-[[2-(methylsulfinyl) phenyl]methyl]-4-oxo-. To a solution example 112, pyrimido [2,1-c][1,4]oxazine-2-carboxamide, 4,6,7,9-tetrahydro-3-hydroxy-9,9-dimethyl-N-[[2-(methylthio)phenyl]methyl]-4-oxo-, (112 mg, 0.3 mmol) in $CH_2Cl_2$ (5 mL) was added 3-chloroperoxybenzoic acid (69 mg, 0.3 mmol; 77%, Aldrich) and the mixture stirred for 5 min. After removing the solvent in vacuo, the residue was purified by preparative reverse phase HPLC (YMC, ODS, 8-15% $CH_3CN/H_2O$-0.1% $CF_3CO_2H$) to provide 58 mg (0.16 mmol, Yield 53%) of the title compound as a white powder after trituration with diethyl ether. $^1$H NMR (300 MHz, $CDCl_3$) δ ppm: 1.56 (6H, s), 2.80 (3H,s), 3.98 (4H, s), 4.60-4.94 (2H, m), 7.38-7.61 (3H, m), 7.65-7.89 (1H, m), 8.34 (1H, t, J=6.4 Hz), 11.82 (1H, s). HRMS (ESI) calcd for $C_{18}H_{22}N_3O_5S$ (M+H) 392.1280, found 392.1281.

EXAMPLE 114

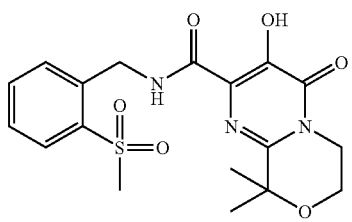

Pyrimido[2,1-c][1,4]oxazine-2-carboxamide, 4,6,7,9-tetrahydro-3-hydroxy-9,9-dimethyl-N-[[2-(methylsulfonyl) phenyl]methyl]-4-oxo-. To a solution of example 112, pyrimido[2,1-c][1,4]oxazine-2-carboxamide, 4,6,7,9-tetrahydro-3-hydroxy-9,9-dimethyl-N-[[2-(methylthio)phenyl] methyl]-4-oxo- (112 mg, 0.3 mmol) in $CH_2Cl_2$ (5 mL) was added 3-chloroperoxybenzoic acid (140 mg, 0.62 mmol; 77%, Aldrich) and the mixture stirred for 20 hrs. After removing the solvent in vacuo, the residue was purified by preparative reverse phase HPLC (YMC, ODS, 15% $CH_3CN/H_2O$-0.1% $CF_3CO_2H$) to provide 61 mg (0.15 mmol, Yield 50%) of the title compound as a white powder after trituration with diethyl ether. $^1$H NMR (300 MHz, $CDCl_3$) δ ppm: 1.56 (6H, s), 3.14 (3H,s), 3.96 (4H, s), 4.83 (2H, d, J=7.0 Hz), 7.39-7.57 (1H, m), 7.60-7.68 (2H, m), 8.02 (1H, d, J=8.4 Hz), 8.65 (1H, t, J=7.0 Hz), 11.78 (1H, brs). HRMS (ESI) calcd for $C_{18}H_{22}N_3O_6S$ (M+H) 408.1229, found 408.1217.

EXAMPLES 115-116

Examples 115-116 can be prepared from the indicated intermediates by hydrogenolysis or trifluoroacetic acid mediated hydrolysis.

EXAMPLE 115

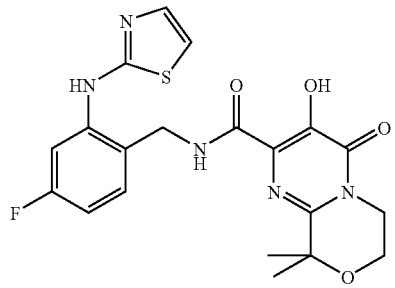

Pyrimido[2,1-c][1,4]oxazine-2-carboxamide, N-[[4-fluoro-2-(2-thiazolylamino)phenyl]methyl]-4,6,7,9-tetrahydro-3-hydroxy-9,9-dimethyl-4-oxo-. The title compound can be prepared from intermediate 163, N-(4-fluoro-2-(thiazol-2-ylamino)benzyl)-3-(benzyloxy)-9,9-dimethyl-4-oxo-4,6,7,9-tetrahydropyrimido[2,1-c][1,4]oxazine-2-carboxamide. $^1$H NMR (400 MHz, DMSO-d6) δ ppm: 11.97 (1H, brs), 9.72 (1H, brs), 9.39 (1H, t, J=6.3 Hz), 8.14 (1H, dd, J=2.5, 12.0 Hz), 7.31-7.28 (2H, m), 6.99 (1H, d, J=3.8 Hz), 6.84 (1H, ddd(dt), J=2.5, 8.3 Hz), 4.52 (2H, d, J=6.3 Hz), 3.96-3.94 (2H, m), 3.82-3.79 (2H, m), 1.54 (6H, s) LCMS ($^+$ESI, M+H$^+$) m/z 446. HRMS (ESI$^+$) calculated for $C_{20}H_{21}FN_5O_4S$ [M+H$^+$]: 446.1298; found: 446.1292.

EXAMPLE 116

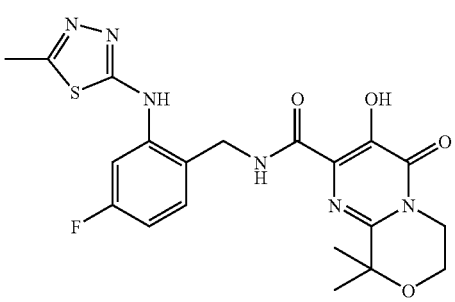

Pyrimido[2,1-c][1,4]oxazine-2-carboxamide, N-[[4-fluoro-2-[(5-methyl-1,3,4-thiadiazol-2-yl)amino]phenyl] methyl]-4,6,7,9-tetrahydro-3-hydroxy-9,9-dimethyl-4-oxo-. The title compound can be prepared from intermediate 164, N-(4-fluoro-2-(5-methyl-1,3,4-thiadiazol-2-ylamino)benzyl)-3-(benzyloxy)-9,9-dimethyl-4-oxo-4,6,7,9-tetrahydropyrimido[2,1-c][1,4]oxazine-2-carboxamide. $^1$H NMR (400 MHz, DMSO-d6) δ ppm: 11.97 (1H, brs), 9.66 (1H, brs), 9.37 (1H, brt, J=6.1 Hz), 7.99 (1H, brd), 7.29 (1H, brt, J=7.1 Hz), 6.88 (1H, ddd(dt), J=2.5, 8.0 Hz), 4.52 (2H, d, J=6.1 Hz), 3.97-3.94 (2H, m), 3.82-3.80 (2H, m), 2.55 (3H, s), 1.54 (6H, s); LCMS (⁺ESI, M+H⁺) m/z 461. HRMS (ESI⁺) calculated for $C_{20}H_{22}FN_6O_4S$ [M+H⁺]: 461.1407; found: 461.1425.

EXAMPLE 117

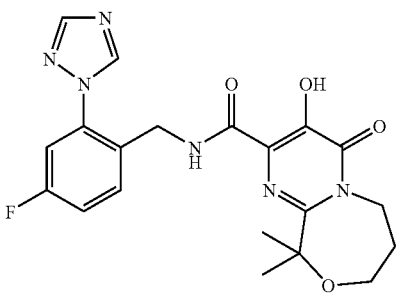

6H-Pyrimido[2,1-c][1,4]oxazepine-2-carboxamide, N-[[4-fluoro-2-(1H-1,2,4-triazol-1-yl)phenyl]methyl]-4,7,8,10-tetrahydro-3-hydroxy-10,10-dimethyl-4-oxo- A solution of intermediate 33, ethyl 2-(2-(3-chloropropoxy)propan-2-yl)-5-hydroxy-6-oxo-1,6-dihydropyrimidine-4-carboxylate, (0.208 g, 0.65 mmol) in anhydrous dimethylformamide (2 mL) was stirred with anhydrous potassium carbonate (0.366 g, 2.6 mmol) at 60° C. for 16 hours. This was treated with intermediate 69, (4-fluoro-2-(1H-1,2,4-triazol-1-yl)phenyl)methanamine hydrochloride, (0.451 g, 2.08 mmol) and triethylamine (0.5 mL, 3.6 mmol) and stirring continued at 100° C. for 16 hours. The solvent was removed by rotary evaporator and the was purified by preparative reverse phase HPLC (C18, 10%-35% $CH_3CN/H_2O$-0.1% trifluoroacetic acid). Fractions containing product were pooled and concentrated by rotary evaporator. The resulting aqueous solution was extracted with ethyl acetate (2×50 mL), and the combined organic fractions dried (sodium sulfate), filtered, and concentrated to dryness. The resulting residue was triturated with a minimal volume of 95% ethanol, and the solid collected by filtration to give 103 mg (0.24 mmol, Yield 37%) of the title compound as a white solid: ¹H NMR (500 MHz, $CDCl_3$) δ ppm: 11.96 (1H, br s), 8.83 (1H, t, J=6.6 Hz), 8.46 (1H, s), 8.17 (1H, s), 7.71 (1H, dd, J=8.5, 6.1 Hz), 7.21 (1H, dt, J=8.2, 2.6 Hz), 7.11 (1H, dd, J=8.4, 2.6 Hz), 4.55 (2H, br), 4.44 (2H, d, J=6.7 Hz), 3.67 (2H, t, J=6.4 Hz), 1.91-1.97 (2H, p J=6.10 Hz), 1.63 (6H, s). ¹³C NMR (125.76 MHz, $CDCl_3$) δ ppm: 167.97, 163.19, 161.20, 158.28, 153.35, 152.90, 147.34, 143.94, 136.89, 134.45, 134.37, 128.65, 128.62, 125.01, 117.09, 116.93, 112.42, 112.23, 82.46, 60.88, 39.13, 38.56, 27.73, 27.36. HRMS [M+H]⁺ calcd for $C_{20}H_{22}N_6O_4F$: 429.16867; found: 429.1687. Anal calcd for $C_{20}H_{21}N_6O_4F \cdot 0.06\ H_2O$: C, 55.93; H, 4.96; N, 19.57; F, 4.42; found: C, 55.80; H, 5.14; N, 19.74; F, 4.46.

EXAMPLE 118

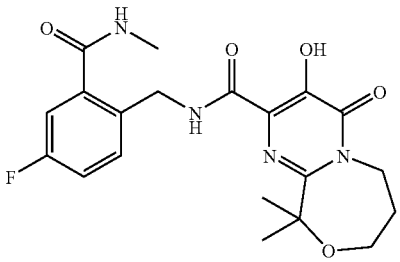

6H-Pyrimido[2,1-c][1,4]oxazepine-2-carboxamide, N-[[4-fluoro-2-[(methylamino)carbonyl]phenyl]methyl]-4,7,8,10-tetrahydro-3-hydroxy-10,10-dimethyl-4-oxo-. The title compound can be prepared from intermediate 148, N-(4-fluoro-2-(methylcarbamoyl)benzyl)-3-(benzyloxy)-10,10-dimethyl-4-oxo-6,7,8,10-tetrahydro-4H-pyrimido[2,1-c][1,4]oxazepine-2-carboxamide according to the method described for example 46. White powder; ¹H NMR (500 MHz, DMSO-D6) δ ppm: 12.17 (1H, s), 9.23 (1H, t, J=6.4 Hz), 8.56 (1H, q, J=4.3 Hz), 7.41 (1H, dd, J=8.6, 5.8 Hz), 7.34 (1H, dd, J=9.2, 2.8 Hz), 7.30 (1H, dt, J=8.6, 2.8 Hz), 4.55 (2H, d, J=6.4 Hz), 4.37 (2H, br), 3.64 (2H, t, J=6.4 Hz), 2.80 (3H, d, J=4.6 Hz), 1.80-1.86 (2H, m), 1.57 (6H, s); HRMS [M+H]⁺ calcd for $C_{20}H_{23}N_4O_5F$: 419.17308; found: 419.1713.

EXAMPLE 119

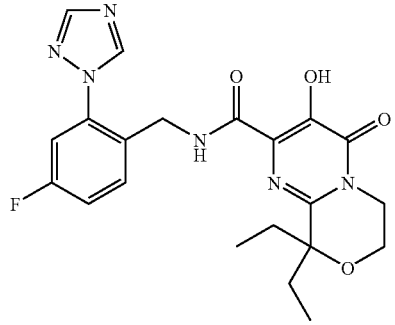

Pyrimido[2,1-c][1,4]oxazine-2-carboxamide, 9,9-diethyl-N-[[4-fluoro-2-(1H-1,2,4-triazol-1-yl)phenyl]methyl]-4,6,7,9-tetrahydro-3-hydroxy-4-oxo-. The title compound can be prepared from intermediate 31, ethyl 9,9-diethyl-3-hydroxy-4-oxo-4,6,7,9-tetrahydropyrimido[2,1-c][1,4]oxazine-2-carboxylate, and intermediate 69, (4-fluoro-2-(1H-1,2,4-triazol-1-yl)phenyl)methanamine hydrochloride, according to the methods described for examples 1, 19 and 20. White powder; ¹H NMR (500 MHz, $CDCl_3$) δ ppm: 11.89 (1H, br s), 8.81 (1H, t, J=6.6 Hz), 8.46 (1H, s), 8.15 (1H, s), 7.69 (1H, dd, J=8.6, 5.8 Hz), 7.22 (1H, dt, J=8.2, 2.6 Hz), 7.12 (1H, dd, J=8.4, 2.6 Hz), 4.45 (2H, d, J=6.7 Hz), 3.95-4.02 (4H, m), 1.95-2.03 (2H, m), 1.87-1.96 (2H, m), 0.86 (6H, t, J=7.5 Hz). ¹³C NMR (125.76 MHz, $CDCl_3$) δ ppm: 167.98, 163.19, 161.20, 157.88, 152.81, 151.29, 146.05, 143.97, 137.00, 136.93, 134.28, 134.21, 128.62, 128.59, 125.85, 117.10, 116.94, 112.58, 112.38, 80.93, 58.63, 43.02, 39.20, 31.43, 7.86. HRMS [M+H]+ calcd for $C_{21}H_{24}N_6O_4F$: 443.18432; found: 443.1845.

EXAMPLE 120

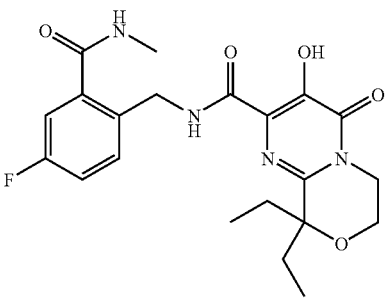

Pyrimido[2,1-c][1,4]oxazine-2-carboxamide, 9,9-diethyl-N-[[4-fluoro-2-[(methylamino)carbonyl]phenyl]methyl]-4,6,7,9-tetrahydro-3-hydroxy-4-oxo-. A solution of intermediate 31, ethyl 9,9-diethyl-3-hydroxy-4-oxo-4,6,7,9-tetrahydropyrimido[2,1-c][1,4]oxazine-2-carboxylate, (0.228 g, 0.77 mmol) in anhydrous dimethylformamide (5 mL) was treated with anhydrous potassium carbonate (0.279 g, 2.0 mmol) followed by benzyl bromide (0.145 g, 0.85 mmol), and the mixture stirred for 16 hours. The mixture was treated with lithium hydroxide (0.042 g, 1.75 mmol) and water (2 mL) and stirred for 20 hours. The reaction mixture was diluted with water (30 mL) and brought to pH 1 with 6 N hydrochloric acid. The crude product was extracted with ethyl acetate (2×30 mL). The combined organic layers were dried (sodium sulfate), filtered, and concentrated to dryness.

A solution of this material, in anhydrous dimethylformamide (4 mL), was treated with HATU (0.32 g, 0.83 mmol) and stirred for 10 minutes. The reaction mixture was treated with intermediate 39, 2-aminomethyl-5-fluoro-N-methyl-benzamide trifluoroacetic acid salt, (0.281 g, 0.94 mmol), followed by dimethylaminopyridine, DMAP, (0.140 g, 1.125 mmol), and stirred at 60° C. for 3 hours. Solvent was removed by rotary evaporator and the residue purified by flash column chromatography, eluting with 50% to 60% ethyl acetate in hexanes. Fractions containing the product were pooled and concentrated to dryness, which gave a white glassy solid. A sample (approximately 10 mg) was further dried under vacuum, and the remainder used in the following reaction: $^1$H NMR (500 MHz, CDCl$_3$) δ ppm: 8.47 (1H, t, J=6.2 Hz), 7.36-7.45 (3H, m), 7.23-7.27 (2H, m), 7.10 (1H, dd, J=8.8, 2.9 Hz), 7.04 (1H, dt, J=8.3, 2.7 Hz), 6.60-6.69 (1H, br), 5.25 (2H, s), 4.50 (2H, d, J=6.2 Hz), 3.94 (4H, s), 2.95 (3H, d, J=5.1 Hz), 1.90-2.02 (5H, m), 0.75-0.82 (6H, m).

A solution of the above compound in dichloromethane (5 mL) and trifluoroacetic acid (5 mL) was stirred for 2 hours. The solvent was removed and the crude product was purified by preparative reverse phase HPLC (C-18 column, 10% to 40% CH$_3$CN/H$_2$O-0.1% CF$_3$CO$_2$H). Fractions containing product were pooled and concentrated in vacuo. The resulting aqueous suspension was extracted with dichloromethane (4×100 mL), and the combined organic extracts, dried (sodium sulfate), filtered, and concentrated to dryness. The residue was recrystallized ethanol/H$_2$O to provide 0.012 g (0.028 mmol, Yield 4%) of the title compound as a white solid. $^1$H NMR (500 MHz, DMSO-D6) δ ppm: 12.10 (1H, s), 9.30 (1H, t, J=6.4 Hz), 8.52 (1H, m), 7.39 (1H, dd, J=8.4, 5.7 Hz), 7.26-7.35 (2H, m), 4.57 (2H, d, J=6.4 Hz), 3.94 (2H, t, J=4.9 Hz), 3.84 (2H, t, J=4.9 Hz), 2.79 (3H, d, J=4.6 Hz), 1.99-2.09 (2H, m), 1.81-1.91 (2H, m), 0.77 (6H, t, J=7.3 Hz). $^{13}$C NMR (125.76 MHz, DMSO-D6) δ ppm: 167.86, 167.57, 159.65, 156.86, 151.21, 145.10, 137.26, 137.21, 132.52, 130.75, 130.68, 125.39, 116.69, 116.52, 114.71, 114.53, 80.04, 57.60, 42.62, 40.05, 30.04, 26.03, 7.47. HRMS [M+H]+ calcd for $C_{21}H_{26}N_4O_5F$: 433.18873; found: 433.1872.

EXAMPLES 121-130

Examples 121-130 can be prepared from the indicated intermediates according to the methods described for examples 121 and 122. Alternatively, the examples can be formed by treating the indicated intermediates with trifluoroacetic acid.

EXAMPLE 121

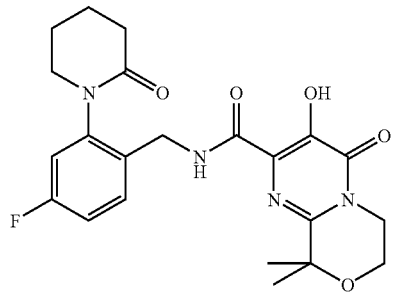

Pyrimido[2,1-c][1,4]oxazine-2-carboxamide, N-[[4-fluoro-2-(2-oxo-1-piperidinyl)phenyl]methyl]-4,6,7,9-tetrahydro-3-hydroxy-9,9-dimethyl-4-oxo-. To intermediate 145, N-(4-fluoro-2-(2-oxopiperidin-1-yl)benzyl)-3-(benzyloxy)-9,9-dimethyl-4-oxo-4,6,7,9-tetrahydropyrimido[2,1-c][1,4]oxazin-4(9H)-one, (100 mg, 0.187 mmol) in ethyl acetate (10 mL) was added palladium (10% on charcoal) (30 mg). The reaction mixture was stirred at 23° C. under a hydrogen atmosphere (balloon) for 3 h. The catalyst was removed by filtration on Celite. The filtrate was concentrated in vacuo and the resulting residue triturated with diethyl ether (10 ml) and dried in vacuo to afford 37 mg (45% yield) of the title compound. IR (KBr, cm$^{-1}$) 3397, 2943, 1636, 1539, 1173. $^1$HNMR 400 MHz (MeOD) δ ppm: 7.51 (1H, dd, (t), J=7.0 Hz), 7.11 (2H, m), 4.70 (1H, d, J=15.3 Hz), 4.24 (1H, d, J=15.3 Hz), 4.05 (2H, m), 3.96 (2H, m,), 3.73 (1H, m), 3.62 (1H, m), 2.63-2.48 (2H, m), 2.03 (4H, broad s), 1.62 (6H, s). LCMS (M+H)+ m/z 445.

EXAMPLE 122

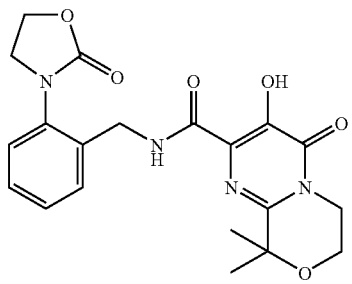

Pyrimido[2,1-c][1,4]oxazine-2-carboxamide, 4,6,7,9-tetrahydro-3-hydroxy-9,9-dimethyl-4-oxo-N-[[2-(2-oxo-3-oxazolidinyl)phenyl]methyl]-. To intermediate 161, N-(4-fluoro-2-(2-oxopiperidin-1-yl)benzyl)-3-(benzyloxy)-9,9-dimethyl-4-oxo-4,6,7,9-tetrahydropyrimido[2,1-c][1,4]oxazin-4(9H)-one (100 mg, 0.187 mmol) in ethyl acetate (10 mL) was added palladium (10% on charcoal) (30 mg). The reaction mixture was stirred at 23° C. under a hydrogen atmosphere (balloon) for 3 h. The catalyst was removed by filtration on Celite. The filtrate was concentrated in vacuo and the resulting residue triturated with diethyl ether (10 ml) and dried in vacuo to afford 37 mg (45%) of the title compound. IR (KBr, cm$^{-1}$) 3397, 2943, 1636, 1539, 1173. $^1$HNMR 400 MHz (MeOD) δ ppm: 7.51 (1H, dd, (t), J=7.0 Hz), 7.11 (2H, m), 4.70 (1H, d, J=15.3 Hz), 4.24 (1H, d, J=15.3 Hz), 4.05 (2H, m), 3.96 (2H, m,), 3.73 (1H, m), 3.62 (1H, m), 2.63-2.48 (2H, m), 2.03 (4H, broad s), 1.62 (6H, s). LCMS (M+H)+ m/z 445.

EXAMPLE 123

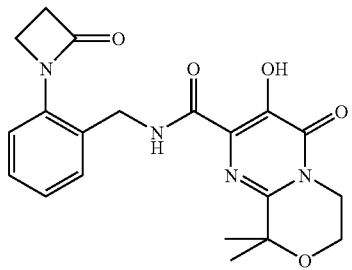

Pyrimido[2,1-c][1,4]oxazine-2-carboxamide, 4,6,7,9-tetrahydro-3-hydroxy-9,9-dimethyl-4-oxo-N-[[2-(2-oxo-1-azetidinyl)phenyl]methyl]-. The title compound can be prepared from intermediate 162, N-(2-(2-oxoazetidin-1-yl)benzyl)-3-(benzyloxy)-9,9-dimethyl-4-oxo-4,6,7,9-tetrahydropyrimido[2,1-c][1,4]oxazine-2-carboxamide. $^1$H NMR (400 MHz, CDCl$_3$) δ ppm: 12.15 (1H, brs), 9.65 (1H, brs), 7.33-7.20 (4H, m), 4.54 (2H, d, J=6.6 Hz), 3.96-3.94 (2H, m), 3.82-3.79 (2H, m), 3.76 (2H, t, J=4.3 Hz), 3.10 (2H, t, J=4.3 Hz), 1.53 (6H, s); LCMS (+ESI, M+H+) m/z 399.

EXAMPLE 124

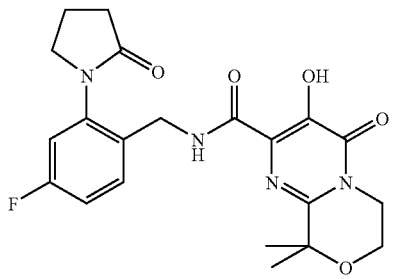

Pyrimido[2,1-c][1,4]oxazine-2-carboxamide, N-[[4-fluoro-2-(2-oxo-1-pyrrolidinyl)phenyl]methyl]-4,6,7,9-tetrahydro-3-hydroxy-9,9-dimethyl-4-oxo. The title compound can be prepared from intermediate 159, N-(4-fluoro-2-(2-oxopyrrolidin-1-yl)benzyl)-3-(benzyloxy)-9,9-dimethyl-4-oxo-4,6,7,9-tetrahydropyrimido[2,1-c][1,4]oxazine-2-carboxamide. IR (KBr, cm$^{-1}$) 3432, 2980, 1689, 1543, 1183. $^1$HNMR 400 MHz (MeOD) δ ppm: 7.53 (1H, dd, J=9.2, 6.3 Hz), 7.11 (2H, m), 4.52 (2H, s), 4.05 (2H, t, J=5.0 Hz), 3.96 (2H, m), 3.87 (2H, t, J=7.1 Hz), 2.61 (2H, t, J=8.0 Hz), 2.26 (2H, m), 1.6 (6H, s). HRMS (ESI+) calculated for C$_{21}$H$_{24}$FN$_4$O$_5$ [M+H+]: 431.1731; found: 431.1714.

EXAMPLE 125

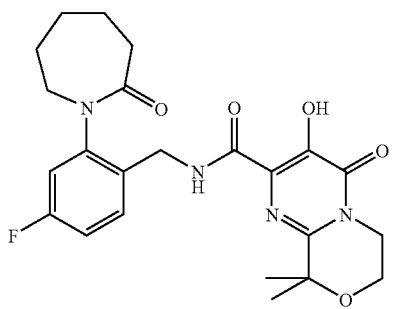

Pyrimido[2,1-c][1,4]oxazine-2-carboxamide, N-[[4-fluoro-2-(hexahydro-2-oxo-1H-azepin-1-yl)phenyl]methyl]-4,6,7,9-tetrahydro-3-hydroxy-9,9-dimethyl-4-oxo-. The title compound can be prepared from intermediate 160, N-(4-fluoro-2-(2-oxoazepan-1-yl)benzyl)-3-(benzyloxy)-9,9-dimethyl-4-oxo-4,6,7,9-tetrahydropyrimido[2,1-c][1,4]oxazine-2 carboxamide. IR (KBr, cm$^{-1}$) 3392, 2934, 1646, 1522, 1292. $^1$HNMR 400 MHz (MeOD) δ ppm: 7.50 (1H, broad s), 7.06 (1H, broad s), 7.01 (1H, d, J=9.0 Hz), 4.64 (1H, d, J$_{AB}$=15.0 Hz), 4.31 (1H, d, J$_{AB}$=15 Hz), 4.04 (2H, m), 3.96

(3H, m), 3.66 (1H, m), 2.86 (1H, m), 2.65 (1H, m), 2.03-1.80 (6H, m), 1.62 (6H, s), (2H, m). LCMS (M+H)+ m/z 459.

EXAMPLE 126

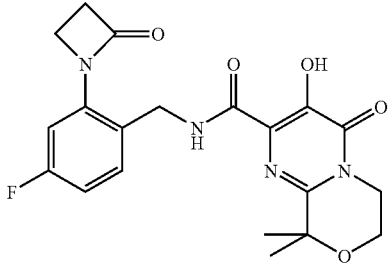

N-(4-Fluoro-2-(2-oxoazetidin-1-yl)benzyl)-3-hydroxy-9,9-dimethyl-4-oxo-4,6,7,9-tetrahydropyrimido[2,1-c][1,4]oxazine-2-carboxamide. The title compound can be prepared from intermediate 146, N-(4-fluoro-2-(2-oxoazetidin-1-yl)benzyl)-3-(benzyloxy)-9,9-dimethyl-4-oxo-4,6,7,9-tetrahydropyrimido[2,1-c][1,4]oxazine-2-carboxamide. $^1$H NMR (400 MHz, DMSO-$d_6$) δ: 9.46 (d, J=6.4 Hz), 7.34 (1H, dd, J=8.5, 6.4 Hz), 7.25 (1H, dd, J=10.2, 2.6 Hz), 7.08 (1H, td, J=8.5, 2.6 Hz), 6.90 (1H, m), 4.52 (2H, d, J=6.4 Hz), 3.96 (2H, t, J=5.0 Hz), 3.83-3.77 (4H, m), 3.11 (2H, t, J=5.0 Hz), 1.53 (6H, s); LCMS (M+H)+ m/z 417.

EXAMPLE 127

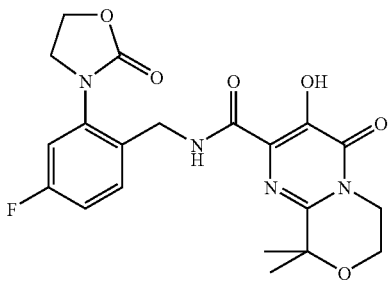

N-(4-Fluoro-2-(2-oxooxazolidin-3-yl)benzyl)-3-hydroxy-9,9-dimethyl-4-oxo-4,6,7,9-tetrahydropyrimido[2,1-c][1,4]oxazine-2-carboxamide. The title compound can be prepared from intermediate 165, N-(4-fluoro-2-(2-oxooxazolidin-3-yl)benzyl)-3-(benzyloxy)-9,9-dimethyl-4-oxo-4,6,7,9-tetrahydropyrimido[2,1-c][1,4]oxazine-2-carboxamide. $^1$H NMR (400 MHz, DMSO-$d_6$) δ ppm: 12.12 (1H, s), 9.34 (1H, t, J=6.2 Hz), 7.41 (1H, m), 7.23 (1H, td, J=8.6, 2.5 Hz), 4.48 (4H, m), 4.06 (2H, t, J=7.7 Hz), 3.97 (2H, t, J=5.0 Hz), 3.83 (2H, t, J=5.0 Hz), 1.55 (6H, s). LCMS (M+H)+ m/z 433.

EXAMPLE 128

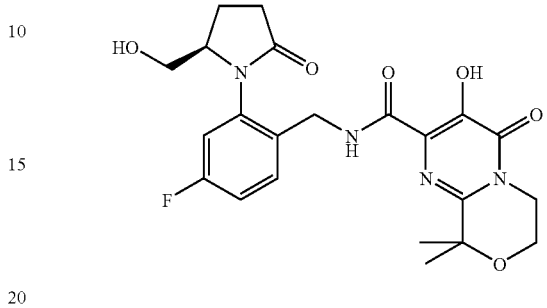

Pyrimido[2,1-c][1,4]oxazine-2-carboxamide, N-[[4-fluoro-2-[(2R)-2-(hydroxymethyl)-5-oxo-1-pyrrolidinyl]phenyl]methyl]-4,6,7,9-tetrahydro-3-hydroxy-9,9-dimethyl-4-oxo-. The title compound can be prepared from intermediate 192, (R)-N-(4-fluoro-2-(2-(hydroxymethyl)-5-oxopyrrolidin-1-yl)benzyl)-3-(benzyloxy)-9,9-dimethyl-4-oxo-4,6,7,9-tetrahydropyrimido[2,1-c][1,4]oxazine-2-carboxamide. IR (KBr, cm$^{-1}$) 3441, 2979, 1684, 1540, 1172. $^1$HNMR 400 MHz (MeOD) δ ppm: 7.56 (1H, m), 7.15 (2H, m), 4.86-4.31 (3H, m), 4.06 (2H, t, 5.0 Hz), 3.98 (2H, t, 5.0 Hz), 3.57 (2H, broad s), 2.72-2.55 (2H, m), 2.41 (1H, m), 2.25 (1H, m), 1.62 (6H, s). LCMS (M+H)+ m/z 461.

EXAMPLE 129

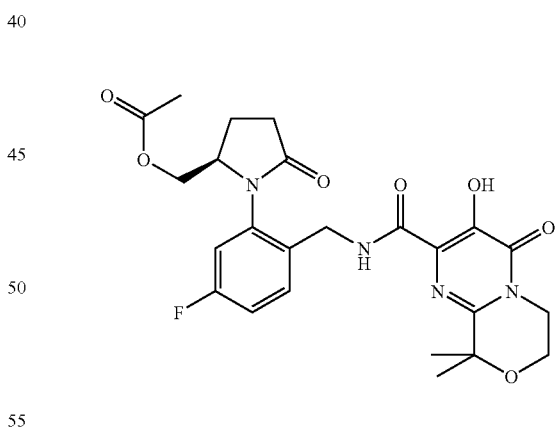

Pyrimido[2,1-c][1,4]oxazine-2-carboxamide, N-[[2-[(2R)-2-[(acetyloxy)methyl]-5-oxo-1-pyrrolidinyl]-4-fluorophenyl]methyl]-4,6,7,9-tetrahydro-3-hydroxy-9,9-dimethyl-4-oxo-. The title compound can be prepared from intermediate 193, (R)-(1-(2-((3-(benzyloxy)-9,9-dimethyl-4-oxo-4,6,7,9-tetrahydropyrimido[2,1-c][1,4]oxazine-2-carboxamido)methyl)-5-fluorophenyl)-5-oxopyrrolidin-2-yl)methyl acetate. $^1$HNMR 400 MHz (MeOD) δ ppm: 7.58 (1H, m), 7.21-7.04 (2H, m), 5.24 (2H, s), 4.66-4.21 (3H, m), 4.02-3.92 (5H, m), 2.73-2.34 (3H, m), 2.23-1.61 (5H, m), 1.60 (6H, s). LCMS (M+H)+ m/z 503.

EXAMPLE 130

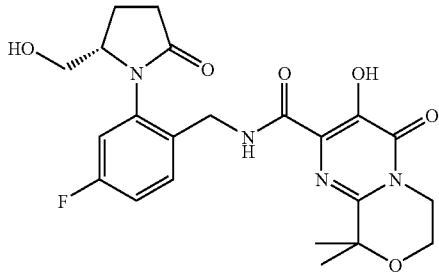

Pyrimido[2,1-c][1,4]oxazine-2-carboxamide, N-[[4-fluoro-2-[(2S)-2-(hydroxymethyl)-5-oxo-1-pyrrolidinyl]phenyl]methyl]-4,6,7,9-tetrahydro-3-hydroxy-9,9-dimethyl-4-oxo-. The title compound can be prepared from intermediate 167, (S)-N-(2-(2-((tert-butyldimethylsilyloxy)methyl)-5-oxopyrrolidin-1-yl)-4-fluorobenzyl)-3-(benzyloxy)-9,9-dimethyl-4-oxo-4,6,7,9-tetrahydropyrimido[2,1-c][1,4]oxazine-2-carboxamide. $^1$HNMR 400 MHz (DMSO) δ ppm: 7.36 (1H, m), 7.18 (2H, m), 5.07 (1H, broad s), 4.66-4.11 (3H, m), 3.95 (2H, t, 5.1 Hz), 3.80 (2H, t, 5.1 Hz), 3.39 (2H, s), 2.43 (1H, m), 2.25 (1H, m), 2.08 (1H, m), 1.51 (6H, s). LCMS (M+H)+ m/z 461.

EXAMPLE 131

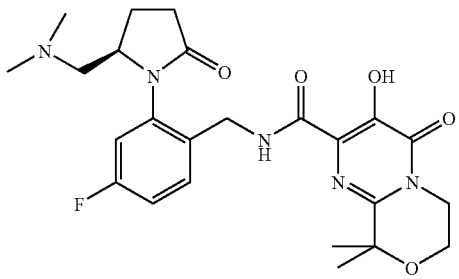

(R)-N-(2-(2-((Dimethylamino)methyl)-5-oxopyrrolidin-1-yl)-4-fluorobenzyl)-3-hydroxy-9,9-dimethyl-4-oxo-4,6,7,9-tetrahydropyrimido[2,1-c][1,4]oxazine-2-carboxamide. To a solution of intermediate 195, (R)-N-(2-(2-(azidomethyl)-5-oxopyrrolidin-1-yl)-4-fluorobenzyl)-3-(benzyloxy)-9,9-dimethyl-4-oxo-4,6,7,9-tetrahydropyrimido[2,1-c][1,4]oxazine-2-carboxamide, (0.050 g, 0.087 mmol) in MeOH (5 mL) was added Palladium (10%) on charcoal (0.020 g) and formaldehyde (0.30 mL, 10 mmol). The reaction mixture was stirred at 23° C. under H$_2$ (balloon) for 5 h. Palladium on charcoal was then removed by filtration and the solvent was evaporated in vacuo. The residue was purified by preparative HPLC (YMC-Pack C-18) to afford the title compound (0.013 g, 29% yield): $^1$H NMR (400 MHz, MeOD) δ ppm: 7.56 (1H, dd, J=7.0 Hz), 7.30-7.17 (2H, m), 4.70 (2H, m), 4.15 (1H, d, J=15.3 Hz), 4.07 (2H, m), 3.99 (2H, m,), 3.54 (1H, m), 2.93 (6H, s), 2.84-2.64 (4H, m), 2.20 (1H, m), 1.65 (6H, s). HRMS calcd for C$_{24}$H$_{31}$N$_5$O$_5$F: 488.2309; found 488.2328.

EXAMPLE 132

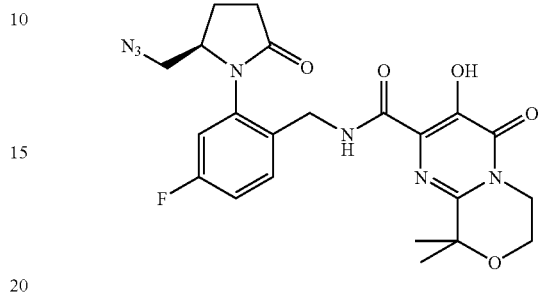

(R)-N-(2-(2-(Azidomethyl)-5-oxopyrrolidin-1-yl)-4-fluorobenzyl)-3-hydroxy-9,9-dimethyl-4-oxo-4,6,7,9-tetrahydropyrimido[2,1-c][1,4]oxazine-2-carboxamide. To a solution of intermediate 195, (R)-N-(2-(2-(azidomethyl)-5-oxopyrrolidin-1-yl)-4-fluorobenzyl)-3-(benzyloxy)-9,9-dimethyl-4-oxo-4,6,7,9-tetrahydropyrimido[2,1-c][1,4]oxazine-2-carboxamide, (0.030 g, 0.052 mmol) in CH$_2$Cl$_2$ (1 mL) was added CF$_3$CO$_2$H (1 mL) at 23° C. The reaction mixture was stirred at 23° C. for 3 h. Toluene (20 mL) was then added and the solvents evaporated in vacuo. The residue was purified by preparative HPLC (YMC-Pack C-18) to afford the title compound (0.008 g, 31%): $^1$H NMR (400 MHz, MeOD) δ ppm: 7.55 (1H, dd, J=6.6 Hz), 7.16 (2H, m), 4.47-4.24 (2H, m), 4.05 (2H, m), 3.98 (2H, m), 3.56 (2H, s), 2.70-2.45 (4H, m), 2.11 (1H, m), 1.64 (3H, s), 1.61 (3H, s). HRMS calcd for C$_{22}$H$_{25}$N$_7$O$_5$F: 486.1901; found 486.1923.

EXAMPLE 133

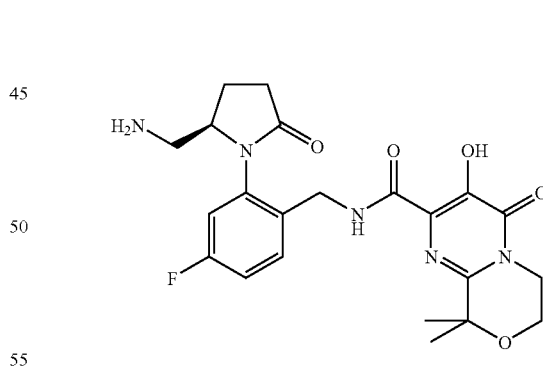

(R)-N-(2-(2-(Aminomethyl)-5-oxopyrrolidin-1-yl)-4-fluorobenzyl)-3-hydroxy-9,9-dimethyl-4-oxo-4,6,7,9-tetrahydropyrimido[2,1-c][1,4]oxazine-2-carboxamide. The title compound can be prepared by hydrogenolysis (H$_2$, 10% Pd—C) of intermediate 195, (R)-N-(2-(2-(azidomethyl)-5-oxopyrrolidin-1-yl)-4-fluorobenzyl)-3-(benzyloxy)-9,9-dimethyl-4-oxo-4,6,7,9-tetrahydropyrimido[2,1-c][1,4]oxazine-2-carboxamide. $^1$H NMR (400 MHz, MeOD) δ ppm: 7.54 (1H, dd, J=7.0 Hz), 7.25-7.13 (2H, m), 4.62 (2H, m), 4.17 (1H, d, J=15.6 Hz), 4.07 (2H, m), 3.99 (2H, m,), 3.23

(2H, d, J=3.1 Hz), 2.79-2.59 (3H, m), 2.14 (1H, m), 1.66 (6H, s). HRMS calcd for $C_{22}H_{27}N_5O_5F$: 460.1996; found 460.2014.

EXAMPLES 134-136

Examples 134-136 can be prepared from the indicated intermediates by hydrogenolysis or trifluoroacetic acid mediated hydrolysis.

EXAMPLE 134

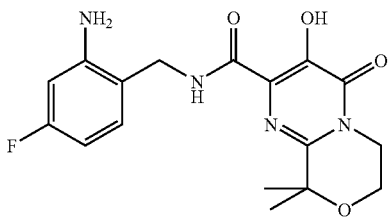

Pyrimido[2,1-c][1,4]oxazine-2-carboxamide, N-[(2-amino-4-fluorophenyl)methyl]-4,6,7,9-tetrahydro-3-hydroxy-9,9-dimethyl-4-oxo-. The title compound can be prepared from intermediate 169, N-(2-amino-4-fluorobenzyl)-3-(benzyloxy)-9,9-dimethyl-4-oxo-4,6,7,9-tetrahydropyrimido[2,1-c][1,4]oxazine-2-carboxamide. IR (KBr, cm$^{-1}$) 3383, 2979, 1636, 1540, 1288. $^1$HNMR 400 MHz (MeOD) δ ppm: 7.14 (1H, dd, J=7.3 Hz), 6.44-6.31 (2H, m), 4.69 (1H, broad s), 4.48 (2H, broad s), 4.03 (2H, t, J=4.6 Hz), 3.95 (2H, t, J=4.6 Hz), 1.62 (6H, s). HRMS (ESI$^+$) calculated for $C_{17}H_{20}FN_4O_4$ [M+H$^+$]:363.1469; found: 363.1454.

EXAMPLE 135

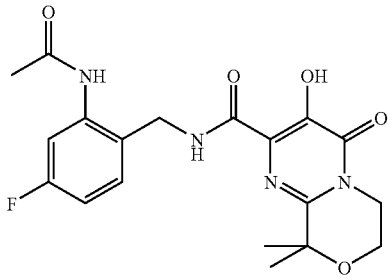

Pyrimido[2,1-c][1,4]oxazine-2-carboxamide, N-[[2-(acetylamino)-4-fluorophenyl]methyl]-4,6,7,9-tetrahydro-3-hydroxy-9,9-dimethyl-4-oxo-. The title compound can be prepared from intermediate 189, N-(2-acetamido-4-fluorobenzyl)-3-(benzyloxy)-9,9-dimethyl-4-oxo-4,6,7,9-tetrahydropyrimido[2,1-c][1,4]oxazine-2-carboxamide.
$^1$HNMR 400 MHz (MeOD) δ ppm: 7.66 (1H, broad d, J=10.5 Hz), 7.40 (1H, broad t, 6.5 Hz), 6.87 (1H, broad t, J=6.5 Hz), 4.55 (2H, m), 4.02 (2H, t, J=5.0 Hz), 3.92 (2H, t, J=5.0 Hz), 2.28 (3H, s), 1.62 (6H, s). HRMS (ESI$^+$) calculated for $C_{19}H_{22}FN_4O_5$ [M+H$^+$]:405.1574; found:405.1571.

EXAMPLE 136

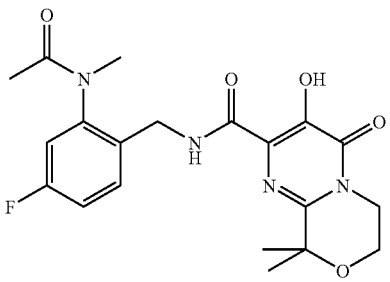

Pyrimido[2,1-c][1,4]oxazine-2-carboxamide, N-[[2-(acetylmethylamino)-4-fluorophenyl]methyl]-4,6,7,9-tetrahydro-3-hydroxy-9,9-dimethyl-4-oxo-. The title compound can be prepared from intermediate 168, N-(4-fluoro-2-(N-methylacetamido)benzyl)-3-(benzyloxy)-9,9-dimethyl-4-oxo-4,6,7,9-tetrahydropyrimido[2,1-c][1,4]oxazine-2-carboxamide. IR (KBr, cm$^{-1}$) 3407, 2979, 1653, 1539, 1116. $^1$HNMR 400 MHz (MeOD) δ ppm: 7.53 (1H, m), 7.24-7.06 (2H, m), 4.61-4.45 (2H, m), 4.08 (2H, t, J=5.1 Hz), 4.00 (2H, t, J=5.1 Hz), 3.40 (0.6H, s), 3.25 (2.4H, s), 1.85 (2.4H, s), 1.81 (0.6H, s), 1.65 (2.4H, s), 1.64 (2.4H, s), 1.62 (1.2H, s). LCMS (M+H)$^+$ m/z 419.

EXAMPLE 137

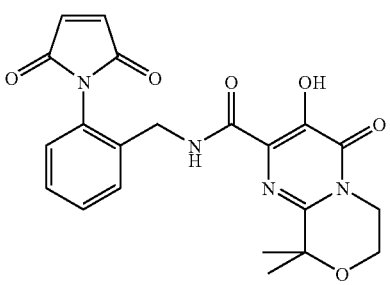

N-(2-(2,5-Dioxo-2H-pyrrol-1(5H)-yl)benzyl)-3-hydroxy-9,9-dimethyl-4-oxo-4,6,7,9-tetrahydropyrimido[2,1-c][1,4]oxazine-2-carboxamide. To a solution of N-(2-aminobenzyl)-3-(benzyloxy)-9,9-dimethyl-4-oxo-4,6,7,9-tetrahydropyrimido[2,1-c][1,4]oxazine-2-carboxamide (0.050 g, 0.114 mmol) in acetic acid (1.5 mL) was added maleic anhydride (0.013 g, 0.131 mmol) and the reaction mixture stirred in a sealed tube at 115 C for 18 h. Acetic acid was evaporated in vacuo and the residue was purified by preparative HPLC (YMC-Pack C-18) to afford the title compound (0.013 g, 27% yield): $^1$H NMR (400 MHz, CDCl$_3$) δ ppm: 8.03 (1H, broad t), 7.59 (1H, m), 7.48 (2H, m), 7.19 (1H, m), 6.92 (2H, s), 4.48 (2H, d, J=6.1 Hz), 4.04 (4H, s), 1.62 (6H, s); HRMS calcd for $C_{21}H_{21}N_4O_6$: 425.1461; found 425.1451.

EXAMPLE 138

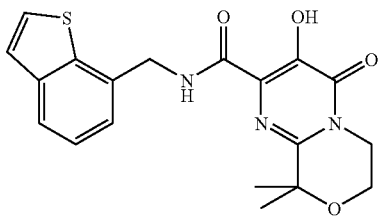

Pyrimido[2,1-c][1,4]oxazine-2-carboxamide, N-(benzo[b]thien-7-ylmethyl)-4,6,7,9-tetrahydro-3-hydroxy-9,9-dimethyl-4-oxo-. To intermediate 147, N-(benzo[b]thiophen-7-ylmethyl)-3-(benzyloxy)-9,9-dimethyl-4-oxo-4,6,7,9-tetrahydropyrimido[2,1-c][1,4]oxazine-2-carboxamide, (60 mg, 0.13 mmol) was added $CF_3CO_2H$ (2 mL) at 23° C. The reaction mixture was stirred at 23° C. for 1.5 h. Toluene (20 mL) was then added and the solvents were evaporated in vacuo. The residue was purified by preparative HPLC (YMC-Pack C-18) to afford the title compound (0.017 g, 34% yield): $^1$H NMR (400 MHz, $CDCl_3$) δ: 8.00 (1H, broad t), 7.86 (1H, d, J=8.0 Hz), 7.51-7.28 (3H, m), 4.93 (2H, d, J=3.9 Hz), 4.05 (4H, s), 1.58 (6H, s). HRMS calcd for $C_{19}H_{20}N_3O_4S$: 386.1175; found 386.1165.

EXAMPLE 139

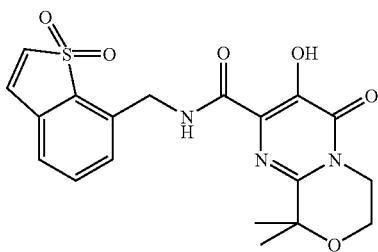

Pyrimido[2,1-c][1,4]oxazine-2-carboxamide, N-[(1,1-dioxidobenzo[b]thien-7-yl)methyl]-4,6,7,9-tetrahydro-3-hydroxy-9,9-dimethyl-4-oxo-. To intermediate 196, N-(benzo[b]thiophen-1,1-dione-7-ylmethyl)-3-(benzyloxy)-9,9-dimethyl-4-oxo-4,6,7,9-. tetrahydropyrimido[2,1-c][1,4]oxazine-2-carboxamide, (0.080 g, 0.16 mmol) was added $CF_3CO_2H$ (2 mL) at 23° C. The reaction mixture was stirred at 23° C. for 2.5 h. Toluene (20 mL) was then added and the solvents evaporated in vacuo. The residue was purified by crystallization with MeOH (10 mL) to afford the title compound (0.037 g, 55% yield). $^1$H NMR (400 MHz, DMSO-$d_6$) δ: 11.87 (1H, s), 9.44 (1H, t, J=6.5 Hz), 7.65 (2H, m), 7.51 (1H, d, J=7.0 Hz), 7.42-7.37 (2H, m), 4.84 (2H, d, J=6.2 Hz), 3.99 (2H, t, 5.4 Hz), 3.85 (2H, t, J=5.4 Hz), 1.59 (6H, s). HRMS calcd for $C_{19}H_{20}N_3O_6S$: 418.1073; found 418.1078.

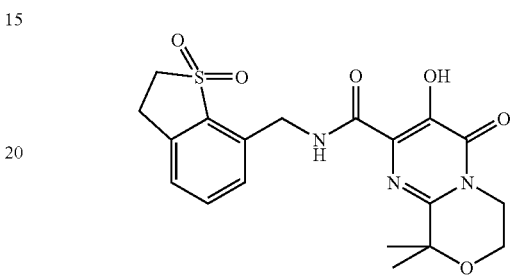

Pyrimido[2,1-c][1,4]oxazine-2-carboxamide, N-[(2,3-dihydro-1,1-dioxidobenzo[b]thien-7-yl)methyl]-4,6,7,9-tetrahydro-3-hydroxy-9,9-dimethyl-4-oxo-. The title compound was obtained from intermediate 196, N-(benzo[b]thiophen-1,1-dione-7-ylmethyl)-3-(benzyloxy)-9,9-dimethyl-4-oxo-4,6,7,9-tetrahydropyrimido[2,1-c][1,4]oxazine-2-carboxamide by reduction, Palladium (10%) on charcoal under $H_2$. $^1$HNMR (400 MHz, CDCl3) δ: 8.65 (1H, s), 7.58-7.49 (2H, m), 7.32 (1H, d, J=7.0 Hz), 4.86 (2H, d, J=6.8 Hz), 3.99 (4H, s), 3.54 (2H, t, J=6.8 Hz), 3.40 (2H, t, J=6.8), 1.61 (6H, s). LCMS (M+H)$^+$ m/z 420.

EXAMPLES 141-146

Examples 141-146, listed in Table 9, can be prepared from intermediate 25, ethyl 3-hydroxy-9,9-dimethyl-4-oxo-4,6,7,9-tetrahydropyrimido[2,1-c][1,4]oxazine-2-carboxylate, according to the methods described for examples 1, 19, and 20. The compounds in the table were characterized by LCMS; (Xterra MS-C18, 4.6×50 mm); eluted with 10% to 100% B, 4.5 min gradient, (A=$H_2O$-0.1% $CF_3CO_2H$, B=$CH_3CN$-0.1% $CF_3CO_2H$); flow rate at 2.5 mL/min. UV detection at 220 nm). Product retention time (RT, minutes) and molecular weight (MS [M+1]) results are listed in the table.

TABLE 9

| Example | Structure | RT | MS |
|---|---|---|---|
| 141 | Pyrimido[2,1-c][1,4]oxazine-2-carboxamide, 4,6,7,9-tetrahydro-3-hydroxy-9,9-dimethyl-4-oxo-N-(2-pyridinylmethyl)- | 1.1 | 331.17 |

TABLE 9-continued

| Example | Structure | RT | MS |
|---|---|---|---|
| 142 | 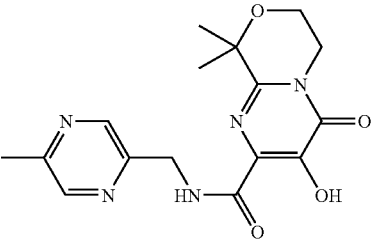 Pyrimido[2,1-c][1,4]oxazine-2-carboxamide, 4,6,7,9-tetrahydro-3-hydroxy-9,9-dimethyl-N-[(5-methylpyrazinyl)methyl]-4-oxo- | 2.07 | 346.18 |
| 143 | 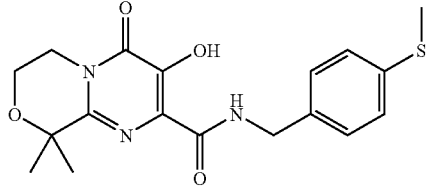 Pyrimido[2,1-c][1,4]oxazine-2-carboxamide, 4,6,7,9-tetrahydro-3-hydroxy-9,9-dimethyl-N-[[4-(methylthio)phenyl]methyl]-4-oxo- | 3.35 | 376.16 |
| 144 | 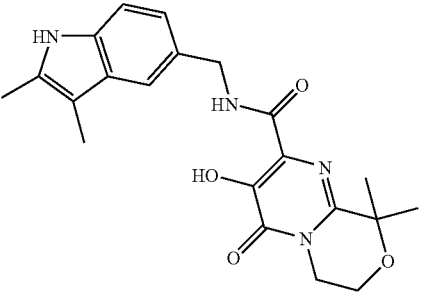 Pyrimido[2,1-c][1,4]oxazine-2-carboxamide, N-[(2,3-dimethyl-1H-indol-5-yl)methyl]-4,6,7,9-tetrahydro-3-hydroxy-9,9-dimethyl-4-oxo- | 2.37 | 397 |
| 145 | 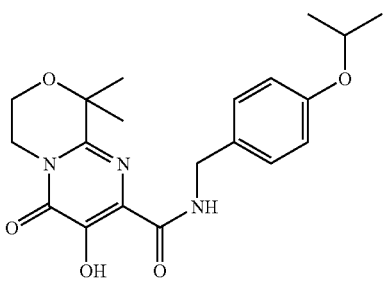 Pyrimido[2,1-c][1,4]oxazine-2-carboxamide, 4,6,7,9-tetrahydro-3-hydroxy-9,9-dimethyl-N-[[4-(1-methylethoxy)phenyl]methyl]-4-oxo- | 2.54 | 388.2 |

TABLE 9-continued

| Example | Structure | RT | MS |
|---|---|---|---|
| 146 | 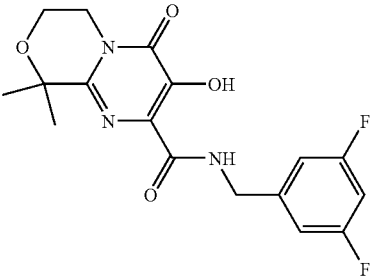 Pyrimido[2,1-c][1,4]oxazine-2-carboxamide, N-[(3,5-difluorophenyl)methyl]-4,6,7,9-tetrahydro-3-hydroxy-9,9-dimethyl-4-oxo- | 3.23 | 366.15 |

EXAMPLE 147

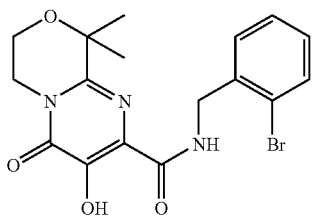

Pyrimido[2,1-c][1,4]oxazine-2-carboxamide, N-[(2-bromophenyl)methyl]-4,6,7,9-tetrahydro-3-hydroxy-9,9-dimethyl-4-oxo-. The title compound can be prepared from intermediate 25, ethyl 3-hydroxy-9,9-dimethyl-4-oxo-4,6,7,9-tetrahydropyrimido[2,1-c][1,4]oxazine-2-carboxylate, and 2-bromobenzylamine according to the methods described for examples 1, 19 and 20. $^1$H NMR (300 MHz, DMSO-D6) δ ppm: 1.58 (s, 1), 3.84 (t, 2), 3.98 (t, 2), 4.54 (d, 2), 7.25 (m, 2), 7.38 (m, 2), 7.64 (d, 1), 9.43 (brm, 1), 12.01 (s, 1).

EXAMPLES 148-200

Examples 148-200, listed in table 10, were synthesized according to the following procedure. To a microwave reaction vessel containing a stir bar, was added Pd(Ph$_3$P)$_4$ (30 mg, 25 μmol), followed by anhydrous dioxane (0.5 mL). To this was added example 147, pyrimido[2,1-c][1,4]oxazine-2-carboxamide, N-[(2-bromophenyl)methyl]-4,6,7,9-tetrahydro-3-hydroxy-9,9-dimethyl-4-oxo-, (50 μmol), boronic acid or boronate ester reagent (200 μmol), anhydrous dioxane (0.5 mL) and 2M K$_3$PO$_4$ aqueous solution (0.25 mL). The reaction vessel was flushed with nitrogen, capped and heated at 120° C. for 10 minutes in a microwave reactor. The reaction mixture was filtered through a Whatman 0.45 μm syringe filter and the crude product purified using preparative HPLC (Xterra MS-C18, 30×50 mm); Eluted with 30% to 100% B, 8 min gradient, (A=10 mM NH$_4$OAC (aq.), B=CH$_3$CN); flow rate at 30 mL/min. UV detection at 220 nm) to give the title compound.

The compounds in the table were characterized by LCMS; (Xterra MS-C18, 4.6×50 mm); eluted with 10% to 100% B, 4.5 min gradient, (A=H$_2$O-0.1% CF$_3$CO$_2$H, B=CH$_3$CN-0.1% CF$_3$CO$_2$H); flow rate at 2.5 mL/min. UV detection at 220 nm). Product retention time (RT, minutes) and observed molecular weight (MS [M+1]) results are listed in the table.

TABLE 10

| Example | Structure | RT | MS |
|---|---|---|---|
| 148 | 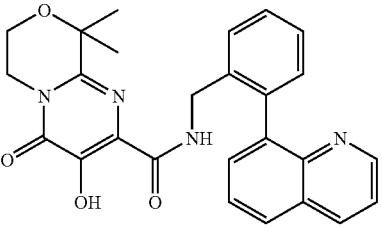 Pyrimido[2,1-c][1,4]oxazine-2-carboxamide, 4,6,7,9-tetrahydro-3-hydroxy-9,9-dimethyl-4-oxo-N-[[2-(8-quinolinyl)phenyl]methyl]- | 2.08 | 457 |

TABLE 10-continued

| Example | Structure | RT | MS |
|---|---|---|---|
| 149 | 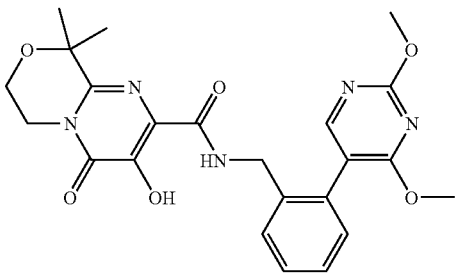<br>Pyrimido[2,1-c][1,4]oxazine-2-carboxamide, N-[[2-(2,4-dimethoxy-5-pyrimidinyl)phenyl]methyl]-4,6,7,9-tetrahydro-3-hydroxy-9,9-dimethyl-4-oxo- | 1.91 | 467.95 |
| 150 | 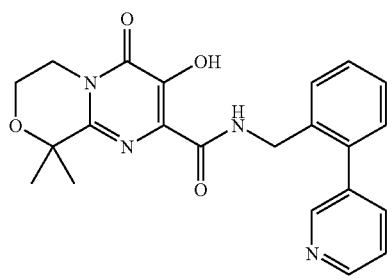<br>Pyrimido[2,1-c][1,4]oxazine-2-carboxamide, 4,6,7,9-tetrahydro-3-hydroxy-9,9-dimethyl-4-oxo-N-[[2-(3-pyridinyl)phenyl]methyl]- | 1.71 | 407 |
| 151 | 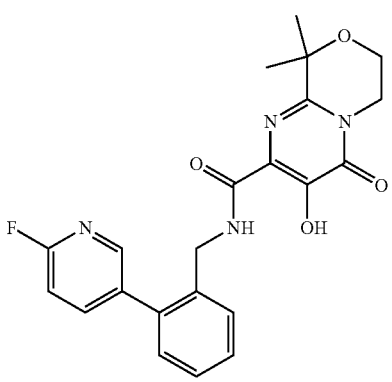<br>Pyrimido[2,1-c][1,4]oxazine-2-carboxamide, 4,6,7,9-tetrahydro-3-hydroxy-9,9-dimethyl-4-oxo-N-[[2-(3-pyridinyl)phenyl]methyl]- | 1.98 | 425.01 |
| 152 | 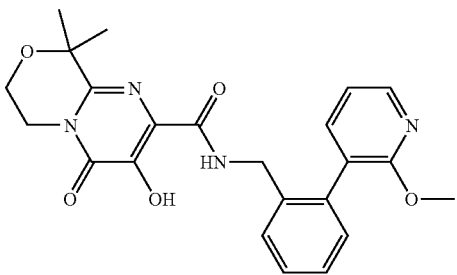<br>Pyrimido[2,1-c][1,4]oxazine-2-carboxamide, 4,6,7,9-tetrahydro-3-hydroxy-N-[[2-(2-methoxy-3-pyridinyl)phenyl]methyl]-9,9-dimethyl-4-oxo- | 2.04 | 437.04 |

TABLE 10-continued

| Example | Structure | RT | MS |
| --- | --- | --- | --- |
| 153 | 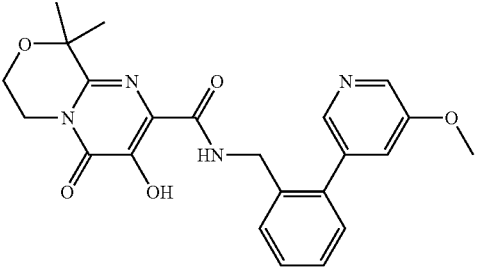 Pyrimido[2,1-c][1,4]oxazine-2-carboxamide, 4,6,7,9-tetrahydro-3-hydroxy-N-[[2-(5-methoxy-3-pyridinyl)phenyl]methyl]-9,9-dimethyl-4-oxo- | 2.1 | 436.97 |
| 154 | 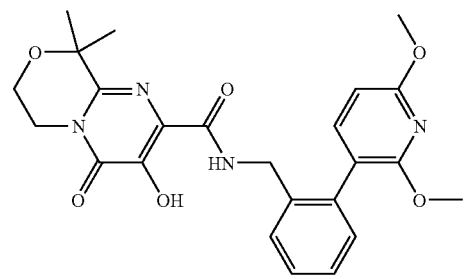 Pyrimido[2,1-c][1,4]oxazine-2-carboxamide, N-[[2-(2,6-dimethoxy-3-pyridinyl)phenyl]methyl]-4,6,7,9-tetrahydro-3-hydroxy-9,9-dimethyl-4-oxo- | 2.41 | 467.01 |
| 155 | 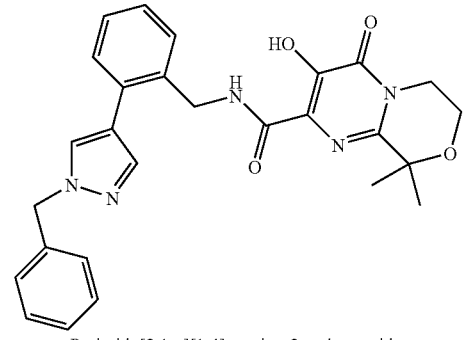 Pyrimido[2,1-c][1,4]oxazine-2-carboxamide, 4,6,7,9-tetrahydro-3-hydroxy-9,9-dimethyl-4-oxo-N-[[2-[1-(phenylmethyl)-1H-pyrazol-4-yl]phenyl]methyl]- | 2.19 | 486.03 |
| 156 | 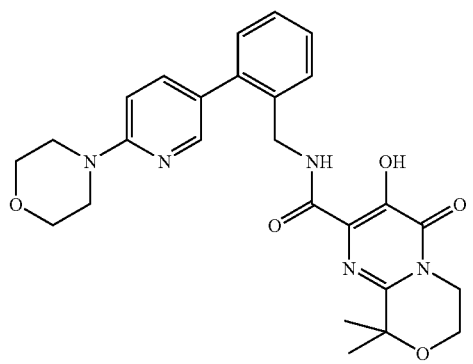 Pyrimido[2,1-c][1,4]oxazine-2-carboxamide, 4,6,7,9-tetrahydro-3-hydroxy-9,9-dimethyl-N-[[2-[6-(4-morpholinyl)-3-pyridinyl]phenyl]methyl]-4-oxo- | 2 | 492.01 |

TABLE 10-continued

| Example | Structure | RT | MS |
|---|---|---|---|
| 157 | 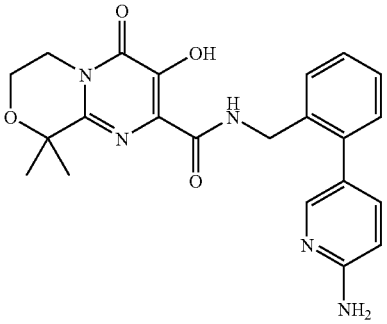Pyrimido[2,1-c][1,4]oxazine-2-carboxamide, N-[[2-(6-amino-3-pyridinyl)phenyl]methyl]-4,6,7,9-tetrahydro-3-hydroxy-9,9-dimethyl-4-oxo- | 3.02 | 454.97 |
| 158 | 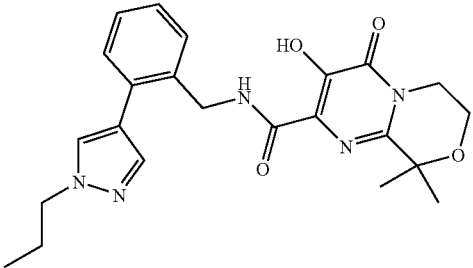Pyrimido[2,1-c][1,4]oxazine-2-carboxamide, 4,6,7,9-tetrahydro-3-hydroxy-9,9-dimethyl-4-oxo-N-[[2-(1-propyl-1H-pyrazol-4-yl)phenyl]methyl]- | 1.99 | 438.04 |
| 159 | 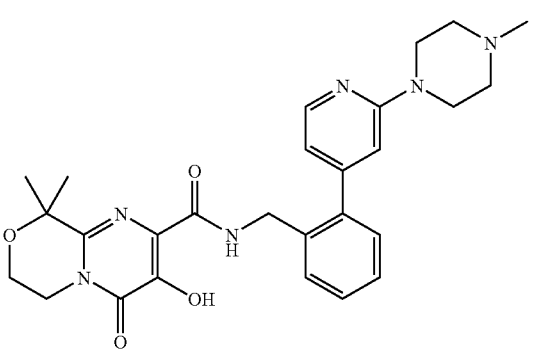Pyrimido[2,1-c][1,4]oxazine-2-carboxamide, 4,6,7,9-tetrahydro-3-hydroxy-9,9-dimethyl-N-[[2-[2-(4-methyl-1-piperazinyl)-4-pyridinyl]phenyl]methyl]-4-oxo- | 1.66 | 505.05 |
| 160 | 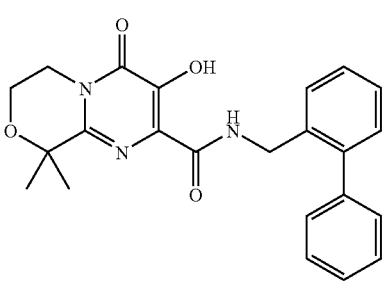Pyrimido[2,1-c][1,4]oxazine-2-carboxamide, N-([1,1'-biphenyl]-2-ylmethyl)-4,6,7,9-tetrahydro-3-hydroxy-9,9-dimethyl-4-oxo- | 3.2 | 406 |

TABLE 10-continued

| Example | Structure | RT | MS |
|---|---|---|---|
| 161 | 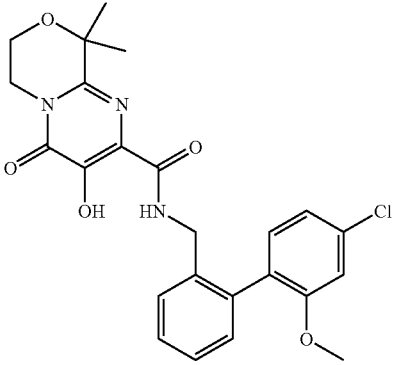 Pyrimido[2,1-c][1,4]oxazine-2-carboxamide, N-[(4'-chloro-2'-methoxy[1,1'-biphenyl]-2-yl)methyl]-4,6,7,9-tetrahydro-3-hydroxy-9,9-dimethyl-4-oxo- | 3.36 | 469.91 |
| 162 | 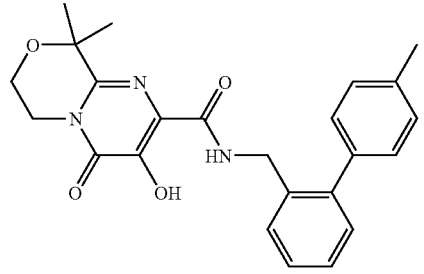 Pyrimido[2,1-c][1,4]oxazine-2-carboxamide, 4,6,7,9-tetrahydro-3-hydroxy-9,9-dimethyl-N-[(4'-methyl[1,1'-biphenyl]-2-yl)methyl]-4-oxo- | 3.39 | 419.97 |
| 163 | 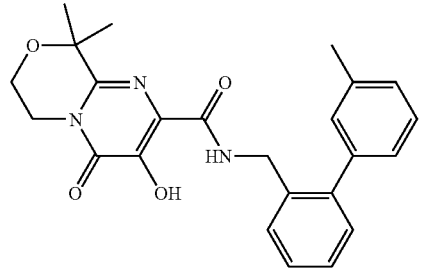 Pyrimido[2,1-c][1,4]oxazine-2-carboxamide, 4,6,7,9-tetrahydro-3-hydroxy-9,9-dimethyl-N-[(3'-methyl[1,1'-biphenyl]-2-yl)methyl]-4-oxo- | 3.36 | 419.97 |
| 164 | 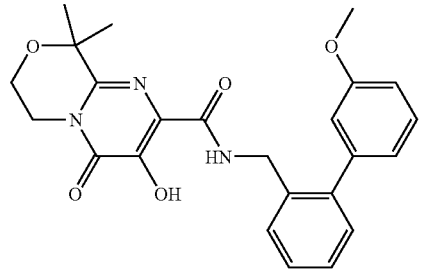 Pyrimido[2,1-c][1,4]oxazine-2-carboxamide, 4,6,7,9-tetrahydro-3-hydroxy-N-[(3'-methoxy[1,1'-biphenyl]-2-yl)methyl]-9,9-dimethyl-4-oxo- | 3.14 | 435.97 |

TABLE 10-continued

| Example | Structure | RT | MS |
|---|---|---|---|
| 165 | 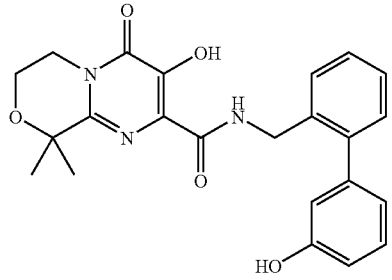Pyrimido[2,1-c][1,4]oxazine-2-carboxamide, 4,6,7,9-tetrahydro-3-hydroxy-N-[(3'-hydroxy[1,1'-biphenyl]-2-yl)methyl]-9,9-dimethyl-4-oxo- | 2.65 | 421.99 |
| 166 | 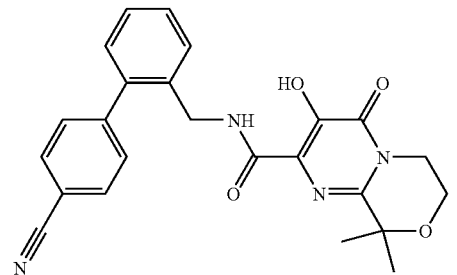Pyrimido[2,1-c][1,4]oxazine-2-carboxamide, N-[(4'-cyano[1,1'-biphenyl]-2-yl)methyl]-4,6,7,9-tetrahydro-3-hydroxy-9,9-dimethyl-4-oxo- | 2.91 | 430.99 |
| 167 | 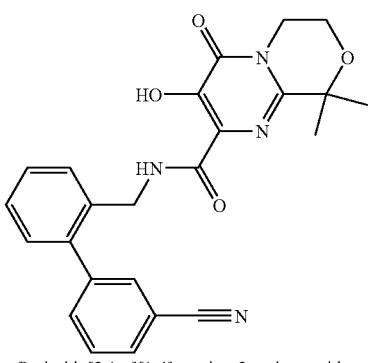Pyrimido[2,1-c][1,4]oxazine-2-carboxamide, N-[(3'-cyano[1,1'-biphenyl]-2-yl)methyl]-4,6,7,9-tetrahydro-3-hydroxy-9,9-dimethyl-4-oxo- | 2.93 | 430.99 |
| 168 | 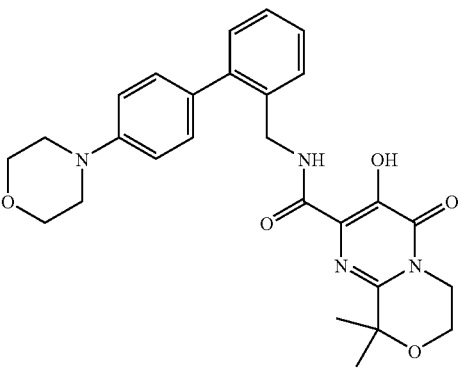Pyrimido[2,1-c][1,4]oxazine-2-carboxamide, 4,6,7,9-tetrahydro-3-hydroxy-9,9-dimethyl-N-[[4'-(4-morpholinyl)[1,1'-biphenyl]-2-yl]methyl]-4-oxo- | 3.02 | 491 |

TABLE 10-continued

| Example | Structure | RT | MS |
|---|---|---|---|
| 169 | 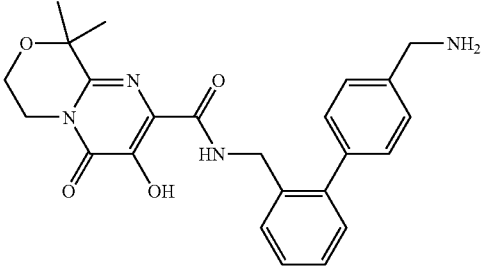<br>Pyrimido[2,1-c][1,4]oxazine-2-carboxamide, 4,6,7,9-tetrahydro-3-hydroxy-9,9-dimethyl-N-[[4'-(4-morpholinyl)[1,1'-biphenyl]-2-yl]methyl]-4-oxo- | 2.11 | 435.02 |
| 170 | 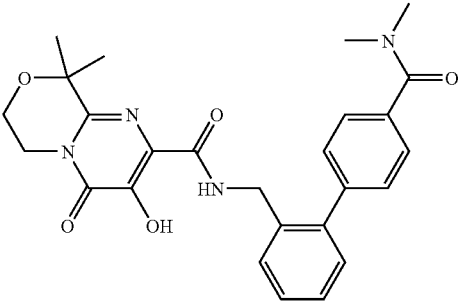<br>Pyrimido[2,1-c][1,4]oxazine-2-carboxamide, N-[[4'-[(dimethylamino)carbonyl][1,1'-biphenyl]-2-yl]methyl]-4,6,7,9-tetrahydro-3-hydroxy-9,9-dimethyl-4-oxo- | 2.54 | 476.96 |
| 171 | 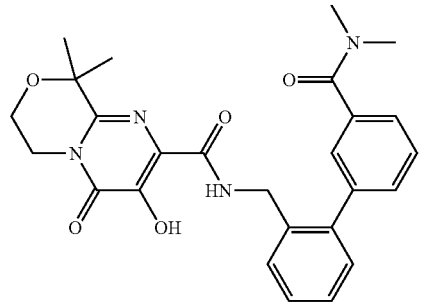<br>Pyrimido[2,1-c][1,4]oxazine-2-carboxamide, N-[3'-[(dimethylamino)carbony][1,1'-biphenyl]-2-yl]methyl]-4,6,7,9-tetrahydro-3-hydroxy-9,9-dimethyl-4-oxo- | 2.53 | 476.96 |
| 172 | 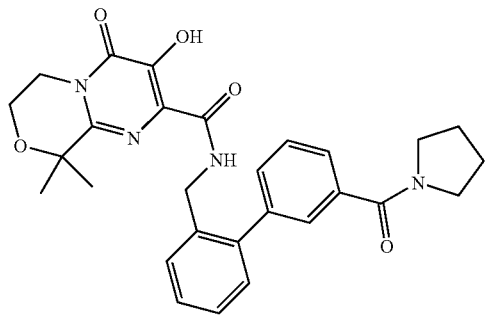<br>Pyrimido[2,1-c][1,4]oxazine-2-carboxamide, 4,6,7,9-tetrahydro-3-hydroxy-9,9-dimethyl-4-oxo-N-[[3'-(1-pyrrolidinylcarbonyl)[1,1'-biphenyl]-2-yl]methyl]- | 2.66 | 502.97 |

TABLE 10-continued

| Example | Structure | RT | MS |
|---|---|---|---|
| 173 | 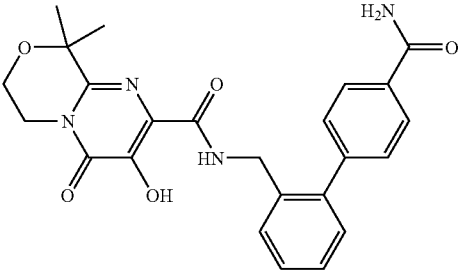<br>Pyrimido[2,1-c][1,4]oxazine-2-carboxamide,<br>N-[[4'-(aminocarbonyl)[1,1'-biphenyl]-2-yl]methyl]-<br>4,6,7,9-tetrahydro-3-hydroxy-9,9-dimethyl-4-oxo- | 2.26 | 448.94 |
| 174 | 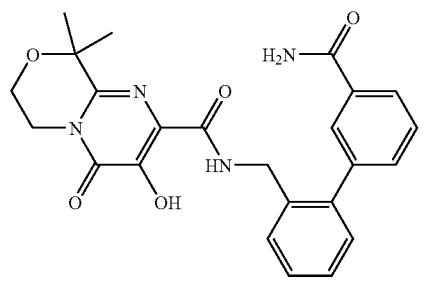<br>Pyrimido[2,1-c][1,4]oxazine-2-carboxamide,<br>N-[[3'-(aminocarbonyl)[1,1'-biphenyl]-2-yl]methyl]-<br>4,6,7,9-tetrahydro-3-hydroxy-9,9-dimethyl-4-oxo- | 2.27 | 448.94 |
| 175 | 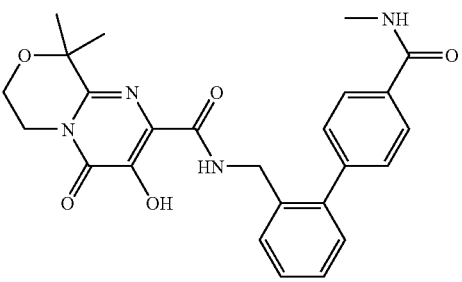<br>Pyrimido[2,1-c][1,4]oxazine-2-carboxamide,<br>4,6,7,9-tetrahydro-3-hydroxy-9,9-dimethyl-N-[[4'-<br>[(methylamino)carbonyl][1,1'-biphenyl]-2-yl]methyl]-4-oxo- | 2.36 | 462.98 |
| 176 | 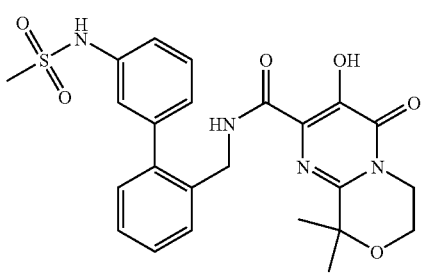<br>Pyrimido[2,1-c][1,4]oxazine-2-carboxamide,<br>4,6,7,9-tetrahydro-3-hydroxy-9,9-dimethyl-N-[[3'-<br>[(methylsulfonyl)amino][1,1'-biphenyl]-2-yl]methyl]-4-oxo- | 2.63 | 498.94 |

TABLE 10-continued

| Example | Structure | RT | MS |
|---|---|---|---|
| 177 | 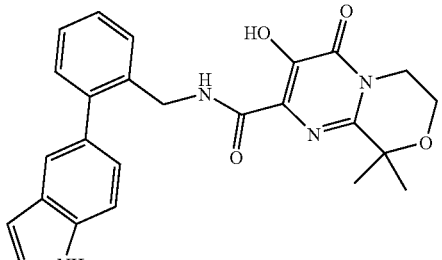 Pyrimido[2,1-c][1,4]oxazine-2-carboxamide, 4,6,7,9-tetrahydro-3-hydroxy-N-[[2-(1H-indol-5-yl)phenyl]methyl]-9,9-dimethyl-4-oxo- | 3 | 444.97 |
| 178 | 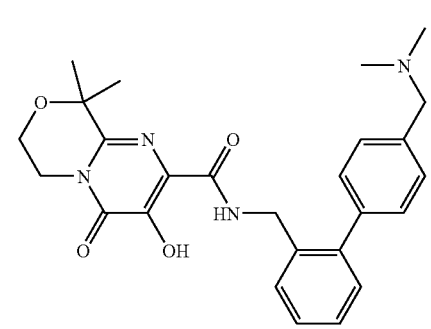 Pyrimido[2,1-c][1,4]oxazine-2-carboxamide, N-[[4'-[(dimethylamino)methyl][1,1'-biphenyl]-2-yl]methyl]-4,6,7,9-tetrahydro-3-hydroxy-9,9-dimethyl-4-oxo- | 2.56 | 462.98 |
| 179 | 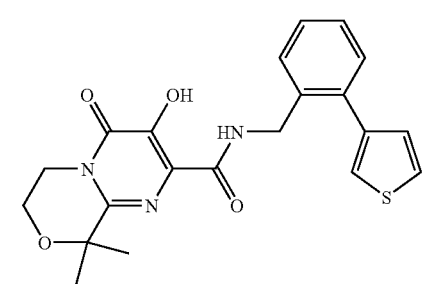 Pyrimido[2,1-c][1,4]oxazine-2-carboxamide, 4,6,7,9-tetrahydro-3-hydroxy-9,9-dimethyl-4-oxo-N-[[2-(3-thienyl)phenyl]methyl]- | 3.09 | 411.98 |
| 180 | 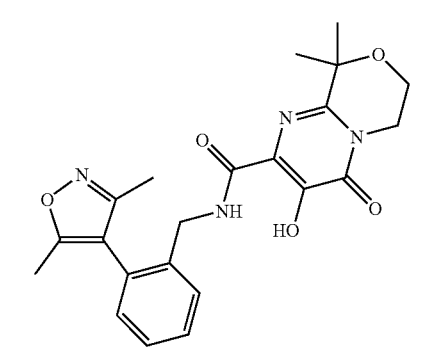 Pyrimido[2,1-c][1,4]oxazine-2-carboxamide, N-[[2-(3,5-dimethyl-4-isoxazolyl)phenyl]methyl]-4,6,7,9-tetrahydro-3-hydroxy-9,9-dimethyl-4-oxo- | 2.66 | 425.01 |

TABLE 10-continued

| Example | Structure | RT | MS |
|---------|-----------|------|--------|
| 181 | 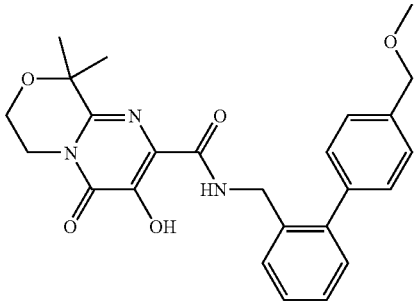<br>Pyrimido[2,1-c][1,4]oxazine-2-carboxamide, 4,6,7,9-tetrahydro-3-hydroxy-N-[[4'-(methoxymethyl)[1,1'-biphenyl]-2-yl]methyl]-9,9-dimethyl-4-oxo- | 3.08 | 450.01 |
| 182 | 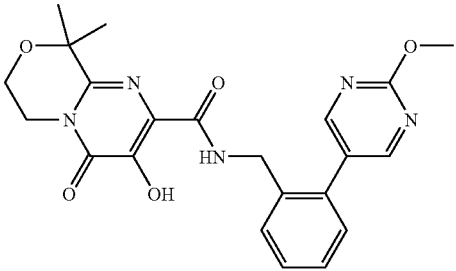<br>Pyrimido[2,1-c][1,4]oxazine-2-carboxamide, 4,6,7,9-tetrahydro-3-hydroxy-N-[[2-(2-methoxy-5-pyrimidinyl)phenyl]methyl]-9,9-dimethyl-4-oxo- | 2.43 | 438 |
| 183 | 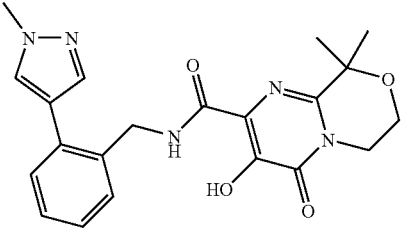<br>Pyrimido[2,1-c][1,4]oxazine-2-carboxamide, 4,6,7,9-tetrahydro-3-hydroxy-9,9-dimethyl-N-[[2-(1-methyl-1H-pyrazol-4-yl)phenyl]methyl]-4-oxo- | 1.71 | 410 |
| 184 | 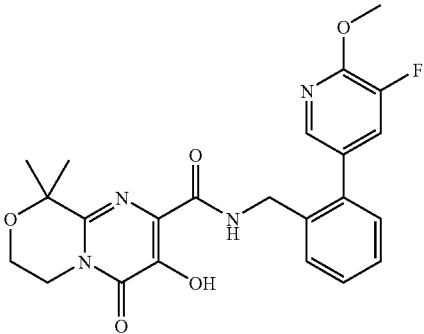<br>Pyrimido[2,1-c][1,4]oxazine-2-carboxamide, N-[[2-(5-fluoro-6-methoxy-3-pyridinyl)phenyl]methyl]-4,6,7,9-tetrahydro-3-hydroxy-9,9-dimethyl-4-oxo- | 3.02 | 455 |

TABLE 10-continued

| Example | Structure | RT | MS |
|---|---|---|---|
| 185 | 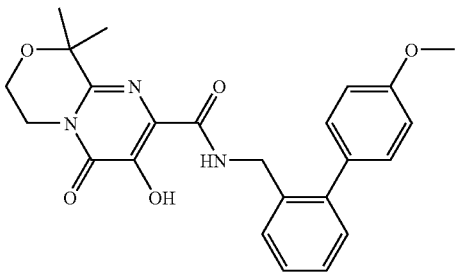 Pyrimido[2,1-c][1,4]oxazine-2-carboxamide, 4,6,7,9-tetrahydro-3-hydroxy-N-[(4'-methoxy[1,1'-biphenyl]-2-yl)methyl]-9,9-dimethyl-4-oxo- | 3.14 | 436 |
| 186 | 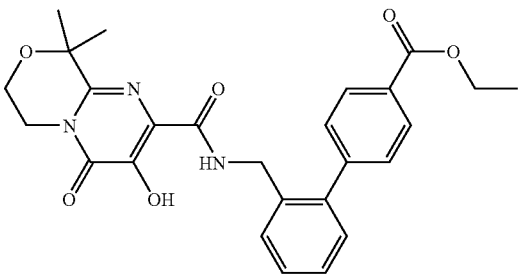 [1,1'-Biphenyl]-4-carboxylic acid,2'-[[[(4,6,7,9-tetrahydro-3-hydroxy-9,9-dimethyl-4-oxopyrimido[2,1-c][1,4]oxazin-2-yl)carbonyl]amino]methyl]-, ethyl ester | 3.30 | 478 |
| 187 | 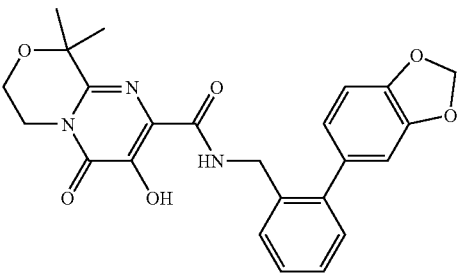 Pyrimido[2,1-c][1,4]oxazine-2-carboxamide, N-[[2-(1,3-benzodioxol-5-yl)phenyl]methyl]-4,6,7,9-tetrahydro-3-hydroxy-9,9-dimethyl-4-oxo- | 2.76 | 450.2 |
| 188 | 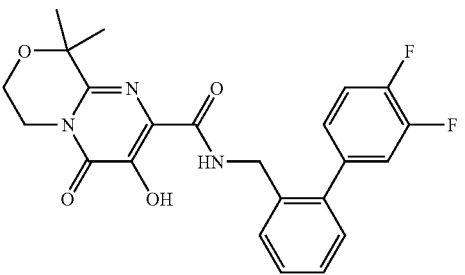 Pyrimido[2,1-c][1,4]oxazine-2-carboxamide, N-[(3',4'-difluoro[1,1'-biphenyl]-2-yl)methyl]-4,6,7,9-tetrahydro-3-hydroxy-9,9-dimethyl-4-oxo- | 2.92 | 442.13 |

TABLE 10-continued

| Example | Structure | RT | MS |
|---|---|---|---|
| 189 | 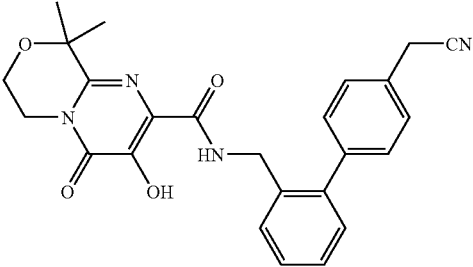 Pyrimido[2,1-c][1,4]oxazine-2-carboxamide, N-[[4'-(cyanomethyl)[1,1'-biphenyl]-2-yl]methyl]-4,6,7,9-terahydro-3-hydroxy-9,9-dimethyl-4-oxo- | 2.57 | 445.15 |
| 190 | 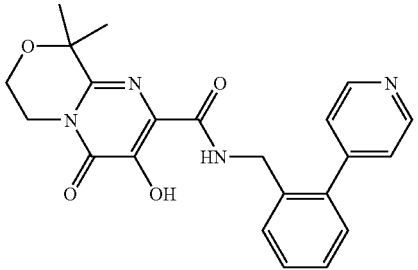 Pyrimido[2,1-c][1,4]oxazine-2-carboxamide, 4,6,7,9-tetrahydro-3-hydroxy-9,9-dimethyl-4-oxo-N-[[2-(4-pyridinyl)phenyl]methyl]- | 1.34 | 407.34 |
| 191 | 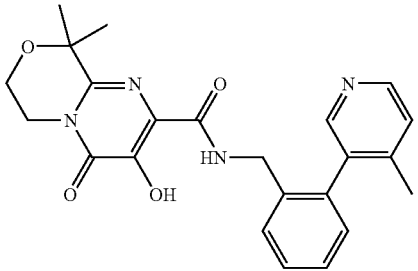 Pyrimido[2,1-c][1,4]oxazine-2-carboxamide, 4,6,7,9-tetrahydro-3-hydroxy-9,9-dimethyl-N-[[2-(4-methyl-3-pyridinyl)phenyl]methyl]-4-oxo- | 1.40 | 421.2 |
| 192 | 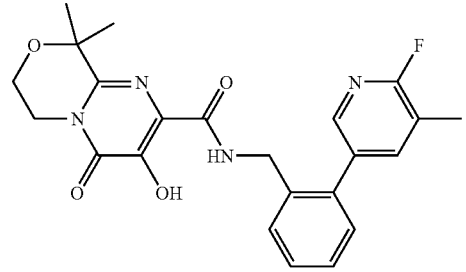 Pyrimido[2,1-c][1,4]oxazine-2-carboxamide, N-[[2-(6-fluoro-5-methyl-3-pyridinyl)phenyl]methyl]-4,6,7,9-tetrahydro-3-hydroxy-9,9-dimethyl-4-oxo- | 2.57 | 439.36 |

TABLE 10-continued

| Example | Structure | RT | MS |
|---|---|---|---|
| 193 | 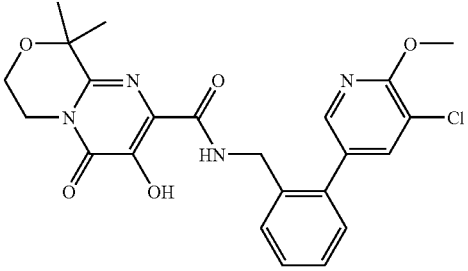<br>Pyrimido[2,1-c][1,4]oxazine-2-carboxamide,<br>N-[[2-(5-chloro-6-methoxy-3-pyridinyl)phenyl]methyl]-<br>4,6,7,9-tetrahydro-3-hydroxy-9,9-dimethyl-4-oxo- | 2.84 | 471.13 |
| 194 | 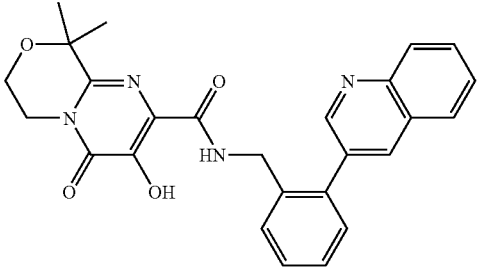<br>Pyrimido[2,1-c][1,4]oxazine-2-carboxamide,<br>4,6,7,9-tetrahydro-3-hydroxy-9,9-dimethyl-4-<br>oxo-N-[[2-(3-quinolinyl)phenyl]methyl]- | 1.62 | 457.26 |
| 195 | 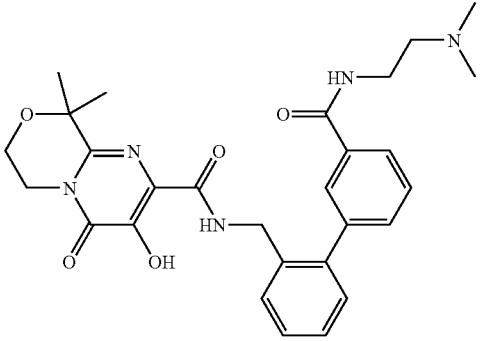<br>Pyrimido[2,1-c][1,4]oxazine-2-carboxamide,<br>N-[[3'-[[[2-(dimethylamino)ethyl]amino]<br>carbonyl][1,1'-biphenyl]-2-yl]methyl]-4,6,7,9-<br>tetrahydro-3-hydroxy-9,9-dimethyl-4-oxo- | 1.57 | 520.31 |
| 196 | 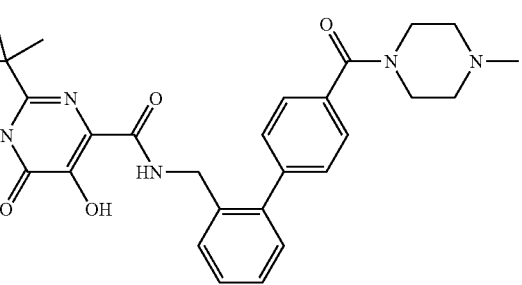<br>Pyrimido[2,1-c][1,4]oxazine-2-carboxamide,<br>4,6,7,9-tetrahydro-3-hydroxy-9,9-dimethyl-N-[[4'-[(4-methyl-1-<br>piperazinyl)carbonyl][1,1'-biphenyl]-2-yl]methyl]-4-oxo- | 1.57 | 532.41 |

TABLE 10-continued

| Example | Structure | RT | MS |
|---|---|---|---|
| 197 | Pyrimido[2,1-c][1,4]oxazine-2-carboxamide, 4,6,7,9-tetrahydro-3-hydroxy-9,9-dimethyl-4-oxo-N-[[2-(5-quinolinyl)phenyl]methyl]- | 1.55 | 457.26 |
| 198 | Pyrimido[2,1-c][1,4]oxazine-2-carboxamide, N-[[2-(3-furanyl)phenyl]methyl]-4,6,7,9-tetrahydro-3-hydroxy-9,9-dimethyl-4-oxo- | 2.86 | 396.2 |
| 199 | Pyrimido[2,1-c][1,4]oxazine-2-carboxamide, N-[[2-(6-ethoxy-3-pyridinyl)phenyl]methyl]-4,6,7,9-tetrahydro-3-hydroxy-9,9-dimethyl-4-oxo- | 3.08 | 451.2 |
| 200 | Pyrimido[2,1-c][1,4]oxazine-2-carboxamide, N-[[2-(1-cyclopenten-1-yl)phenyl]methyl]-4,6,7,9-tetrahydro-3-hydroxy-9,9-dimethyl-4-oxo- | 3.33 | 396.34 |

EXAMPLE 201

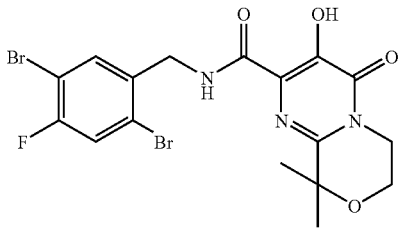

Pyrimido[2,1-c][1,4]oxazine-2-carboxamide, N-[(4-fluoro-2,5-dibromophenyl)methyl]-4,6,7,9-tetrahydro-3-hydroxy-9,9-dimethyl-4-oxo. A mixture of (2,5-dibromo-4-fluorophenyl)methanamine (1 mmol), intermediate 25 (0.268 g, 1 mmol) and triethylamine (0.5 mL, 3.5 mmol) in ethanol/dimethylformamide (1:1, 3 mL) was heated at 100° C. for 6 h. After cooling, the reaction mixture was purified by preparative HPLC to afford the title compound (0.31 g, 62% yield) as an off-white solid. $^1$H NMR (500 MHz, CDCl$_3$) δ ppm: 11.72 (1H, s), 8.08 (1H, t, J=6.1 Hz), 7.61 (1H, d, J=7.0 Hz), 7.38 (1H, d, J=7.6 Hz), 4.61 (2H, d, J=6.4 Hz), 4.02 (4H, s), 1.59 (6H, s).

EXAMPLE 202

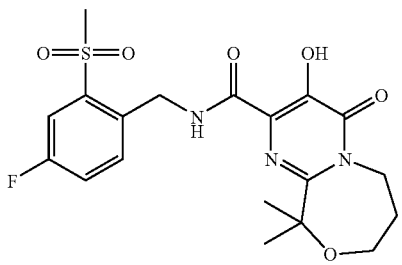

6H-Pyrimido[2,1-c][1,4]oxazepine-2-carboxamide, N-[[4-fluoro-2-(methylsulfonyl)phenyl]methyl]-4,7,8,10-tetrahydro-3-hydroxy-10,10-dimethyl-4-oxo-. Off-white solid. $^1$H NMR (500 MHz, CDCl$_3$) δ ppm: 11.77 (1H, br s), 8.55 (1H, t, J=6.3 Hz), 7.75 (1H, dd, J=8.1, 2.6 Hz), 7.72 (1H, dd, J=8.5, 5.2 Hz), 7.34 (1H, td, J=8.0, 2.6 Hz), 4.81 (2H, d, J=6.7 Hz), 4.54 (2H, br), 3.65 (2H, t, J=6.1 Hz), 3.18 (3H, s), 1.93 (2H, m), 1.59 (6H, s); $^{13}$C NMR (126 MHz, CDCl$_3$) δ ppm: 168.14, 163.14, 161.13, 158.23, 153.73, 147.26, 140.77, 140.72, 135.31, 135.25, 132.83, 132.80, 124.83, 121.69 121.52, 117.63, 117.43, 82.56, 60.80, 45.14, 40.24, 38.62, 27.76, 27.35. HRMS (ESI) calcd for C$_{19}$H$_{23}$N$_3$O$_6$FS (M+H): 440.1292; found: 440.1300. Anal. Calcd for C$_{19}$H$_{22}$N$_3$O$_6$FS.0.06 H$_2$O: C, 51.80; H, 5.06; N, 9.54; F, 4.31; found C, 51.83; H, 4.97; N, 9.29; F, 4.12.

EXAMPLE 203

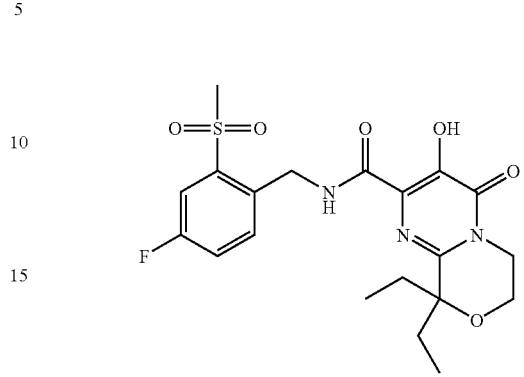

Pyrimido[2,1-c][1,4]oxazine-2-carboxamide, 9,9-diethyl-N-[[4-fluoro-2-(methylsulfonyl)phenyl]methyl]-4,6,7,9-tetrahydro-3-hydroxy-4-oxo-. $^1$H NMR (500 MHz, CDCl$_3$) δ ppm: 11.74 (1H, s), 8.54 (1H, t, J=6.6 Hz), 7.75 (1H, dd, J=8.2, 2.7 Hz), 7.71 (1H, dd, J=8.5, 5.2 Hz), 7.34 (1H, td, J=8.0, 2.6 Hz), 4.82 (2H, d, J=7.0 Hz), 3.94-4.00 (4H, m), 3.17 (3H, s), 1.93-2.00 (2 H, m), 1.84-1.92 (2H, m), 0.83 (6H, t, J=7.3 Hz); $^{13}$C NMR (126 MHz, CDCl$_3$) δ ppm: 168.26, 163.13, 161.11, 157.83, 151.66, 146.05, 140.69, 140.64, 135.13, 135.07, 132.80, 132.77, 125.63, 121.65, 121.48, 117.65, 117.45, 81.03, 58.51, 45.14, 43.08, 40.33, 31.38, 7.87. HRMS (ESI) calcd for C$_{20}$H$_{25}$N$_3$O$_6$FS (M+H): 454.1448; found: 454.1448. Anal. calcd for C$_{20}$H$_{24}$N$_3$O$_6$FS: C, 52.97; H, 5.33; N, 9.27; S, 7.07; found: C, 53.01; H, 5.60; N, 9.10; S, 7.00.

EXAMPLE 204

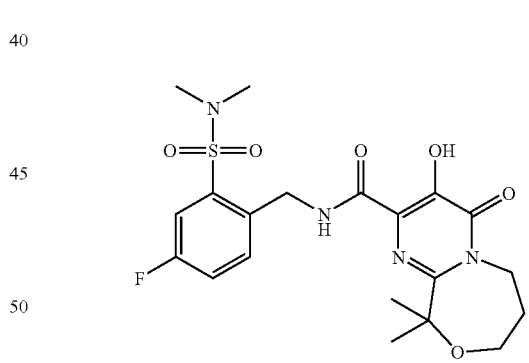

6H-Pyrimido[2,1-c][1,4]oxazepine-2-carboxamide, N-[[2-[(dimethylamino)sulfonyl]-4-fluorophenyl]methyl]-4,7,8,10-tetrahydro-3-hydroxy-10,10-dimethyl-4-oxo-. Pale orange solid. $^1$H NMR (500 MHz, CDCl$_3$) δ ppm: 11.87 (1H, br s), 8.59 (1H, t, J=6.4 Hz), 7.69 (1H, dd, J=8.5, 5.2 Hz), 7.49 (1H, dd, J=8.2, 2.4 Hz), 7.26 (1H, td, J=7.7, 3.2 Hz), 4.79 (2H, d, J=6.7 Hz), 4.53 (2H, br), 3.65 (2H, t, J=6.1 Hz), 2.90 (6H, s), 1.89-1.96 (2H, m), 1.57-1.61 (6H, s); $^{13}$C NMR (126 MHz, CDCl$_3$) δ ppm: 168.03, 162.71, 160.70, 158.29, 153.57, 147.23, 138.51, 138.46, 135.30, 135.25, 132.70, 132.67, 124.99, 120.40, 120.24, 116.93, 116.73, 82.59, 60.79, 58.57, 40.26, 38.58, 37.59, 27.74, 27.36, 18.55. HRMS (ESI) calcd for C$_{20}$H$_{26}$N$_4$O$_6$FS (M+H) 469.1557; found 469.1557. Anal.

calcd for $C_{20}H_{26}N_4O_6FS \cdot CH_3CH_2OH$: C, 51.29; H, 6.07; N, 10.89; S, 6.01; F, 3.69; found C, 51.29; H, 6.33; N, 10.85; S, 6.01; F, 3.54.

EXAMPLE 205

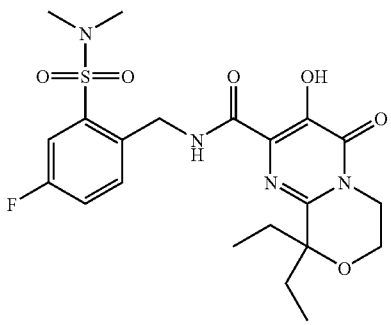

Pyrimido[2,1-c][1,4]oxazine-2-carboxamide, N-[[2-[(dimethylamino)sulfonyl]-4-fluorophenyl]methyl]-9,9-diethyl-4,6,7,9-tetrahydro-3-hydroxy-4-oxo-. White glassy solid. $^1$H NMR (500 MHz, CDCl$_3$) δ ppm: 11.85 (1H, br), 8.59 (1H, t, J=6.4 Hz), 7.68 (1H, dd, J=8.5, 5.2 Hz), 7.49 (1H, dd, J=8.2, 2.4 Hz), 7.24-7.30 (1H, m), 4.80 (2H, d, J=7.0 Hz), 3.94-4.01 (4H, m), 2.90 (6H, s), 1.93-2.01 (2H, m), 1.85-1.93 (2H, m), 0.83 (6H, t, J=7.3 Hz); $^{13}$C NMR (126 MHz, CDCl$_3$) δ ppm: 168.04, 162.70, 160.70, 158.06, 151.44, 145.95, 138.53, 138.49, 135.17, 135.12, 132.62, 132.59, 125.95, 120.37, 120.21, 116.87, 116.68, 81.08, 58.51, 43.11, 40.32, 37.58, 31.35, 7.87. HRMS (ESI) calcd for $C_{21}H_{28}N_4O_6FS$ (M+H) 483.1714; found 483.1702. Anal. calcd for $C_{21}H_{27}N_4O_6FS \cdot 0.15\ CF_3CO_2H$: C, 51.20; H, 5.48; N, 11.21; F, 5.51; S, 6.42; found: C, 51.10; H, 5.23; N, 11.21; F, 5.49; S, 6.32.

EXAMPLE 206

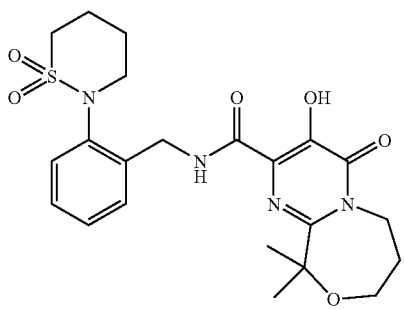

6H-pyrimido[2,1-c][1,4]oxazepine-2-carboxamide, 4,7,8,10-tetrahydro-3-hydroxy-10,10-dimethyl-4-oxo-N-[[2-(tetrahydro-1,1-dioxido-2H-1,2-thiazin-2-yl)phenyl]methyl]-. Off-white solid. $^1$H NMR (500 MHz, CDCl$_3$) δ ppm: 12.18 (1H, br s), 8.14-8.25 (1H, br), 7.41-7.50 (2H, m), 7.31-7.39 (2H, m), 4.96 (1H, dd, J=14.0, 8.9 Hz), 4.54 (2H, br s), 4.44 (1H, dd, J=14.2, 3.2 Hz), 3.83-3.92 (1H, m), 3.65 (2H, br), 3.38-3.46 (1H, m), 3.18-3.28 (2H, m), 2.32-2.42 (2H, m), 1.89-1.98 (4H, m), 1.55 (6H, d, J=15.9 Hz); $^{13}$C NMR (126 MHz, CDCl$_3$) δ ppm: 168.22, 158.38, 153.54, 147.32, 138.80, 137.00, 130.88, 129.47, 129.29, 127.68, 125.17, 82.60, 60.74, 54.15, 51.05, 39.11, 38.63, 27.76, 27.73, 27.36, 25.04, 24.32. HRMS (ESI) calcd for $C_{22}H_{29}N_4O_6S$ (M+H): 477.1808; found: 477.1794. Anal. calcd for $C_{22}H_{28}N_4O_6S \cdot 0.5\ CH_3CH_2OH$: C, 55.45; H, 5.92; N, 11.76; S, 6.73; found: C, 55.36; H, 6.11; N, 11.46; S, 6.48.

EXAMPLE 207

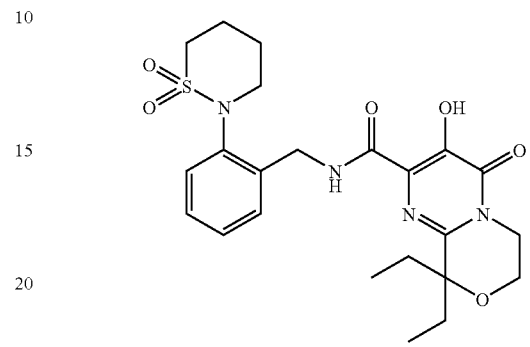

Pyrimido[2,1-c][1,4]oxazine-2-carboxamide, 4,6,7,9-tetrahydro-3-hydroxy-9,9-diethyl-4-oxo-N-[[2-(tetrahydro-1,1-dioxido-2H-1,2-thiazin-2-yl)phenyl]methyl]. Off-white crystalline solid. $^1$H NMR (500 MHz, CDCl$_3$) δ ppm: 12.11 (1H, br s), 8.20 (1H, br), 7.42-7.48 (2H, m), 7.33-7.40 (2H, m), 4.93 (1H, dd, J=14.2, 8.4 Hz), 4.45 (1H, dd, J=14.2, 3.8 Hz), 3.94-4.02 (4H, m), 3.87 (1H, ddd, J=13.0, 9.9, 3.7 Hz), 3.39-3.46 (1H, m), 3.15-3.24 (2H, m), 2.29-2.46 (2H, m), 1.79-2.04 (6H, m), 0.81 (3H, t, J=6.7 Hz), 0.78 (3H, t, J=7.3 Hz); $^{13}$C NMR (126 MHz, CDCl$_3$) δ ppm: 168.25, 157.91, 151.43, 146.14, 139.14, 136.81, 130.79, 129.46, 129.25, 127.90, 125.96, 81.15, 58.55, 54.22, 51.09, 43.03, 39.57, 31.21, 25.03, 24.34, 7.82, 7.68. HRMS (ESI) calcd for $C_{23}H_{31}N_4O_6S$ (M+H): 491.1964; found: 491.1953. Anal. calcd for $C_{23}H_{30}N_4O_6S$: C, 56.12; H, 6.48; N, 10.91; S, 6.24; found: C, 56.14; H, 6.44; N, 11.07; S, 6.05.

EXAMPLE 208

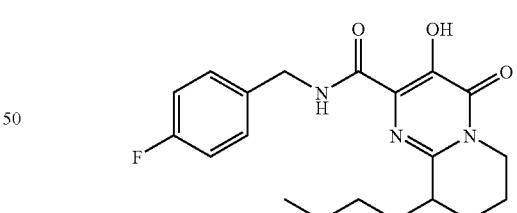

Pyrimido[2,1-c][1,4]oxazine-2-carboxamide, N-[(4-fluorophenyl)methyl]-4,6,7,9-tetrahydro-3-hydroxy-9-[2-(methylthio)ethyl]-4-oxo-. A solution of intermediate 141, N-(4-fluorobenzyl)-3-(benzyloxy)-9-(2-(methylthio)ethyl)-4-oxo-4,6,7,9-tetrahydropyrimido[2,1-c][1,4]oxazine-2-carboxamide in 4 mL CF$_3$CO$_2$H was stirred at 60° C. for 1 hr then concentrated. The residue was dissolved in CH$_2$Cl$_2$ and washed with water then concentrated. Trituration with hexanes gave the title compound as a solid. $^1$H NMR (300 MHz, CDCl$_3$) δ ppm: 12.03 (1 H, s) 7.75 (1 H, m) 6.84-7.40 (4 H, m) 4.39-4.72 (3 H, m) 4.04-4.36 (2 H, m) 3.68-3.92 (2 H, m)

2.49-2.73 (2 H, m) 2.07-2.50 (2 H, m) 2.02 (3 H, s); HRMS (ESI) calcd for $C_{18}H_{20}FN_3O_4S$ (M+H): 394.1237, found: 394.1234.

EXAMPLE 209

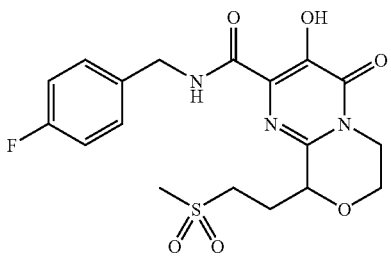

Pyrimido[2,1-c][1,4]oxazine-2-carboxamide, N-[(4-fluorophenyl)methyl]-4,6,7,9-tetrahydro-3-hydroxy-9-[2-(methylsulfonyl)ethyl]-4-oxo-. A solution of example 208, pyrimido[2,1-c][1,4]oxazine-2-carboxamide, N-[(4-fluorophenyl)methyl]-4,6,7,9-tetrahydro-3-hydroxy-9-[2-(methylthio)ethyl]-4-oxo-, (40 mg, 0.11 mmol) in 2 mL $CH_2Cl_2$ was treated with excess m-chloroperbenzoic acid (100 mg, 0.4 mmol) and stirred at room temperature for 20 hrs. The reaction mixture was washed with water and concentrated. The crude material was purified by reverse phase HPLC (C18, 12% $CH_3CN/H_2O$). The fractions containing the product were concentrated and lyophilized to afford 5 mg (12% yield) of the title compound. $^1$H NMR (300 MHz, $CDCl_3$) δ ppm: 12.10-12.27 (1 H, s) 7.80-8.02 (1 H, m) 7.25-7.39 (2 H, m) 6.90-7.09 (2 H, m) 4.05-4.72 (5 H, m) 3.73-3.99 (2 H, m) 3.02-3.34 (2 H, m) 2.86-2.91 (3 H, s) 2.35-2.78 (2 H, m); HRMS (ESI) calcd for $C_{18}H_{20}FN_3O_6S$ (M+H): 426.1135, found: 426.1143.

EXAMPLE 210

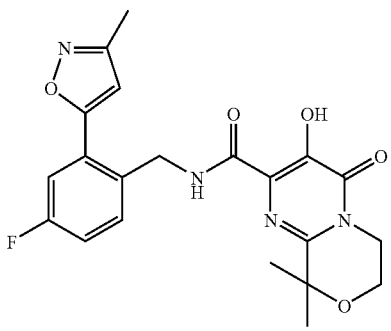

Pyrimido[2,1-c][1,4]oxazine-2-carboxamide, N-[[4-fluoro-2-(3-methyl-5-isoxazolyl)phenyl]methyl]-4,6,7,9-tetrahydro-3-hydroxy-9,9-dimethyl-4-oxo-. The title compound can be prepared from intermediate 180, N-(4-fluoro-2-(3-methylisoxazol-5-yl)benzyl)-3-(benzyloxy)-9,9-dimethyl-4-oxo-4,6,7,9-tetrahydropyrimido[2,1-c][1,4]oxazine-2-carboxamide. $^1$HNMR 400 MHz ($CDCl_3$) δ ppm: 1.59 (6H, s, 2×$CH_3$), 2.42 (3H, s, $CH_3$), 4.03 (4H, s, 2×$CH_2$), 4.74 (2H, d, J=6.6 Hz, $NCH_2$), 6.40 (1H, s, aromatic), 7.18 (1H, m, aromatic), 7.32 (1H, dd, J=2.5 Hz and J=9.1 Hz, aromatic), 7.59 (1H, dd, J=5.6 Hz and J=8.6 Hz, aromatic), 8.29 (1H, broad t, NH), 11.87 (1H, s, OH). HRMS (ESI$^+$) calculated for $C_{21}H_{22}FN_4O_5$ [M+H$^+$]: 429.1574; found: 429.1584.

EXAMPLE 211

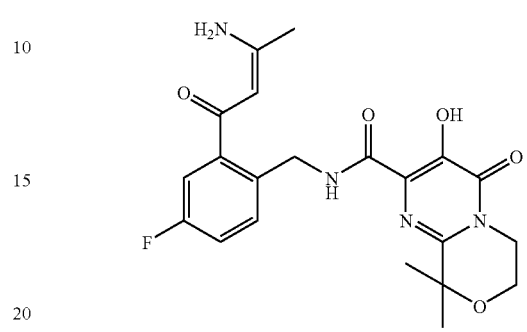

Pyrimido[2,1-c][1,4]oxazine-2-carboxamide, N-[[2-[(2Z)-3-amino-1-oxo-2-butenyl]-4-fluorophenyl]methyl]-4,6,7,9-tetrahydro-3-hydroxy-9,9-dimethyl-4-oxo-. $^1$HNMR 400 MHz ($CDCl_3$) δ ppm: 1.63 (6H, s, 2×$CH_3$), 2.11 (3H, s, $CH_3$), 4.03 (4H, s, 2×$CH_2$), 4.58 (2H, d, J=6.5 Hz, $NCH_2$), 5.38 (1H, broad, NH), 5.49 (1H, s, CH), 7.09 (1H, m, aromatic), 7.29 (1H, dd, J=3.0 Hz and J=9.1 Hz, aromatic), 7.48 (1H, dd, J=5.6 Hz and J=8.6 Hz, aromatic), 9.19 (1H, broad t, NH), 10.26 (1H, broad, NH), 12.21 (1H, s, OH).

EXAMPLE 212

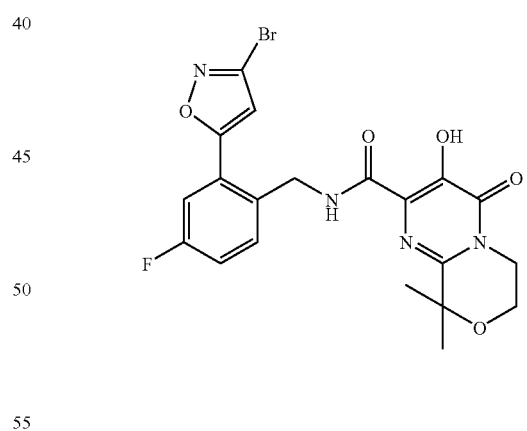

Pyrimido[2,1-c][1,4]oxazine-2-carboxamide, N-[[2-(3-bromo-5-isoxazolyl)-4-fluorophenyl]methyl]-4,6,7,9-tetrahydro-3-hydroxy-9,9-dimethyl-4-oxo-. The title compound can be prepared from intermediate 181, N-(2-(3-bromoisoxazol-5-yl)-4-fluorobenzyl)-3-(benzyloxy)-9,9-dimethyl-4-oxo-4,6,7,9-tetrahydropyrimido[2,1-c][1,4]oxazine-2-carboxamide. $^1$HNMR 400 MHz ($CDCl_3$) δ ppm: 1.60 (6H, s, 2×$CH_3$), 4.03 (4H, s, 2×$CH_2$), 4.74 (2H, d, J=7.1 Hz, $NCH_2$), 6.63 (1H, s, aromatic), 7.24 (1H, m, aromatic), 7.32 (1H, dd, J=2.5 Hz and J=9.1 Hz, aromatic), 7.63 (1H, dd, J=5.5 Hz and J=8.6 Hz, aromatic), 8.20 (1H, broad t, NH), 11.77 (1H, s, OH).

EXAMPLE 213

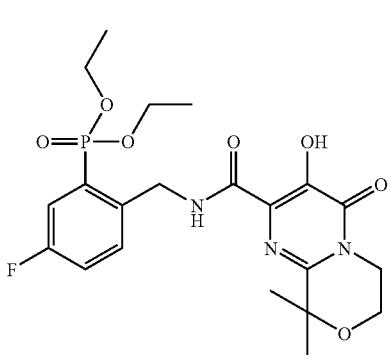

Phosphonic acid, [5-fluoro-2-[[[(4,6,7,9-tetrahydro-3-hydroxy-9,9-dimethyl-4-oxopyrimido[2,1-c][1,4]oxazin-2-yl)carbonyl]amino]methyl]phenyl]-, diethyl ester. Hydrogenolysis of intermediate 187, diethyl 2-((3-(benzyloxy)-9,9-dimethyl-4-oxo-4,6,7,9-tetrahydropyrimido[2,1-c][1,4]oxazine-2-carboxamido)methyl)-5-fluorophenylphosphonate (0.089 g, 0.15 mmol) gave 0.065 g (90% yield) of the title compound as a white solid: mp 124° C. $^1$HNMR 400 MHz (CDCl$_3$) δ ppm: 1.39 (6H, t, J=7.1 Hz, 2×CH$_3$), 1.63 (6H, s, 2×CH$_3$), 4.02 (4H, s, 2×CH$_2$), 4.20 (4H, m, 2×OCH$_2$), 4.78 (2H, d, J=6.6 Hz, NCH$_2$), 7.25 (1H, m, aromatic), 7.49 (1H, m, aromatic), 7.63 (1H, m, aromatic), 9.12 (1H, broad t, NH)., 12.1 (1H, broad, OH). HRMS (ESI$^+$) calculated for C$_{21}$H$_{28}$FN$_3$O$_7$P [M+H$^+$]: 484.1649; found: 484.1646.

EXAMPLE 214

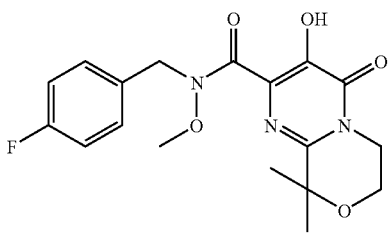

Pyrimido[2,1-c][1,4]oxazine-2-carboxamide, N-[(4-fluorophenyl)methyl]-4,6,7,9-tetrahydro-3-hydroxy-N-methoxy-9,9-dimethyl-4-oxo-. The title compound can be prepared from intermediate 171, N-(4-fluorobenzyl)-3-(benzyloxy)-N-methoxy-9,9-dimethyl-4-oxo-4,6,7,9-tetrahydropyrimido[2,1-c][1,4]oxazine-2-carboxamide. $^1$HNMR 400 MHz (DMSO-d$_6$) δ ppm: (mixture of rotamers) 1.52 (6H, s, 2×CH$_3$), 3.59 (3H, s, OCH$_3$), 3.89 (2H, broad, CH$_2$), 4.01 (2H, broad, CH$_2$), 4.68 and 4.91 (2H, broad, NCH$_2$), 7.18 (2H, m, aromatics), 7.43 (2H, m, aromatics), 9.88 and 10.2 (1H, broad, OH).

EXAMPLE 215

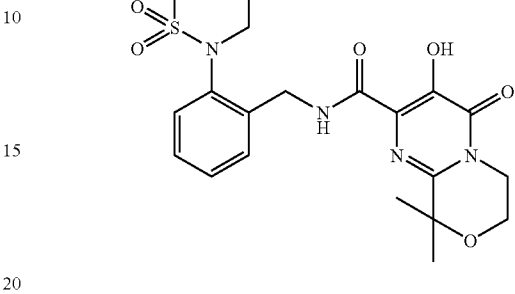

Pyrimido[2,1-c][1,4]oxazine-2-carboxamide, 4,6,7,9-tetrahydro-3-hydroxy-9,9-dimethyl-4-oxo-N-[[2-(tetrahydro-1,1-dioxido-2H-1,2-thiazin-2-yl)phenyl]methyl]-. The title compound can be prepared from intermediate 101. Pale brown solid. $^1$H-NMR (300 MHz, CDCl$_3$) δ ppm: 12.11 (1H, s), 8.32-8.29 (1H, m), 7.46-7.42 (2H, m), 7.36-7.32 (2H, m), 4.92 (1H, dd, J=14.3, 8.8 Hz), 4.40 (1H, dd, J=14.1, 3.5 Hz), 3.97 (4H, s), 3.90-3.81 (1H, m), 3.47-3.37 (1H, m), 3.24-3.18 (2H, m), 2.42-2.28 (2H, m), 1.97-1.86 (2H, m), 1.54 (3H, s), 1.50 (3H, s). HRMS [M+H]$^+$ calcd for C$_{21}$H$_{27}$N$_4$SO$_6$: 463.1651; found: 463.1669. Anal calcd for C$_{21}$H$_{26}$N$_4$SO$_6$: C, 54.53; H, 5.67; N, 12.11; S, 6.93; found: C, 54.53; H, 5.41; N, 12.40; S, 6.69.

EXAMPLE 216

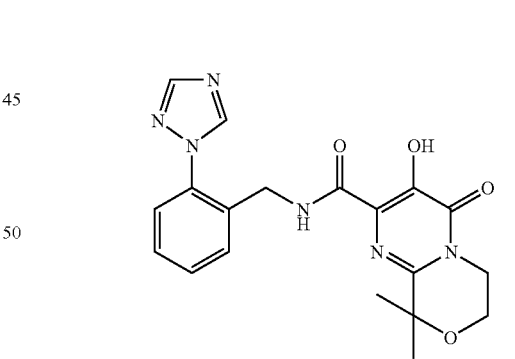

Pyrimido[2,1-c][1,4]oxazine-2-carboxamide, 4,6,7,9-tetrahydro-3-hydroxy-9,9-dimethyl-4-oxo-N-[[2-(1H-1,2,4-triazol-1-yl)phenyl]methyl]-. White solid. $^1$H-NMR (300 MHz, CDCl$_3$) δ ppm: 11.94 (1H, s), 8.86 (1H, t, J=6.2 Hz), 8.42 (1H, s), 8.16 (1H, s), 7.66 (1H, dd, J=7.3, 1.8 Hz), 7.51-7.42 (2H, m), 7.35-7.32 (1H, m), 4.45 (2H, d, J=6.6 Hz), 3.98 (4H, s), 1.59 (6H, s). HRMS [M+H]$^+$ calcd for $C_{19}H_{21}N_6O_4$: 397.1624; found: 397.1609. Anal calcd for $C_{19}H_{20}N_6O_4$: C, 57.57; H, 5.08; N, 21.20; found: C, 57.40; H, 4.96; N, 21.09.

EXAMPLE 217

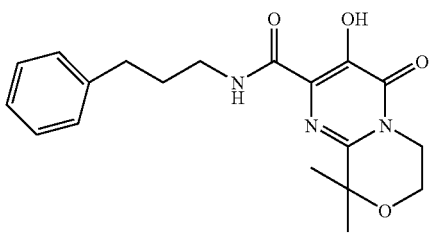

Pyrimido[2,1-c][1,4]oxazine-2-carboxamide, 4,6,7,9-tetrahydro-3-hydroxy-9,9-dimethyl-4-oxo-N-(3-phenylpropyl)-$^1$H NMR (500 MHz, DMSO-D6) δ ppm: 1.56 (s, 6 H) 1.82-1.89 (m, 2 H) 2.62 (t, J=7.48 Hz, 2 H) 3.31 (m, 2 H) 3.82 (t, J=5.04 Hz, 2 H) 3.97 (t, J=5.04 Hz, 2 H) 7.16-7.24 (m, 3 H) 7.29 (m, 2 H) 8.91 (s, 1 H) 12.41 (s, 1 H). Anal calcd for $C_{19}H_{23}N_3O_4$: C, 63.85; H, 6.48; N, 11.75. Found: C, 63.56; H, 6.67; N, 12.01.

EXAMPLES 218-259

Examples 218-259, in table 11, were prepared using methods similar to those described for examples 1, 19, 20. The compounds were characterized by LCMS with the observed retention time (RT, minutes) and molecular weight (MS [M+1]) listed in the table.

TABLE 11

| Example | Structure | RT | MS |
|---|---|---|---|
| 218 | Pyrimido[2,1-c][1,4]oxazine-2-carboxamide, N-(1,3-benzodioxol-5-ylmethyl)-4,6,7,9-tetrahydro-3-hydroxy-9,9-dimethyl-4-oxo- | 1.55 | 374.2 |
| 219 | Pyrimido[2,1-c][1,4]oxazine-2-carboxamide, 4,6,7,9-tetrahydro-3-hydroxy-9,9-dimethyl-4-oxo-N-(phenylmethyl)- | 1.60 | 330.2 |
| 220 | Pyrimido[2,1-c][1,4]oxazine-2-carboxamide, N-[(3-fluorophenyl)methyl]-4,6,7,9-tetrahydro-3-hydroxy-9,9-dimethyl-4-oxo- | 1.63 | 348.2 |

TABLE 11-continued

| Example | Structure | RT | MS |
|---|---|---|---|
| 221 | 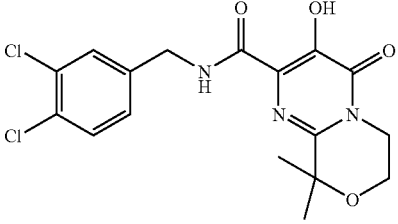<br>Pyrimido[2,1-c][1,4]oxazine-2-carboxamide,<br>N-[(3,4-dichlorophenyl)methyl]-4,6,7,9-<br>tetrahydro-3-hydroxy-9,9-dimethyl-4-oxo- | 1.99 | 398.16 |
| 222 | 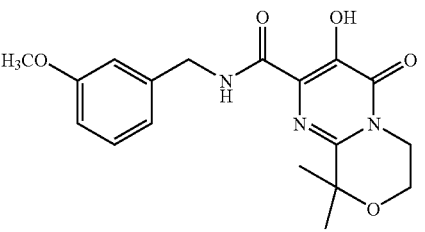<br>Pyrimido[2,1-c][1,4]oxazine-2-carboxamide,<br>4,6,7,9-tetrahydro-3-hydroxy-N-<br>[(3-methoxyphenyl)methyl]-9,9-dimethyl-4-oxo- | 1.61 | 360.2 |
| 223 | 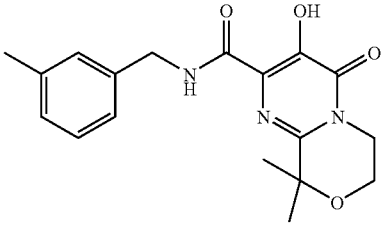<br>Pyrimido[2,1-c][1,4]oxazine-2-carboxamide,<br>4,6,7,9-tetrahydro-3-hydroxy-9,9-dimethyl-N-<br>[(3-methylphenyl)methyl]-4-oxo- | 1.79 | 344.2 |
| 224 | 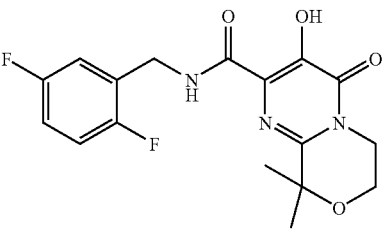<br>Pyrimido[2,1-c][1,4]oxazine-2-carboxamide,<br>N-[(2,5-difluorophenyl)methyl]-4,6,7,9-<br>tetrahydro-3-hydroxy-9,9-dimethyl-4-oxo- | 1.65 | 366.2 |
| 225 | 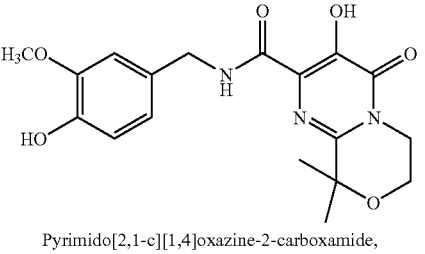<br>Pyrimido[2,1-c][1,4]oxazine-2-carboxamide,<br>4,6,7,9-tetrahydro-3-hydroxy-N-[(4-hydroxy-3-<br>methoxyphenyl)methyl]-9,9-dimethyl-4-oxo- | 1.27 | 376.2 |

TABLE 11-continued

| Example | Structure | RT | MS |
|---|---|---|---|
| 226 | 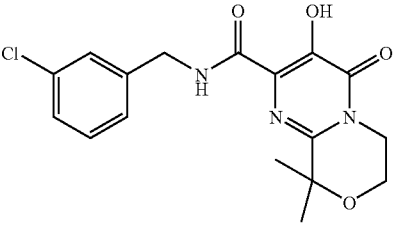<br>Pyrimido[2,1-c][1,4]oxazine-2-carboxamide,<br>N-[(3-chlorophenyl)methyl]-4,6,7,9-tetrahydro-<br>3-hydroxy-9,9-dimethyl-4-oxo- | 1.80 | 364.2 |
| 227 | 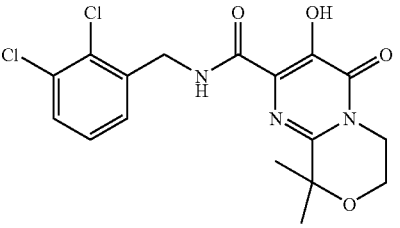<br>Pyrimido[2,1-c][1,4]oxazine-2-carboxamide,<br>N-[(2,3-dichlorophenyl)methyl]-4,6,7,9-<br>tetrahydro-3-hydroxy-9,9-dimethyl-4-oxo- | 2.00 | 398.2 |
| 228 | 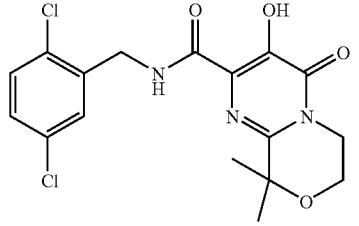<br>Pyrimido[2,1-c][1,4]oxazine-2-carboxamide,<br>N-[(2,5-dichlorophenyl)methyl]-4,6,7,9-<br>tetrahydro-3-hydroxy-9,9-dimethyl-4-oxo- | 1.97 | 398.1 |
| 229 | 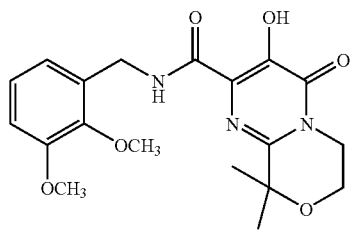<br>Pyrimido[2,1-c][1,4]oxazine-2-carboxamide,<br>N-[(2,3-dimethoxyphenyl)methyl]-4,6,7,9-<br>tetrahydro-3-hydroxy-9,9-dimethyl-4-oxo- | 1.64 | 390.2 |
| 230 | 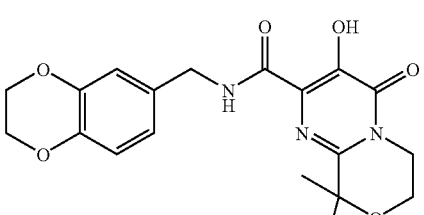<br>Pyrimido[2,1-c][1,4]oxazine-2-carboxamide,<br>N-[(2,3-dihydro-1,4-benzodioxin-6-yl)methyl]-<br>4,6,7,9-tetrahydro-3-hydroxy-9,9-dimethyl-4-oxo- | 1.64 | 390.24 |

TABLE 11-continued

| Example | Structure | RT | MS |
|---|---|---|---|
| 231 | 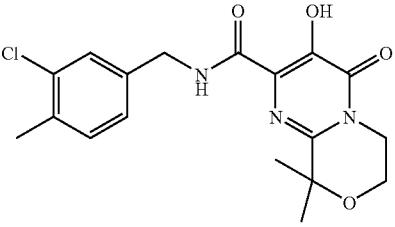<br>Pyrimido[2,1-c][1,4]oxazine-2-carboxamide,<br>N-[(3-chloro-4-methylphenyl)methyl]-4,6,7,9-<br>tetrahydro-3-hydroxy-9,9-dimethyl-4-oxo- | 2.01 | 378.1 |
| 232 | 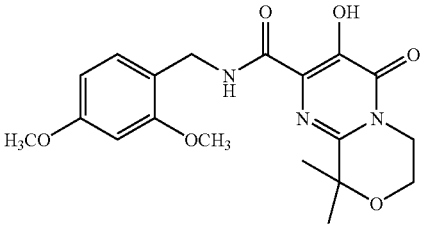<br>Pyrimido[2,1-c][1,4]oxazine-2-carboxamide,<br>N-[(2,4-dimethoxyphenyl)methyl]-4,6,7,9-<br>tetrahydro-3-hydroxy-9,9-dimethyl-4-oxo- | 1.75 | 390.2 |
| 233 | 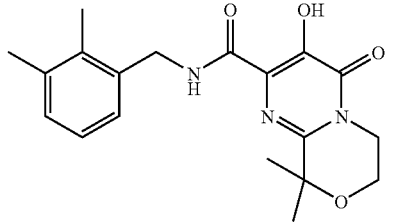<br>Pyrimido[2,1-c][1,4]oxazine-2-carboxamide,<br>N-[(2,3-dimethylphenyl)methyl]-4,6,7,9-<br>tetrahydro-3-hydroxy-9,9-dimethyl-4-oxo- | 1.92 | 358.2 |
| 234 | 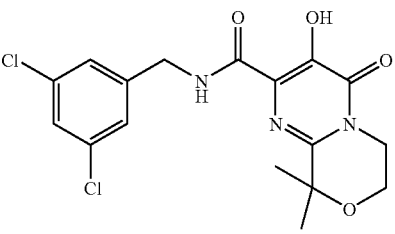<br>Pyrimido[2,1-c][1,4]oxazine-2-carboxamide,<br>N-[(3,5-dichlorophenyl)methyl]-4,6,7,9-<br>tetrahydro-3-hydroxy-9,9-dimethyl-4-oxo- | 2.01 | 398.0 |
| 235 | 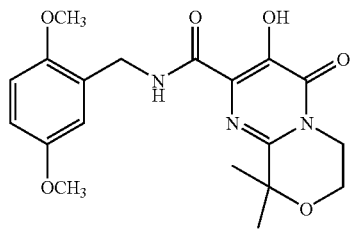<br>Pyrimido[2,1-c][1,4]oxazine-2-carboxamide,<br>N-[(2,5-dimethoxyphenyl)methyl]-4,6,7,9-<br>tetrahydro-3-hydroxy-9,9-dimethyl-4-oxo- | 1.71 | 390.1 |

TABLE 11-continued

| Example | Structure | RT | MS |
|---|---|---|---|
| 236 | 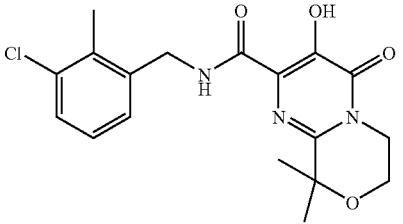<br>Pyrimido[2,1-c][1,4]oxazine-2-carboxamide, N-[(3-chloro-2-methylphenyl)methyl]-4,6,7,9-tetrahydro-3-hydroxy-9,9-dimethyl-4-oxo- | 1.98 | 378.1 |
| 237 | 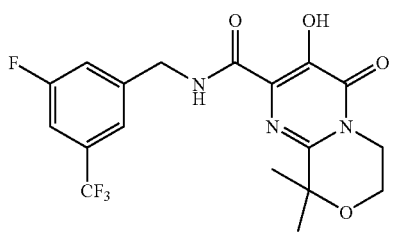<br>Pyrimido[2,1-c][1,4]oxazine-2-carboxamide, N-[[3-fluoro-5-(trifluoromethyl)phenyl]methyl]-4,6,7,9-tetrahydro-3-hydroxy-9,9-dimehyl-4-oxo- | 1.95 | 416.1 |
| 238 | 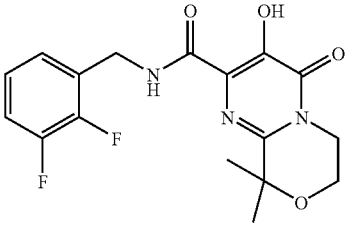<br>Pyrimido[2,1-c][1,4]oxazine-2-carboxamide, N-[(2,3-difluorophenyl)methyl]-4,6,7,9-tetrahydro-3-hydroxy-9,9-dimethyl-4-oxo- | 1.70 | 366.0 |
| 239 | 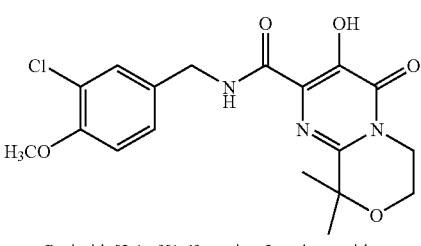<br>Pyrimido[2,1-c][1,4]oxazine-2-carboxamide, N-[(3-chloro-4-methoxyphenyl)methyl]-4,6,7,9-tetrahydro-3-hydroxy-9,9-dimethyl-4-oxo- | 1.71 | 394.0 |
| 240 | 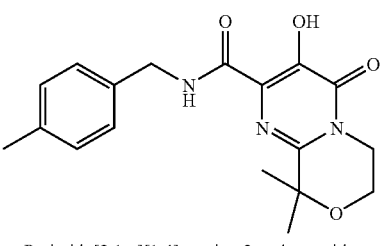<br>Pyrimido[2,1-c][1,4]oxazine-2-carboxamide, 4,6,7,9-tetrahydro-3-hydroxy-9,9-dimethyl-N-[(4-methylphenyl)methyl]-4-oxo- | 1.80 | 344.0 |

TABLE 11-continued

| Example | Structure | RT | MS |
|---|---|---|---|
| 241 | 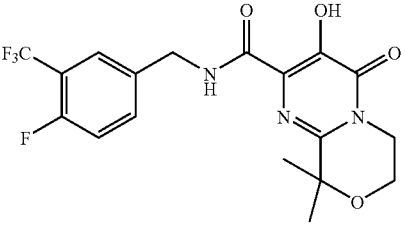<br>Pyrimido[2,1-c][1,4]oxazine-2-carboxamide,<br>N-[[4-fluoro-3-(trifluoromethyl)phenyl]methyl]-<br>4,6,7,9-tetrahydro-3-hydroxy-9,9-dimethyl-4-oxo- | 1.90 | 416.1 |
| 242 | 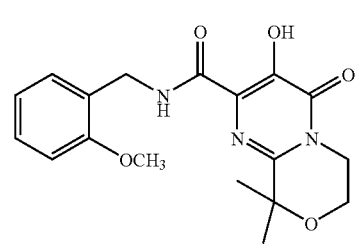<br>Pyrimido[2,1-c][1,4]oxazine-2-carboxamide,<br>4,6,7,9-tetrahydro-3-hydroxy-N-[(2-methoxyphenyl)<br>methyl]-9,9-dimethyl-4-oxo- | 1.80 | 360.1 |
| 243 | 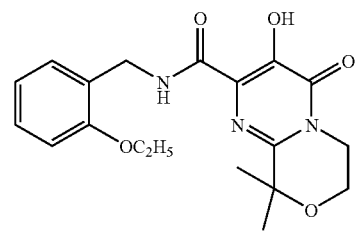<br>Pyrimido[2,1-c][1,4]oxazine-2-carboxamide,<br>N-[(2-ethoxyphenyl)methyl]-4,6,7,9-<br>tetrahydro-3-hydroxy-9,9-dimethyl-4-oxo- | 1.90 | 374.1 |
| 244 | 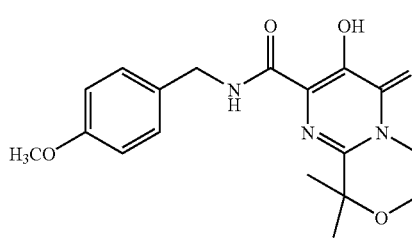<br>Pyrimido[2,1-c][1,4]oxazine-2-carboxamide,<br>4,6,7,9-tetrahydro-3-hydroxy-N-[(4-methoxyphenyl)<br>methyl]-9,9-dimethyl-4-oxo- | 1.60 | 360.1 |
| 245 | 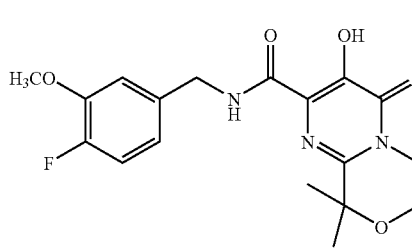<br>Pyrimido[2,1-c][1,4]oxazine-2-carboxamide,<br>N-[(4-fluoro-3-methoxyphenyl)methyl]-4,6,7,9-<br>tetrahydro-3-hydroxy-9,9-dimethyl-4-oxo- | 1.23 | 378.1 |

TABLE 11-continued

| Example | Structure | RT | MS |
|---|---|---|---|
| 246 | 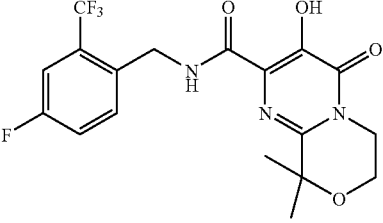<br>Pyrimido[2,1-c][1,4]oxazine-2-carboxamide, N-[[4-fluoro-2-(trifluoromethyl)phenyl]methyl]-4,6,7,9-tetrahydro-3-hydroxy-9,9-dimethyl-4-oxo- | 1.99 | 416.1 |
| 247 | 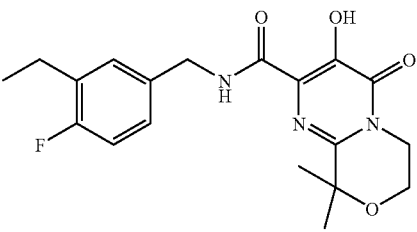<br>Pyrimido[2,1-c][1,4]oxazine-2-carboxamide, N-[(3-ethyl-4-fluorophenyl)methyl]-4,6,7,9-tetrahydro-3-hydroxy-9,9-dimethyl-4-oxo- | 1.98 | 376.1 |
| 248 | 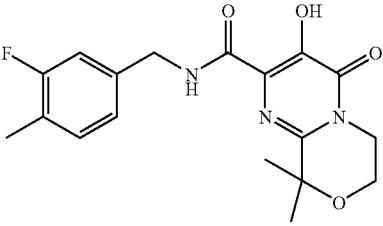<br>Pyrimido[2,1-c][1,4]oxazine-2-carboxamide, N-[(3-fluoro-4-methylphenyl)methyl]-4,6,7,9-tetrahydro-3-hydroxy-9,9-dimethyl-4-oxo- | 1.83 | 362.1 |
| 249 | 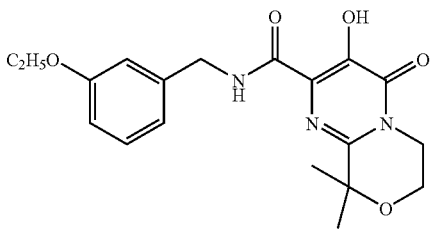<br>Pyrimido[2,1-c][1,4]oxazine-2-carboxamide, N-[(3-ethoxyphenyl)methyl]-4,6,7,9-tetrahydro-3-hydroxy-9,9-dimethyl-4-oxo- | 1.77 | 374.1 |
| 250 | 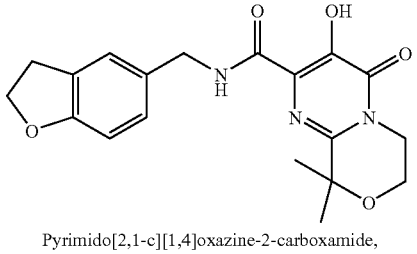<br>Pyrimido[2,1-c][1,4]oxazine-2-carboxamide, N-[(2,3-dihydro-5-benzofuranyl)methyl]-4,6,7,9-tetrahydro-3-hydroxy-9,9-dimethyl-4-oxo- | 1.59 | 372.0 |

TABLE 11-continued

| Example | Structure | RT | MS |
|---|---|---|---|
| 251 | 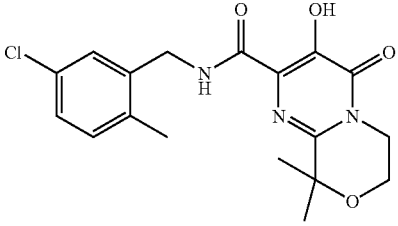

Pyrimido[2,1-c][1,4]oxazine-2-carboxamide, N-[(5-chloro-2-methylphenyl)methyl]-4,6,7,9-tetrahydro-3-hydroxy-9,9-dimethyl-4-oxo- | 1.96 | 378.1 |
| 252 | 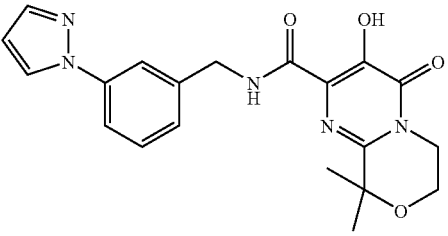

Pyrimido[2,1-c][1,4]oxazine-2-carboxamide, 4,6,7,9-tetrahydro-3-hydroxy-9,9-dimethyl-4-oxo-N-[[3-(1H-pyrazol-1-yl)phenyl]methyl]- | 1.50 | 396.27 |
| 253 | 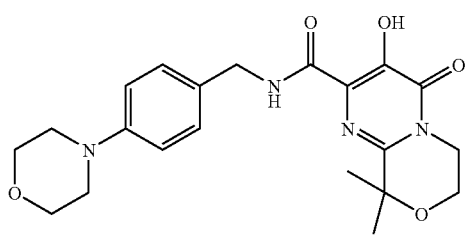

Pyrimido[2,1-c][1,4]oxazine-2-carboxamide, 4,6,7,9-tetrahydro-3-hydroxy-9,9-dimethyl-N-[[4-(4-morpholinyl)phenyl]methyl]-4-oxo- | 1.27 | 415.29 |
| 254 | 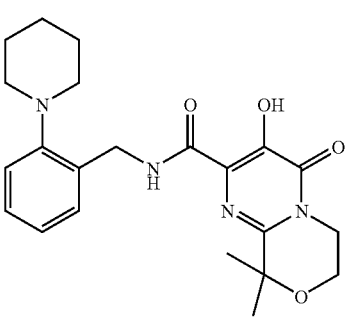

Pyrimido[2,1-c][1,4]oxazine-2-carboxamide, 4,6,7,9-tetrahydro-3-hydroxy-9,9-dimethyl-4-oxo-N-[[2-(1-piperidinyl)phenyl]methyl]- | 1.12 | 413.31 |
| 255 | 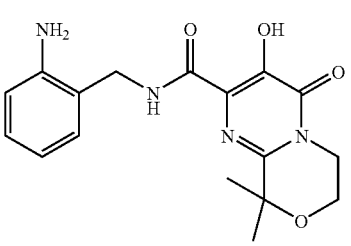

Pyrimido[2,1-c][1,4]oxazine-2-carboxamide, N-[(2-aminophenyl)methyl]-4,6,7,9-tetrahydro-3-hydroxy-9,9-dimethyl-4-oxo- | 1.05 | 345.26 |

TABLE 11-continued

| Example | Structure | RT | MS |
|---|---|---|---|
| 256 | 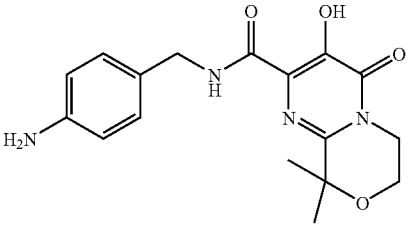<br>Pyrimido[2,1-c][1,4]oxazine-2-carboxamide, N-[(4-aminophenyl)methyl]-4,6,7,9-tetrahydro-3-hydroxy-9,9-dimethyl-4-oxo- | 0.98 | 345.25 |
| 257 | 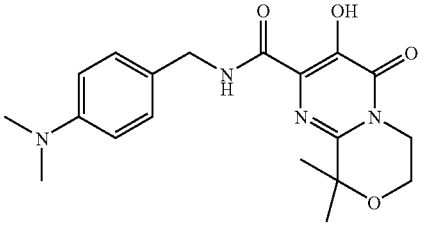<br>Pyrimido[2,1-c][1,4]oxazine-2-carboxamide, N-[[4-(dimethylamino)phenyl]methyl]-4,6,7,9-tetrahydro-3-hydroxy-9,9-dimethyl-4-oxo- | 0.98 | 373.29 |
| 258 | 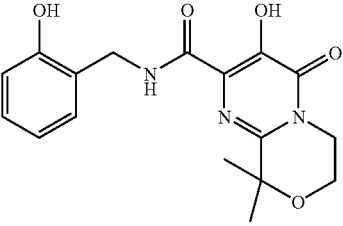<br>Pyrimido[2,1-c][1,4]oxazine-2-carboxamide, 4,6,7,9-tetrahydro-3-hydroxy-N-[(2-hydroxyphenyl)methyl]-9,9-dimethyl-4-oxo- | 1.44 | 346.24 |
| 259 | 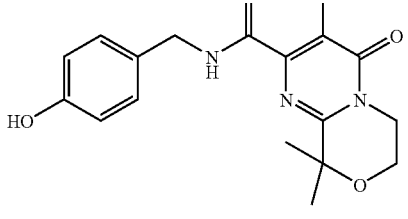<br>Pyrimido[2,1-c][1,4]oxazine-2-carboxamide, 4,6,7,9-tetrahydro-3-hydroxy-N-[(4-hydroxyphenyl)methyl]-9,9-dimethyl-4-oxo- | 1.22 | 346.24 |

EXAMPLES 260-278

Examples 260-278 were prepared according to the methods used for the preparation of the compounds in table 3 and characterized by LCMS.

EXAMPLE 260

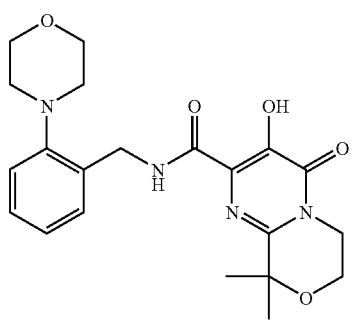

Pyrimido[2,1-c][1,4]oxazine-2-carboxamide, 4,6,7,9-tetrahydro-3-hydroxy-9,9-dimethyl-N-[[2-(4-morpholinyl)phenyl]methyl]-4-oxo-. LCMS: HPLC retention time=4.03 min, MS=[M+1] 415.23.

EXAMPLE 261

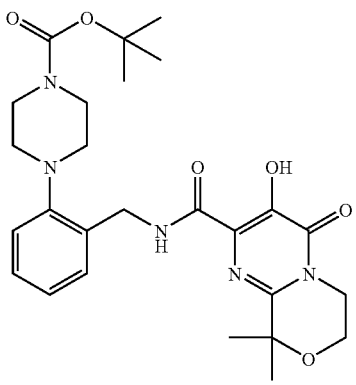

1-Piperazinecarboxylic acid, 4-[2-[[[(4,6,7,9-tetrahydro-3-hydroxy-9,9-dimethyl-4-oxopyrimido[2,1-c][1,4]oxazin-2-yl)carbonyl]amino]methyl]phenyl]-, 1,1-dimethylethyl ester. LCMS: HPLC retention time=4.93 min, MS=[M+1] 514.24.

EXAMPLE 262

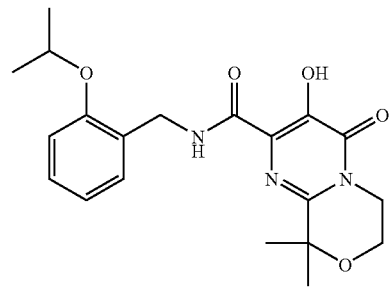

Pyrimido[2,1-c][1,4]oxazine-2-carboxamide, 4,6,7,9-tetrahydro-3-hydroxy-9,9-dimethyl-N-[[2-(1-methylethoxy)phenyl]methyl]-4-oxo-. LCMS: HPLC retention time=4.66 min, MS=[M+1] 388.21.

EXAMPLE 263

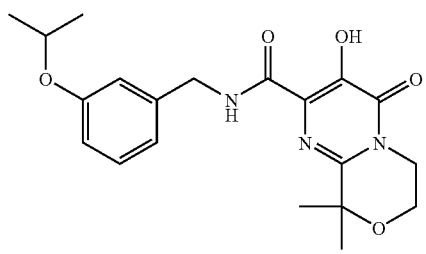

Pyrimido[2,1-c][1,4]oxazine-2-carboxamide, 4,6,7,9-tetrahydro-3-hydroxy-9,9-dimethyl-N-[[3-(1-methylethoxy)phenyl]methyl]-4-oxo-. LCMS: HPLC retention time=3.97 min., MS=[M+1] 4388.21.

EXAMPLE 264

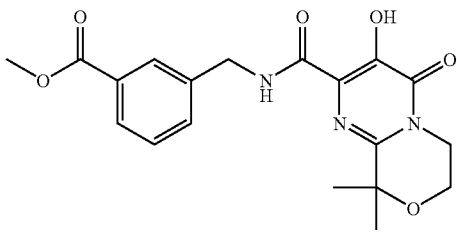

Benzoic acid, 3-[[[(4,6,7,9-tetrahydro-3-hydroxy-9,9-dimethyl-4-oxopyrimido[2,1-c][1,4]oxazin-2-yl)carbonyl]

amino]methyl]-, methyl ester. LCMS: HPLC retention time=3.97 min, MS=[M+1] 388.18.

EXAMPLE 265

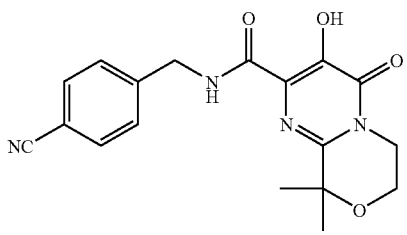

Pyrimido[2,1-c][1,4]oxazine-2-carboxamide, N-[(4-cyanophenyl)methyl]-4,6,7,9-tetrahydro-3-hydroxy-9,9-dimethyl-4-oxo-. LCMS: HPLC retention time=3.59 min, MS=[M+1] 355.2.

EXAMPLE 266

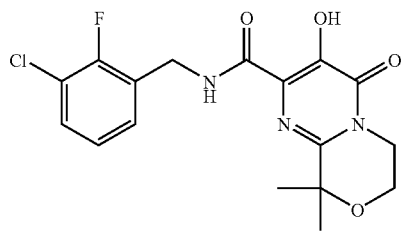

Pyrimido[2,1-c][1,4]oxazine-2-carboxamide, N-[(3-chloro-2-fluorophenyl)methyl]-4,6,7,9-tetrahydro-3-hydroxy-9,9-dimethyl-4-oxo-. LCMS: HPLC retention time=4.47 min, MS=[M+1] 382.14.

EXAMPLE 267

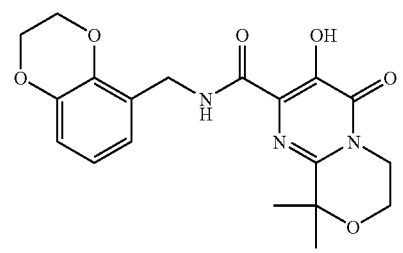

Pyrimido[2,1-c][1,4]oxazine-2-carboxamide, N-[(2,3-dihydro-1,4-benzodioxin-5-yl)methyl]-4,6,7,9-tetrahydro-3-hydroxy-9,9-dimethyl-4-oxo-. LCMS: HPLC retention time=4.15 min, MS=[M+1] 388.2.

EXAMPLE 268

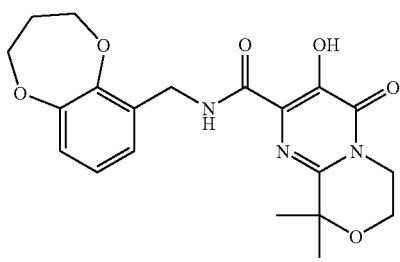

Pyrimido[2,1-c][1,4]oxazine-2-carboxamide, N-[(3,4-dihydro-2H-1,5-benzodioxepin-6-yl)methyl]-4,6,7,9-tetrahydro-3-hydroxy-9,9-dimethyl-4-oxo-. LCMS: HPLC retention time=4.12 min, MS=[M+1] 402.21.

EXAMPLE 269

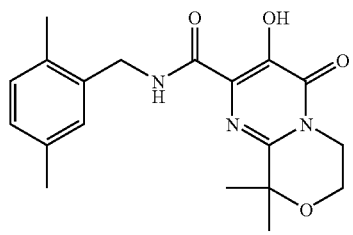

Pyrimido[2,1-c][1,4]oxazine-2-carboxamide, N-[(2,5-dimethylphenyl)methyl]-4,6,7,9-tetrahydro-3-hydroxy-9,9-dimethyl-4-oxo-. LCMS: HPLC retention time=4.64 min, MS=[M+1] 358.22.

EXAMPLE 270

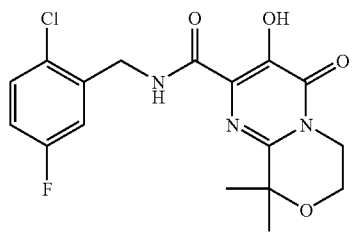

Pyrimido[2,1-c][1,4]oxazine-2-carboxamide, N-[(5-chloro-2-fluorophenyl)methyl]-4,6,7,9-tetrahydro-3-hydroxy-9,9-dimethyl-4-oxo-. LCMS: HPLC retention time=4.44 min, MS=[M+1] 382.15.

EXAMPLE 271

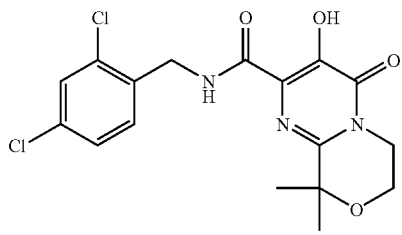

Pyrimido[2,1-c][1,4]oxazine-2-carboxamide, N-[(2,4-dichlorophenyl)methyl]-4,6,7,9-tetrahydro-3-hydroxy-9,9-dimethyl-4-oxo-. LCMS: HPLC retention time=4.88 min, MS=[M+1] 398.11.

EXAMPLE 272

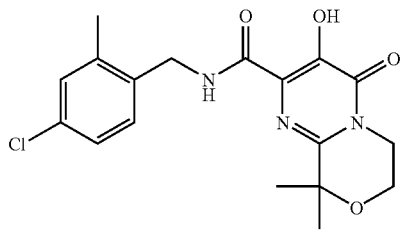

Pyrimido[2,1-c][1,4]oxazine-2-carboxamide, N-[(4-chloro-2-methylphenyl)methyl]-4,6,7,9-tetrahydro-3-hydroxy-9,9-dimethyl-4-oxo-. LCMS: HPLC retention time=4.69 min, MS=[M+1] 378.17.

EXAMPLE 273

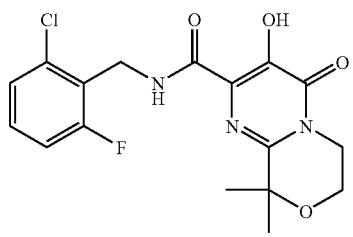

Pyrimido[2,1-c][1,4]oxazine-2-carboxamide, N-[(2-chloro-6-fluorophenyl)methyl]-4,6,7,9-tetrahydro-3-hydroxy-9,9-dimethyl-4-oxo-. LCMS: HPLC retention time=4.39 min, MS=[M+1] 382.13.

EXAMPLE 274

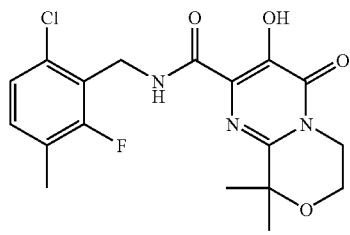

Pyrimido[2,1-c][1,4]oxazine-2-carboxamide, N-[(6-chloro-2-fluoro-3-methylphenyl)methyl]-4,6,7,9-tetrahydro-3-hydroxy-9,9-dimethyl-4-oxo-. LCMS: HPLC retention time=4.74 min, MS=[M+1] 396.14.

EXAMPLE 275

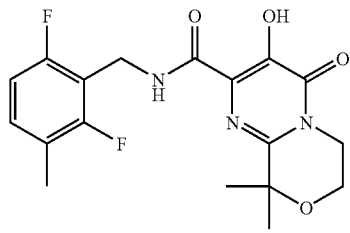

Pyrimido[2,1-c][1,4]oxazine-2-carboxamide, N-[(2,6-difluoro-3-methylphenyl)methyl]-4,6,7,9-tetrahydro-3-hydroxy-9,9-dimethyl-4-oxo-. LCMS: HPLC retention time=4.49 min, MS=[M+1] 380.18.

EXAMPLE 276

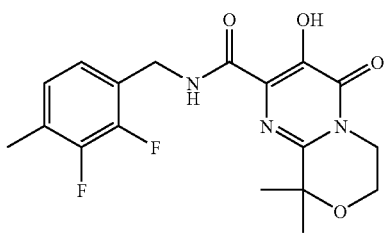

Pyrimido[2,1-c][1,4]oxazine-2-carboxamide, N-[(2,3-difluoro-4-methylphenyl)methyl]-4,6,7,9-tetrahydro-3-hydroxy-9,9-dimethyl-4-oxo-. LCMS: HPLC retention time=4.53 min, MS=[M+1] 380.18.

EXAMPLE 277

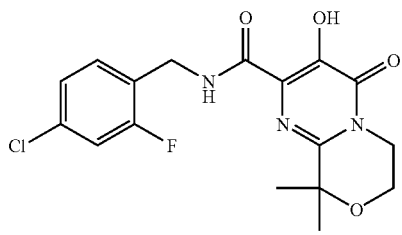

Pyrimido[2,1-c][1,4]oxazine-2-carboxamide, N-[(4-chloro-2-fluorophenyl)methyl]-4,6,7,9-tetrahydro-3-hydroxy-9,9-dimethyl-4-oxo-. LCMS: HPLC retention time=4.57 min, MS=[M+1] 382.13.

EXAMPLE 278

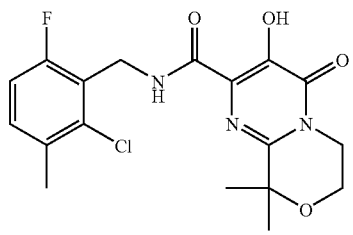

Pyrimido[2,1-c][1,4]oxazine-2-carboxamide, N-[(2-chloro-6-fluoro-3-methylphenyl)methyl]-4,6,7,9-tetrahydro-3-hydroxy-9,9-dimethyl-4-oxo-. LCMS: HPLC retention time=4.68 min, MS=[M+1] 396.16.

EXAMPLE 279

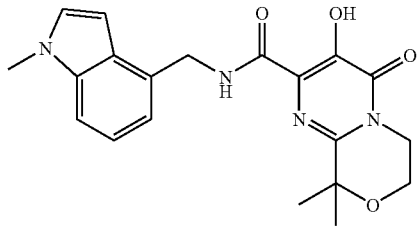

Pyrimido[2,1-c][1,4]oxazine-2-carboxamide, 4,6,7,9-tetrahydro-3-hydroxy-9,9-dimethyl-N-[(1-methyl-1H-indol-4-yl)methyl]-4-oxo-. $^1$H NMR (500 MHz, DMSO-d$_6$) δ ppm: 1.56 (s, 6), 3.79 (s, 3), 3.82 (m, 2), 3.97 (m, 2), 4.76 (d, 2), 6.62 (d, 1), 6.96 (d, 1), 7.12 (m, 1), 7.27-7.38 (overlapping m, 2). HRMS [M+1] calcd for $C_{20}H_{23}N_4O_4$, 383.1641; found, 383.1717. Anal calcd for $C_{20}H_{22}N_4O_4$: C, 62.81; H, 5.79; N, 14.65. Found: C, 62.88; H, 6.08; N, 13.56.

EXAMPLE 280

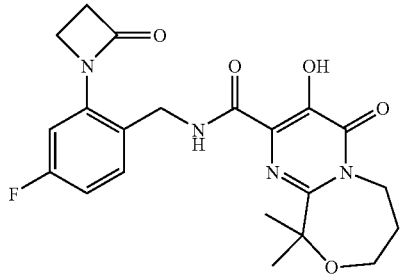

6H-Pyrimido[2,1-c][1,4]oxazepine-2-carboxamide, N-[[4-fluoro-2-(2-oxo-1-azetidinyl)phenyl]methyl]-4,7,8,10-tetrahydro-3-hydroxy-10,10-dimethyl-4-oxo-. $^1$H NMR (400 MHz, DMSO-d$_6$) δ: 12.17 (1H, s), 9.28 (1H, broad s), 7.37 (1H, dd, J=8.2, 6.7 Hz), 7.23 (1H, dd, J=10.2, 2.4 Hz), 7.04 (1H, m), 4.51 (2H, broad s), 4.35 (2H, broad s), 3.79 (2H, t, J=4.4 Hz), 3.62 (2H, m), 3.11 (2H, t, J=4.4 Hz), 1.81 (2H, m), 1.55 (6H, s). LCMS (M+H)$^+$ m/z 431.

EXAMPLE 281

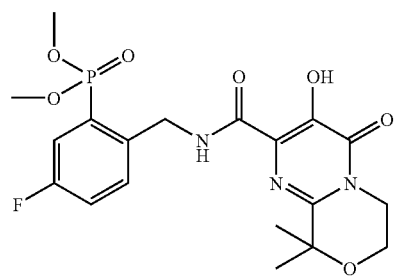

Phosphonic acid, [5-fluoro-2-[[[(4,6,7,9-tetrahydro-3-hydroxy-9,9-dimethyl-4-oxopyrimido[2,1-c][1,4]oxazin-2-yl)carbonyl]amino]methyl]phenyl]-, dimethyl ester. Hydrogenation of dimethyl 2-((3-(benzyloxy)-9,9-dimethyl-4-oxo-4,6,7,9-tetrahydropyrimido[2,1-c][1,4]oxazine-2-carboxamido)methyl)-5-fluorophenylphosphonate (0.030 g, 0.055 mmol) gave 0.018 g (72%) of the title compound as a white solid $^1$HNMR 400 MHz (CDCl$_3$) δ (ppm): 1.63 (6H, s, 2×CH$_3$), 3.84 (3H, s, OCH$_3$), 3.87 (3H, s, OCH$_3$), 4.03 (4H, s, 2×CH$_2$), 4.77 (2H, d, J=6.5 Hz, NCH$_2$), 7.28 (1H, m, aromatic), 7.47 (1H, m, aromatic), 7.65 (1H, m, aromatic), 9.0 (1H, broad t, NH) 12.0 (1H, broad, OH). MS (ESI$^+$) m/z 456 [M+H$^+$].

EXAMPLE 282

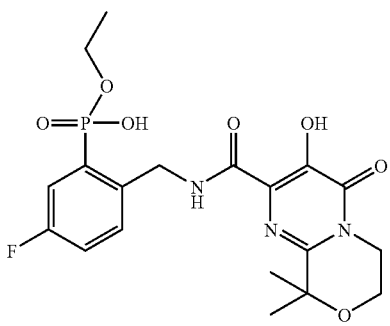

Phosphonic acid, [5-fluoro-2-[[[(4,6,7,9-tetrahydro-3-hydroxy-9,9-dimethyl-4-oxopyrimido[2,1-c][1,4]oxazin-2-yl)carbonyl]amino]methyl]phenyl]-, monoethyl ester. The title compound can be prepared from intermediate 188, ethyl hydrogen 2-((3-(benzyloxy)-9,9-dimethyl-4-oxo-4,6,7,9-tetrahydropyrimido[2,1-c][1,4]oxazine-2-carboxamido)methyl)-5-fluorophenylphosphonate. $^1$HNMR 400 MHz (CDCl$_3$) δ (ppm): 1.32 (3H, t, J=7.1 Hz, CH$_3$), 1.60 (6H, s, 2×CH$_3$), 4.02 (4H, s, 2×CH$_2$), 4.12 (2H, m, OCH$_2$), 4.83 (2H, broad, NCH$_2$), 7.18 (1H, m, aromatic), 7.54 (2H, m, aromatics), 8.49 (1H, broad, NH). HRMS (ESI$^+$) calculated for C$_{19}$H$_{24}$FN$_3$O$_7$P [M+H$^+$]: 456.1336; found: 456.1353.

We claim:

1. A composition useful for treating HIV infections comprising a therapeutic amount of the compound

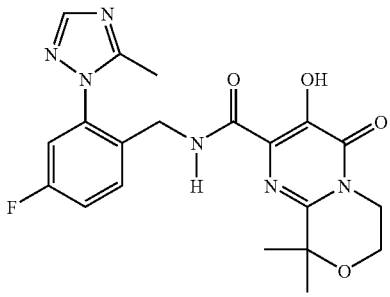

and a pharmaceutically acceptable carrier.

2. The composition of claim 1 further comprising a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

3. A method for treating HIV infection comprising administering a therapeutically effective amount of the compound

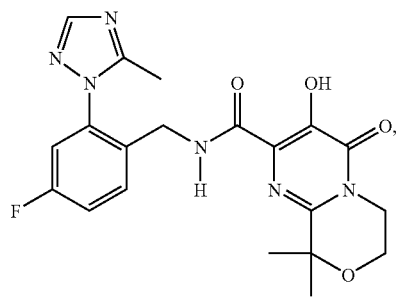

or a pharmaceutically acceptable salt thereof, to a patient in need thereof.

4. The method of claim 3 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *

UNITED STATES PATENT AND TRADEMARK OFFICE
CERTIFICATE OF CORRECTION

PATENT NO. : 7,511,037 B2  Page 1 of 1
APPLICATION NO. : 11/505149
DATED : March 31, 2009
INVENTOR(S) : B. Narasimhulu Naidu et al.

It is certified that error appears in the above-identified patent and that said Letters Patent is hereby corrected as shown below:

On the Title Page:

Item (54), change "N-[[4-FLUORO-2-(5-METHY-lH-1,2,4-TRIAZOL-l-YL)PHENYL]METHYL]-4-,6,7,9-TETRAHYDRO-3-HYDROXY-9,9-DIMETHYL-4-OXO-PYRIMIDO[2,l-C][l,4]OXAZINE-2-CARBOXAMIDE AS AN HIV INTEGRASE INHIBITOR" to -- N-[[4-FLUORO-2-(5-METHYL-lH-1,2,4-TRIAZOL-l-YL)PHENYL]METHYL]-4,6,7,9-TETRAHYDRO-3-HYDROXY-9,9-DIMETHYL-4-OXO-PYRIMIDO[2,l-c][l,4]OXAZINE-2-CARBOXAMIDE AS AN HIV INTEGRASE INHIBITOR --.

In the Specification:

Column 1, lines 1 to 6, change "N-[[4-FLUORO-2-(5-METHY-lH-1,2,4-TRIAZOL-l-YL)PHENYL]METHYL]-4-,6,7,9-TETRAHYDRO-3-HYDROXY-9,9-DIMETHYL-4-OXO-PYRIMIDO[2,l-C][l,4]OXAZINE-2-CARBOXAMIDE AS AN HIV INTEGRASE INHIBITOR" to -- N-[[4-FLUORO-2-(5-METHYL-lH-1,2,4-TRIAZOL-l-YL)PHENYL]METHYL]-4,6,7,9-TETRAHYDRO-3-HYDROXY-9,9-DIMETHYL-4-OXO-PYRIMIDO[2,l-c][l,4]OXAZINE-2-CARBOXAMIDE AS AN HIV INTEGRASE INHIBITOR --.

Column 1, line 8, change "CROSS REFERENCE" to -- CROSS-REFERENCE --.

Signed and Sealed this
Nineteenth Day of April, 2011

David J. Kappos
*Director of the United States Patent and Trademark Office*